United States Patent
Vigneault et al.

(10) Patent No.: US 10,393,743 B2
(45) Date of Patent: Aug. 27, 2019

(54) METHODS OF SELECTING T CELL RECEPTORS USING AFFINITY OLIGONUCLEOTIDE CONJUGATES

(71) Applicant: AbVitro LLC, Boston, MA (US)

(72) Inventors: Francois Vigneault, Seattle, WA (US); Adrian Wrangham Briggs, Seattle, WA (US); Stephen J. Goldfless, Seattle, WA (US); Brian J. Belmont, Seattle, WA (US)

(73) Assignee: AbVitro LLC, Seattle, WA (US)

( * ) Notice: Subject to any disclaimer, the term of this patent is extended or adjusted under 35 U.S.C. 154(b) by 104 days.

(21) Appl. No.: 15/405,301

(22) Filed: Jan. 12, 2017

(65) Prior Publication Data

US 2017/0268056 A1    Sep. 21, 2017

Related U.S. Application Data

(63) Continuation-in-part of application No. PCT/US2016/053598, filed on Sep. 24, 2016.
(Continued)

(51) Int. Cl.
*C12P 19/34* (2006.01)
*G01N 33/569* (2006.01)
(Continued)

(52) U.S. Cl.
CPC ... *G01N 33/56972* (2013.01); *C12N 15/1065* (2013.01); *C12Q 1/6804* (2013.01);
(Continued)

(58) Field of Classification Search
None
See application file for complete search history.

(56) References Cited

U.S. PATENT DOCUMENTS

| 5,635,363 A | 6/1997 | Altman et al. |
| 6,143,495 A | 11/2000 | Lizardi et al. |

(Continued)

FOREIGN PATENT DOCUMENTS

| WO | WO-2012048340 A2 | 4/2012 |
| WO | WO-2012048341 A1 | 4/2012 |

(Continued)

OTHER PUBLICATIONS

Andersen et al., Parallel detection of antigen-specific T cell responses by combinatorial encoding of MHC multimers, Nat Protoc., 7(5): 891-902 (2012).
(Continued)

*Primary Examiner* — Kenneth R Horlick
(74) *Attorney, Agent, or Firm* — Finnegan, Henderson, Farabow, Garrett & Dunner, LLP

(57) ABSTRACT

Provided herein are methods and compositions for single cell characterization using affinity-oligonucleotide conjugates, including tetramer-oligonucleotide conjugates (e.g., pMHC-oligonucleotide). In some aspects, such methods may comprise the steps of: forming a vessel comprising an affinity-oligonucleotide conjugate and a T cell; attaching a vessel barcoded polynucleotide or complement thereof to: (a) an oligonucleotide portion of a pMHC-oligonucleotide conjugate, and (b) a T cell receptor (TCR) polynucleotide originating from the T cell; and sequencing the oligonucleotide portion or a complement thereof and the TCR polynucleotide or a complement thereof. Additional methods provided herein include determining the binding affinity of a T cell receptor (TCR) to a pMHC-oligonucleotide. Compositions of the present invention encompass a plurality of vessels, wherein a vessel of the plurality of vessels may comprise a single T cell; and a vessel barcoded polynucle-
(Continued)

otide, wherein the vessel may further comprise a pMHC-oligonucleotide conjugate.

31 Claims, 29 Drawing Sheets

Specification includes a Sequence Listing.

Related U.S. Application Data

(60) Provisional application No. 62/232,209, filed on Sep. 24, 2015.

(51) Int. Cl.
    *C12Q 1/6804*    (2018.01)
    *C12Q 1/6869*    (2018.01)
    *C12N 15/10*     (2006.01)
    *C12Q 1/6881*    (2018.01)
    *G01N 33/68*     (2006.01)

(52) U.S. Cl.
CPC ......... *C12Q 1/6869* (2013.01); *C12Q 1/6881* (2013.01); *G01N 33/6872* (2013.01); *C12Q 2600/158* (2013.01); *G01N 2333/7051* (2013.01); *G01N 2333/70514* (2013.01); *G01N 2333/70517* (2013.01); *G01N 2333/70539* (2013.01); *G01N 2458/10* (2013.01)

(56) References Cited

U.S. PATENT DOCUMENTS

| | | | |
|---|---|---|---|
| 6,413,495 B1 | 7/2002 | Aizawa et al. | |
| 7,902,121 B2 | 3/2011 | Chen et al. | |
| 2017/0343545 A1* | 11/2017 | Hadrup | C07K 14/70539 |
| 2018/0180601 A1* | 6/2018 | Pedersen | G01N 33/533 |

FOREIGN PATENT DOCUMENTS

| | | |
|---|---|---|
| WO | WO-2014144495 A1 | 9/2014 |
| WO | WO-2014145047 A1 | 9/2014 |
| WO | WO-2015006379 A2 | 1/2015 |
| WO | WO-2015153788 A1 | 10/2015 |
| WO | WO-2015185067 A1 | 12/2015 |
| WO | WO-2016100977 A1 | 6/2016 |

OTHER PUBLICATIONS

Bentzen et al., Large-scale detection of antigen-specific T cells using peptide-MHC-I multimers labeled with DNA barcodes, Nat Biotechnol., 34(10): 1037-1045 (2016).

DeKosky et al., High-throughput sequencing of the paired human immunoglobulin heavy and light chain repertoire, Nat Biotechnol., 31(2): 166-169 (2013).

International Search Report and Written Opinion dated Jan. 4, 2017 for International Application No. PCT/US2016/053598.

International Search Report and Written Opinion dated Jun. 6, 2017 for International Application No. PCT/US2017/013274.

Macosko et al., Highly Parallel Genome-wide Expression Profiling of Individual Cells Using Nanoliter Droplets, Cell, 161(5): 1202-1214 (2015).

* cited by examiner

|  | \multicolumn{4}{c}{protein} |
| --- | --- | --- | --- | --- |
| 3,682 TCR Vβ droplet barcodes | CD4 | CD8 | undef | TOTAL |
| mRNA CD4 | 33.0% | 1.4% | 0.4% | 34.8% |
| mRNA CD8 | 0.7% | 16.6% | 0.1% | 17.4% |
| mRNA undef | 30.7% | 13.5% | 3.6% | 47.8% |
| TOTAL | 64.5% | 31.5% | 4.0% | 100.0% |

FIG. 3D

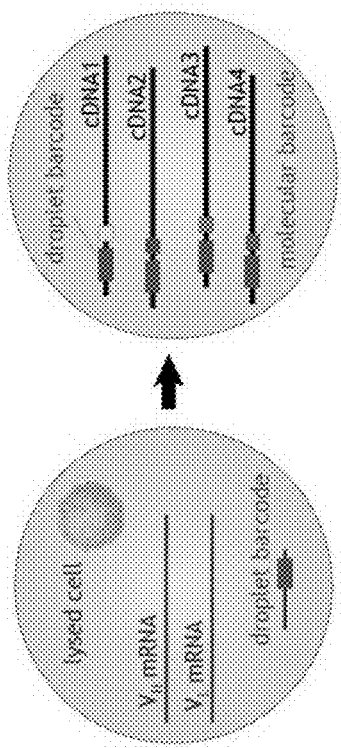
FIG. 5A
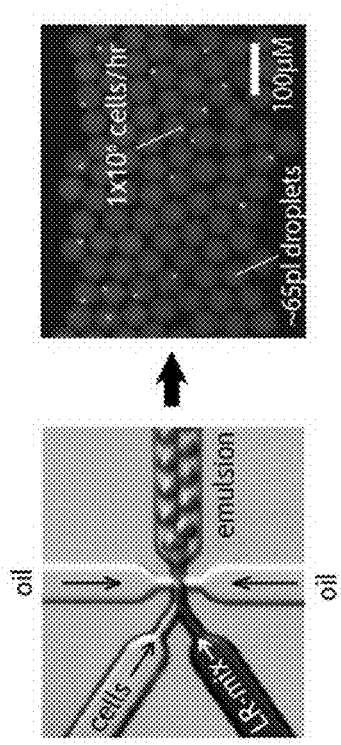
FIG. 5B
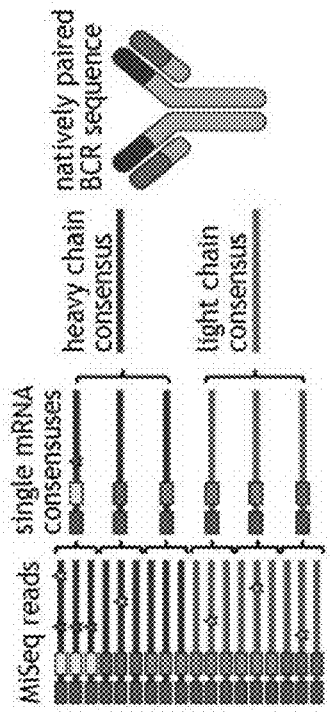
FIG. 5C
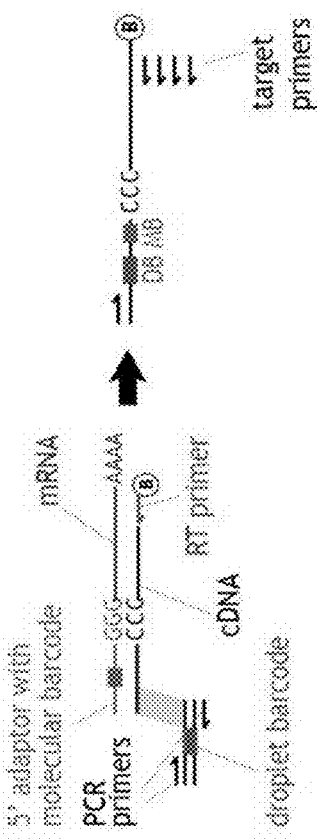
FIG. 5D
FIG. 5

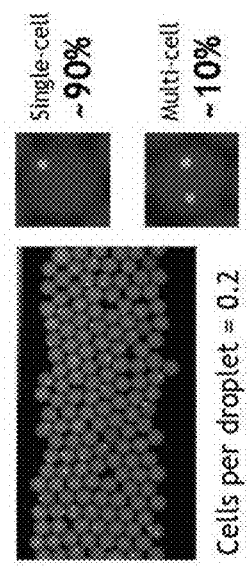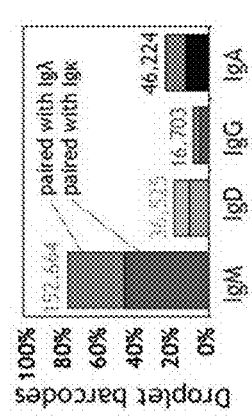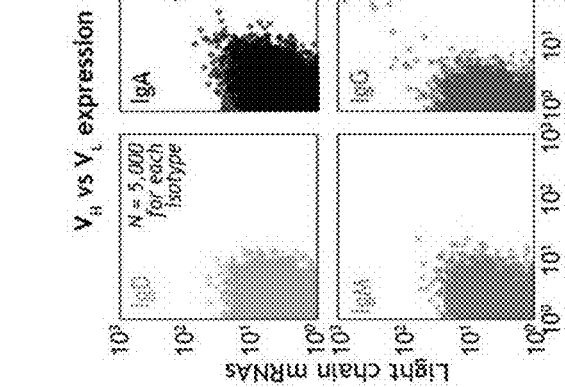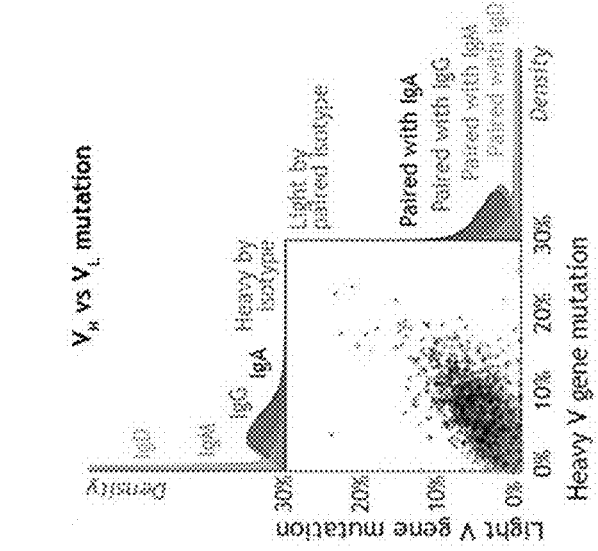
FIG. 6

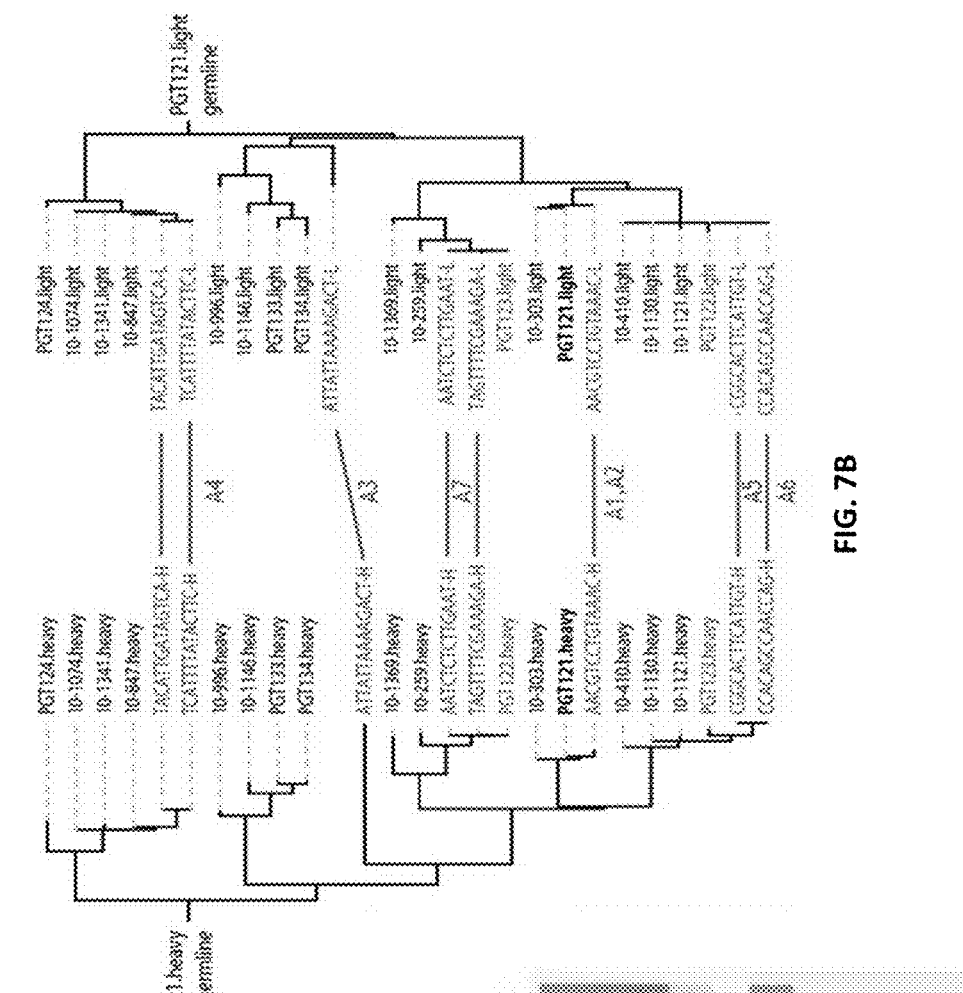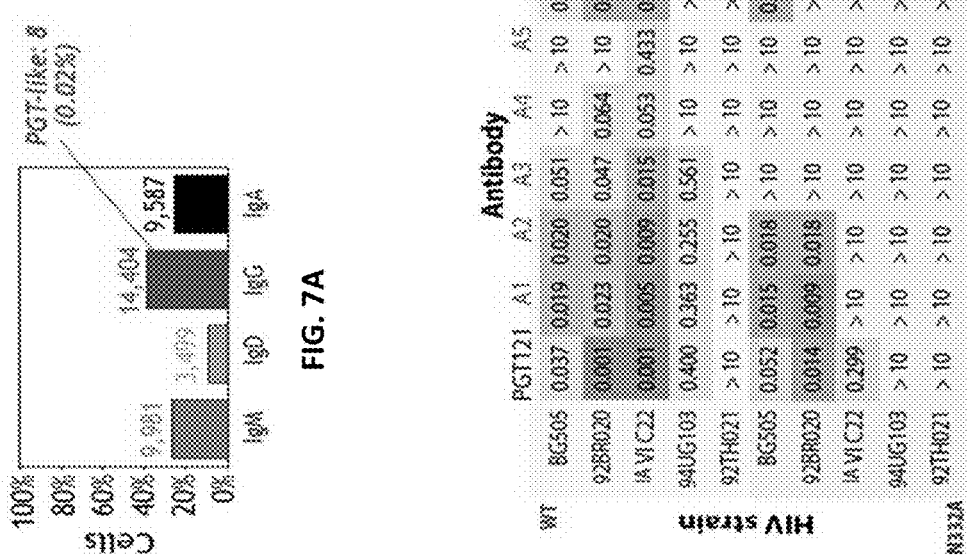
FIG. 7A
FIG. 7B
FIG. 7C
FIG. 7

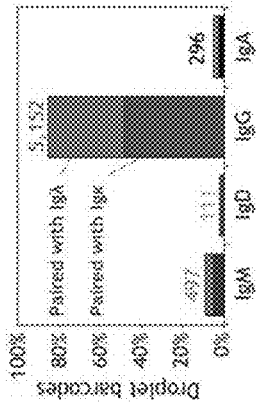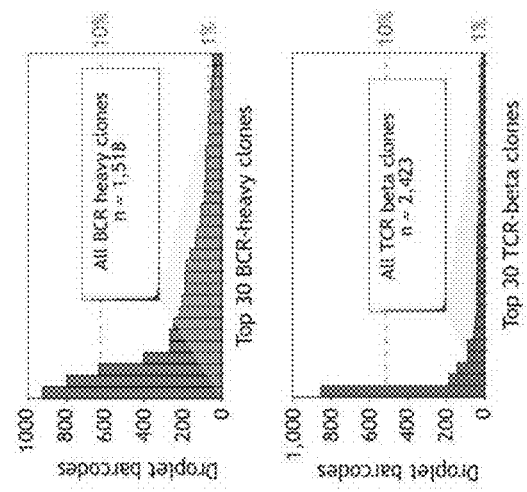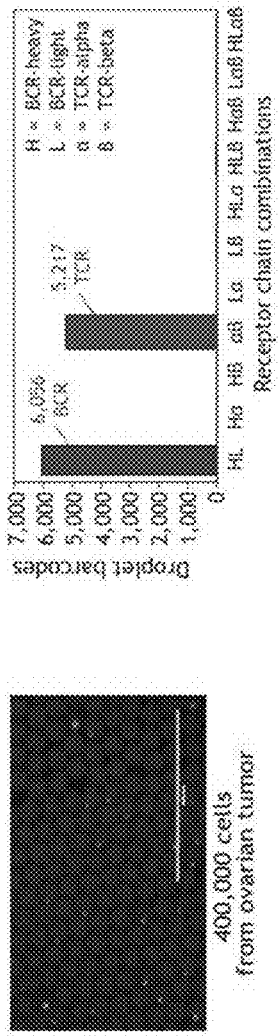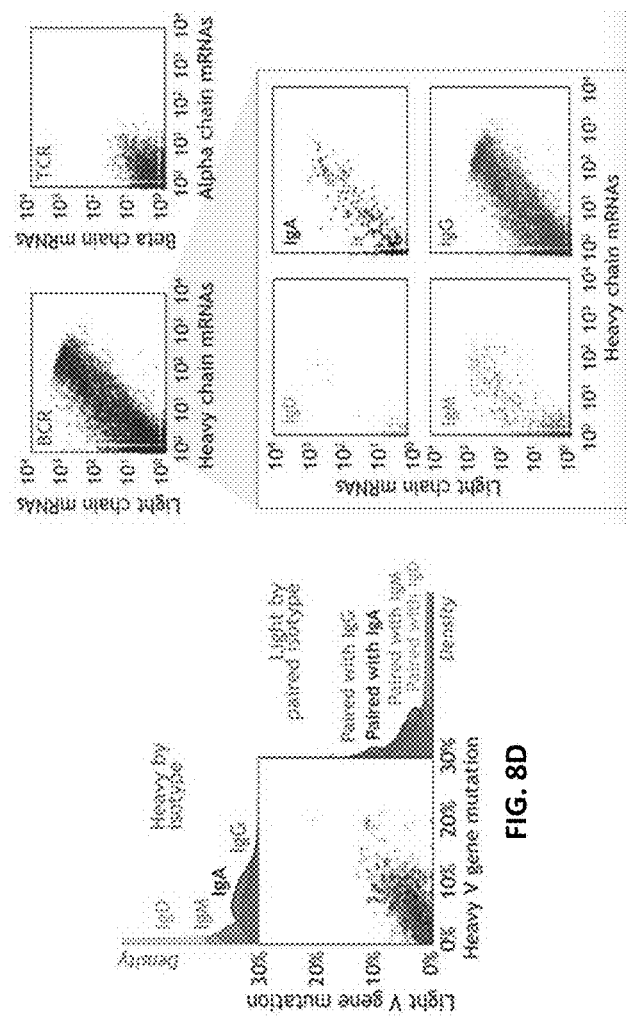
FIG. 8

METHODS OF SELECTING T CELL RECEPTORS USING AFFINITY OLIGONUCLEOTIDE CONJUGATES

CROSS-REFERENCE

This application claims priority to International Patent Application No. PCT/US2016/053598 filed Sep. 24, 2016, which claims priority to U.S. Provisional Application No. 62/232,209 filed Sep. 24, 2015; each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 29, 2016, is named 44243-711_601_SL.txt and is 3,426 bytes in size.

BACKGROUND

Many cell types can be identified and categorized by the abundance of specific sets of proteins endogenously expressed and located on their plasma membranes. This phenomenon enables the study of cells using a process known as immunophenotyping, in which cells are incubated with and bound by fluorescently-labeled antibodies that are specific to known surface proteins of the cells. Flow cytometry is commonly used to measure the levels of the surface-bound antibodies for each cell. However, flow cytometry-based approaches are limited by the number of fluorophores that can be used concurrently in the same experiment. Further, the number of fluorophores that can be used concurrently in the same experiment using flow cytometry-based approaches is limited by spectral overlap. Additionally, flow cytometry is not amenable to many biologically-relevant assays and subsequent DNA sequencing.

SUMMARY

Thus, a need exists for methods of characterizing, e.g., immunophenotyping, single cells without these limitations. Unlike flow cytometry-based approaches, the methods described herein use a sequence readout to analyze proteins of individual cells and are not limited by the number of fluorophores that can be used concurrently in the same experiment or their spectral overlap. Further, the methods described herein are amenable to many biologically-relevant assays and subsequent DNA sequencing. The methods described herein utilize affinity-oligonucleotide conjugates (e.g., antibody-oligonucleotide conjugates or tetramer-oligonucleotide conjugates). The oligonucleotide of the conjugate comprises an Antigen ID (AID) sequence that is barcoded to a surface antigen that the affinity portion of the affinity-oligonucleotide conjugate specifically binds. Thus, using the methods described herein, an antigen (e.g., a surface protein) of a single cell can be analyzed without a need for fluorophores. For example, a surface protein of a single cell that is displayed can be identified from the Antigen ID sequence. As another example, a T cell receptor (TCR) or B cell receptor (BCR) of a single cell that is displayed can be identified from the Antigen ID sequence. In some aspects, the binding affinity of a TCR or BCR displayed on the surface of a cell may be determined using the affinity-oligonucleotide conjugated described herein. One or more of the surface proteins of a single cell can be used to define the single cell's identity, characteristics or relevance.

The affinity-oligonucleotide conjugate of the methods described herein that can be used to overcome the problems of slow cell sorting, reduced target yield associated with cell sorting, limited number of output streams, and selected bins that do not correspond to a quantified property of the affinity-oligonucleotide conjugate, such as affinity. The exemplary affinity-oligonucleotide conjugate depicted can replace or enhance sorting with single-cell measurements of tetramer binding in vessels. The exemplary affinity-oligonucleotide conjugate depicted can be used in the methods described herein to simultaneously acquire TCR pair sequences, clone abundance, and relative tetramer affinities. For example, an affinity-oligonucleotide conjugate that is a tetramer-oligonucleotide conjugate can be used in the methods described herein to simultaneously acquire TCR pair sequences that bind to the peptide of the tetramer, determine the affinity of binding of the TCR to a Major Histocompatibility Complex (MHC)-peptide complex of the tetramer-oligonucleotide conjugate, and differentiate between TCRs with a low binding affinity as compared with TCRs with a high binding affinity for a MHC-peptide complex of the tetramer-oligonucleotide conjugate. As another example, an affinity-oligonucleotide conjugate that is a tetramer-oligonucleotide conjugate can be used in the methods described herein to simultaneously acquire BCR pair sequences that bind to the B-cell receptor antigen of the tetramer, determine the affinity of binding of the BCR to a B-cell receptor antigen of the tetramer-oligonucleotide conjugate, and differentiate between BCRs with a low binding affinity as compared with BCRs with a high binding affinity for a B-cell receptor antigen of the tetramer-oligonucleotide conjugate.

A method of characterizing, e.g., immunophenotyping, cells in vessels (e.g., emulsion) with affinity-oligonucleotide conjugates is described herein. In some embodiments, the method is used to identify cell subsets in a manner compatible with emulsion-based single cell analysis. In some embodiments, the method is used to identify immune cells specific for an antigen in a manner compatible with emulsion-based single cell analysis. In some embodiments, prior to cellular analysis, surface protein-specific antibodies are conjugated to oligonucleotides. In some embodiments, the oligonucleotides are designed to contain a sequence motif which is unique to the target-specificity of the conjugated antibody. In some embodiments, the oligonucleotides are designed to contain a sequence motif which is unique to the target-specificity of the conjugated tetramer. The oligonucleotide can be conjugated to the affinity portion of the affinity-oligonucleotide conjugate (e.g., an antibody or tetramer) covalently or non-covalently (e.g., biotin-oligonucleotide to streptavidin-antibody).

A method can comprise incubating cells in a mixture or a solution with one or more affinity-oligonucleotide conjugates. The cells can be washed to remove unbound affinity-oligonucleotide conjugates. Cells are then encapsulated in vessels, e.g., an emulsion. The cells can be present in the vessels at a single cell per vessel density. Thus, the affinity-oligonucleotide conjugates within a vessel, e.g., droplet, are bound to the cell surface, e.g., through a specific antibody-surface protein interaction. The method can comprise attaching a vessel-specific DNA sequence (e.g., a unique vessel barcode) to the affinity-conjugated oligonucleotides. Additional cellular DNA or mRNA analysis, phenotypic measurements, functional testing, cell-sorting or other reactions can be carried out prior to, concurrently with, or after barcoding the affinity-conjugated oligonucleotide, (e.g., with a DNA barcode).

A method can comprise incubating cells in a mixture or a solution with one or more tetramer-oligonucleotide conjugates. The cells can be washed to remove unbound tetramer-oligonucleotide conjugates. Cells are then encapsulated in vessels, e.g., an emulsion. The cells can be present in the vessels at a single cell per vessel density. Thus, the tetramer-oligonucleotide conjugates within a vessel, e.g., droplet, are bound to the cell surface, e.g., through a specific TCR-MHC-peptide complex interaction or through a specific BCR-B-cell receptor antigen of a tetramer interaction. The method can comprise attaching a vessel-specific DNA sequence (e.g., a unique vessel barcode) to the tetramer-conjugated oligonucleotides. Additional cellular DNA or mRNA analysis, phenotypic measurements, functional testing, cell-sorting or other reactions can be carried out prior to, concurrently with, or after barcoding the tetramer-conjugated oligonucleotide, (e.g., with a DNA barcode).

A method can comprise extracting nucleic acids from the emulsion, for example, subsequent to the emulsion experimentation. Extracted nucleic acids can be prepared for sequencing and sequenced (e.g., using next generation sequencing technology). A method can comprise sequencing polynucleotide molecules from the vessels that contain both an Antigen ID sequence and droplet-specific barcode sequence. The Antigen ID sequence can define the specific cell surface protein bound by the oligonucleotide-conjugated antibody. The Antigen ID sequence can define the specific antibody of the oligonucleotide-conjugated antibody that binds to a particular cell surface protein. The Antigen ID sequence can define the specific MHC-peptide complex of the oligonucleotide-conjugated tetramer that binds to a particular cell TCR. The Antigen ID sequence can define the specific B-cell receptor antigen of the oligonucleotide-conjugated tetramer that binds to a particular cell BCR. Thus, the Antigen ID sequence can indicate which surface protein the analyzed cell expressed. In a vessel harboring a single cell, all sequences containing a shared droplet-specific barcode sequence are associated with a single cell. Therefore, a single cell can be analyzed as displaying a set of surface proteins which can be used to define its identity, characteristics or relevance. For example, a single cell can be analyzed as displaying a TCR with a certain affinity to a MHC-peptide complex in which the sequence of that TCR can also be identified or a single cell can be analyzed as displaying a BCR with a certain affinity to a B cell receptor antigen of a tetramer in which the sequence of that BCR can also be identified.

In one aspect, a method is provided comprising performing a reaction in a plurality of vessels, the reaction comprising attaching a vessel barcoded polynucleotide comprising a vessel barcode sequence to an oligonucleotide of an affinity-oligonucleotide conjugate bound to a target antigen of a single cell isolated in a vessel of a plurality of vessels. In one aspect, a method is provided comprising performing a reaction in a plurality of vessels, the reaction comprising attaching a vessel barcoded polynucleotide comprising a vessel barcode sequence to an oligonucleotide of a tetramer-oligonucleotide conjugate bound to a TCR of a single cell isolated in a vessel of a plurality of vessels. In one aspect, a method is provided comprising performing a reaction in a plurality of vessels, the reaction comprising attaching a vessel barcoded polynucleotide comprising a vessel barcode sequence to an oligonucleotide of a tetramer-oligonucleotide conjugate bound to a BCR of a single cell isolated in a vessel of a plurality of vessels.

In one aspect, provided herein is a method comprising, performing a reaction in a vessel of a plurality of vessels, the reaction comprising attaching a vessel barcoded polynucleotide, which comprises a vessel barcode sequence, to an oligonucleotide portion of an affinity-oligonucleotide conjugate, wherein the affinity-oligonucleotide conjugate binds to a target antigen expressed by a cell in the vessel of the plurality of vessels. In one aspect, provided herein is a method comprising, performing a reaction in a vessel of a plurality of vessels, the reaction comprising attaching a vessel barcoded polynucleotide, which comprises a vessel barcode sequence, to an oligonucleotide portion of a tetramer-oligonucleotide conjugate, wherein the tetramer-oligonucleotide conjugate binds to a TCR expressed by a cell in the vessel of the plurality of vessels. In one aspect, provided herein is a method comprising, performing a reaction in a vessel of a plurality of vessels, the reaction comprising attaching a vessel barcoded polynucleotide, which comprises a vessel barcode sequence, to an oligonucleotide portion of a tetramer-oligonucleotide conjugate, wherein the tetramer-oligonucleotide conjugate binds to a BCR expressed by a cell in the vessel of the plurality of vessels.

In some embodiments, the cell is a single cell contained within the vessel. In some embodiments, the vessel comprises two or more vessels of the plurality of vessels. In some embodiments, the vessel comprises each vessel of the plurality of vessels. In some embodiments, the reaction takes place in two or more vessels of the plurality of vessels. In some embodiments, the cell in each vessel is from a same sample. In some embodiments, the cell in a vessel of a first plurality of vessels of the two or more pluralities of vessels is from a same sample as the cell in a vessel in a second plurality of vessels of the two or more pluralities of vessels. In some embodiments, the oligonucleotide portion comprises an antigen identification sequence (AID). In some embodiments, the AID is barcoded to the target antigen or the affinity portion of the affinity-oligonucleotide conjugate. In some embodiments, the AID is barcoded to a TCR with a known specificity or the MHC-peptide complex of the tetramer-oligonucleotide conjugate. In some embodiments, the AID is barcoded to a BCR with a known specificity or the B-cell receptor antigen of the tetramer-oligonucleotide conjugate.

In some embodiments, the oligonucleotide further comprises an antigen identification sequence (AID) barcoded to the target antigen or the affinity portion of the affinity-oligonucleotide conjugate. In some embodiments, the oligonucleotide further comprises an antigen identification sequence (AID) barcoded to a TCR with a known specificity or the MHC-peptide complex of the tetramer-oligonucleotide conjugate. In some embodiments, the antigen identification sequence (AID) is a known sequence.

In some embodiments, the vessel barcoded polynucleotide is from a template vessel barcoded polynucleotide in the vessel.

In some embodiments, the method further comprises sequencing the oligonucleotide or an amplicon thereof to obtain sequence information.

In some embodiments, the method further comprises determining a characteristic of the single cell based on the sequence information. In some embodiments, the sequence information comprises the antigen identification (AID) sequence. In some embodiments, the method further comprises determining a characteristic of the single cell based on the sequence information. In some embodiments, the characteristic is a phenotype. In some embodiments, the phenotype is an immunophenotype. In some embodiments, the characteristic is affinity. In some embodiments the affinity is of a MHC-peptide complex. In some embodiments affinity is relative affinity of a MHC-peptide complex (e.g., TCRs with higher binding affinity compared to TCRs with lower binding affinity). In some embodiments the affinity is of a BCR. In some embodiments affinity is relative affinity of a BCR (e.g., BCRs with higher binding affinity compared to BCRs with lower binding affinity).

In some embodiments, the method further comprises contacting the affinity-oligonucleotide conjugate to a plurality of cells comprising the single cell. In some embodiments, the method further comprises contacting the tetramer-oligonucleotide conjugate to a plurality of cells comprising the single cell. In some embodiments, the contacting is before the single cell is isolated in the vessel. In some embodiments, the method further comprises washing the plurality of cells after the contacting.

In some embodiments, the vessel does not comprise an affinity-oligonucleotide conjugate that is not bound to a target antigen. In some embodiments, the vessel does not comprise a tetramer-oligonucleotide conjugate that is not bound to a TCR. In some embodiments, the vessel does not comprise a tetramer-oligonucleotide conjugate that is not bound to a BCR.

In some embodiments, the method further comprises isolating the single cell in the vessel. In some embodiments, the single cell is bound to the affinity-oligonucleotide conjugate before the isolating.

In some embodiments, the method further comprises lysing the single cell. In some embodiments, the lysing is after the single cell is isolated in the vessel.

In some embodiments, the plurality of cells is a plurality of unsorted cells. In some embodiments, the plurality of cells is a plurality of sorted cells. In some embodiments, the plurality of cells is a plurality of enriched cells.

In some embodiments, the vessel barcode sequence of a vessel barcoded polynucleotide or amplicon thereof in a first vessel of the plurality of vessels is a different than the vessel barcode sequence of a vessel barcoded polynucleotide or amplicon thereof in a second vessel of the plurality of vessels. In some embodiments, the vessel barcode sequence of each vessel barcoded polynucleotide or amplicon thereof in a single vessel of the plurality of vessels comprises a same vessel barcode sequence. In some embodiments, the vessel barcode sequence of each vessel barcoded polynucleotide and amplicon thereof in any single vessel of the plurality of vessels is unique to the vessel barcode sequence of each vessel barcoded polynucleotide and amplicon thereof in any other single vessel of the plurality of vessels.

In some embodiments, the method further comprises attaching a vessel barcoded polynucleotide to a cell polynucleotide from the single cell. In some embodiments, the attaching a vessel barcoded polynucleotide to an oligonucleotide of an affinity-oligonucleotide conjugate and the attaching a vessel barcoded polynucleotide to a cell polynucleotide from the single cell are performed simultaneously.

In some embodiments, the method further comprises amplifying the oligonucleotide or a complement thereof. In some embodiments, the method further comprises amplifying the cell polynucleotide or a complement thereof. In some embodiments, the amplifying the oligonucleotide or a complement thereof and the amplifying the cell polynucleotide or a complement thereof are performed simultaneously.

In some embodiments, the vessel barcode sequence of the cell polynucleotide and the vessel barcode sequence of the oligonucleotide are the same.

In some embodiments, the method further comprises pooling oligonucleotides or amplicons thereof from two or more vessels of the plurality of vessels. In some embodiments, the method further comprises pooling oligonucleotides or amplicons thereof and cell polynucleotides or amplicons thereof from two or more vessels of the plurality of vessels. In some embodiments, the pooling is before sequencing.

In some embodiments, the affinity-oligonucleotide conjugate comprises a plurality of different affinity-oligonucleotide conjugates. In some embodiments, each affinity-oligonucleotide conjugate of the plurality of affinity-oligonucleotide conjugates comprises a unique antigen identification (AID) sequence. In some embodiments, the oligonucleotide comprises an affinity molecular barcode (AMB) sequence that is barcoded to a single affinity-oligonucleotide conjugate molecule of a plurality of affinity-oligonucleotide conjugate molecules. In some embodiments, each affinity-oligonucleotide conjugate molecule of the plurality of affinity-oligonucleotide conjugate molecules comprises a unique affinity molecular barcode (AMB) sequence.

In some embodiments, the methods and conjugates described herein comprise a plurality of different tetramer-oligonucleotide conjugates. In some embodiments, each tetramer-oligonucleotide conjugate of the plurality of affinity-oligonucleotide conjugates comprises a unique antigen identification (AID) sequence. In some embodiments, the oligonucleotide comprises an affinity molecular barcode (AMB) sequence that is barcoded to a single tetramer-oligonucleotide conjugate molecule of a plurality of tetramer-oligonucleotide conjugate molecules. In some embodiments, each tetramer-oligonucleotide conjugate molecule of the plurality of tetramer-oligonucleotide conjugate molecules comprises a unique affinity molecular barcode (AMB) sequence.

In some embodiments, the oligonucleotide comprises a fusion sequence and the attaching comprises attaching the vessel barcoded polynucleotide to the fusion sequence. In some embodiments, the oligonucleotide comprises a primer binding sequence. In some embodiments, the oligonucleotide comprises a constant sequence.

In some embodiments, the method further comprises sequencing the oligonucleotide, complements thereof, amplified products thereof, or a combination thereof, thereby producing oligonucleotide sequence reads.

In some embodiments, the method further comprises comparing one or more first oligonucleotide sequence reads to one or more second oligonucleotide sequence reads. In some embodiments, the method further comprises analyzing the oligonucleotide sequence reads. In some embodiments, the method further comprises analyzing vessel barcode sequences of the oligonucleotide sequence reads. In some embodiments, the method further comprises analyzing antigen identification (AID) sequences of the oligonucleotide sequence reads. In some embodiments, the method further comprises analyzing affinity molecular barcode (AMB) sequences of the oligonucleotide sequence reads. In some embodiments, the analyzing comprises determining a frequency of one or more vessel barcode sequences, one or more AID sequences, one or more affinity molecular barcode (AMB) sequences, or a combination thereof. In some embodiments, the analyzing comprises comparing. In some embodiments, the method further comprises comparing antigen identification (AID) sequences of oligonucleotide sequence reads to affinity molecular barcode (AMB) sequences of oligonucleotide sequence reads.

In some embodiments, the method further comprises sequencing the cell polynucleotide, complements thereof, amplified products thereof, or a combination thereof, thereby producing cell polynucleotide sequence reads. In some embodiments, the method further comprises comparing oligonucleotide sequence reads to the cell polynucleotide sequence reads. In some embodiments, the method further comprises comparing vessel barcode sequences of oligonucleotide sequence reads to vessel barcode sequences of the cell polynucleotide sequence reads. In some embodiments, the method further comprises comparing the cell polynucleotide sequence reads. In some embodiments, the method further comprises analyzing vessel barcode sequences of the cell polynucleotide sequence reads. In some embodiments, the method further comprises analyzing molecular barcode sequences of the cell polynucleotide sequence reads.

In some embodiments, the method further comprises determining a characteristic of a cell based on the analyzing or the comparing. In some embodiments, the method further comprises selecting an antibody, BCR, or TCR based on the oligonucleotide sequence reads. In some embodiments, the method comprises selecting an antibody, BCR, or TCR based on the cell polynucleotide sequence reads.

In some embodiments, the method further comprises determining an affinity of a tetramer for a TCR or BCR and/or an affinity of a TCR or BCR for a tetramer based on the analyzing or comparing. In some embodiments, the number of sequencing reads is indicative of affinity of the tetramer for a TCR or a BCR. In some embodiments, a higher number of sequence reads for a single cell indicates higher binding affinity of a tetramer-oligonucleotide conjugate and/or TCR or BCR as compared to a single cell with a lower number of sequencing reads. Binding affinity of a tetramer can be indicative of the binding of a MHC-peptide complex of the tetramer or a B-cell receptor antigen of the tetramer.

In some embodiments, a method of determining an affinity of a TCR or BCR for a tetramer oligonucleotide conjugate comprises incubating one or a plurality of T cells in the presence of one or a plurality of tetramer oligonucleotide conjugates, wherein the plurality of tetramer oligonucleotide conjugates may each comprise unique identifier barcodes. In some embodiments, the method further comprises isolating each cell-tetramer complex and sequencing at least a portion of the oligonucleotide or a complementary sequence thereof conjugated to the tetrameric complex as described herein. In some embodiments, the method further comprises counting the number of sequencing reads obtained during the sequencing for each unique barcode sequence. In some embodiments, the method further comprises analyzing or comparing the sequencing information to a standard curve. In some embodiments, the method further comprises determining an affinity of the TCR or BCR for the tetramer, or the tetramer for the TCR or BCR, based on the sequencing, or the analyzing or comparing of the sequencing information. In some embodiments, the vessel barcoded polynucleotide attached to the oligonucleotide and the vessel barcoded polynucleotide attached to the cell polynucleotide are from a same template vessel barcoded polynucleotide in the vessel. In some embodiments, the vessel barcoded polynucleotide attached to the oligonucleotide is an amplification product of a template vessel barcoded polynucleotide.

In some embodiments, the vessel barcoded polynucleotide attached to the cell polynucleotide is an amplification product of the template vessel barcoded polynucleotide.

In some embodiments, the vessel comprises a solid support. In some embodiments, the vessel does not comprise a solid support. In some embodiments, each vessel of the plurality of vessels comprises a single cell. In some embodiments, the vessel is a well, an emulsion, or a droplet. In some embodiments, the template vessel barcoded polynucleotide is not bound to a solid support. In some embodiments, the template vessel barcoded polynucleotide is bound to a solid support.

In some embodiments, the method further comprises attaching a molecular barcode sequence of a molecular barcoded polynucleotide of a plurality of molecular barcoded polynucleotides to the cell polynucleotide, wherein the molecular barcode sequence is barcoded to a single cell polynucleotide molecule and amplicons thereof.

In some embodiments, the attaching comprises ligating the vessel polynucleotide to the oligonucleotide. In some embodiments, the attaching comprises attaching the vessel polynucleotide to the oligonucleotide with an enzyme. In some embodiments, the attaching comprises hybridizing the vessel polynucleotide to the oligonucleotide. In some embodiments, the attaching further comprises extending the oligonucleotide. In some embodiments, the attaching comprises amplifying a template vessel barcoded polynucleotide.

In some embodiments, the oligonucleotide is double stranded. In some embodiments, the oligonucleotide is single stranded. In some embodiments, the oligonucleotide is DNA. In some embodiments, the oligonucleotide is RNA.

In some embodiments, the cell polynucleotide comprises a variable region sequence. In some embodiments, the method further comprises pairing native chain sequences containing a variable region sequence. In some embodiments, the cell polynucleotide is DNA. In some embodiments, the cell polynucleotide is RNA. In some embodiments, the RNA is mRNA.

In some embodiments, the single cell is a B-cell. In some embodiments, the single cell is a T-cell.

In some embodiments, the affinity portion of the affinity-oligonucleotide conjugate binds to an extracellular antigen of the single cell. In some embodiments, the extracellular antigen of the single cell is an antigen specific to an immune cell. In some embodiments, the extracellular antigen of the single cell is an antigen specific to a T-cell. In some embodiments, the extracellular antigen is CD4. In some embodiments, the extracellular antigen is CD8. In some embodiments, the extracellular antigen of the single cell is an antigen specific to a B-cell. In some embodiments, the extracellular antigen is an immunoglobulin.

In some embodiments, the affinity portion of the affinity oligonucleotide conjugate is an antibody or fragment thereof. In some embodiments, the affinity portion of the affinity oligonucleotide conjugate is a peptide. In some embodiments, the affinity portion of the affinity oligonucleotide conjugate is a protein. In some embodiments, the affinity portion of the affinity oligonucleotide conjugate is an aptamer. In some embodiments, the affinity portion of the affinity oligonucleotide conjugate is a small molecule. In some embodiments, the affinity portion of the affinity oligonucleotide conjugate is a drug. In some embodiments, the affinity portion of the affinity oligonucleotide conjugate is a cell. In some embodiments, the cell is an antigen presenting cell (APC). In some embodiments, the affinity portion of the affinity oligonucleotide conjugate comprises a MHC-peptide complex. In some embodiments, the affinity portion of the affinity oligonucleotide conjugate comprises a major histocompatibility complex (MHC). In some embodiments, the MHC is in a soluble and/or multimeric (e.g., tetrameric) form. In some embodiments, the MHC is bound to a peptide. In some embodiments, the peptide is a synthetic peptide. In some embodiments, the MHC binds to a T-cell receptor (TCR) and/or a TCR-like binding molecule, such as a TCR-like antibody or immunoglobulin or chimeric antigen receptor, e.g., of the single cell.

In some embodiments, the affinity portion of the tetramer-oligonucleotide conjugate comprises a MHC-peptide complex. In some embodiments, the affinity portion of the tetramer-oligonucleotide conjugate comprises a major histocompatibility complex (MHC) in a soluble and/or multimeric (e.g., tetrameric) form. In some embodiments, the MHC is bound to a streptavidin protein, which is complexed with a central biotin protein, allowing for up to four MHC-streptavidin complexes to be joined into a multimeric complex (for example, as depicted in FIG. 10A). In some embodiments, the MHC is associated with a peptide. In some embodiments, the MHC is associated with a peptide via a covalent or non-covalent linkage. In some embodiments, the peptide is a synthetic peptide. In some embodiments, the peptide is a synthetic peptide. In some embodiments, the MHC binds to a TCR and/or a TCR-like binding molecule, such as a TCR-like antibody or immunoglobulin or chimeric antigen receptor, e.g., of the single cell. In some embodiments, the affinity portion of the tetramer-oligonucleotide conjugate comprises a B-cell receptor antigen in a soluble and/or multimeric (e.g., tetrameric) form. In some embodiments, the B-cell receptor antigen was previously administered to cells or to a subject. In some embodiments, the B-cell receptor antigen binds to a BCR and/or a BCR-like binding molecule, such as a chimeric antigen receptor, e.g., of the single cell.

In some embodiments, the affinity portion specifically binds to an antigen-recognizing molecule and/or immunoreceptor, such as an antibody or immunoglobulin or portion or fusion thereof, an engineered immunoreceptor, a chimeric antigen receptor (CAR), or a TCR. In some such embodiments, the affinity portion comprises an antigen or epitope or portion thereof recognized by the antibody or receptor such as the CAR. In some embodiments, the affinity portion comprises an antibody or antigen-binding fragment thereof that specifically binds to the immunoreceptor. In some aspects, the antibody or antigen-binding fragment thereof specifically binds to a variable and/or antigen-binding portion of the receptor, such as an idiotope. In some aspects, the affinity molecule is an anti-idiotypic antibody or fragment thereof.

In some embodiments, the affinity portion of the affinity oligonucleotide conjugate comprises a major histocompatibility complex (MHC) or functional or binding portion thereof. In some embodiments, the affinity portion comprises a multimer of the MHC, optionally a tetramer of the MHC. In some embodiments, the MHC is in a soluble form. In some embodiments, the MHC is bound to a peptide and/or contains a peptide within a groove of the MHC. In some embodiments, the peptide is a synthetic peptide. In some embodiments, the MHC binds to a T-cell receptor (TCR) of the single cell. In some embodiments, the affinity portion comprises a peptide that binds to an antibody or a chimeric antigen receptor (CAR) and/or wherein the target is an antibody or a CAR. In some embodiments, the affinity portion is or comprises an antigen or an epitope specifically recognized by the antibody or the chimeric antigen receptor and/or comprises an antibody that specifically binds thereto, optionally an anti-idiotypic antibody that specifically binds to an antigen binding portion thereof.

In one aspect, provided is a composition comprising a plurality of vessels each comprising a single cell from a sample comprising a plurality of cells, an affinity-oligonucleotide conjugate bound to a target antigen of the single cell, and a vessel barcoded polynucleotide comprising a vessel barcode sequence. In some embodiments, the vessel barcoded polynucleotide or a complement thereof is attached to the oligonucleotide of the affinity-oligonucleotide conjugate.

In one aspect, provided is a composition comprising a plurality of vessels each comprising a single cell from a sample comprising a plurality of cells, a tetramer-oligonucleotide conjugate bound to a TCR or BCR of the single cell, and a vessel barcoded polynucleotide comprising a vessel barcode sequence. In some embodiments, the vessel barcoded polynucleotide or a complement thereof is attached to the oligonucleotide of the tetramer-oligonucleotide conjugate. In one aspect, provided is a composition comprising a plurality of vessels each comprising a single lysed cell from a sample comprising a plurality of cells, and an affinity-oligonucleotide conjugate bound to a target antigen of the single lysed cell; wherein the oligonucleotide of the affinity-oligonucleotide conjugate comprises a vessel barcode sequence, and wherein a cell polynucleotide from the single lysed cell comprises the same vessel barcode sequence.

In one aspect, provided is a composition comprising a plurality of vessels each comprising a single lysed cell from a sample comprising a plurality of cells, and a tetramer-oligonucleotide conjugate bound to a TCR or BCR of the single lysed cell; wherein the oligonucleotide of the tetramer-oligonucleotide conjugate comprises a vessel barcode sequence, and wherein a cell polynucleotide from the single lysed cell comprises the same vessel barcode sequence. In one aspect, provided herein is a composition comprising a plurality of vessels, wherein a vessel of the plurality of vessels comprises a single cell from a sample comprising a plurality of cells, and a vessel barcoded polynucleotide comprising a vessel barcode sequence wherein the vessel further comprises an affinity-oligonucleotide conjugate that binds to a target antigen of the single cell, or an oligonucleotide portion therefrom.

In one aspect, provided herein is a composition comprising a plurality of vessels, wherein a vessel of the plurality of vessels comprises a single cell from a sample comprising a plurality of cells, and a vessel barcoded polynucleotide comprising a vessel barcode sequence wherein the vessel further comprises a tetramer-oligonucleotide conjugate that binds to a TCR or BCR of the single cell, or an oligonucleotide portion therefrom.

In some embodiments, a reaction takes place in two or more vessels of the plurality of vessels. In some embodiments, the vessel comprises each vessel of the plurality of vessels. In some embodiments, the plurality of vessels comprises two or more pluralities of vessels. In some embodiments, the cell in each vessel is from a same sample. In some embodiments, the cell in a vessel of a first plurality of vessels of the two or more pluralities of vessels is from a same sample as the cell in a vessel in a second plurality of vessels of the two or more pluralities of vessels. In some embodiments, the vessel barcoded polynucleotide or a complement thereof is attached to the oligonucleotide of the affinity-oligonucleotide conjugate. In some embodiments, the vessel barcoded polynucleotide or a complement thereof is attached to the oligonucleotide of the tetramer-oligonucleotide conjugate. In some embodiments, the single cell is lysed.

In one aspect, provided herein is a composition comprising a plurality of vessels, wherein a vessel of the plurality of vessels comprises a single lysed cell from a sample comprising a plurality of cells, and an affinity-oligonucleotide conjugate comprising an affinity portion that binds to a target antigen of the single lysed cell, or an oligonucleotide portion of the affinity-oligonucleotide conjugate; wherein the oligonucleotide portion of the affinity-oligonucleotide conjugate comprises a vessel barcode sequence, and wherein a cell polynucleotide from the single lysed cell comprises the same vessel barcode sequence.

In one aspect, provided herein is a composition comprising a plurality of vessels, wherein a vessel of the plurality of vessels comprises a single lysed cell from a sample comprising a plurality of cells, and a tetramer-oligonucleotide conjugate comprising an affinity portion that binds to a TCR or BCR of the single lysed cell, or an oligonucleotide portion of the tetramer-oligonucleotide conjugate; wherein the oligonucleotide portion of the tetramer-oligonucleotide conjugate comprises a vessel barcode sequence, and wherein a cell polynucleotide from the single lysed cell comprises the same vessel barcode sequence.

In one aspect, provided is a kit, comprising: a first container comprising a first oligonucleotide comprising a first antigen identification (AID) sequence, wherein the first AID sequence is a known sequence; a second container comprising a second oligonucleotide comprising a second antigen identification (AID) sequence, wherein the second AID sequence is a known sequence and is different than the first AID sequence; one or more third containers comprising reagents capable of conjugating the first oligonucleotide to a first affinity molecule and reagents capable of conjugating the second oligonucleotide to a second affinity molecule; a set of instructions describing how to conjugate the first oligonucleotide to the first affinity molecule and the second oligonucleotide to the second affinity molecule.

In one aspect, provided is a kit, comprising: a first container comprising a first oligonucleotide comprising a first antigen identification (AID) sequence, wherein the first AID sequence is a known sequence; a second container comprising a second oligonucleotide comprising a second antigen identification (AID) sequence, wherein the second AID sequence is a known sequence and is different than the first AID sequence; one or more third containers comprising reagents capable of conjugating the first oligonucleotide to a first tetramer and reagents capable of conjugating the second oligonucleotide to a second tetramer; a set of instructions describing how to conjugate the first oligonucleotide to the first tetramer and the second oligonucleotide to the second tetramer molecule.

In one aspect, provided is a kit, comprising: a first container comprising an oligonucleotide comprising an antigen identification (AID) sequence, wherein the AID sequence is a known sequence; a second container comprising reagents capable of conjugating the oligonucleotide to an affinity molecule; a third container comprising a plurality of vessel barcoded polynucleotides; and a set of instructions describing how to attach a vessel barcoded polynucleotide of the plurality of vessel barcoded polynucleotides to the oligonucleotide when conjugated to the affinity molecule.

In one aspect, provided is a kit, comprising: a first container comprising an oligonucleotide comprising an antigen identification (AID) sequence, wherein the AID sequence is a known sequence; a second container comprising reagents capable of conjugating the oligonucleotide to a tetramer; a third container comprising a plurality of vessel barcoded polynucleotides; and a set of instructions describing how to attach a vessel barcoded polynucleotide of the plurality of vessel barcoded polynucleotides to the oligonucleotide when conjugated to the tetramer.

The methods and compositions disclosed herein can be used for tumor profiling. For example, the methods can comprise linking cell phenotypes with an immune repertoire in patient samples to identify tumor reactive TCRs. The methods and compositions disclosed herein can be used for adoptive cell therapy. For example, the methods can comprise genetic analysis of T cells without sorting. For example, the methods can comprise combining T cell clonal information (using TCR) with gene expression patterns during product manufacture and treatment. In some embodiments, the methods disclosed herein may be used to track, characterize, monitor, and/or assess adoptively transferred cells obtained from a patient prior to, during the course of, or after adoptive cell therapy. The methods and compositions disclosed herein can be used to identify TCRs against known targets. For example, the methods can comprise identifying high affinity clones that may respond highly to antigen, but proliferate poorly. The methods and compositions disclosed herein can be used for cell sample multiplexing. For example, an emulsion containing pooled cell samples contacted to one or more affinity-oligonucleotide conjugates can be used to identify original cell samples while processing multiple samples at the same time.

The methods and compositions disclosed herein can be used for multiplexed TCR or BCR affinity measurement by sequencing. The methods and compositions disclosed herein can be used for quantifying binding affinity of the TCRs or BCRs of a single cell for a tetramer of the tetramer-oligonucleotide conjugate.

Furthermore, this quantification can be sensitive to tetramer-oligonucleotide conjugate concentration, in which the binding affinity signal can be dependent on the tetramer-oligonucleotide conjugate concentration (e.g., decreasing tetramer-oligonucleotide conjugate concentration results in a corresponding decrease in binding affinity signal). Additionally, the method and compositions disclosed herein can be used for distinguishing antigen specific cells from non-specific cells. For example, distinguishing between cells with TCRs or BCRs that bind the tetramer of the tetramer-oligonucleotide conjugate versus cells with TCRs or BCRs that do not bind the tetramer of the tetramer-oligonucleotide conjugate. Furthermore, one advantage of the methods and compositions disclosed herein is the ability to distinguish the population of antigen specific cells (i.e., tetramer+ cells) from non-specific cells (i.e., tetramer-cells) without the use of flow cytometry gating to separate these two populations. Often times, flow cytometry gating can be a "best guess" of population separation based on the separation of the tetramer+ population from the tetramer-population on the flow cytometry plot, which can be inexact and therefore, can result in loss of cells from each population or mischaracterization of a cell. In contrast, the methods and compositions described herein do not rely on gating techniques to distinguish populations of cells, but instead can be a high throughput method that individually quantifies the binding affinity of each cell in a sample. Furthermore, the methods and compositions disclosed herein can be used to distinguish between a cell with TCRs that have high binding affinity for a MHC-peptide (i.e., high binder) and a cell with TCRs that have low binding affinity for a MHC-peptide (i.e., low binder) as wells to distinguish between high binding affinity cells and low binding affinity cells within a sample using the high-throughput methods described herein.

INCORPORATION BY REFERENCE

All publications, patents, and patent applications mentioned in this specification are herein incorporated by reference in their entirety for all purposes, to the same extent as if each individual publication, patent, or patent application was specifically and individually indicated to be incorporated by reference.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 3D depicts an exemplary table of simultaneous mRNA and protein detection of CD4 and CD8 from unsorted T-cells in emulsion. From 30,000 input T-cells, 3,682 TCR pairs were recovered. Frequencies of TCR pairs called as CD4$^+$ or CD8$^+$ by mRNA vs protein (based on molecular counting, majority rule) are shown in a matrix.

FIG. 5 exemplifies results from a method of single immune cell barcoding in an emulsion.

FIG. 5A is an exemplary depiction of two aqueous streams containing cells and lysis/reaction (LR) mix being passed into oil that produces monodisperse emulsion at over 8 million droplets per hour.

FIG. 5B is an exemplary depiction showing that cells within the vessels are lysed and subjected to molecular- and droplet-specific barcoding in a single reaction.

FIG. 5C is an exemplary depiction showing that target mRNA is reverse transcribed and template switch-tagged with a universal adaptor sequence. Subsequently PCR amplification occurs of a droplet barcode template initially diluted to ~1 molecule per droplet. Amplified barcodes are appended to template-switched cDNAs by complementary overlap extension. Products are recovered from the emulsion and purified using a biotin on the RT primer, before additional library processing steps and high throughput sequencing.

FIG. 5D is an exemplary depiction showing that dual barcoding allows clustering of sequencing reads into their molecules and droplets of origin, reconstructing the native receptor chain pairings while minimizing sequencing errors and amplification biases.

FIG. 6 exemplifies results from a method of BCR recovery from isolated healthy B-cells.

FIG. 6A is an exemplary depiction of droplets in which 3 million B-cells were passed into an emulsion at 0.2 cells/ droplet resulting in ~90% of occupied cells containing single cells.

FIG. 6B is an exemplary depiction of $V_H V_L$ pairing precision. After emulsion barcoding and sequencing, data was enriched for data from single-cell droplets and $V_H V_L$ pairing precision was estimated using pair consistency among expanded clones.

FIG. 6C is an exemplary graph of droplet barcode percentage vs. Ig isotype. Heavy chain isotype (most abundant isotype within each droplet) and light chain locus usage for 259,368 filtered $V_H V_L$ pairs are shown.

FIG. 6D is an exemplary graph of rank abundance of the 100 most frequent heavy chain clones in each of six independent emulsion fractions. 0.05% overall frequency is marked.

FIG. 6E is an exemplary graph of $V_H$ vs $V_L$ expression within cells as estimated by number of captured mRNAs within each droplet barcode. 5,000 points are shown for each isotype.

FIG. 6F is an exemplary graph of $V_H$ versus $V_L$ mutation correlation for BCR pairs and density distributions within each isotype.

FIG. 7 exemplifies results from a method of HIV broad neutralizing antibody (bNAb) discovery.

FIG. 7A is an exemplary graph of heavy chain isotype distribution of 38,620 recovered $V_H V_L$ pairs from B-cells from an HIV elite controller were entered into emulsion. A rare proportion of the IgG chains aligned well to previously known bNAbs ("PGT-like").

FIG. 7B is an exemplary depiction of phylogenetic trees of complete VDJ amino acid sequences of known bNAbs (black) plus the newly recovered ones (red, labeled with droplet barcode), with heavy (left) and light chains (right) plotted separately. Potentially mismatched antibodies PGT122 and PGT123 are blue.

FIG. 7C is an exemplary depiction of neutralization activity ($IC_{50}$, μg/mL) of 8 newly discovered PGT-like variants against ten strains of HIV, compared to a control stock of PGT121.

FIG. 8 exemplifies results from a method of characterization of TILs from an ovarian tumor.

FIG. 8A is an exemplary depiction of droplets in which 400,000 unsorted dissociated cells from an ovarian tumor were entered into emulsion and BCR and TCR pairs were simultaneously recovered by emulsion barcoding.

FIG. 8B is an exemplary graph of droplet barcodes vs. receptor chain combinations showing the numbers of all $V_H/V_L$ and $V\alpha/V\beta$ combinations observed within droplet barcodes after filtering.

FIG. 8C is an exemplary graph of droplet barcode percentage vs. heavy chain isotype distribution of recovered BCR pairs.

FIG. 8D is an exemplary graph of $V_H$ vs $V_L$ mutation correlation for BCR pairs and density distributions within each isotype.

FIG. 8E depicts exemplary graphs of the numbers of captured mRNAs for TCR pairs and BCR pairs overall (top) and for different isotypes (bottom).

FIG. 8F depicts exemplary graphs of clonal analysis showing the rank abundance of the 30 most frequent BCR heavy chain clones (top) and the 30 most frequent TCR beta chain clones in each of six independent emulsion fractions. 1% and 10% overall frequency levels are shown.

FIG. 9A depicts an exemplary schematic showing 2 vessels each containing a single cell bound to an antibody-oligonucleotide conjugate are depicted. (DB1—droplet barcode 1; DB2—droplet barcode 2; MB1—molecular barcode 1; MB2—molecular barcode 2; AID—antigen ID barcode; AMB1—antibody molecular barcode 1; AMB2—antibody molecular barcode 2).

FIG. 9B depicts an exemplary schematic showing 2 vessels each containing RNA molecules from a lysed cell of a vessel from FIG. 9A. The RNA molecules are reverse transcribed and non-template nucleotides are added to the end of the cDNA molecule created by the reverse transcription. Molecular barcodes are hybridized to the non-template nucleotides added to the end of the cDNA molecule created by the reverse transcription.

FIG. 9C depicts an exemplary schematic showing 2 vessels each containing a template barcoded polynucleotide that is amplified and attached to the cDNA of a vessel from FIG. 9B via hybridization and the cDNA is extended (top). The extended cDNA is then amplified (bottom).

FIG. 9D depicts an exemplary schematic showing that RNA-MB-DB species with the same molecular barcode (MB) attached to the same identical RNA sequences is likely the result of PCR duplication. RNA-MB-DB species with two different MBs that are attached to the same identical RNA sequences (RNA1-MB1-DB and RNA1-MB2-DB) are two independent RNA molecules of origin and not of PCR duplication.

FIG. 9E depicts an exemplary schematic showing that DB-AMB-AID species with the same antibody molecular barcode (AMB) attached to a sequence with the same droplet barcode (DB) and antigen ID barcode (AID) is likely the result of PCR duplication. DB1-AMB1-AID1 and DB1-AMB2-AID1 species with two different AMBs attached to sequences with the same droplet barcode (DB) and antigen ID barcode (AID) are two independent oligonucleotide molecules from two independent antibody oligonucleotide conjugate molecules each with an antibody that specifically binds to the same target antigen attached to the same single cell in a vessel, and not of PCR duplication. DB1-AMBn-AID1 and DB1-AMBn-AID2 species with two different AIDs attached to sequences with the same droplet barcode (DB) and a same or different antibody molecular barcodes (AMBs) are two independent oligonucleotide molecules from two independent antibody oligonucleotide conjugate molecules attached to the same single cell in a vessel, wherein one of the antibody oligonucleotide conjugate molecules has an antibody that specifically binds to a first target antigen and the other antibody oligonucleotide conjugate molecule has an antibody that specifically binds to a second target antigen.

DETAILED DESCRIPTION

Figure 1:
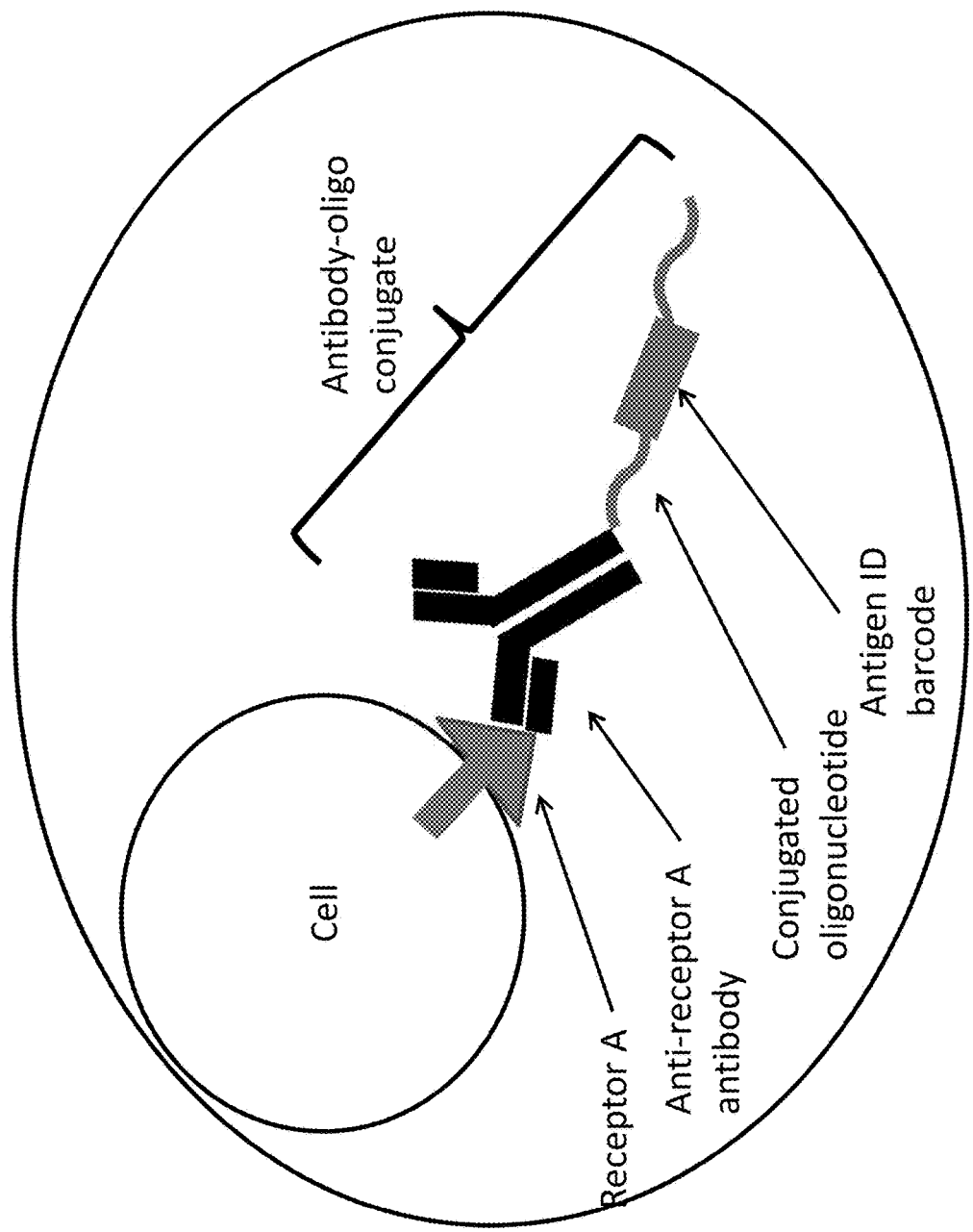
FIG. 1 depicts an exemplary schematic of a vessel of the methods described herein.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

It is an object of the invention to provide methods and compositions for phenotyping single cells (e.g., immune cells using affinity-oligonucleotide conjugates (e.g., antibody-oligonucleotide conjugates) (e.g., in emulsions).

Definitions

The term "antibody" herein thus is used in the broadest sense and includes polyclonal and monoclonal antibodies, including intact antibodies and functional (antigen-binding) antibody fragments thereof, including fragment antigen binding (Fab) fragments, F(ab')2 fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme), MacCallum et al., J. Mol. Biol. 262: 732-745 (1996), "Antibody-antigen interactions: Contact analysis and binding site topography," J. Mol. Biol. 262, 732-745." ("Contact" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Pltickthun A, "Yet another numbering scheme for immunoglobulin variable domains: an automatic modeling and analysis tool," J Mol Biol, 2001 Jun. 8; 309(3):657-70, ("Aho" numbering scheme).

The boundaries of a given CDR or FR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Table A, below, lists exemplary position boundaries of CDR-L1, CDR-L2, CDR-L3 and CDR-H1, CDR-H2, CDR-H3 as identified by Kabat, Chothia, and Contact schemes, respectively. For CDR-H1, residue numbering is listed using both the Kabat and Chothia numbering schemes. FRs are located between CDRs, for example, with FR-L1 located between CDR-L1 and CDR-L2, and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE A

| CDR | Kabat | Chothia | Contact |
|---|---|---|---|
| CDR-L1 | L24--L34 | L24--L34 | L30--L36 |
| CDR-L2 | L50--L56 | L50--L56 | L46--L55 |
| CDR-L3 | L89--L97 | L89--L97 | L89--L96 |
| CDR-H1 (Kabat Numbering[1]) | H31--H35B | H26--H32 . . . 34 | H30--H35B |
| CDR-H1 (Chothia Numbering[2]) | H31--H35 | H26--H32 | H30--H35 |
| CDR-H2 | H50--H65 | H52--H56 | H47--H58 |
| CDR-H3 | H95--H102 | H95--H102 | H93--H101 |

Thus, unless otherwise specified, a "CDR" or "complementary determining region," or individual specified CDRs (e.g., "CDR-H1, CDR-H2), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given VH or VL amino acid sequence, it is understood that such a CDR has a sequence of the corresponding CDR (e.g., CDR-H3) within the variable region, as defined by any of the aforementioned schemes. In some embodiments, specified CDR sequences are specified.

Likewise, unless otherwise specified, a FR or individual specified FR(s) (e.g., FR-H1, FR-H2), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, or Contact method. In other cases, the particular amino acid sequence of a CDR or FR is given.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150: 880-887 (1993); Clarkson et al., Nature 352:624-628 (1991).

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. In particular embodiments, the antibodies are single-chain antibody fragments comprising a variable heavy chain region and/or a variable light chain region, such as scFvs.

Unless otherwise stated, the term "TCR" should be understood to encompass full TCRs as well as antigen-binding portions or antigen-binding fragments (also called MHC-peptide binding fragments) thereof. In some embodiments, the TCR is an intact or full-length TCR. In some embodiments, the TCR is an antigen-binding portion that is less than a full-length TCR but that binds to a specific antigenic peptide bound to (i.e., in the context of) an MHC molecule, i.e., an MHC-peptide complex. In some cases, an antigen-binding portion or fragment of a TCR can contain only a portion of the structural domains of a full-length or intact TCR, but yet is able to bind the epitope (e.g., MHC-peptide complex) to which the full TCR binds. In some cases, an antigen-binding portion or fragment of a TCR contains the variable domains of a TCR, such as variable α chain and variable β chain of a TCR, sufficient to form a binding site for binding to a specific MHC-peptide complex, such as generally where each chain contains three complementarity determining regions. Polypeptides or proteins having a binding domain which is an antigen-binding domain or is homologous to an antigen-binding domain are included. Complementarity determining region (CDR) grafted antibodies and TCRs and other humanized antibodies and TCRs (including CDR modifications and framework region modifications) are also contemplated by these terms. It should be noted that while reference may be made only to immunoglobulin chains (e.g., heavy chains and lights chains), the disclosed invention can be applied to multiple other different types of paired sequences, e.g., T-cell receptor chain pairs (TCRα and TCRβ chains and TCRγ and TCRδ chains), and is not limited to immunoglobulins.

The ability of T-cells to recognize antigens associated with various cancers or infectious organisms is conferred by its TCR, which is made up of both an alpha (α) chain and a beta (β) chain or a gamma (γ) and a delta (δ) chain. The proteins which make up these chains are encoded by DNA, which employs a unique mechanism for generating the tremendous diversity of the TCR. This multi-subunit immune recognition receptor associates with the CD3 complex and binds peptides presented by the MHC class I and II proteins on the surface of antigen-presenting cells (APCs). Binding of a TCR to the antigenic peptide on the APC is a central event in T-cell activation, which occurs at an immunological synapse at the point of contact between the T-cell and the APC.

Each TCR comprises variable complementarity determining regions (CDRs), as well as framework regions (FRs). The amino acid sequence of the third complementarity-determining region (CDR3) loops of the α and β chain variable domains largely determines the sequence diversity of αβ T-cells arising from recombination between variable (Vβ), diversity (Dβ), and joining (Jβ) gene segments in the β chain locus, and between analogous Vα and Jα gene segments in the α chain locus, respectively. The existence of multiple such gene segments in the TCR α and β chain loci allows for a large number of distinct CDR3 sequences to be encoded. Independent addition and deletion of nucleotides at the Vβ-Dβ, Dβ-Jβ, and Vα-Jα junctions during the process of TCR gene rearrangement further increases CDR3 sequence diversity. In this respect, immunocompetence is reflected in the diversity of TCRs.

Immunoglobulins (Igs) expressed by B-cells are in some aspects proteins consisting of four polypeptide chains, two heavy chains (IgHs) and two light chains (IgLs), forming an $H_2L_2$ structure. Each pair of IgH and IgL chains contains a hypervariable domain, consisting of a $V_L$ and a $V_H$ region, and a constant domain. The IgH chains of Igs are of several types, μ, δ, γ, α, and β. The diversity of Igs within an individual is mainly determined by the hypervariable domain. Similar to the TCR, the V domain of IgH chains is created by the combinatorial joining of the $V_H$, $D_H$, and $J_H$ gene segments. Independent addition and deletion of nucleotides at the $V_H$-$D_H$, $D_H$-$J_H$, and $V_H$-$J_H$ junctions during the process of Ig gene rearrangement further increases hypervariable domain sequence diversity. Here, immunocompetence is reflected in the diversity of Igs.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150: 880-887 (1993); Clarkson et al., Nature 352:624-628 (1991).

An "affinity portion" refers to a portion of the affinity-oligonucleotide conjugate that interacts with a target antigen. Exemplary affinity portions include antibodies, peptides, proteins, aptamers, small molecules, drugs, cells, MHCs and others.

A "hypervariable region" refers to the amino acid residues of an antibody or TCR which are responsible for antigen-binding. The hypervariable region comprises amino acid residues from a complementarity determining region or CDR. Framework or FR residues are those variable domain residues other than the hypervariable region residues as herein defined.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

Also provided are TCR fragments, including antigen-binding fragments. In some embodiments, the TCR is an antigen-binding portion thereof, such as a variant of a full-length TCR not containing the transmembrane and/or cytoplasmic region(s) thereof, which may be referred to as a full soluble TCR. In some embodiments, the TCR is a dimeric TCR (dTCR). In some embodiments, the TCR is a single-chain TCR (scTCR), such as a scTCR having a structure as described in PCT patent publication numbers WO 03/020763, WO 04/033685, or WO 2011/044186. In certain embodiments, the TCR is a single-chain TCR fragment comprising an alpha chain variable region linked to a beta chain variable region, such as a scTv. In some embodiments, an scTv is also referred to as an scFv A single-chain Fv or scFv refers in some aspects to antibody or TCR fragments that comprise the variable heavy chain ($V_H$) and variable light chain ($V_L$) domains of an antibody or the variable alpha or gamma chain (Vα or Vγ) and variable beta or delta chain (Vβ or Vδ) domains of a TCR, wherein these domains are present in a single polypeptide chain. Generally, the Fv polypeptide further comprises a polypeptide linker between the $V_H$ and $V_L$ domains or Vα and Vβ domains or Vγ and Vδ domains which enables the sFv to form the desired structure for antigen binding.

A diabody refers in some aspects to small antibody and/or TCR fragments with two antigen-binding sites, which fragments comprise a $V_H$ connected to a $V_L$ in the same polypeptide chain ($V_H$-$V_L$) or a Vα connected to a Vβ in the same polypeptide chain (Vα-Vβ) or a Vγ connected to a Vδ in the same polypeptide chain (Vγ-Vδ). By using a linker that is too short to allow pairing between the two domains on the same chain, the domains are forced to pair with the complementary domains of another chain and create two antigen-binding sites. Exemplary diabodies are described more fully in, for example, EP404097 and WO93111161.

A bispecific antibody or bispecific TCR refers in some aspects to an antibody or TCR that shows specificities to two different types of antigens. The terms as used herein specifically include, without limitation, antibodies and TCRs which show binding specificity for a target antigen and to another target that facilitates delivery to a particular tissue. Similarly, multi-specific antibodies and TCRs have two or more binding specificities.

A linear antibody or "linear TC refers in some aspects to a pair of tandem Fd segments (e.g., $V_H$-$C_{H1}$-$V_H$-$C_{H1}$ or Vα-$Cα_1$-Vα-$Cα_1$) which form a pair of antigen binding regions. Linear antibodies and TCRs can be bispecific or monospecific, for example, as described by Zapata et al., Protein Eng. 8(10):1057-1062 (1995).

An antigen-binding domain refers in some aspects to one or more fragments of an antibody or TCR that retain the ability to specifically bind to an antigen. Non-limiting examples of antibody fragments included within such terms include, but are not limited to, (i) a Fab fragment, a monovalent fragment consisting of the $V_L$, $V_H$, $C_L$ and $C_{H1}$ domains; (ii) a F(ab')$_2$ fragment, a bivalent fragment containing two Fab fragments linked by a disulfide bridge at the hinge region; (iii) a Fd fragment consisting of the $V_H$ and $C_{H1}$ domains; (iv) a Fv fragment containing the $V_L$ and $V_H$ domains of a single arm of an antibody, including scFvs, (v) a dAb fragment (Ward et al., (1989) Nature 341:544 546), which containing a $V_H$ domain; and (vi) an isolated CDR. Additionally included in this definition are antibodies comprising a single heavy chain and a single light chain or TCRs with a single alpha chain or a single beta chain.

"F(ab')$_2$" and "Fab'" moieties can be produced by treating an Ig with a protease such as pepsin and papain, and include antibody fragments generated by digesting immunoglobulin near the disulfide bonds existing between the hinge regions in each of the two heavy chains. For example, papain cleaves IgG upstream of the disulfide bonds existing between the hinge regions in each of the two heavy chains to generate two homologous antibody fragments in which a light chain composed of $V_L$ and $C_L$, and a heavy chain fragment composed of $V_H$ and $C_{H\gamma 1}$ (γ1 region in the constant region of the heavy chain) are connected at their C terminal regions through a disulfide bond. Each of these two homologous antibody fragments is called 'Fab'. Pepsin also cleaves IgG downstream of the disulfide bonds existing between the hinge regions in each of the two heavy chains to generate an antibody fragment slightly larger than the fragment in which the two above-mentioned 'Fab' are connected at the hinge region. This antibody fragment is called F('ab')$_2$. The Fab fragment also contains the constant domain of the light chain and the first constant domain ($C_H 1$) of the heavy chain. 'Fab' fragments differ from Fab fragments by the addition of a few residues at the carboxyl terminus of the heavy chain $C_H 1$ domain including one or more cysteine(s) from the antibody hinge region. Fab'-SH is the designation herein for Fab' in which the cysteine residue(s) of the constant domains bear a free thiol group. F(ab')$_2$ antibody fragments originally are produced as pairs of Fab' fragments which have hinge cysteines between them.

Fv refers in some aspects to an antibody or TCR fragment which contains a complete antigen-recognition and antigen-binding site. This region consists of a dimer of one heavy chain and one light chain variable domain or one TCRα chain and one TCRβ chain or one TCRγ chain and one TCRδ chain in tight, non-covalent association. It is in this configuration that the three CDRs of each variable domain interact to define an antigen-binding site on the surface of the $V_H$-$V_L$ dimer or Vα-Vβ dimer or Vγ-Vδ dimer. Collectively, a combination of one or more of the CDRs from each of the $V_H$ and $V_L$ chains or Vα-Vβ chains or Vγ-Vδ chains confers antigen-binding specificity to the antibody or TCR. For example, it would be understood that, for example, the CDRH3 and CDRL3 could be sufficient to confer antigen-binding specificity to an antibody or TCR when transferred to $V_H$ and $V_L$ chains or Vα and Vβ chains or Vγ-Vδ chains of a recipient selected antibody, TCR, or antigen-binding fragment thereof and this combination of CDRs can be tested for binding, affinity, etc. Even a single variable domain (or half of an Fv comprising only three CDRs specific for an antigen) has the ability to recognize and bind antigen, although likely at a lower affinity than when combined with a second variable domain. Furthermore, although the two domains of a Fv fragment ($V_L$ and $V_H$ or Vα and Vβ or Vγ and Vδ), are coded for by separate genes, they can be joined using recombinant methods by a synthetic linker that enables them to be made as a single protein chain in which the $V_L$ and $V_H$ or Vα and Vβ or Vγ and Vδ chain regions pair to form monovalent molecules (known as single chain Fv (scFv); Bird et al. (1988) Science 242:423-426; Huston et al. (1988) Proc. Natl. Acad. Sci. USA 85:5879-5883; and Osbourn et al. (1998) Nat. Biotechnol. 16:778). Such scFvs are also intended to be encompassed within the term "antigen-binding portion" of an antibody. Any $V_H$ and $V_L$ sequences of specific scFv can be linked to an Fc region cDNA or genomic sequences, in order to generate expression vectors encoding complete Ig (e.g., IgG) molecules or other isotypes. $V_H$ and $V_L$ can also be used in the generation of Fab, Fv or other fragments of Igs using either protein chemistry or recombinant DNA technology.

Antigen-binding polypeptides also include heavy chain dimers such as, for example, antibodies from camelids and sharks. Camelid and shark antibodies comprise a homodimeric pair of two chains of V-like and C-like domains (neither has a light chain). Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called $V_{HH}$ domains. Shark Ig-NARs comprise a homodimer of one variable domain (termed a V-NAR domain) and five C-like constant domains (C-NAR domains). In camelids, the diversity of antibody repertoire is determined by the CDRs 1, 2, and 3 in the $V_H$ or $V_{HH}$ regions. The CDR3 in the camel $V_{HH}$ region is characterized by its relatively long length, averaging 16 amino acids (Muyldermans et al., 1994, Protein Engineering 7(9): 1129).

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

The terms "polypeptide" and "protein" are used interchangeably to refer to a polymer of amino acid residues, and are not limited to a minimum length. Polypeptides, including the provided antibodies and antibody chains and other peptides, e.g., linkers and binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

A "germline sequence" refers to a genetic sequence from the germline (the haploid gametes and those diploid cells from which they are formed). Germline DNA contains multiple gene segments that encode a single Ig heavy or light chain, or a single TCRα or TCRβ chain, or a single TCRγ or TCRδ chain. These gene segments are carried in the germ cells but cannot be transcribed and translated until they are arranged into functional genes. During B-cell and T-cell differentiation in the bone marrow, these gene segments are randomly shuffled by a dynamic genetic system capable of generating more than $10^8$ specificities. Most of these gene segments are published and collected by the germline database.

Affinity refers to the equilibrium constant for the reversible binding of two agents and is expressed as $K_D$. Affinity of a binding protein to a ligand such as affinity of an antibody for an epitope or such as affinity for a TCR for a MCH-peptide complex can be, for example, from about 100 nanomolar (nM) to about 0.1 nM, from about 100 nM to about 1 picomolar (pM), or from about 100 nM to about 1 femtomolar (fM). The term "avidity" refers to the resistance of a complex of two or more agents to dissociation after dilution.

An epitope refers in some aspects to a portion of an antigen or other macromolecule capable of forming a binding interaction with the variable region binding pocket of an antibody or TCR. Such binding interactions can be manifested as an intermolecular contact with one or more amino acid residues of one or more CDRs. Antigen binding can involve, for example, a CDR3, a CDR3 pair, or in some instances, interactions of up to all six CDRs of the $V_H$ and $V_L$ chains. An epitope can be a linear peptide sequence (i.e., "continuous") or can be composed of noncontiguous amino acid sequences (i.e., "conformational" or "discontinuous"). An antibody or TCR can recognize one or more amino acid sequences; therefore an epitope can define more than one distinct amino acid sequence. In some aspects, a TCR can recognize one or more amino acid sequences or epitopes in the context of an MHC. Epitopes recognized by antibodies and TCRs can be determined by peptide mapping and sequence analysis techniques well known to one of skill in the art. Binding interactions are manifested as intermolecular contacts with one or more amino acid residues of a CDR.

In some embodiments, reference to an antibody or TCR with specific binding refers to a situation in which an antibody or TCR will not show any significant binding to molecules other than the antigen containing the epitope recognized by the antibody or TCR. The term is also applicable where for example, an antigen binding domain is specific for a particular epitope which is carried by a number of antigens, in which case the selected antibody, TCR, or antigen-binding fragment thereof carrying the antigen binding domain will be able to bind to the various antigens carrying the epitope. The terms "preferentially binds" or "specifically binds" mean that the antibodies, TCRs, or fragments thereof bind to an epitope with greater affinity than it binds unrelated amino acid sequences, and, if cross-reactive to other polypeptides containing the epitope, are not toxic at the levels at which they are formulated for administration to human use. In one aspect, such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody, TCR, or fragment thereof for unrelated amino acid sequences. The term "binding" refers to a direct association between two molecules, due to, for example, covalent, electrostatic, hydrophobic, and ionic and/or hydrogen-bond interactions under physiological conditions, and includes interactions such as salt bridges and water bridges, as well as any other conventional means of binding.

The term "binding" refers to a direct association between two molecules, due to, for example, covalent, electrostatic, hydrophobic, and ionic and/or hydrogen-bond interactions under physiological conditions, and includes interactions such as salt bridges and water bridges, as well as any other conventional means of binding.

In some aspects, the term "tetramer" may refer to a complex comprising four subunits bound to a single molecule of streptavidin, which can bind to and thus identify a population of cells. A subunit can be a MHC-peptide complex. A subunit may be a MHC without an associated peptide. A subunit can be a B-cell receptor antigen. A population of cells identified by a tetramer can be a population that expresses a receptor, such as a TCR or BCR, that binds to a subunit of the tetramer. The population of cells can be antigen specific T cells. The population of cells can be antigen specific B cells. A tetramer can be fluorescently labeled. As used herein MHC-peptide tetramer can be used interchangeably with pMHC.

"Pharmaceutically acceptable" refers to molecular entities and compositions that are physiologically tolerable and do not typically produce an allergic or similar untoward reaction, such as gastric upset, dizziness and the like, when administered to a human.

"Prevention" refers to prophylaxis, prevention of onset of symptoms, prevention of progression of a disease or disorder associated with excess levels of protein or correlated with protein activity.

"Inhibition," "treatment" and "treating" are used interchangeably and refer to, for example, stasis of symptoms, prolongation of survival, partial or full amelioration of symptoms, and partial or full eradication of a condition, disease or disorder associated with excess levels of protein or correlated with protein activity. For example, treatment of cancer includes, but is not limited to, stasis, partial or total elimination of a cancerous growth or tumor. Treatment or partial elimination includes, for example, a fold reduction in growth or tumor size and/or volume such as about 2-fold, about 3-fold, about 4-fold, about 5-fold, about 10-fold, about 20-fold, about 50-fold, or any fold reduction in between.

Similarly, treatment or partial elimination can include a percent reduction in growth or tumor size and/or volume of about 1%, 2%, 3%, 4%, 5%, 10%, 20%, 30%, 40%, 50%, 60%, 70%, 80%, 90%, 95% or any percentage reduction in between.

A neutralizing antibody or neutralizing TCR refers in some aspects to any antibody or TCR that inhibits replication of a pathogen, such as a virus or bacteria, regardless of the mechanism by which neutralization is achieved.

An antibody repertoire or TCR repertoire refers to a collection of antibodies, TCRs, or fragments thereof. An antibody repertoire can, for example, be used to select a particular antibody or screen for a particular property, such as binding ability, binding specificity, ability of gastrointestinal transport, stability, affinity, and the like. The term specifically includes antibody and TCR libraries, including all forms of combinatorial libraries, such as, for example, antibody phage display libraries, including, without limitation, single-chain Fv (scFv) and Fab antibody phage display libraries from any source, including naïve, synthetic and semi-synthetic libraries.

A "target nucleic acid molecule," "target polynucleotide," "target polynucleotide molecule," refers to any nucleic acid of interest.

A polymerase chain reaction (PCR) refers to an in vitro amplification reaction of polynucleotide sequences by the simultaneous primer extension of complementary strands of a double stranded polynucleotide. PCR reactions produce copies of a template polynucleotide flanked by primer binding sites. The result, with two primers, is an exponential increase in template polynucleotide copy number of both strands with each cycle, because with each cycle both strands are replicated. The polynucleotide duplex has termini corresponding to the ends of primers used. PCR can comprise one or more repetitions of denaturing a template polynucleotide, annealing primers to primer binding sites, and extending the primers by a DNA or RNA polymerase in the presence of nucleotides. Particular temperatures, durations at each step, and rates of change between steps depend on many factors well-known to those of ordinary skill in the art. (McPherson et al., IRL Press, Oxford (1991 and 1995)). For example, in a conventional PCR using Taq DNA polymerase, a double stranded template polynucleotide can be denatured at a temperature >90° C., primers can be annealed at a temperature in the range 50-75° C., and primers can be extended at a temperature in the range 72-78° C. In some embodiments, PCR comprises Reverse transcription PCR (RT-PCR), real-time PCR, nested PCR, quantitative PCR, multiplexed PCR, or the like. In some embodiments, PCR does not comprise RT-PCR. (U.S. Pat. Nos. 5,168,038, 5,210,015, 6,174,670, 6,569,627, and 5,925,517; Mackay et al., Nucleic Acids Research, 30: 1292-1305 (2002)). RT-PCR comprises a PCR reaction preceded by a reverse transcription reaction and a resulting cDNA is amplified, Nested PCR comprises a two-stage PCR wherein an amplicon of a first PCR reaction using a first set of primers becomes the sample for a second PCR reaction using a second primer set, at least one of which binds to an interior location of an amplicon of a first PCR reaction. Multiplexed PCR comprises a PCR reaction, wherein a plurality of polynucleotide sequences is subjected to PCR in the same reaction mixture simultaneously. PCR reaction volumes can be anywhere from 0.2 pL-1000 µL. Quantitative PCR comprises a PCR reaction designed to measure an absolute or relative amount, abundance, or concentration of one or more sequences in a sample. Quantitative measurements can include comparing one or more reference sequences or standards to a polynucleotide sequence of interest. (Freeman et al., Biotechniques, 26: 112-126 (1999); Becker-Andre et al., Nucleic Acids Research, 17: 9437-9447 (1989); Zimmerman et al., Biotechniques, 21: 268-279 (1996); Diviacco et al., Gene, 122: 3013-3020 (1992); Becker-Andre et al., Nucleic Acids Research, 17: 9437-9446 (1989)).

"Nucleotide," "nucleoside," "nucleotide residue," and "nucleoside residue," as used herein, can mean a deoxyribonucleotide or ribonucleotide residue, or other similar nucleoside analogue capable of serving as a component of a primer suitable for use in an amplification reaction (e.g., PCR reaction). Such nucleosides and derivatives thereof can be used as the building blocks of the primers described herein, except where indicated otherwise. Nothing in this application is meant to preclude the utilization of nucleoside derivatives or bases that have been chemical modified to enhance their stability or usefulness in an amplification reaction, provided that the chemical modification does not interfere with their recognition by a polymerase as deoxyguanine, deoxycytosine, deoxythymidine, or deoxyadenine, as appropriate. In some embodiments, nucleotide analogs can stabilize hybrid formation. In some embodiments, nucleotide analogs can destabilize hybrid formation. In some embodiments, nucleotide analogs can enhance hybridization specificity. In some embodiments, nucleotide analogs can reduce hybridization specificity.

A "nucleic acid", or grammatical equivalents, refers to either a single nucleotide or at least two nucleotides covalently linked together.

A "polynucleotide" or grammatical equivalents refers to at least two nucleotides covalently linked together. A polynucleotide comprises a molecule containing two or more nucleotides. A polynucleotide comprises polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatives of nucleotide bases. The backbone of the polynucleotide can comprise sugars and phosphate groups, or modified or substituted sugar or phosphate groups. A polynucleotide may comprise modified nucleotides, such as methylated nucleotides and nucleotide analogs. The sequence of nucleotides may be interrupted by non-nucleotide components. A polynucleotide can include other molecules, such as another hybridized polynucleotide. Polynucleotides include sequences of deoxyribonucleic acid (DNA), ribonucleic acid (RNA), or both. Non-limiting examples of polynucleotides include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), cDNA, recombinant polynucleotides, branched polynucleotides, plasmids, vectors, isolated DNA of a sequence, isolated RNA of a sequence, nucleic acid probes, and primers. Polynucleotides can be isolated from natural sources, recombinant, or artificially synthesized.

Polynucleotides can include nonstandard nucleotides, such as nucleotide analogs or modified nucleotides. In some embodiments, nonstandard nucleotides can stabilize hybrid formation. In some embodiments, nonstandard nucleotides can destabilize hybrid formation. In some embodiments, nonstandard nucleotides can enhance hybridization specificity. In some embodiments, nonstandard nucleotides can reduce hybridization specificity. Examples of nonstandard nucleotide modifications include 2' O-Me, 2' O-allyl, 2' O-propargyl, 2' O-alkyl, 2' fluoro, 2' arabino, 2' xylo, 2' fluoro arabino, phosphorothioate, phosphorodithioate, phosphoroamidates, 2' Amino, 5-alkyl-substituted pyrimidine, 3' deoxyguanosine, 5-halo-substituted pyrimidine, alkyl-substituted purine, halo-substituted purine, bicyclic nucleotides, 2'MOE, PNA molecules, LNA-molecules, LNA-like molecules, diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methyl guanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxy acetic acid (v), 5-methyl-2-thiouracil, 3-(3-amino-3-N-2-carboxypropyl) uracil, (acp3)w, 2,6-diaminopurine, and derivatives thereof.

A "subject", "individual", "host" or "patient" refers to a living organisms such as mammals. Examples of subjects and hosts include, but are not limited to, horses, cows, camels, sheep, pigs, goats, dogs, cats, rabbits, guinea pigs, rats, mice (e.g., humanized mice), gerbils, non-human primates (e.g., macaques), humans and the like, non-mammals, including, e.g., non-mammalian vertebrates, such as birds (e.g., chickens or ducks) fish (e.g., sharks) or frogs (e.g., *Xenopus*), and non-mammalian invertebrates, as well as transgenic species thereof. In certain aspects, a subject refers to a single organism (e.g., human). In certain aspects, or a group of individuals composing a small cohort having either a common immune factor to study and/or disease, and/or a cohort of individuals without the disease (e.g., negative/normal control) are provided. A subject from whom samples are obtained can either be inflicted with a disease and/or disorder (e.g., one or more allergies, infections, cancers or autoimmune disorders or the like) and can be compared against a negative control subject which is not affected by the disease.

A "kit" refers to a delivery system for delivering materials or reagents for carrying out a method disclosed herein. In some embodiments, kits include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains a plurality of primers.

A polypeptide refers in some aspects to a molecule comprising at least two amino acids. In some embodiments, the polypeptide consists of a single peptide. In some embodiments, a polypeptide comprises two or more peptides. For example, a polypeptide can comprise at least about 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 peptides or amino acids. Examples of polypeptides include, but are not limited to, amino acid chains, proteins, peptides, hormones, polypeptide saccharides, lipids, glycolipids, phospholipids, antibodies, enzymes, kinases, receptors, transcription factors, and ligands.

A sample refers in some aspects to a biological, environmental, medical, subject, or patient sample or a sample containing a polynucleotide, such as a target polynucleotide.

Affinity-Oligonucleotide Conjugates

An affinity-oligonucleotide conjugate comprises an affinity molecule portion (e.g., an antibody or MHC-peptide complex) and an oligonucleotide portion. An antigen identification sequence of the affinity-oligonucleotide conjugate's oligonucleotide can be used to identify the one or more antigens to which the affinity-oligonucleotide conjugate specifically interacts. In some embodiments, the oligonucleotide is attached covalently to the affinity portion of the conjugate. In some embodiments, the oligonucleotide is attached non-covalently to the affinity portion of the conjugate. An affinity-oligonucleotide conjugate can be a tetramer-oligonucleotide conjugate. A tetramer-oligonucleotide conjugate can comprise a tetramer (e.g., B-cell receptor antigen tetramer or MHC-peptide complex tetramer) and an oligonucleotide portion. An antigen identification sequence of the tetramer-oligonucleotide conjugate's oligonucleotide can be used to identify the one or more antigens to which the tetramer-oligonucleotide conjugate specifically interacts. In some embodiments, the oligonucleotide is attached covalently to the affinity portion or tetramer of the conjugate. In some embodiments, the oligonucleotide is attached non-covalently to the affinity portion or tetramer of the conjugate.

In some embodiments, an affinity-oligonucleotide conjugate comprises a single affinity portion. In some embodiments, affinity-oligonucleotide conjugates are multivalent affinity-oligonucleotide conjugates. For example, multivalent affinity-oligonucleotide conjugates can comprise antigen-binding domains of at least two affinity molecules conjugated to one or more oligonucleotide(s). For example, multivalent affinity-oligonucleotide conjugates may comprise antigen-binding domains of at least about 2, 3, 4, 5, 6, 7, 8, 9, 10, 20, 50, 100, 200, 500, or 1,000 affinity molecules conjugated to one or more oligonucleotides. In some embodiments, an affinity-oligonucleotide conjugate comprises a single oligonucleotide. In some embodiments, an affinity-oligonucleotide conjugate comprises 2 or more oligonucleotides. For example, an affinity-oligonucleotide conjugate can comprise at least about 2, 3, 4, 5, 6, 7, 8, 9, 10, 20, 50, 100, 200, 500, or 1,000 oligonucleotides conjugated to one or more affinity molecules (e.g., an antibody or MHC-peptide complex). In some embodiments, an affinity-oligonucleotide conjugate comprises 2 or more oligonucleotides containing a same Antigen ID (AID) sequence. For example, an affinity-oligonucleotide conjugate can comprise at least about 2, 3, 4, 5, 6, 7, 8, 9, 10, 20, 50, 100, 200, 500, or 1,000 oligonucleotides containing a same AID sequence Affinity Portion of Affinity-Oligonucleotide Conjugates An affinity portion (or domain) of an affinity-oligonucleotide conjugate comprises the region, molecule, domain, portion, fragment, or moiety of an affinity-oligonucleotide conjugate that binds to a target antigen. Thus, an affinity portion confers the ability to bind or specifically bind to a given target antigen, such as an extracellular domain of a cell-surface protein. In some embodiments, an affinity portion does not substantially interact with an antigen of another affinity-oligonucleotide conjugate comprising a different Antigen ID sequence. In some embodiments, an affinity portion is a molecule that can contain a nucleic acid, or to which an oligonucleotide can be attached, without substantially abolishing the binding of the affinity portion to a target antigen.

An affinity portion of an affinity-oligonucleotide conjugate can be a nucleic acid molecule or can be proteinaceous. Affinity portions include, but are not limited to, RNAs, DNAs, RNA-DNA hybrids, small molecules (e.g., drugs), aptamers, polypeptides, proteins, antibodies and fragments thereof, TCRs and fragments thereof, viruses, virus particles, cells, fragments thereof, and combinations thereof. (See, e.g., Fredriksson et al., (2002) Nat Biotech 20:473-77; Gullberg et al., (2004) PNAS, 101:8420-24). For example, an affinity portion can be a single-stranded RNA, a double-stranded RNA, a single-stranded DNA, a double-stranded DNA, a DNA or RNA comprising one or more double stranded regions and one or more single stranded regions, an RNA-DNA hybrid, a small molecule, an aptamer, a polypeptide, a protein, an antibody, an antibody fragment, a TCR, a TCR fragment, an MHC, an MHC-peptide complex, a virus particle, a cell, or any combination thereof.

In some embodiments, an affinity portion of an affinity-oligonucleotide conjugate targets a cell. For example, an affinity portion of an affinity-oligonucleotide conjugate can target a T-cell or a B-cell. In some embodiments, an affinity portion of an affinity-oligonucleotide conjugate targets a particular cell type or cell subset. For example, an affinity portion of an affinity-oligonucleotide conjugate can target a $CD4^+$ T-cell or a $CD8^+$ T-cell. For example, an affinity portion of an affinity-oligonucleotide conjugate can target a T-cell comprising a TCR that specifically recognizes a particular antigen. For example, an affinity portion of an affinity-oligonucleotide conjugate can target a T-cell comprising a TCR that specifically recognizes a particular MHC-peptide complex.

In some embodiments, an affinity portion of an affinity-oligonucleotide conjugate targets an extracellular domain of a target of a cell. For example, an affinity portion of an affinity-oligonucleotide conjugate can target an extracellular domain of a receptor of a cell, e.g., a T-cell receptor (TCR). For example, an affinity portion of an affinity-oligonucleotide conjugate can target a glycosylated region of an extracellular domain of a receptor of a cell. For example, an affinity portion of an affinity-oligonucleotide conjugate can target a ligand binding region of an extracellular domain of a receptor of a cell. For example, an affinity portion of an affinity-oligonucleotide conjugate can target a region of an extracellular domain of a receptor of a cell that does not bind to a ligand.

In some embodiments, an affinity portion of a tetramer-oligonucleotide conjugate comprises a MHC-peptide complex. In some embodiments, the MHC-peptide complex targets a TCR. In some embodiments, an affinity portion of a tetramer-oligonucleotide conjugate comprises a B-cell receptor antigen. In some embodiments, the B-cell receptor antigen targets a BCR.

Proteins

In some embodiments, an affinity portion is a polypeptide, a protein, or any fragment thereof. In some embodiments, an affinity portion of an affinity-oligonucleotide conjugate is a protein. In some embodiments, an affinity portion of an affinity-oligonucleotide conjugate is a peptide. For example, an affinity portion of an affinity-oligonucleotide conjugate can be an antibody, such as a binding domain of an antibody. For example, an affinity portion of an affinity-oligonucleotide conjugate can be a MHC-peptide complex. For example, an affinity portion can be a purified polypeptide, an isolated polypeptide, a fusion tagged polypeptide, a polypeptide attached to or spanning the membrane of a cell or a virus or virion, a cytoplasmic protein, an intracellular protein, an extracellular protein, a kinase, a phosphatase, an aromatase, a helicase, a protease, an oxidoreductase, a reductase, a transferase, a hydrolase, a lyase, an isomerase, a glycosylase, a extracellular matrix protein, a ligase, an ion transporter, a channel, a pore, an apoptotic protein, a cell adhesion protein, a pathogenic protein, an aberrantly expressed protein, an transcription factor, a transcription regulator, a translation protein, a chaperone, a secreted protein, a ligand, a hormone, a cytokine, a chemokine, a nuclear protein, a receptor, a transmembrane receptor, a signal transducer, an antibody, a membrane protein, an integral membrane protein, a peripheral membrane protein, a cell wall protein, a globular protein, a fibrous protein, a glycoprotein, a lipoprotein, a chromosomal protein, any fragment thereof, or any combination thereof. In some embodiments, an affinity portion is a heterologous polypeptide. In some embodiments, an affinity portion is a protein overexpressed in a cell using molecular techniques, such as transfection. In some embodiments, an affinity portion is recombinant polypeptide. For example, an affinity portion can comprise samples produced in bacterial (e.g., *E. coli*), yeast, mammalian, or insect cells (e.g., proteins overexpressed by the organisms). In some embodiments, an affinity portion is a polypeptide containing a mutation, insertion, deletion, or polymorphism. In some embodiments, an affinity portion is an antigen, such as a polypeptide used to immunize an organism or to generate an immune response in an organism, such as for antibody production.

In some embodiments, an affinity portion of a tetramer-oligonucleotide conjugate is a tetramer. In some embodiments, a subunit of a tetramer is a protein. In some embodiments, a subunit of a tetramer is a peptide. In some embodiments, a subunit of a tetramer is a complex of proteins and/or peptides. In some embodiments, a complex of proteins and/or peptides may be covalently or non-covalently linked and/or associated. For example, an affinity portion of an tetramer-oligonucleotide conjugate can be a MHC-peptide complex. Some non-limiting examples of the peptide in the MHC-peptide complex can be a peptide from a purified polypeptide, an isolated polypeptide, a fusion tagged polypeptide, a polypeptide attached to or spanning the membrane of a cell or a virus or virion, a cytoplasmic protein, an intracellular protein, an extracellular protein, a kinase, a phosphatase, an aromatase, a helicase, a protease, an oxidoreductase, a reductase, a transferase, a hydrolase, a lyase, an isomerase, a glycosylase, a extracellular matrix protein, a ligase, an ion transporter, a channel, a pore, an apoptotic protein, a cell adhesion protein, a pathogenic protein, an aberrantly expressed protein, an transcription factor, a transcription regulator, a translation protein, a chaperone, a secreted protein, a ligand, a hormone, a cytokine, a chemokine, a nuclear protein, a receptor, a transmembrane receptor, a signal transducer, an antibody, a membrane protein, an integral membrane protein, a peripheral membrane protein, a cell wall protein, a globular protein, a fibrous protein, a glycoprotein, a lipoprotein, a chromosomal protein, any fragment thereof, or any combination thereof. In some embodiments, the peptide is derived from a disease associated antigen. For example, in some aspects, the peptide is or may be derived from a tumor-associated antigen, including a universal tumor antigen, a virally-associated antigen, an autoimmune-associated antigen, an inflammatory-associated antigen, a bacterially-associated antigen, or any combination thereof. In some embodiments, an affinity portion is a protein overexpressed in a cell using molecular techniques, such as transfection. In some embodiments, an affinity portion is recombinant polypeptide. For example, an affinity portion can comprise samples produced in bacterial (e.g., E. coli), yeast, mammalian, or insect cells (e.g., proteins overexpressed by the organisms). In some embodiments, an affinity portion is a polypeptide containing a mutation, insertion, deletion, or polymorphism. In some embodiments, an affinity portion is an antigen, such as a polypeptide used to immunize an organism or to generate an immune response in an organism, such as for antibody production. As another example, an affinity portion of an tetramer-oligonucleotide conjugate can be a B-cell receptor antigen. A B-cell receptor antigen can be a subunit of a tetramer.

Antibodies

In some embodiments, an affinity portion in an antibody, e.g., a binding fragment of an antibody. An antibody can specifically bind to a particular spatial and polar organization of another molecule. For example, an antibody can be a purified antibody, an isolated antibody, a fragment of an antibody, or a fusion tagged antibody. In some embodiments, an antibody is overexpressed in a cell using molecular techniques, such as transfection. In some embodiments, an antibody is a recombinant antibody. An antibody can specifically bind to a particular spatial and polar organization of another molecule, such as a cell surface molecule. An antibody can be monoclonal, polyclonal, or a recombinant antibody, and can be prepared by techniques that are well known in the art such as immunization of a host and collection of sera (polyclonal) or by preparing continuous hybrid cell lines and collecting the secreted protein (monoclonal), or by cloning and expressing nucleotide sequences, or mutagenized versions thereof, coding at least for the amino acid sequences required for specific binding of natural antibodies. In addition, aggregates, polymers, and conjugates of immunoglobulins or their fragments can be used where appropriate so long as binding affinity for a particular molecule is maintained. Examples of antibody fragments include a Fab fragment, a monovalent fragment consisting of the $V_L$, $V_H$, $C_L$ and $C_{H1}$ domains; a F(ab)$_2$ fragment, a bivalent fragment comprising two Fab fragments linked by a disulfide bridge at the hinge region; an Fd fragment consisting of the $V_H$ and $C_{H1}$ domains; an Fv fragment consisting of the $V_L$ and $V_H$ domains of a single arm of an antibody; a single domain antibody (dAb) fragment (Ward et al., (1989) Nature 341:544-46), which consists of a $V_H$ domain; and an isolated CDR and a single chain Fragment (scFv) in which the $V_L$ and $V_H$ regions pair to form monovalent molecules (known as single chain Fv (scFv); See, e.g., Bird et al., (1988) Science 242:423-26; and Huston et al., (1988) PNAS 85:5879-83). Thus, antibody fragments include Fab, F(ab)$_2$, scFv, Fv, dAb, and the like. Although the two domains $V_L$ and $V_H$ are coded for by separate genes, they can be joined, using recombinant methods, by an artificial peptide linker that enables them to be made as a single protein chain. Such single chain antibodies include one or more antigen binding moieties. These antibody fragments can be obtained using conventional techniques known to those of skill in the art, and the fragments can be screened for utility in the same manner as are intact antibodies. Antibodies can be human, humanized, chimeric, isolated, dog, cat, donkey, sheep, any plant, animal, or mammal.

MHCs

The recognition of antigenic structures by the cellular immune system in some cases is mediated by surface-expressed major histocompatibility complexes (MHC). Cells, such as antigen-presenting cells (APCs), in some aspects process proteins such as antigens into short peptides, which may be presented in a specific peptide binding fold of the MHC molecule and in some aspects can thus be recognized by T-cells. Specific recognition of the epitope (peptide fragment) by the T-cell receptor (TCR) generally requires simultaneous interaction with the MHC molecule. A stable multimeric complex can be prepared with MHC protein subunits containing a bound peptide. The MHC-antigen complex can form a stable structure with T-cells recognizing the complex through their antigen receptor, thereby allowing for the binding to T-cells that specifically recognize the antigen. An affinity portion of an affinity-oligonucleotide conjugate or of a tetramer-oligonucleotide conjugate can target a T-cell. An affinity portion of an affinity-oligonucleotide conjugate can specifically target a T-cell. An affinity portion of an affinity-oligonucleotide conjugate or of a tetramer-oligonucleotide conjugate can target a T-cell receptor or TCR-like molecule, such as a TCR-like CAR. An affinity portion of an affinity-oligonucleotide conjugate can specifically target a T-cell receptor. For example, an affinity portion of an affinity-oligonucleotide conjugate or of a tetramer-oligonucleotide conjugate can comprise a MHC molecule. For example, an affinity portion of an affinity-oligonucleotide conjugate or of a tetramer-oligonucleotide conjugate can comprise a MHC-peptide complex (MHC-p). An affinity portion of an affinity-oligonucleotide conjugate or of a tetramer-oligonucleotide conjugate can have the formula $(A-B-P)_n$, where A is an α-chain of a MHC class I or an MHC class II protein, B is a β-chain of a class II MHC protein or $β_2$ microglobulin for a MHC class I protein, and P is a peptide. In some embodiments, n is 1. In some embodiments, n is greater than or equal to 2. The MHC protein subunits can be a soluble form. For example, soluble MHC protein subunits can be derived from native MHC protein subunits by deletion of a transmembrane domain or portion thereof. In some embodiments, MHC protein subunits do not comprise a cytoplasmic domain. In some embodiments, MHC protein subunits do not comprise a transmembrane domain.

The peptide (P) can be from about 6 to 12 amino acids in length for complexes with class I MHC proteins, e.g., about 8 to 10 amino acids. The peptide can be from about 6 to 20 amino acids in length for complexes with class II MHC proteins, e.g., about 10 to 18 amino acids. The peptides may have a sequence derived from a wide variety of proteins. The peptides can be T-cell epitopes. The epitope sequences from a number of antigens are known in the art. Alternatively, the epitope sequence may be empirically determined, by isolating and sequencing peptides bound to native MHC proteins, by synthesis of a series of peptides from the target sequence, then assaying for T-cell reactivity to the different peptides, or by producing a series of binding complexes with different peptides and quantitating the T-cell binding. Preparation of fragments, identifying sequences, and identifying the minimal sequence is described in U.S. Pat. No. 5,019,384 and references cited therein. Peptides may be prepared in a variety of ways. Conveniently, they can be synthesized by conventional techniques employing automatic synthesizers, or may be synthesized manually. Alternatively, DNA sequences can be prepared which encode the particular peptide and may be cloned and expressed to provide the desired peptide. In this instance a methionine may be the first amino acid. In addition, peptides may be produced by recombinant methods as a fusion to proteins that are one of a specific binding pair, allowing purification of the fusion protein by means of affinity reagents, followed by proteolytic cleavage, usually at an engineered site to yield the desired peptide (see, e.g., Driscoll et al. (1993) J. Mol. Bio. 232:342-350). The peptides may also be isolated from natural sources and purified by known techniques, including, for example, chromatography on ion exchange materials, separation by size, immunoaffinity chromatography and electrophoresis.

In some embodiments, the α- and β-subunits are separately produced and allowed to associate in vitro to form a stable heteroduplex complex (see, e.g., Altman et al. (1993) or Garboczi et al. (1992)). In some embodiments, the α- and β-subunits are expressed together in a single cell. In some embodiments, a single molecule having the α- and β-subunits is used. For example, a single-chain heterodimer can be created by fusing together the two subunits using a short peptide linker, e.g., a 15 to 25 amino acid peptide or linker (see, e.g., Bedzyk et al. (1990) J. Biol. Chem. 265:18615). Soluble heterodimers may also be produced by isolation of a native heterodimer and cleavage with a protease, e.g., papain, to produce a soluble product.

Soluble subunits can be independently expressed from a DNA construct encoding a truncated protein. For expression, the DNA sequences can be inserted into an appropriate expression vector, where the native transcriptional initiation region may be employed or an exogenous transcriptional initiation region, e.g., a promoter other than the promoter which is associated with the gene in the normally occurring chromosome. The promoter may be introduced by recombinant methods in vitro, or as the result of homologous integration of the sequence into a chromosome. Transcriptional initiation regions are known for a wide variety of expression hosts. The expression hosts may involve prokaryotes or eukaryotes, particularly E. coli, B. subtilis, mammalian cells, such as CHO cells, COS cells, monkey kidney cells, lymphoid cells, human cell lines, and the like.

The subunits can be expressed in a suitable host cell, and, if necessary, solubilized. The two subunits can be combined with a peptide and allowed to fold in vitro to form a stable heterodimer complex with intrachain disulfide bonded domains. The peptide may be included in the initial folding reaction, or may be added to the empty heterodimer in a later step. The MHC binding site may be free of peptides prior to addition of the peptide. The exception will be those cases where it is desirable to label the T cells with a natural peptide-MHC complex, such as those that may be present on the surface of cells that are a target for autoimmune attack, etc. The MHC heterodimer will bind to a peptide in the groove formed by the two membrane distal domains, either α2 and α1 for class I, or α1 and β1 for class II. Conditions that permit folding and association of the subunits and peptide are known in the art (see, e.g., for Altman et al. (1993) and Garboczi et al. (1992)). As one example of permissive conditions, roughly equimolar amounts of solubilized α and β subunits are mixed in a solution of urea. Refolding is initiated by dilution or dialysis into a buffered solution without urea. Peptides are loaded into empty class II heterodimers at about pH 5 to 5.5 for about 1 to 3 days, followed by neutralization, concentration and buffer exchange. However, it will be readily understood by one of skill in the art that the specific folding conditions are not critical for the practice of the invention.

In some embodiments, a monomeric complex (α-β-P) can be multimerized. For example, a multimer can be formed by binding the monomers to a multivalent entity through specific attachment sites on the α or β subunit. In some embodiments, a multimer is be formed by chemical cross-linking of the monomers. A number of reagents capable of cross-linking proteins are known in the art, including, but not limited to azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, formaldehyde and succinimidyl 4-[N-maleimidomethyl] cyclohexane-1-carboxylate. An attachment site for binding to a multivalent entity may be naturally occurring, or may be introduced through genetic engineering. The site can be a specific binding pair member or one that is modified to provide a specific binding pair member, where the complementary pair has a multiplicity of specific binding sites. Binding to the complementary binding member can be a chemical reaction, epitope-receptor binding or hapten-receptor binding where a hapten is linked to the subunit chain. In a preferred embodiment, one of the subunits is fused to an amino acid sequence providing a recognition site for a modifying enzyme. The recognition sequence will usually be fused proximal to the carboxy terminus of one of the subunit to avoid potential hindrance at the antigenic peptide binding site. Conveniently, an expression cassette will include the sequence encoding the recognition site.

Modifying enzymes of interest include BirA, various glycosylases, farnesyl protein transferase, protein kinases and the like. The subunit may be reacted with the modifying enzyme at any convenient time, usually after formation of the monomer. The group introduced by the modifying enzyme, e.g., biotin, sugar, phosphate, farnesyl, etc. provides a complementary binding pair member, or a unique site for further modification, such as chemical cross-linking, biotinylation, etc. that will provide a complementary binding pair member. An alternative strategy is to introduce an unpaired cysteine residue to the subunit, thereby introducing a unique and chemically reactive site for binding. The attachment site may also be a naturally occurring or introduced epitope, where the multivalent binding partner will be an antibody, e.g., IgG, IgM, etc. Any modification will be at a site, e.g., C-terminal proximal, that will not interfere with binding. Exemplary of multimer formation is the introduction of the recognition sequence for the enzyme BirA, which catalyzes biotinylation of the protein substrate. The monomer with a biotinylated subunit is then bound to a multivalent binding partner, e.g., streptavidin or avidin, to which biotin binds with extremely high affinity. Streptavidin has a valency of 4, providing a multimer of $(\alpha-\beta-P)_4$. The multivalent binding partner may be free in solution, or may be attached to an insoluble support. Examples of suitable insoluble supports include beads, e.g., magnetic beads, membranes and microtiter plates. These are typically made of glass, plastic (e.g., polystyrene), polysaccharides, nylon or nitrocellulose. Attachment to an insoluble support is useful when the binding complex is to be used for separation of T cells.

B-Cell Receptor Antigen

B cells, such as small populations of B cells or B cell subsets, can recognize antigens via B-cell receptors (BCRs). Tetramers with subunits of B-cell receptor antigens can be used to identify and study these B cells or B cell subsets. B-cell receptor antigens include any antigen with an epitope capable of inducing an immune response via the BCR. For example, a B-cell receptor antigen can be an antigen that has been used to immunize a subject. A B-cell receptor antigen can be made into a tetramer by using a small, linear-peptide portion of a B-cell receptor antigen, in which the peptide portion contains the BCR epitope. The small, linearized peptide portion can then be expressed with a biotinylation site in an expression vector and purified as a monomer to be used in a tetramer. The monomer with a biotinylated subunit can then be bound to a multivalent binding partner, e.g., streptavidin or avidin, to which biotin binds with extremely high affinity. Streptavidin has a valency of 4, providing a tetramer of B-cell receptor antigen. The resulting tetramer can be purified using a size exclusion column.

Cells

In some embodiments, an affinity portion of an affinity-oligonucleotide conjugate is a cell. For example, an affinity portion can be an intact cell, a cell treated with a compound (e.g., a drug), a fixed cell, a lysed cell, or any combination thereof. In some embodiments, an affinity portion is a single cell. For example, an affinity portion of an affinity-oligonucleotide conjugate can be a T-cell or a B-cell. In some embodiments, an affinity portion is a plurality of cells. In some embodiments, an affinity portion is a T-cell. In some embodiments, an affinity portion is B-cell. In some embodiments, an affinity portion is an antigen presenting cell (APC). In some embodiments, an affinity portion of an affinity-oligonucleotide conjugate is a particular cell type or cell subset. For example, an affinity portion of an affinity-oligonucleotide conjugate can be a $CD4^+$ T-cell or a $CD8^+$ T-cell. For example, an affinity portion of an affinity-oligonucleotide conjugate can be a T-cell comprising a TCR that specifically recognizes a particular antigen. For example, an affinity portion of an affinity-oligonucleotide conjugate can be a T-cell comprising a TCR that specifically recognizes a particular MHC-peptide complex. In some embodiments, an affinity portion is a cell.

Small Molecules

In some embodiments, an affinity portion of an affinity-oligonucleotide conjugate is a small molecule, such as a drug. For example, a small molecule can be a macrocyclic molecule, an inhibitor, a drug, or chemical compound. In some embodiments, a small molecule contains no more than five hydrogen bond donors. In some embodiments, a small molecule contains no more than ten hydrogen bond acceptors. In some embodiments, a small molecule has a molecular weight of 500 Daltons or less. In some embodiments, a small molecule has a molecular weight of from about 180 to 500 Daltons. In some embodiments, a small molecule contains an octanol-water partition coefficient lop P of no more than five. In some embodiments, a small molecule has a partition coefficient log P of from −0.4 to 5.6. In some embodiments, a small molecule has a molar refractivity of from 40 to 130. In some embodiments, a small molecule contains from about 20 to about 70 atoms. In some embodiments, a small molecule has a polar surface area of 140 $Angstroms^2$ or less.

Nucleic Acids

In some embodiments, an affinity portion is a polymeric form of ribonucleotides and/or deoxyribonucleotides (adenine, guanine, thymine, or cytosine), such as DNA or RNA (e.g., mRNA). DNA includes double-stranded DNA found in linear DNA molecules (e.g., restriction fragments), viruses, plasmids, and chromosomes. In some embodiments, a polynucleotide affinity portion is single-stranded, double stranded, small interfering RNA (siRNA), messenger RNA (mRNA), transfer RNA (tRNA), a chromosome, a gene, a noncoding genomic sequence, genomic DNA (e.g., fragmented genomic DNA), a purified polynucleotide, an isolated polynucleotide, a hybridized polynucleotide, a transcription factor binding site, mitochondrial DNA, ribosomal RNA, a eukaryotic polynucleotide, a prokaryotic polynucleotide, a synthesized polynucleotide, a ligated polynucleotide, a recombinant polynucleotide, a polynucleotide containing a nucleic acid analogue, a methylated polynucleotide, a demethylated polynucleotide, any fragment thereof, or any combination thereof. In some embodiments, an affinity portion is a polynucleotide comprising double stranded region and an end that is not double stranded (e.g., a 5' or 3' overhang region). In some embodiments, an affinity portion is a recombinant polynucleotide. In some embodiments, an affinity portion is a heterologous polynucleotide. For example, an affinity portion can comprise polynucleotides produced in bacterial (e.g., E. coli), yeast, mammalian, or insect cells (e.g., polynucleotides heterologous to the organisms). In some embodiments, an affinity portion is a polynucleotide containing a mutation, insertion, deletion, or polymorphism.

In some embodiments, an affinity portion is an aptamer. An aptamer is an isolated nucleic acid molecule that binds with high specificity and affinity to a target analyte, such as a protein. An aptamer is a three dimensional structure held in certain conformation(s) that provides chemical contacts to specifically bind its given target. Although aptamers are nucleic acid based molecules, there is a fundamental difference between aptamers and other nucleic acid molecules such as genes and mRNA. In the latter, the nucleic acid structure encodes information through its linear base sequence and thus this sequence is of importance to the function of information storage. In complete contrast, aptamer function, which is based upon the specific binding of a target molecule, is not entirely dependent on a conserved linear base sequence (a non-coding sequence), but rather a particular secondary/tertiary/quaternary structure. Any coding potential that an aptamer may possess is entirely fortuitous and plays no role whatsoever in the binding of an aptamer to its cognate target. Aptamers must also be differentiated from the naturally occurring nucleic acid sequences that bind to certain proteins. These latter sequences are naturally occurring sequences embedded within the genome of the organism that bind to a specialized sub-group of proteins that are involved in the transcription, translation, and transportation of naturally occurring nucleic acids (e.g., nucleic acid-binding proteins). Aptamers on the other hand are short, isolated, non-naturally occurring nucleic acid molecules. While aptamers can be identified that bind nucleic acid-binding proteins, in most cases such aptamers have little or no sequence identity to the sequences recognized by the nucleic acid-binding proteins in nature. More importantly, aptamers can bind virtually any protein (not just nucleic acid-binding proteins) as well as almost any target of interest including small molecules, carbohydrates, peptides, etc. For most targets, even proteins, a naturally occurring nucleic acid sequence to which it binds does not exist. For those targets that do have such a sequence, e.g., nucleic acid-binding proteins, such sequences will differ from aptamers as a result of the relatively low binding affinity used in nature as compared to tightly binding aptamers. Aptamers are capable of specifically binding to selected targets and modulating the targets activity or binding interactions, e.g., through binding, aptamers may block their target's ability to function. The functional property of specific binding to a target is an inherent property an aptamer. A typical aptamer is 6-35 kDa in size (20-100 nucleotides), binds its target with micromolar to sub-nanomolar affinity, and may discriminate against closely related targets (e.g., aptamers may selectively bind related proteins from the same gene family). Aptamers are capable of using commonly seen intermolecular interactions such as hydrogen bonding, electrostatic complementarities, hydrophobic contacts, and steric exclusion to bind with a specific target. Aptamers have a number of desirable characteristics for use as therapeutics and diagnostics including high specificity and affinity, low immunogenicity, biological efficacy, and excellent pharmacokinetic properties. An aptamer can comprise a molecular stem and loop structure formed from the hybridization of complementary polynucleotides that are covalently linked (e.g., a hairpin loop structure). The stem comprises the hybridized polynucleotides and the loop is the region that covalently links the two complementary polynucleotides.

In some embodiments, an affinity portion is a plurality of affinity portions, such as a mixture or library of affinity portions. In some embodiments, an affinity portion is a plurality of different an affinity portions. For example, an affinity portion can comprise a plurality of at least about 2, 3, 4, 5, 6, 7, 8, 9, 10, 15, 20, 30, 40, 50, 60, 70, 80, 90, 100, 200, 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 25,000, or 30,000 affinity portions.

Oligonucleotide Portion of Affinity-Oligonucleotide Conjugates

The oligonucleotide portion of the affinity-oligonucleotide conjugate is a nucleic acid that is coupled to the affinity portion of the affinity-oligonucleotide conjugate. In some embodiments, the oligonucleotide portion of the tetramer-oligonucleotide conjugate is a nucleic acid that is coupled to the affinity portion of the tetramer-oligonucleotide conjugate. In some embodiments, the oligonucleotide portion of the tetramer-oligonucleotide conjugate is a nucleic acid that is coupled to one or more core elements of the tetramer complex. For example, a nucleic acid may be conjugated to a monomeric or tetrameric streptavidin core. Exemplary schematics of a tetramer-oligonucleotide conjugate are depicted in FIGS. 10A, 10B, 13, 14, and 18. In some embodiments, the oligonucleotide is coupled directly to the affinity portion. In some embodiments, the oligonucleotide is coupled indirectly to the affinity portion. In some embodiments, the oligonucleotide is coupled non-covalently to the affinity portion. In some embodiments, the oligonucleotide is coupled covalently to the affinity portion. In some embodiments, the oligonucleotide is a synthesized oligonucleotide. In preferred embodiments, an oligonucleotide does not substantially interact with a target analyte of the affinity portion directly.

The oligonucleotide coupled to the affinity portion of the affinity-oligonucleotide conjugate or tetramer-oligonucleotide conjugate can comprise one or more barcode sequences. For example, the oligonucleotide coupled to the affinity portion of the affinity-oligonucleotide conjugate or tetramer-oligonucleotide conjugate can comprise an Antigen ID (AID) sequence and an antigen molecular barcode (AMB) sequence. An oligonucleotide can comprise an Antigen ID (AID) sequence, a fusion sequence, a primer site, a molecular barcode sequence, a constant sequence, or any combination thereof.

The oligonucleotide may contain a chemical modification to enable conjugation to the affinity portion of the affinity-oligonucleotide conjugate (e.g., amine, thiol or biotin) or tetramer-oligonucleotide conjugate.

An oligonucleotide can comprise a plurality of oligonucleotides. The plurality oligonucleotides can be comprised by a plurality of affinity-oligonucleotide conjugates or a plurality of tetramer-oligonucleotide conjugates. For example, an oligonucleotide can comprise a plurality of at least about 2, 3, 4, 5, 6, 7, 8, 9, 10, 15, 20, 30, 40, 50, 60, 70, 80, 90, 100, 200, 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 25,000, or 30,000 oligonucleotides. For example, a plurality of at least about 2, 3, 4, 5, 6, 7, 8, 9, 10, 15, 20, 30, 40, 50, 60, 70, 80, 90, 100, 200, 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 25,000, or 30,000 oligonucleotides can be comprised by a plurality of at least about 2, 3, 4, 5, 6, 7, 8, 9, 10, 15, 20, 30, 40, 50, 60, 70, 80, 90, 100, 200, 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 25,000, or 30,000 affinity-oligonucleotide conjugates or tetramer-oligonucleotide conjugates.

An oligonucleotide can comprise an oligonucleotide barcode sequence, an oligonucleotide fusion sequence, an oligonucleotide primer binding sequence, an oligonucleotide constant sequence, or any combination thereof.

Oligonucleotide Antigen ID (AID) Sequence

An oligonucleotide can comprise an oligonucleotide antigen barcode sequence or compliment thereof. An oligonucleotide antigen barcode can allow for identification of an affinity-oligonucleotide complex or tetramer oligonucleotide complex comprising the oligonucleotide antigen barcode. An oligonucleotide antigen barcode can allow for identification of an affinity portion to which the oligonucleotide antigen barcode is attached. An oligonucleotide antigen barcode can be used to identify an affinity portion from a plurality of different affinity portions that binds to different target analytes. An oligonucleotide antigen barcode can be barcoded to an affinity-oligonucleotide complex exclusively or a tetramer-oligonucleotide complex exclusively. An oligonucleotide antigen barcode can be barcoded to an affinity portion exclusively. Thus, an oligonucleotide antigen barcode sequence can be barcoded to a specific affinity portion.

An oligonucleotide antigen barcode can be a unique barcode sequence. For example, any one oligonucleotide antigen barcode of a plurality of oligonucleotide antigen barcodes can be a unique barcode sequence. The number of different antigen barcode sequences theoretically possible can be directly dependent on the length of the barcode sequence. For example, if a DNA barcode with randomly assembled adenine, thymidine, guanosine and cytidine nucleotides can be used, the theoretical maximal number of barcode sequences possible can be 1,048,576 for a length of ten nucleotides, and can be 1,073,741,824 for a length of fifteen nucleotides. An oligonucleotide antigen barcode sequence can comprise a sequence of at least 3, 4, 5, 6, 7, 8, 9, 10, 11, 12, 13, 14, 15, 16, 17, 18, 19, 20, 25, 30, 40, 45, or 50 or more consecutive nucleotides. An oligonucleotide can comprise two or more oligonucleotide antigen barcode sequences or compliments thereof. An oligonucleotide antigen barcode sequence can comprise a randomly assembled sequence of nucleotides. An oligonucleotide antigen barcode sequence can be a degenerate sequence. An oligonucleotide antigen barcode sequence can be a known sequence. An oligonucleotide antigen barcode sequence can be a predefined sequence. In a preferred embodiment, an oligonucleotide antigen barcode sequence is a known, unique sequence that is barcoded to an affinity portion to which it is coupled such that a signal containing the oligonucleotide antigen barcode (e.g., a sequence read) or compliment thereof can be used to identify an affinity portion of a plurality of different affinity portions that interact with different target analytes.

For example, the oligonucleotide coupled to the affinity portion of the affinity-oligonucleotide conjugate can comprise a barcode that is an Antigen ID (AID) sequence. The AID sequence can be barcoded to the affinity portion of the affinity-oligonucleotide conjugate. The AID sequence can be barcoded to the antigen that the affinity portion targets. The AID sequence can be used to identify the affinity portion of the affinity-oligonucleotide conjugate and/or the antigen that the affinity portion targets. For example, the AID sequence can be barcoded to the antibody of an antibody-oligonucleotide conjugate. For example, the AID sequence can be barcoded to the antigen that the antibody of an antibody-oligonucleotide conjugate targets. For example, the AID sequence can be used to immunophenotype cells. For example, the AID sequence can be barcoded to the peptide of an MHC-peptide complex.

The AID sequence can be unique for each antigen targeted by the affinity portion of the affinity-oligonucleotide conjugates. The AID sequence can be unique for the affinity portion of the affinity-oligonucleotide conjugates. For example, the AID sequence can be unique for each antibody that specifically binds to a different target antigen of a cell. In some embodiments, the AID sequence is a defined sequence. In some embodiments, the AID sequence is a known sequence. The AID sequence for each oligonucleotide can be determined by sequencing the oligonucleotide or amplification products of the oligonucleotide, e.g., by next generation sequencing.

Oligonucleotide Molecular Barcode Sequence

An oligonucleotide can comprise an oligonucleotide molecular barcode sequence or compliment thereof. An oligonucleotide barcode can allow for identification of a molecule of an affinity-oligonucleotide complex comprising the oligonucleotide barcode. An oligonucleotide molecular barcode can be barcoded to a molecule of an affinity-oligonucleotide complex exclusively. An oligonucleotide molecular barcode can be barcoded to a molecule of an affinity portion exclusively. Thus, an oligonucleotide molecular barcode sequence can be barcoded to a specific molecule of an affinity portion.

An oligonucleotide molecular barcode can be a unique barcode sequence. For example, any one oligonucleotide molecular barcode of a plurality of oligonucleotide molecular barcodes can be a unique barcode sequence. The number of different molecular barcode sequences theoretically possible can be directly dependent on the length of the barcode sequence. For example, if a DNA barcode with randomly assembled adenine, thymidine, guanosine and cytidine nucleotides can be used, the theoretical maximal number of barcode sequences possible can be 1,048,576 for a length of ten nucleotides, and can be 1,073,741,824 for a length of fifteen nucleotides. An oligonucleotide molecular barcode sequence can comprise a sequence of at least 3, 4, 5, 6, 7, 8, 9, 10, 11, 12, 13, 14, 15, 16, 17, 18, 19, 20, 25, 30, 40, 45, or 50 or more consecutive nucleotides. An oligonucleotide can comprise two or more oligonucleotide molecular barcode sequences or compliments thereof. An oligonucleotide molecular barcode sequence can comprise a randomly assembled sequence of nucleotides. An oligonucleotide molecular barcode sequence can be a degenerate sequence. An oligonucleotide molecular barcode sequence can be a known sequence. An oligonucleotide molecular barcode sequence can be a predefined sequence. In a preferred embodiment, an oligonucleotide molecular barcode sequence is a unique sequence can be used to identify an affinity portion molecule of a plurality of affinity portion molecules that interacted with a target analyte.

For example, the oligonucleotide coupled to the affinity portion of the affinity-oligonucleotide conjugate can comprise a barcode that is an antigen molecular barcode (AMB) sequence. An antigen molecular barcode (AMB) sequence can be unique for each oligonucleotide molecule of an affinity-oligonucleotide conjugate. An AMB sequence can enable the counting of the number of oligonucleotide molecules of an affinity-oligonucleotide conjugate that are bound to an antigen, such as an antigen of an individual cell in a vessel, e.g., an emulsion droplet. The AMB sequence for each oligonucleotide can be determined by sequencing the oligonucleotide or amplification products of the oligonucleotide, e.g., by next generation sequencing.

Oligonucleotide Fusion Sequence

The oligonucleotide coupled to the affinity portion of the affinity-oligonucleotide conjugate or tetramer-oligonucleotide conjugate can comprise a fusion sequence. The fusion sequence can allow for PCR extension of a droplet-specific barcode sequence onto the oligonucleotide of the affinity-oligonucleotide conjugate, e.g., a cell surface-bound affinity-oligonucleotide conjugate, or tetramer-oligonucleotide conjugate, e.g., a TCR or BCR-bound tetramer-oligonucleotide conjugate. The fusion sequence of each oligonucleotide of a plurality of oligonucleotides can be identical. The fusion sequence can comprise a sequence that is complementary to a sequence of a droplet barcode. In some embodiments, the fusion sequence is located at the end of the oligonucleotide. In some embodiments, the fusion sequence at the end of the oligonucleotide is not directly conjugated to an affinity portion of the antibody-oligonucleotide conjugate or tetramer-oligonucleotide conjugate. In some embodiments, the fusion sequence at the end of the oligonucleotide comprises a free end.

The fusion sequence can comprise a region complementary to a region of a 3' tagging polynucleotide, such as a polynucleotide comprising a vessel barcode. The fusion sequence can comprise a region complementary to a complement of region of polynucleotide, such as a polynucleotide comprising a vessel barcode. For example, the fusion sequence can comprise a 3' region, such as a 3' terminal region, that is complementary to a 3' tagging polynucleotide or complement thereof containing a barcode, such as a vessel barcode.

A 3' tagging polynucleotide can be a polynucleotide used to add nucleic acids to a 3' end of a target polynucleotide, such as an oligonucleotide of an affinity-oligonucleotide conjugate or tetramer-oligonucleotide conjugate. A 3' tagging polynucleotide can be a polynucleotide used as a template to add nucleic acids to a 3' end of a target polynucleotide, such as an oligonucleotide of an affinity-oligonucleotide conjugate or tetramer-oligonucleotide conjugate. A 3' tagging polynucleotide can be a polynucleotide that hybridizes to a 3' end of a target polynucleotide, such as an oligonucleotide of an affinity-oligonucleotide conjugate or tetramer-oligonucleotide conjugate. A 3' tagging polynucleotide can be a polynucleotide that contains a 3' region, such as a 3' terminal region, that hybridizes to a 3' end of a target polynucleotide, such as an oligonucleotide of an affinity-oligonucleotide conjugate or tetramer-oligonucleotide conjugate.

In some embodiments, a 3' tagging polynucleotide is a vessel barcoded polynucleotide. The vessel barcode can be added to the oligonucleotide of the affinity oligonucleotide conjugate or tetramer-oligonucleotide conjugate. For example, the vessel barcode can be hybridized to the oligonucleotide of the affinity oligonucleotide conjugate or tetramer-oligonucleotide conjugate. A vessel barcoded polynucleotide can comprise a 3' region, such as a 3' terminal region, that hybridizes to a 3' end of an oligonucleotide of an affinity-oligonucleotide conjugate or tetramer-oligonucleotide conjugate.

In some embodiments, a 3' tagging polynucleotide is an amplified product. In some embodiments, a 3' tagging polynucleotide is an amplified product originating from a single molecule. In some embodiments, a 3' tagging polynucleotide is an amplified product of a vessel barcoded polynucleotide. In some embodiments, a 3' tagging polynucleotide is an amplified product originating from a single vessel barcoded polynucleotide. The region 5' to the 3' region that hybridizes to a 3' end of an oligonucleotide of an affinity-oligonucleotide conjugate can comprise a region complementary to a primer or complement thereof. The region 5' to the 3' region that hybridizes to a 3' end of an oligonucleotide of an affinity-oligonucleotide conjugate can comprise a region complementary to a primer that can be used to amplify the oligonucleotide of the affinity-oligonucleotide conjugate or tetramer-oligonucleotide conjugate. For example, a primer set comprising a first primer that is complementary to the region 5' to the 3' region that hybridizes to a 3' end of an oligonucleotide of an affinity-oligonucleotide conjugate, tetramer-oligonucleotide conjugate or a complement thereof and a second primer that is complementary to the primer site of the oligonucleotide of an affinity-oligonucleotide conjugate or tetramer-oligonucleotide conjugate can be used to amplify the oligonucleotide of an affinity-oligonucleotide conjugate or tetramer-oligonucleotide conjugate.

The region 5' to the 3' region that hybridizes to a 3' end of an oligonucleotide of an affinity-oligonucleotide conjugate can comprise a region complementary to a primer or complement thereof that was used to amplify the vessel barcoded polynucleotide.

An oligonucleotide fusion sequence can be at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more consecutive nucleotides. An oligonucleotide fusion sequence can be a sequence of known length. An oligonucleotide fusion sequence can be a known sequence. An oligonucleotide fusion sequence can be a predefined sequence. An oligonucleotide fusion sequence can be an unknown sequence of known length. An oligonucleotide fusion sequence can be a known sequence of known length.

Oligonucleotide Constant Sequence

The oligonucleotide coupled to the affinity portion of the affinity-oligonucleotide conjugate or tetramer-oligonucleotide conjugate can comprise a constant sequence. The constant sequence is optional. The constant sequence of each oligonucleotide of a plurality of affinity-oligonucleotide conjugates or tetramer-oligonucleotide conjugates can be identical.

An oligonucleotide constant sequence can be used to increase the length of the oligonucleotide or to separate one or more of an oligonucleotide barcode, oligonucleotide fusion, and an oligonucleotide primer binding site from each other. In some embodiments, an oligonucleotide does not comprise an oligonucleotide constant sequence. For example, an oligonucleotide can be coupled to an affinity portion at an end of the oligonucleotide comprising an oligonucleotide primer binding site.

In some embodiments, an oligonucleotide constant sequence is attached to an affinity portion of an affinity-oligonucleotide complex or tetramer-oligonucleotide complex. In some embodiments, an oligonucleotide constant is located upstream of an oligonucleotide primer binding sequence. For example, an oligonucleotide constant sequence can be located 5' to an oligonucleotide primer binding sequence. In some embodiments, an oligonucleotide constant is located downstream of an oligonucleotide primer binding sequence. For example, an oligonucleotide constant sequence can be located 3' to an oligonucleotide primer binding sequence. In some embodiments, an oligonucleotide constant is located upstream of an oligonucleotide barcode. For example, an oligonucleotide constant sequence can be located 5' to an oligonucleotide barcode. In some embodiments, an oligonucleotide constant is located downstream of an oligonucleotide barcode. For example, an oligonucleotide constant sequence can be located 3' to an oligonucleotide barcode. In some embodiments, an oligonucleotide constant is located upstream of an oligonucleotide fusion sequence. For example, an oligonucleotide constant sequence can be located 5' to an oligonucleotide fusion sequence.

In some embodiments, an oligonucleotide constant sequence is interposed between an oligonucleotide primer binding sequence and an affinity portion of an affinity-oligonucleotide complex or tetramer-oligonucleotide complex. For example, an oligonucleotide constant sequence can be located 5' to an oligonucleotide primer binding sequence and attached to an affinity portion of an oligonucleotide. In some embodiments, an oligonucleotide constant sequence is interposed between an oligonucleotide primer binding sequence and an oligonucleotide barcode. For example, an oligonucleotide constant sequence can be located 3' to an oligonucleotide primer binding sequence and 5' to an oligonucleotide barcode. In some embodiments, an oligonucleotide constant is interposed between an oligonucleotide fusion sequence and an oligonucleotide barcode. For example, an oligonucleotide constant sequence can be located 3' to an oligonucleotide barcode and 5' to an oligonucleotide fusion sequence.

An oligonucleotide constant sequence can be at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 200, 250, 300, 400, 500 or more consecutive nucleotides. An oligonucleotide constant sequence can comprise a nonrandom sequence of nucleotides. An oligonucleotide constant sequence can be a sequence of known length. An oligonucleotide constant sequence can be a known sequence. An oligonucleotide constant sequence can be a predefined sequence. An oligonucleotide constant sequence can be an unknown sequence of known length. An oligonucleotide constant sequence can be a known sequence of known length.

Oligonucleotide Primer Binding Site

The oligonucleotide coupled to the affinity portion of the affinity-oligonucleotide conjugate or tetramer-oligonucleotide conjugate can comprise a primer site. The primer site can comprise a sequence that is complementary to a primer, such as an amplification primer. An oligonucleotide primer binding sequence can be used as a primer binding site for a reaction, such as amplification or sequencing. An oligonucleotide primer binding sequence can be a first primer binding sequence for a pair of primers used for a reaction, such as amplification or sequencing. For example, an oligonucleotide primer binding sequence can be a forward primer binding site. For example, an oligonucleotide primer binding site can be a reverse primer binding site. For example, an oligonucleotide primer binding site can be a forward primer binding site and a primer binding sequence of a vessel barcoded polynucleotide attached to the oligonucleotide can be a reverse primer binding sequence. In some embodiments, an oligonucleotide primer binding sequence is a universal primer binding sequence.

An oligonucleotide primer binding sequence and a primer binding sequence of a polynucleotide attached to the oligonucleotide (e.g., of a vessel barcoded polynucleotide) can comprise melting temperatures that differ by no more than 6, 5, 4, 3, 2, or 1 degree Celsius. The nucleotide sequence of an oligonucleotide primer binding sequence and a primer binding sequence of a polynucleotide attached to the oligonucleotide can differ such that a polynucleotide that hybridizes to the oligonucleotide primer binding sequence does not hybridize to the primer binding sequence of the polynucleotide attached to the oligonucleotide. The nucleotide sequence of an oligonucleotide primer binding sequence and a primer binding sequence of a polynucleotide attached to the oligonucleotide can differ such that a polynucleotide that hybridizes to the primer binding sequence of a polynucleotide attached to the oligonucleotide does not hybridize to the oligonucleotide primer binding sequence.

Arrangement of Oligonucleotide Elements

An oligonucleotide can be arranged in an order such that an oligonucleotide fusion sequence is located at one end of the oligonucleotide. An oligonucleotide can be arranged in an order such that it contains an oligonucleotide barcode upstream of the oligonucleotide fusion sequence. An oligonucleotide can be arranged in an order such that it contains an oligonucleotide primer binding sequence upstream of the oligonucleotide barcode. An oligonucleotide can be arranged in an order such that an oligonucleotide constant sequence is located upstream or downstream of the oligonucleotide primer binding sequence. An oligonucleotide can be arranged in an order such that an oligonucleotide constant sequence is located upstream of the oligonucleotide barcode sequence. An oligonucleotide can be arranged in an order such that an oligonucleotide constant sequence is located at one end of the oligonucleotide, for example, an end of the oligonucleotide that does not contain the oligonucleotide fusion sequence. For example, an oligonucleotide can be arranged in an order of the oligonucleotide fusion sequence, the oligonucleotide barcode sequence, the oligonucleotide primer binding sequence, and the oligonucleotide constant sequence. For example, an oligonucleotide can be arranged in an order of the oligonucleotide fusion sequence, the oligonucleotide barcode sequence, the oligonucleotide primer binding sequence, and the oligonucleotide constant sequence propagating toward from the affinity portion. For example, an oligonucleotide can be arranged in the order of the oligonucleotide fusion sequence, the oligonucleotide barcode sequence, the oligonucleotide primer binding sequence, and the oligonucleotide constant sequence from the 5' end to the 3' end or from the 3' end to the 5' end. For example, an oligonucleotide can comprise a 5' end oligonucleotide fusion sequence, a unique oligonucleotide barcode sequence, a reverse oligonucleotide primer binding sequence, and a 3' oligonucleotide constant sequence attached to an affinity portion (e.g., via a primary amine group attached to the 3'end) in that order. For example, an oligonucleotide attached to an affinity portion can be arranged, propagating toward the affinity portion, in the order of the oligonucleotide fusion sequence, the oligonucleotide barcode sequence, the oligonucleotide constant sequence, and the oligonucleotide primer binding site sequence.

An oligonucleotide can be arranged in an order such that a fusion sequence is located at one end of oligonucleotide. An oligonucleotide can be arranged in an order such that a fusion sequence is located downstream of an AID sequence. An oligonucleotide can be arranged in an order such that a fusion sequence is located downstream of an AMB sequence. An oligonucleotide can be arranged in an order such that a fusion sequence is located downstream of a constant sequence. An oligonucleotide can be arranged in an order such that a fusion sequence is located downstream of a primer site.

An oligonucleotide can be arranged in an order such that a primer site is located at one end of oligonucleotide. An oligonucleotide can be arranged in an order such that a primer site is located upstream of an AID sequence. An oligonucleotide can be arranged in an order such that a primer site is located upstream of an AMB sequence. An oligonucleotide can be arranged in an order such that a primer site is located upstream of a constant sequence. An oligonucleotide can be arranged in an order such that a primer site is located upstream of a fusion sequence.

An oligonucleotide can be arranged in an order such that it contains an AID sequence upstream of the fusion sequence. An oligonucleotide can be arranged in an order such that it contains an AID sequence downstream of the primer site. An AID sequence can be located upstream or downstream of an AMB sequence. An AID sequence can be located upstream or downstream of a constant sequence. An oligonucleotide can be arranged in an order such that it contains an AID sequence between a fusion sequence and a primer site.

An oligonucleotide can be arranged in an order such that it contains an AMB sequence upstream of the fusion sequence. An oligonucleotide can be arranged in an order such that it contains an AMB sequence downstream of the primer site. An AMB sequence can be located upstream or downstream of an AID sequence. An AMB sequence can be located upstream or downstream of a constant sequence. An oligonucleotide can be arranged in an order such that it contains an AMB sequence between a fusion sequence and a primer site.

An oligonucleotide can be arranged in an order such that it contains a constant sequence upstream of the fusion sequence. An oligonucleotide can be arranged in an order such that it contains a constant sequence downstream of the primer site. A constant sequence can be located upstream or downstream of an AID sequence. A constant sequence can be located upstream or downstream of an AMB sequence. An oligonucleotide can be arranged in an order such that it contains a constant sequence between a fusion sequence and a primer site.

An oligonucleotide can be arranged in an order such that an AMB sequence and/or an AID sequence is not located at one end of the oligonucleotide, for example, an end of the oligonucleotide that contains the fusion sequence or primer site. For example, an oligonucleotide can be arranged in an order of the fusion sequence, the AID sequence, the AMB sequence, and the primer site. For example, an oligonucleotide can be arranged in an order of the fusion sequence, the AMB sequence, the AID sequence, and the primer site.

For example, an oligonucleotide can be arranged in an order of the fusion sequence, the AID sequence, the AMB sequence, the constant sequence, and the primer site. For example, an oligonucleotide can be arranged in an order of the fusion sequence, the AMB sequence, the AID sequence, the constant sequence, and the primer site. For example, an oligonucleotide can be arranged in an order of the fusion sequence, the constant sequence, the AID sequence, the AMB sequence, and the primer site. For example, an oligonucleotide can be arranged in an order of the fusion sequence, the constant sequence, the AMB sequence, the AID sequence, and the primer site. For example, an oligonucleotide can be arranged in an order of the fusion sequence, the AID sequence, the constant sequence, the AMB sequence, and the primer site. For example, an oligonucleotide can be arranged in an order of the fusion sequence, the AMB sequence, the constant sequence, the AID sequence, and the primer site.

For example, an oligonucleotide can be arranged in an order of the fusion sequence, the AID sequence, the AMB sequence, the constant sequence, and the primer site, propagating toward the affinity portion of the affinity-oligonucleotide conjugate. For example, an oligonucleotide can be arranged in the order of the fusion sequence, the AID sequence, the AMB sequence, the constant sequence, and the primer site, from the 5' end to the 3' end of the oligonucleotide. For example, an oligonucleotide can comprise a 5' end fusion sequence, an AID sequence, an AMB sequence, a constant sequence, and a 3' primer site attached to an affinity portion of the affinity-oligonucleotide conjugate (e.g., via a primary amine group of an antibody attached to the 3'end of the oligonucleotide) in that order.

Affinity-Oligonucleotide Conjugate Preparation

The affinity-oligonucleotide conjugates or tetramer-oligonucleotide conjugates employed in the methods and compositions described herein may be prepared using any convenient method. An affinity portion can be coupled directly or indirectly (e.g., via a linker) to an oligonucleotide. An affinity portion can be coupled covalently (e.g., via chemical cross-linking) or non-covalently (e.g., via streptavidin-biotin) to an oligonucleotide. The design and preparation of affinity-oligonucleotide conjugates is widely described in the art, including various different affinity portions which may be used, the design of oligonucleotides for proximity ligation assays, and the coupling of such oligonucleotides to the affinity portions to form the affinity-oligonucleotide conjugates. The details and principles described in the art may be applied to the design of the affinity-oligonucleotide conjugates for use in the methods of the invention (See, e.g., WO2007107743, and U.S. Pat. Nos. 7,306,904 and 6,878,515).

A direct coupling reaction between an oligonucleotide and an affinity portion may be utilized, for example, where each possesses a functional group (e.g., a substituent or chemical handle) capable of reacting with a functional group on the other. Functional groups may be present on the oligonucleotide or affinity portion, or introduced onto these components (e.g., via oxidation reactions, reduction reactions, cleavage reactions and the like). Methods for producing nucleic acid/polypeptide conjugates have been described (See, e.g., U.S. Pat. No. 5,733,523).

Functional groups of an antibody or a polypeptide that can be used for coupling to an oligonucleotide include, but are not limited to carbohydrates, thiol groups (HS—) of amino acids, amine groups ($H_2N$—) of amino acids, and carboxy groups of amino acids. For example, carbohydrate structures can be oxidized to aldehydes, and reacted with a $H_2NNH$ group containing compound to form the functional group —C=NH—NH—. For example, thiol groups can be reacted with a thiol-reactive group to form a thioether or disulfide. For example, free thiol groups of proteins may be introduced into proteins by thiolation or splitting of disulfides in native cysteine residues. For example, an amino group (e.g., of an amino-terminus or an omega amino group of a lysine residue) may be reacted with an electrophilic group (e.g., an activated carboxy group) to form an amide group. For example, a carboxy group (e.g., a carboxy-terminus or a carboxy group of a diacidic alpha amino acid) may be activated and contacted with an amino group to form an amide group. Other exemplary functional groups include, e.g., SPDP, carbodiimide, glutaraldehyde, and the like.

In an exemplary embodiment, an oligonucleotide is covalently coupled to an affinity portion using a commercial kit ("All-in-One Antibody-Oligonucleotide Conjugation Kit"; Solulink, Inc.). For example, first, a 3'-amino-oligonucleotide can be derivatized with Sulfo-S-4FB. Second, an affinity portion can be modified with an S-HyNic group. Third, the HyNic-modified affinity portion can be reacted with the 4FB-modified oligonucleotide to yield a bis-arylhydrazone mediated affinity-oligonucleotide conjugate. Excess 4FB-modified oligonucleotide can be further removed via a magnetic affinity matrix. The overall affinity portion recovery can be at least about 95%, 96%, 97%, 98%, 99%, or 100% free of HyNic-modified affinity portion and 4FB-modified oligonucleotide. The bis-arylhydrazone bond can be stable to both heat (e.g., 94° C.) and pH (e.g., 3-10).

Where linking groups are employed, such linkers may be chosen to provide for covalent attachment or non-covalent attachment of the affinity portion and oligonucleotide through the linking group. A variety of suitable linkers are known in the art. In some embodiments, the linker is at least about 50 or 100 Daltons 100 Daltons. In some embodiments, the linker is at most about 300; 500; 1,000; 10,000, or 100,000 Daltons. A linker can comprise a functional group at either end with a reactive functionality capable of bonding to the oligonucleotide. A linker can comprise a functional group at either end with a reactive functionality capable of bonding to the affinity portion. Functional groups may be present on the oligonucleotide, affinity portion, and/or linker, or introduced onto these components (e.g., via oxidation reactions, reduction reactions, cleavage reactions and the like).

Exemplary linkers include polymers, aliphatic hydrocarbon chains, unsaturated hydrocarbon chains, polypeptides, polynucleotides, cyclic linkers, acyclic linkers, carbohydrates, ethers, polyamines, and others known in the art. Exemplary functional groups of linkers include nucleophilic functional groups (e.g., amines, amino groups hydroxy groups, sulfhydryl groups, amino groups, alcohols, thiols, and hydrazides), electrophilic functional groups (e.g., aldehydes, esters, vinyl ketones, epoxides, isocyanates, and maleimides), and functional groups capable of cycloaddition reactions, forming disulfide bonds, or binding to metals. For example, functional groups of linkers can be primary amines, secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, maleimides, azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

In other embodiments, the affinity-oligonucleotide conjugates or tetramer-oligonucleotide conjugates may be produced using in vitro protocols that yield affinity-oligonucleotide conjugates or tetramer-oligonucleotide conjugates, such as producing the affinity portion in vitro from vectors which encode the affinity portion. Examples of such in vitro protocols of interest include: RepA based protocols (See, e.g., Fitzgerald et al., Drug Discov Today (2000) 5:253-58 and WO9837186), ribosome display based protocols (See, e.g., Hanes et al., PNAS (1997) 94:4937-42; Roberts et al., Curr Opin Chem Biol (1999) June; 3: 268-73; Schaffitzel et al., J Immunol Methods (1999) Dec. 10; 231:119-35; and WO9854312), etc.

Techniques for conjugating nucleic acid molecules to antibodies, are well-known in the art (See, e.g., Arnon et al, "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al, "Antibodies For Drug Delivery," in Controlled Drug Delivery (Robinson et al. eds., Marcel Deiker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al, 1982, Immunol. Rev. 62: 119-58. See also, e.g., PCT publication WO 89/12624.) For example, a nucleic acid molecule can be covalently attached to lysines or cysteines on the antibody, such as through N-hydroxysuccinimide ester or maleimide functionality respectively.

Target Antigens

A target antigen of an affinity portion can be a nucleic acid molecule or can be proteinaceous, such as a target protein or peptide. A target antigen may be a compound or composition that is present on a cell in a sample. In some embodiments, a target antigen can be a compound or composition capable of eliciting a cell-mediated immune response (that is, an adaptive immune response), particularly in a mammal, such as a human. In some embodiments, a target antigen can be recognized by a T cell in the context of the MHC molecule. Target antigens include, but is not limited to, cells, tissue extracts, tissue or cell lysates, proteins, individually or as a mixture, a plurality of proteins, peptides, mixtures of peptides, lipids, carbohydrates, sugars, and the like. A target antigen can be characteristic of a disease, such as an infectious disease, an autoimmune disease, or a cancer. A target antigen can be, for example, a viral antigen, a bacterial antigen, a cancer antigen, etc.

In some embodiments, a target antigen is a viral antigen. Viral antigens include, for example, a viral coat protein, an influenza viral antigen, an HIV antigen, a Hepatitis B antigen, or a Hepatitis C antigen.

In some embodiments, a target antigen is a cancer antigen (e.g., protein, peptide, lipid, carbohydrate, etc.) that is solely or predominantly expressed or over-expressed by a tumor cell or cancer cell, such that the antigen is associated with the tumor or cancer. A cancer antigen may be a cancer antigen of only one type of cancer or tumor, such that the cancer antigen is associated with or characteristic of only one type of cancer or tumor. Alternatively, a cancer antigen may be a cancer antigen (e.g., may be characteristic) of more than one type of cancer or tumor. For example, a cancer antigen may be expressed by both breast and prostate cancer cells and not expressed at all by normal, non-tumor, or non-cancer cells, or expressed only minimally. A cancer antigen may a melanoma cancer antigen or a breast cancer antigen. Exemplary cancer antigens include those of the group consisting of gp100. MART-1, NY-ESO-1, a member of the MAGE family of proteins, e.g., MAGE-A1, mesothelin, Tyrosinase, TRP-1, TRP-2, PMSA, Her-2, and p53.

A target antigen can be naturally, artificially, synthetically, or recombinantly produced. Thus, a target antigen can be a synthetic, recombinant, isolated, and/or purified protein, polypeptide, or peptide. Methods of making or obtaining such antigens are known in the art. For example, suitable methods of de novo synthesizing polypeptides and proteins (e.g., antigenic polypeptides and proteins) are described in Chan et al., Fmoc Solid Phase Peptide Synthesis, Oxford University Press. Oxford, United Kingdom, 2005; Peptide and Protein Drug Analysis, ed. Reid, R., Marcel Dekker, Inc., 2000; Epitope Mapping. ed. Westwood et al., Oxford University Press. Oxford. United Kingdom, 2000; and U.S. Pat. No. 5,449,752. Also, polypeptides and proteins (e.g., antigenic polypeptides and proteins) can be recombinantly produced using nucleic acids which encode the polypeptide or protein using standard recombinant methods. See, for instance, Sambrook et al., Molecular Cloning: A Laboratory Manual, 3rd ed. Cold Spring Harbor Press, Cold Spring Harbor, N.Y. 2001; and Ausubel et al., Current Protocols in Molecular Biology. Greene Publishing Associates and John Wiley & Sons, N Y. 1994. The nucleotide sequences of many antigens are known in the art and are available from the GenBank database of the National Center for Biotechnology Information (NCBI) website. Further, an antigen can be isolated and/or purified from a source, such as a plant, a bacterium, an insect, a mammal, e.g., a rat, a human, etc. Methods of isolation and purification are well-known in the art.

An antigen can be a free antigen, e.g., unbound antigenic peptide (e.g., a free peptide), or can be a bound antigen, e.g., an MHC-peptide tetramer or an antigenic peptide presented by a carrier cell which was pulsed with the peptide.

In some embodiments, a target analyte is a membrane bound protein. In one embodiment, the membrane bound protein is CD4, a classical type I membrane protein with a single transmembrane (TM) domain. (Carr et al., (1989) *J. Biol. Chem.* 264:21286-95). In another embodiment, the membrane bound protein is GPR77, a multi-spanning, G-protein coupled receptor (GPCR) membrane protein. (Cain & Monk, (2002) *J. Biol. Chem.* 277:7165-69).

Additional exemplary membrane bound proteins include, but are not limited to, GPCRs (e.g., adrenergic receptors, angiotensin receptors, cholecystokinin receptors, muscarinic acetylcholine receptors, neurotensin receptors, galanin receptors, dopamine receptors, opioid receptors, erotonin receptors, somatostatin receptors, etc.), ion channels (e.g., nicotinic acetylcholine receptors, sodium channels, potassium channels, etc.), receptor tyrosine kinases, receptor serine/threonine kinases, receptor guanylate cyclases, growth factor and hormone receptors (e.g., epidermal growth factor (EGF) receptor), and others. Mutant or modified variants of membrane-bound proteins may also be used. For example, some single or multiple point mutations of GPCRs retain function and are involved in disease (See, e.g., Stadel et al., (1997) *Trends in Pharmacological Review* 18:430-37).

Single Cell Characterization, Cell Polynucleotide Barcoding, and Chain Pairing

The methods described herein can comprise characterizing cells utilizing affinity-oligonucleotide conjugates or tetramer-oligonucleotide conjugates. A plurality of cells can be contacted to one or more affinity-oligonucleotide conjugates or one or more tetramer-oligonucleotide conjugates. Cells can be washed to remove unbound conjugates. Cells can be isolated in vessels as single cells. Affinity-oligonucleotide conjugates bound to isolated cells can be modified to contain a vessel barcode sequence, such as by attaching a vessel barcoded polynucleotide to the oligonucleotide of the conjugates. Tetramer-oligonucleotide conjugates bound to isolated cells can be modified to contain a vessel barcode sequence, such as by attaching a vessel barcoded polynucleotide to the oligonucleotide of the conjugates.

A polynucleotide harboring a vessel barcode can also be introduced during formation of the vessels. These vessel barcoded polynucleotides can carry degenerate barcodes such that each oligonucleotide containing a vessel barcode contains a unique identity code corresponding to the vessel they are in.

Oligonucleotides can be amplified and amplified products of the reaction can be recovered from the vessels. Amplified products can be PCR enriched to add next-generation sequencing (NGS) tags. The library can be sequenced using a high throughput sequencing platform followed by analysis of vessel barcode sequences and/or AID sequences and/or AMB sequences. Because each single cell is isolated in its respective vessel, for each vessel barcode observed twice, the amplified oligonucleotide products sequenced originated from the same vessel and therefore from a unique single cell. Because each AID of an oligonucleotide is barcoded to the affinity-portion of the affinity-oligonucleotide conjugate or tetramer-oligonucleotide conjugates to which it is attached and each single cell is isolated in its respective vessel, for each AID observed for sequences containing the same vessel barcode, the amplified oligonucleotide products sequenced originated from a particular affinity-oligonucleotide conjugate bound to a single cell in the same vessel. For each different AMB, individually, observed among a set of sequences all containing the same vessel barcode, the amplified oligonucleotide products having the AMB in the set sequenced originated from a different (as compared to the other individual AMBs) single oligonucleotide portion of a single affinity-oligonucleotide conjugate molecule bound to a cell in the same vessel, e.g., in cases in which single-cell vessels are used, bout to the single cell in the vessel. For each single AMB observed, all amplified oligonucleotide products with sequences containing that same vessel barcode originated from an oligonucleotide portion of a single (the same) affinity-oligonucleotide conjugate molecule or tetramer-oligonucleotide conjugate molecule (e.g., representing PCR duplicates or amplicons). Thus, each oligonucleotide observed with a given combination of a specific AMB and a specific vessel barcode indicates a single molecule of affinity-oligonucleotide conjugate bound to a single cell or tetramer-oligonucleotide conjugate bound to a single cell; thus, detection of a given number (e.g., 2, 3, 4, or more) of multiple oligonucleotides sequenced with such AMB/vessel barcode combination is indicative of the number (e.g., the 2, 3, 4, or more) of affinity-oligonucleotide conjugates bound to a single cell or tetramer-oligonucleotide conjugates bound to a single cell, e.g., within the cell population or sample assayed. Thus, such number can be indicative of the number of molecules on the cell to which the given affinity portion of the affinity-oligonucleotide conjugate is designed to bind, e.g., number of copies expressed on or in the single cell.

In some embodiments, the methods described herein further comprise barcoding polynucleotides derived from cells and/or polynucleotides in the vessel that are distinct from the affinity-oligonucleotide conjugates or tetramer-oligonucleotide conjugates and distinct from portions or copies thereof. For example, single cells encapsulated in vessels that are or were bound to affinity-oligonucleotide conjugates or tetramer-oligonucleotide conjugates can be lysed and further polynucleotides, such as polynucleotides from or within the single cell can be barcoded. In some embodiments, an oligonucleotide portion of an affinity-oligonucleotide conjugate or tetramer-oligonucleotide conjugate in the vessel, e.g., one that is or was bound to a single cell in the vessel, and/or copy or amplified product thereof, can be barcoded with a vessel barcode sequence. In some embodiments, one or more cell polynucleotides from the single cell can be barcoded with the same vessel barcoded sequence; such additional one or more cell polynucleotides in some embodiments are further barcoded with molecular barcodes.

T-cell receptor chain pairs and antibody immunoglobulin chain pairs are both types of immune receptors. In some embodiments, the cell polynucleotide is an antibody immunoglobulin chain (or portion)-encoding polynucleotide; in some embodiments, it is or comprises a TCR (or portion)-encoding polynucleotide. In some embodiments, the antigen bound by the affinity-oligonucleotide conjugate is a TCR or antibody or chain or portion thereof. In one aspect, the methods described herein further comprise generating polynucleotide libraries for high-throughput sequencing and diagnostics. In one aspect, the methods described herein further comprise developing human derived library panels for antibody and/or TCR discovery from patient or cohorts with specific common attributes. The disclosed invention can be applied to multiple different types of paired variable sequences, e.g., T-cell receptor chain pairs and antibody immunoglobulin chain pairs, together with single cell characterization using affinity-oligonucleotide conjugates. For example, polynucleotides complementary to cell polynucleotides, such as heavy and/or light chain, e.g., $V_H$ and/or $V_L$, antibody chains and/or alpha and/or beta and/or gamma and/or delta chains, e.g., $V\alpha/V\beta$ and $V\gamma/V\delta$ T-cell receptor (TCR) chains (such as those derived from framework portions thereof), can be introduced during formation of (or included within) the vessels. A polynucleotide harboring a vessel barcode can also be introduced during formation of (or included within) a vessel. These vessel barcoded polynucleotides can carry degenerate barcodes such that each cell polynucleotide containing a vessel barcode contains a unique identity code corresponding to the vessel it is in during the reaction(s). Thus in some such embodiments, a plurality of polynucleotides with the same unique identity code are deemed to have originated from the same vessel and in some aspects thus from a single cell. A plurality of polynucleotides harboring a molecular barcode can also be introduced during formation of or included in the vessels. These molecular barcoded polynucleotides can carry degenerate barcodes such that each cell polynucleotide molecule containing a molecular barcode contains a unique identity code corresponding to a single cell polynucleotide molecule from which they came. The millions of single immune cells can be lysed inside the emulsion and cell transcripts, such as $V_H$ and $V_L$ and/or $V\alpha/V\beta$ and/or $V\gamma/V\delta$ chain transcripts, can be reverse transcribed or copied using primers, followed by tagging with a vessel barcode and a molecular barcode, and PCR amplification of the barcoded polynucleotides. Each $V_H$ and $V_L$ and/or $V\alpha/V\beta$ and/or $V\gamma/V\delta$ chain stemming from a single immune cell (e.g., a B-cell or T-cell) can be virtually linked to each other with the same vessel barcode identity.

The $V_H$ and $V_L$ and/or $V\alpha/V\beta$ and/or $V\gamma/V\delta$ chains can then be recovered from the vessels and PCR enriched in order to add next-generation sequencing (NGS) tags. The library can be sequenced using a high throughput sequencing platform followed by analysis of repertoire diversity, antibody frequency, CDR3 characterization, somatic hypermutation phylogeny analysis, etc. A database of correctly matched $V_H$ and $V_L$ and/or Vα/Vβ and/or Vγ/Vδ pairs can be generated by deconvoluting the vessel and molecular barcode sequences. Because each single immune cell are isolated in their respective vessel, for each vessel barcode observed twice, the transcripts sequenced originated from the same emulsion droplets and therefore from a unique single cell. For each different molecular barcode observed, for sequences containing the same vessel barcode, the transcripts sequenced originated from a different transcript molecule from a single cell. For each same molecular barcode observed, for sequences containing the same vessel barcode, the transcripts sequenced originated from a same transcript molecule from a single cell (e.g., PCR duplicates).

In parallel to the sequencing, a library of $V_H$ and $V_L$ and/or Vα/Vβ and/or Vγ/Vδ chains recovered from the vessels can be cloned into antibody expression vectors and co-transfected for yeast display screening. Cloning this identical library pool is the preferred method compared to splitting a biological sample at the beginning, as some rare immune cells would only be captured in one, or the other assay. The library of human derived $V_H$ and $V_L$ and/or Vα and Vβ and/or Vγ and Vδ chains can be expressed regardless of correct or incorrect pair matching as with classic display assays. Yeast display can then be performed against one or more antigen targets to enrich for potential antibody candidates.

Positive candidate antibodies emerging from display technologies, such as a yeast display, can be sequenced and queried against the barcode database of matched pairs. Each yeast displayed $V_H$ and/or Vα and/or Vγ chain can be matched back to its respective $V_L$ or Vβ or Vδ chain, respectively, and each yeast displayed $V_L$ and/or Vβ and/or Vδ chain can be matched back to its respective $V_H$ or Vα or Vγ chain, respectively. These correctly paired candidates can be gene synthesized and expressed in mammalian cell lines and functionally validated against the target of interest. These candidates can be fully human antibodies and/or TCRs.

Samples

In some embodiments, Any sample containing polynucleotides can be used in the methods described herein. Any sample containing a cell generally can be used in the methods described herein. For example, a sample can be a biological sample from a subject or from a sample derived therefrom containing RNA or DNA. The polynucleotides can be extracted from the biological sample, or the sample can be directly subjected to the methods without extraction or purification of the polynucleotides. The sample can be extracted or isolated DNA or RNA. A sample can also be total RNA or DNA extracted from a biological specimen, a cDNA library, viral, or genomic DNA. In one embodiment, polynucleotides are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the polynucleotides are obtained from a single cell. Polynucleotides can be obtained directly from an organism or from a biological sample obtained from an organism. Any tissue or body fluid specimen may be used as a source for nucleic acid for use in the invention. Polynucleotides can also be isolated from cultured cells, such as a primary cell culture or a cell line. The cells or tissues from which template nucleic acids are obtained can be infected with a virus or other intracellular pathogen.

In certain embodiments, antibody or TCR-producing immune cells can be isolated from the blood or other biological samples of a subject or host, such as a human or other animal, such as a human or other animal that has been immunized or that is suffering from an infection, cancer, an autoimmune condition, or any other diseases to identify a pathogen-, tumor-, and/or disease specific antibody or TCR of potential clinical significance. For example, the human may be diagnosed with a disease, be exhibiting symptoms of a disease, not be diagnosed with a disease, or not be exhibiting symptoms of a disease. For example, the human may be one that was exposed to and/or who can make useful antibodies or TCRs against an infectious agent (e.g., viruses, bacteria, parasites, prions, etc), antigen, or disease. For example, the animal may be one that was exposed to and/or who can make useful antibodies or TCRs against an infectious agent (e.g., viruses, bacteria, parasites, prions, etc), antigen, or disease. Certain immune cells from immunized hosts make antibodies or TCRs to one or more target antigens in question and/or one or more unknown antigens. In the present invention the lymphocyte pool can be enriched for the desired immune cells by any suitable method, such as screening and sorting the cells using fluorescence-activated cell sorting (FACS), magnetic activated cell sorting (MACS), panning or other screening method to generate a plurality of immune cells from a sample, such as an immune cell library, before antibody chains are sequenced, antibodies are made, or an expression library is/are made. In contrast to prior art enrichment methods, which provide only a few subsets of immune cells expressing different antibodies, and therefore only a few naturally occurring combinations of variable domains, the immune cell library of the present invention contains at least 2 subsets of or individual immune cells expressing different antibodies or TCRs. For example, the immune cell library of the present invention can contain at least 5, 10, 100, 250, 500, 750, 1000, 2500, 5000, 10000, 25000, 50000, 75000, 10000, 250000, 500000, 750000, 1000000, 2500000, 5000000, 7500000, or 10000000 subsets of or individual immune cells expressing different antibodies or TCRs. The methods of the present invention maximize immune cell recovery, and afford very high diversity.

T cells can be obtained from a number of sources, including peripheral blood mononuclear cells, bone marrow, thymus, tissue biopsy, tumor, lymph node tissue, gut associated lymphoid tissue, mucosa associated lymphoid tissue, spleen tissue, or any other lymphoid tissue, and tumors. T cells can be obtained from T cell lines and from autologous or allogeneic sources. T cells may be obtained from a single individual or a population of individuals, for example, a population of individual who all suffer from the same disease, such as, a cancer or an infectious disease. In some embodiments, cells from the circulating blood of an individual are obtained by apheresis or leukapheresis. The apheresis product typically contains lymphocytes, including T cells, monocytes, granulocytes, B cells, other nucleated while blood cells, red blood cells, and platelets. In one embodiment, the cells collected by apheresis or leukapheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge. After washing, the cells may be resuspended in a variety of biocompatible buffers, such as, for example. Ca++/Mg++ free PBS. Alternatively, the undesirable components of the apheresis sample may be removed and the cells directly resuspended in culture media. In other embodiments, T cells are isolated from peripheral blood lymphocytes by lysing the red blood cells and by centrifugation through a PERCOLL™ gradient. A specific subpopulation of T cells, such as $CD28^+$, $CD4^+$, $CD8^+$, $CD45RA^+$, and CD45RO+ T cells, can be further isolated by positive or negative selection techniques. For example, $CD3^+$, $CD28^+$ T cells can be positively selected using CD3/CD28 conjugated magnetic beads (e.g., DYNABEADS® M-450 CD3/CD28 T Cell Expander). In some embodiments, enrichment of a T cell population by negative selection can be accomplished with a combination of antibodies directed to surface markers unique to the negatively selected cells. One such method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD1 lb, CD16, HLA-DR, and CD8. Another method of preparing T cells for stimulation is to freeze the cells after the washing step, which does not require the monocyte-removal step. Wishing not to be bound by theory, the freeze and subsequent thaw step provides a more uniform product by removing granulocytes and, to some extent, monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° C. per minute and stored in the vapor phase of a liquid nitrogen storage tank.

In some embodiments, immune cells from non-immunized human or non-human donors are utilized. The naive repertoire of an animal (the repertoire before antigen challenge) provides the animal with antibodies or TCRs that can bind with moderate affinity ($K_A$ of about $1\times10^{-6}$ to $1\times10^{-7}$ M) to essentially any non-self-molecule. The sequence diversity of antibody or TCR binding sites is not encoded directly in the germline but is assembled in a combinatorial manner from V gene segments. Immunizations trigger any immune cell making a $V_H$-$V_L$ or Vα-Vβ or Vγ-Vδ combination that binds the immunogen to proliferate (clonal expansion) and to secrete the corresponding antibody as noted above. However, the use of spleen cells and/or immune cells or other peripheral blood lymphocytes (PBLs) from an unimmunized subject can provide a better representation of the possible antibody or TCR repertoire, and also permits the construction of a subsequent B-cell or T-cell antibody or TCR library using any animal species.

In some cases, in order to obtain sufficient nucleic acid for testing, a blood volume of at least 0.001, 0.005, 0.01, 0.05, 0.1, 0.5, 1, 2, 3, 4, 5, 10, 20, 25, 30, 35, 40, 45, or 50 mL is drawn.

In some cases, the starting material is peripheral blood. The peripheral blood cells can be enriched for a particular cell type (e.g., mononuclear cells; red blood cells; $CD4^+$ cells; $CD8^+$ cells; immune cells; T cells, NK cells, or the like). The peripheral blood cells can also be selectively depleted of a particular cell type (e.g., mononuclear cells; red blood cells; $CD4^+$ cells; $CD8^+$ cells; immune cells; T cells, NK cells, or the like).

In some cases, the starting material can be a tissue sample comprising a solid tissue, with non-limiting examples including brain, liver, lung, kidney, prostate, ovary, spleen, lymph node (including tonsil), thyroid, pancreas, heart, skeletal muscle, intestine, larynx, esophagus, and stomach. In other cases, the starting material can be cells containing nucleic acids, immune cells, and in particular B-cells or T-cells. In some cases, the starting material can be a sample containing nucleic acids, from any organism, from which genetic material can be obtained. In some cases, a sample is a fluid, e.g., blood, saliva, lymph, or urine.

A sample can be taken from a subject with a condition. In some cases, the subject from whom a sample is taken can be a patient, for example, a cancer patient or a patient suspected of having cancer. The subject can be a mammal, e.g., a human, and can be male or female. In some cases, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some cases, non-nucleic acid materials can be removed from the starting material using enzymatic treatments (such as protease digestion).

In some cases, blood can be collected into an apparatus containing a magnesium chelator including but not limited to EDTA, and is stored at 4° C. Optionally, a calcium chelator, including but not limited to EGTA, can be added. In another case, a cell lysis inhibitor is added to the blood including but not limited to formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, or cleavable crosslinkers.

In some cases when the extracted material comprises single-stranded RNA, double-stranded RNA, or DNA-RNA hybrid, these molecules can be converted to double-stranded DNA using techniques known in the field. For example, reverse transcriptase can be employed to synthesize DNA from RNA molecules. In some cases, conversion of RNA to DNA can require a prior ligation step, to ligate a linker fragment to the RNA, thereby permitting use of universal primers to initiate reverse transcription. In other cases, the poly-A tail of an mRNA molecule, for example, can be used to initiate reverse transcription. Following conversion to DNA, the methods detailed herein can be used, in some cases, to further capture, select, tag, or isolate a desired sequence.

Nucleic acid molecules include deoxyribonucleic acid (DNA) and/or ribonucleic acid (RNA). Nucleic acid molecules can be synthetic or derived from naturally occurring sources. In one embodiment, nucleic acid molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the nucleic acid molecules are obtained from a single cell. Biological samples for use in the present invention include viral particles or preparations. Nucleic acid molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules can also be isolated from cultured cells, such as a primary cell culture or a cell line. The cells or tissues from which template nucleic acids are obtained can be infected with a virus or other intracellular pathogen.

A sample can also be total RNA extracted from a biological specimen, a cDNA library, viral, or genomic DNA. In certain embodiments, the nucleic acid molecules are bound as to other target molecules such as proteins, enzymes, substrates, antibodies, binding agents, beads, small molecules, peptides, or any other molecule Generally, nucleic acid can be extracted from a biological sample by a variety of techniques such as those described by Sambrook and Russell, Molecular Cloning: A Laboratory Manual, Third Edition, Cold Spring Harbor, N.Y. (2001). Nucleic acid molecules may be single-stranded, double-stranded, or double-stranded with single-stranded regions (for example, stem- and loop-structures).

Methods of DNA extraction are well-known in the art. A classical DNA isolation protocol is based on extraction using organic solvents such as a mixture of phenol and chloroform, followed by precipitation with ethanol (J. Sambrook et al., "Molecular Cloning: A Laboratory Manual," 1989, 2nd Ed., Cold Spring Harbour Laboratory Press: New York, N.Y.). Other methods include: salting out DNA extraction (P. Sunnucks et al., Genetics, 1996, 144: 747-756; S. M. Aljanabi et al., Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). A variety of kits are commercially available for extracting DNA from biological samples (e.g., BD Biosciences Clontech (Palo Alto, Calif.): Epicentre Technologies (Madison, Wis.); Gentra Systems, Inc. (Minneapolis, Minn.); MicroProbe Corp. (Bothell, Wash.); Organon Teknika (Durham, N.C.); and Qiagen Inc. (Valencia, Calif.)).

Methods of RNA extraction are also well known in the art (e.g., J. Sambrook et al., "Molecular Cloning: A Laboratory Manual" 1989, 211d Ed., Cold Spring Harbour Laboratory Press: New York) and kits for RNA extraction from bodily fluids are commercially available (e.g., Ambion, Inc. (Austin, Tex.); Amersham Biosciences (Piscataway, N.J.); BD Biosciences Clontech (Palo Alto, Calif.); BioRad Laboratories (Hercules, Calif.); Dynal Biotech Inc. (Lake Success, N.Y.); Epicentre Technologies (Madison, Wis.); Gentra Systems, Inc. (Minneapolis, Minn.); GIBCO BRL (Gaithersburg, Md.); Invitrogen Life Technologies (Carlsbad, Calif.); MicroProbe Corp. (Bothell, Wash.); Organon Teknika (Durham, N.C.); Promega, Inc. (Madison, Wis.); and Qiagen Inc. (Valencia, Calif.)).

One or more samples can be from one or more sources. One or more of samples may be from two or more sources. One or more of samples may be from one or more subjects. One or more of samples may be from two or more subjects. One or more of samples may be from the same subject. One or more subjects may be from the same species. One or more subjects may be from different species. The one or more subjects may be healthy. The one or more subjects may be affected by a disease, disorder or condition.

In some embodiments, a sample is a fluid, such as blood, saliva, lymph, urine, cerebrospinal fluid, seminal fluid, sputum, stool, or tissue homogenates.

A sample can be taken from a subject with a condition. In some embodiments, the subject from whom a sample is taken can be a patient, for example, a cancer patient or a patient suspected of having cancer. The subject can be a mammal, e.g., a human, and can be male or female. In some embodiments, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some embodiments, the polynucleotides are bound to other target molecules such as proteins, enzymes, substrates, antibodies, binding agents, beads, small molecules, peptides, or any other molecule. In some embodiments, the polynucleotides are not bound to a solid support. Nucleic acids can be extracted from a biological sample by a variety of techniques (Sambrook et al., Molecular Cloning: A Laboratory Manual, Third Edition, Cold Spring Harbor, N.Y. (2001)).

In some embodiments, the sample is saliva. In some embodiments, the sample is whole blood. In some embodiments, in order to obtain sufficient amount of polynucleotides for testing, a blood volume of at least about 0.001, 0.005, 0.01, 0.05, 0.1, 0.5, 1, 2, 3, 4, 5, 10, 20, 25, 30, 35, 40, 45, or 50 mL is drawn. In some embodiments, blood can be collected into an apparatus containing a magnesium chelator including but not limited to EDTA, and is stored at 4° C. Optionally, a calcium chelator, including but not limited to EGTA, can be added.

In some embodiments, a cell lysis inhibitor is added to the blood including but not limited to formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, or cleavable crosslinkers. In some embodiments, non-nucleic acid materials can be removed from the starting material using enzymatic treatments (such as protease digestion).

A plurality of samples may comprise at least 2, 3, 4, 5, 10, 20, 30, 40, 50, 60, 70, 80, 90 or 100 or more samples. The plurality of samples may comprise at least about 100, 200, 300, 400, 500, 600, 700, 800, 900 or 1000 or more samples. The plurality of samples may comprise at least about 1000, 2000, 3000, 4000, 5000, 6000, 7000, 8000 samples, 9000, or 10,000 samples, or 100,000 samples, or 1,000,000 or more samples. The plurality of samples may comprise at least about 10,000 samples.

The one or more polynucleotides in a first sample may be different from one or more polynucleotides in a second sample. The one or more polynucleotides in a first sample may be different from one or more polynucleotides in a plurality of samples. One or more polynucleotides in a sample can comprise at least about 80%, 85%, 90%, 95%, 96%, 97%, 98%, 99%, or 100% sequence identity. In some embodiments, one or more polynucleotides in a sample can differ by less than about 100, 90, 80, 70, 60, 50, 40, 30, 25, 20, 25, 10, 9, 8, 7, 6, 5, 4, 3, 2, or 1 nucleotide or base pair. A plurality of polynucleotides in one or more samples of the plurality of samples can comprise two or more identical sequences. At least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 98%, 99% or 100% of the total polynucleotides in one or more of the plurality of samples can comprise the same sequence. A plurality of polynucleotides in one or more samples of the plurality of samples may comprise at least two different sequences. At least about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% of the total polynucleotides in one or more of the plurality of samples may comprise at least two different sequences. In some embodiments, one or more polynucleotides are variants of each other. For example, one or more polynucleotides may contain single nucleotide polymorphisms or other types of mutations. In another example, one or more polynucleotides are splice variants.

A first sample may comprise one or more cells and the second sample may comprise one or more cells. The one or more cells of the first sample may be of the same cell type as the one or more cells of the second sample. The one or more cells of the first sample may be of a different cell type as one or more different cells of the plurality of samples.

The plurality of samples may be obtained concurrently. A plurality of samples can be obtained at the same time. The plurality of samples can be obtained sequentially. A plurality of samples can be obtained over a course of years, e.g., 100 years, 10 years, 5 years, 4 years, 3 years, 2 years or 1 year of obtaining one or more different samples. One or more samples can be obtained within about one year of obtaining one or more different samples. One or more samples can be obtained within 12 months, 11 months, 10 months, 9 months, 8 months, 7 months, 6 months, 4 months, 3 months, 2 months or 1 month of obtaining one or more different samples. One or more samples can be obtained within 30 days, 28 days, 26 days, 24 days, 21 days, 20 days, 18 days, 17 days, 16 days, 15 days, 14 days, 13 days, 12 days, 11 days, 10 days, 9 days, 8 days, 7 days, 6 days, 5 days, 4 days, 3 days, 2 days or 1 day of obtaining one or more different samples. One or more samples can be obtained within about 24 hours, 22 hours, 20 hours, 18 hours, 16 hours, 14 hours, 12 hours, 10 hours, 8 hours, 6 hours, 4 hours, 2 hours or 1 hour of obtaining one or more different samples. One or more samples can be obtained within about 60 seconds, 45 seconds, 30 seconds, 20 seconds, 10 seconds, 5 seconds, 2 seconds or 1 second of obtaining one or more different samples. One or more samples can be obtained within less than one second of obtaining one or more different samples.

The different polynucleotides of a sample can be present in the sample at different concentrations or amounts (e.g., different number of molecules). For example, the concentration or amount of one polynucleotide can be greater than the concentration or amount of another polynucleotide in the sample. In some embodiments, the concentration or amount of at least one polynucleotide in the sample is at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times greater than the concentration or amount of at least one other polynucleotide in the sample. In another example, the concentration or amount of one polynucleotide is less than the concentration or amount of another polynucleotide in the sample. The concentration or amount of at least one polynucleotide in the sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times less than the concentration or amount of at least one other polynucleotide in the sample.

In some embodiments, two or more samples may contain different amounts or concentrations of the polynucleotides. In some embodiments, the concentration or amount of one polynucleotide in one sample may be greater than the concentration or amount of the same polynucleotide in a different sample. For example, a blood sample might contain a higher amount of a particular polynucleotide than a urine sample. Alternatively, a single sample can divided into two or more subsamples. The subsamples may contain different amounts or concentrations of the same polynucleotide. The concentration or amount of at least one polynucleotide in one sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times greater than the concentration or amount of the same polynucleotide in another sample. Alternatively, the concentration or amount of one polynucleotide in one sample may be less than the concentration or amount of the same polynucleotide in a different sample. For example, the concentration or amount of at least one polynucleotide in one sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times less than the concentration or amount of the same polynucleotide in another sample.

Target Polynucleotides

In some cases, methods provided herein are directed to amplification and sequencing of a target polynucleotide molecule, such as a polynucleotide molecule from a cell, an oligonucleotide of an affinity-oligonucleotide conjugate, or amplicons thereof. In some cases, methods provided herein are directed to amplification and sequencing of at least one region of a target polynucleotide molecule. In some cases, methods provided herein are directed to amplification and sequencing of at least one target polynucleotide molecule. In one aspect, target polynucleotides are oligonucleotides of affinity-oligonucleotide conjugates. In one aspect, target polynucleotides are RNA. In some embodiments, target RNA polynucleotides are mRNA. In some embodiments, target RNA polynucleotides are polyadenylated. In some embodiments, the RNA polynucleotides are not polyadenylated. In some embodiments, the target polynucleotides are DNA polynucleotides. For example, target polynucleotides include cDNA. The DNA polynucleotides may be genomic DNA. The DNA polynucleotides may comprise exons, introns, untranslated regions, or any combination thereof.

In one aspect, target polynucleotides are genomic nucleic acids. DNA derived from the genetic material in the chromosomes of a particular organism can be genomic DNA. In some embodiments, target polynucleotides include sequences comprising variable regions of an antibody or TCR produced by an immune cell. In some embodiments, target polynucleotides include sequences comprising a variable region of a heavy chain of an antibody produced by an immune cell. In some embodiments, target polynucleotides include sequences comprising a variable region of a light chain of an antibody produced by an immune cell. In some embodiments, target polynucleotides include sequences comprising a variable region of an alpha chain of a TCR produced by an immune cell. In some embodiments, target polynucleotides include sequences comprising a variable region of a beta chain of a TCR produced by an immune cell. In some embodiments, target polynucleotides include sequences comprising a variable region of a gamma chain of a TCR produced by an immune cell. In some embodiments, target polynucleotides include sequences comprising a variable region of a delta chain of a TCR produced by an immune cell. For example, target polynucleotides may include a polynucleotide template used to generate products of a reverse transcription reaction or primer extension reaction, and also include the reverse transcription reaction or primer extension reaction products themselves. For example, target polynucleotides include polynucleotides of interest that can be subjected to a reverse transcription reaction or a primer extension reaction.

In some embodiments, target polynucleotides include sequences comprising AIDs of oligonucleotides of affinity-oligonucleotide conjugates or tetramer-oligonucleotide conjugates. In some embodiments, target polynucleotides include sequences comprising AMDs of oligonucleotides of affinity-oligonucleotide conjugates or tetramer-oligonucleotide conjugates. For example, target polynucleotides include RNA or DNA. For example, target polynucleotides include synthesized oligonucleotides. For example, target polynucleotides include oligonucleotides containing an AID and/or an AMB.

Target polynucleotides can be obtained from virtually any source and can be prepared using methods known in the art. For example, target polynucleotides can be directly isolated without amplification using methods known in the art, including without limitation extracting a fragment of genomic DNA or mRNA from an organism or a cell (e.g., an immune cell) to obtain target polynucleotides. A target polynucleotide can also encompass cDNA generated from RNA (such as mRNA) through reverse transcription-PCR. In some cases, a target polynucleotide is an RNA molecule. In some cases, a target polynucleotide is an mRNA molecule, or a cDNA produced from the mRNA molecule. In some cases, a target polynucleotide is an mRNA molecule, or cDNA molecule produced from the mRNA molecule, from a single immune cell. In some cases, target polynucleotides are mRNA molecules, or cDNA molecules produced from the mRNA molecules, from individual immune cells. In some cases, target polynucleotides are mRNA molecules encoding an antibody sequence from a single immune cell. In some cases, target polynucleotides are mRNA molecules encoding heavy chain antibody sequences from individual immune cells. In some cases, target polynucleotides are mRNA molecules encoding a heavy chain antibody sequence from a single immune cell. In some cases, target polynucleotides are mRNA molecules encoding light chain antibody sequences from individual immune cells. In some cases, target polynucleotides are mRNA molecules encoding a light chain antibody sequence from a single immune cell. In some cases, target polynucleotides are mRNA molecules encoding antibody variable sequences from individual immune cells. In some cases, target polynucleotides are mRNA molecules encoding a variable antibody sequence from a single immune cell. In some cases, target polynucleotides are mRNA molecules encoding variable light chain antibody sequences from individual immune cells. In some cases, target polynucleotides are mRNA molecules encoding a variable light chain antibody sequence from a single immune cell. In some cases, target polynucleotides are mRNA molecules encoding variable heavy chain antibody sequences from individual immune cells. In some cases, target polynucleotides are mRNA molecules encoding a variable heavy chain antibody sequence from a single immune cell. In some cases, a target polynucleotide can be a cell-free nucleic acid, e.g., DNA or RNA. In some cases, target polynucleotides are mRNA molecules encoding variable alpha, beta, gamma, and/or delta chain TCR sequences from individual immune cells. In some cases, target polynucleotides are mRNA molecules encoding $V_H$ and/or $V_L$ BCR sequences from individual immune cells.

The methods described herein can be used to generate a library of polynucleotides from one or more target polynucleotides for sequencing. In some embodiments, libraries can be generated from two or more regions of a target polynucleotide. In some embodiments, methods libraries can be generated from two or more target polynucleotides. In some embodiments, target polynucleotides are genomic nucleic acids or DNA derived from chromosomes. In some embodiments, target polynucleotides include sequences comprising a variant, such as a polymorphism or mutation. In some embodiments, target polynucleotides include DNA and not RNA. In some embodiments, target polynucleotides include RNA and not DNA. In some embodiments, target polynucleotides include DNA and RNA. In some embodiments, a target polynucleotide is a single stranded polynucleotide. In some embodiments, a target polynucleotide is a double stranded polynucleotide. In some embodiments, a target polynucleotide is a single strand of a double stranded polynucleotide.

Target polynucleotides can be synthesized or obtained from any biological sample and prepared using methods known in the art. In some embodiments, target polynucleotides are directly isolated without amplification. Methods for direct isolation are known in the art. Non-limiting examples include extracting genomic DNA or mRNA from a biological sample, organism or, cell. In some embodiments, one or more target polynucleotides are purified from a biological sample. In some embodiments, a target polynucleotide is not purified from the biological sample in which it is contained. In some embodiments, a target polynucleotide is isolated from a biological sample. In some embodiments, a target polynucleotide is not isolated from the biological sample in which it is contained. In some embodiments, a target polynucleotide can be a cell-free nucleic acid. In some embodiments, a target polynucleotide can be a fragmented nucleic acid. In some embodiments, a target polynucleotide can be a transcribed nucleic acid. In some embodiments, a target polynucleotide is a modified polynucleotide. In some embodiments, a target polynucleotide is a non-modified polynucleotide.

In some embodiments, a target polynucleotide is an oligonucleotide from an affinity-oligonucleotide conjugate or tetramer-oligonucleotide conjugate. In some embodiments, a plurality of target polynucleotides comprises a plurality of oligonucleotides from a plurality of affinity-oligonucleotide conjugates or plurality of tetramer-oligonucleotide conjugates. In some embodiments, a plurality of target polynucleotides comprises 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, or 1000 or more oligonucleotides from a plurality of affinity-oligonucleotide conjugates or tetramer-oligonucleotide conjugates. In some embodiments, a plurality of target polynucleotides comprises a plurality of oligonucleotides from 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, or 1000 or more affinity-oligonucleotide conjugates or tetramer-oligonucleotide conjugates. In some embodiments, a plurality of target polynucleotides comprises 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, or 1000 or more oligonucleotides from 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, or 1000 or more affinity-oligonucleotide conjugates or tetramer-oligonucleotide conjugates.

In some embodiments, a target polynucleotide comprises an AID sequence. In some embodiments, a plurality of target polynucleotides comprises 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, or 1000 or more AID sequences. In some embodiments, a target polynucleotide comprises an AMB sequence. In some embodiments, a plurality of target polynucleotides comprises at least 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$ $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ or more AMB sequences.

In some embodiments, a target polynucleotide is a polynucleotide from a single cell. In some embodiments, target polynucleotides are from individual cells. In some embodiments, a target polynucleotide is a polynucleotide from a sample containing a plurality of cells.

In some embodiments, a target polynucleotide encodes a biomarker sequence. In some embodiments, a target polynucleotide encodes two or more biomarker sequences. In some embodiments, a plurality of target polynucleotides encodes a biomarker sequence. In some embodiments, a plurality of target polynucleotides encodes two or more biomarker sequences. In some embodiments, a plurality of target polynucleotides encodes 3, 4, 5, 6, 7, 8, 9, 10, 20, 30, 40, 50, 60, 70, 80, 90, or 100 or more biomarker sequences.

In some embodiments, a plurality of target polynucleotides comprises a panel of oligonucleotide sequences. In some embodiments, a plurality of target polynucleotides comprises a panel of immunoglobulin sequences. For example, a panel of immunoglobulin sequences can be $V_H$ and/or $V_L$ sequences. In some embodiments, a plurality of target polynucleotides comprises a panel of TCR sequences. In a panel of immunoglobulin or TCR sequences contains 1, 2, 3, 4, 5, 6, 7, 8, 9, or 10 immunoglobulin or TCR sequences. In some embodiments, a plurality of target polynucleotides comprises a panel of BCR sequences. For example, a panel of BCR sequences can be $V_H$ and/or $V_L$ sequences. In some embodiments, a panel of immunoglobulin, BCR, or TCR sequences contains at least about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$ $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ immunoglobulin, BCR, or TCR sequences. In some embodiments, a panel of immunoglobulin, BCR, or TCR sequences contains at most about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ immunoglobulin, BCR, or TCR sequences. In some embodiments, a panel of immunoglobulin, BCR, or TCR sequences contains from about 10-20, 10-30, 10-40, 10-30, 10-40, 10-50, 10-60, 10-70, 10-80, 10-90, 10-100, 50-60, 50-70, 50-80, 50-90, 50-100, 100-200, 100-300, 100-400, 100-300, 100-400, 100-500, 100-600, 100-700, 100-800, 100-900, 100-1000, 500-600, 500-700, 500-800, 500-900, 500-1000, 1000-2000, 1000-3000, 1000-4000, 1000-3000, 1000-4000, 1000-5000, 1000-6000, 1000-7000, 1000-8000, 1000-9000, 1000-10000, 5000-6000, 5000-7000, 5000-8000, 5000-9000, 5000-10000, $1\text{-}1\times10^5$, $1\text{-}2\times10^5$, $1\text{-}3\times10^5$, $1\text{-}4\times10^5$, $1\text{-}5\times10^5$, $1\text{-}6\times10^5$, $1\text{-}7\times10^5$, $1\text{-}8\times10^5$, $9\times10^5$, $1\text{-}1\times10^6$, $1\text{-}2\times10^6$, $1\text{-}3\times10^6$, $1\text{-}4\times10^6$, $1\text{-}5\times10^6$, $1\text{-}6\times10^6$, $1\text{-}7\times10^6$, $1\text{-}8\times10^6$, $9\times10^6$, $1\times10^7$, $1\text{-}2\times10^7$, $1\text{-}3\times10^7$, $1\text{-}4\times10^7$, $1\text{-}5\times10^7$, $1\text{-}6\times10^7$, $1\text{-}7\times10^7$, $1\text{-}8\times10^7$, $1\text{-}9\times10^7$, $1\text{-}1\times10^8$, $1\text{-}2\times10^8$, $1\text{-}3\times10^8$, $1\text{-}4\times10^8$, $1\text{-}5\times10^8$, $1\text{-}6\times10^8$, $1\text{-}7\times10^8$, $1\text{-}8\times10^8$, $1\text{-}9\times10^8$, $1\text{-}1\times10^9$, $1\text{-}2\times10^9$, $1\text{-}3\times10^9$, $1\text{-}4\times10^9$, $1\text{-}5\times10^9$, $1\text{-}6\times10^9$, $1\text{-}7\times10^9$, $1\text{-}8\times10^9$, $1\text{-}9\times10^9$, $1\text{-}1\times10^{10}$, $1\text{-}2\times10^{10}$, $1\text{-}3\times10^{10}$, $1\text{-}4\times10^{10}$, $1\text{-}5\times10^{10}$, $1\text{-}6\times10^{10}$, $1\text{-}7\times10^{10}$, $1\text{-}8\times10^{10}$, $1\text{-}9\times10^{10}$, $1\text{-}1\times10^{11}$, $1\text{-}2\times10^{11}$, $1\text{-}3\times10^{11}$, $1\text{-}4\times10^{11}$, $1\text{-}5\times10^{11}$, $1\text{-}6\times10^{11}$, $1\text{-}7\times10^{11}$, $1\text{-}8\times10^{11}$, $1\text{-}9\times10^{11}$, $1\text{-}1\times10^{12}$, $1\text{-}2\times10^{12}$, $1\text{-}3\times10^{12}$, $1\text{-}4\times10^{12}$, $1\text{-}5\times10^{12}$, $1\text{-}6\times10^{12}$, $1\text{-}7\times10^{12}$, $1\text{-}8\times10^{12}$, or $1\text{-}9\times10^{12}$ immunoglobulin, BCR, or TCR sequences.

In some embodiments, a target polynucleotide is about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is at least about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is at most about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is from about 10-20, 10-30, 10-40, 10-30, 10-40, 10-50, 10-60, 10-70, 10-80, 10-90, 10-100, 50-60, 50-70, 50-80, 50-90, 50-100, 100-200, 100-300, 100-400, 100-300, 100-400, 100-500, 100-600, 100-700, 100-800, 100-900, 100-1000, 500-600, 500-700, 500-800, 500-900, 500-1000, 1000-2000, 1000-3000, 1000-4000, 1000-3000, 1000-4000, 1000-5000, 1000-6000, 1000-7000, 1000-8000, 1000-9000, 1000-10000, 5000-6000, 5000-7000, 5000-8000, 5000-9000, or 5000-10000 bases or base-pairs in length. In some embodiments, the average length of the target polynucleotides, or fragments thereof, can be less than about 100, 200, 300, 400, 500, or 800 base pairs, or less than about 5, 10, 20, 30, 40, 50, 60, 70, 80, 90, 100, 110, 120, 130, 140, 150, 160, 170, 180, 190, or 200 nucleotides, or less than about 1, 2, 5, 10, 20, 30, 40, 50, 60, 70, 80, 90, 100 kilobases. In some embodiments, a target sequence from a relative short template, such as a sample containing a target polynucleotide, is about 40, 45, 50, 55, 60, 65, 70, 75, 80, 85, 90, 95, or 100 bases. In certain embodiments, sequencing data are aligned against known or expected sequences using a database containing sequences or immunoglobulin or TCR sequences associated with a disease or condition.

In some embodiments, a method further comprises determining a germ line sequence of the first cell polynucleotide, the second cell polynucleotide, or both wherein the first cell polynucleotide comprises an IgH or $V_H$ sequence, and wherein the second cell polynucleotide comprises an IgL or $V_L$ sequence, or any combination thereof. In some embodiments, a method further comprises determining a variance of the sequence of the IgL IgH, $V_H$, $V_L$, or any combination thereof from a sequence of those of the germ line. In some embodiments, a method further comprises determining at least one of the total number of unique IgH sequences; the total number of unique IgL sequences; the total number of unique IgH and IgL sequences; the total number of unique paired IgL and IgH sequences; the frequency of an IgH sequence, or an IgL sequence; or the frequency of a combination of an IgH sequence and an IgL sequence against one or more others.

In some embodiments, a method further comprises determining a germ line sequence of the first cell polynucleotide, the second cell polynucleotide, or both wherein the first cell polynucleotide comprises a TCRα or Vα sequence, and wherein the second cell polynucleotide comprises TCRβ or Vβ sequence, or any combination thereof. In some embodiments, a method further comprises determining a variance of the sequence of the TCRα, TCRβ, Vα, Vβ, or any combination thereof from a sequence of those of the germ line.

In some embodiments, a method further comprises determining at least one of the total number of unique TCRα, sequences; the total number of unique TCRβ sequences; the total number of unique TCRα, and TCRβ sequences; the total number of unique paired TCRβ and TCRα, sequences; the frequency of a TCRα sequence, or a TCRβ sequence; or the frequency of a combination of a TCRα sequence and a TCRβ sequence against one or more others. In some embodiments, a method further comprises determining a germ line sequence of the first cell polynucleotide, the second cell polynucleotide, or both wherein the first cell polynucleotide comprises a TCRγ or Vγ sequence, and wherein the second cell polynucleotide comprises TCRδ or Vδ sequence, or any combination thereof. In some embodiments, a method further comprises determining a variance of the sequence of the TCRγ, TCRδ, Vγ, Vδ, or any combination thereof from a sequence of those of the germ line. In some embodiments, a method further comprises determining at least one of the total number of unique TCRγ, sequences; the total number of unique TCRδ sequences; the total number of unique TCRγ, and TCRδ sequences; the total number of unique paired TCRδ and TCRγ, sequences; the frequency of a TCRγ sequence, or a TCRδ sequence; or the frequency of a combination of a TCRγ sequence and a TCRδ sequence against one or more others. In some embodiments, a method further comprises determining at least one of the total number of sequences from a first gene; the total number of sequences from a second gene; the total number of unique sequences from a first gene; the total number of unique sequences from a second gene; or the frequency of a sequence from a first gene, or a sequence from a second gene.

In some embodiments, a method further comprises selecting an antibody or TCR based on a total quantity of one or more pairs of individually paired IgL and IgH sequences, or TCRα and TCRβ sequences, or TCRγ and TCRδ sequences, and a variance from a germ line. In some embodiments, a method further comprises selecting an antibody or TCR based on one or more IgL or IgH sequences, TCRα and TCRβ sequences, or TCRγ and TCRδ sequences, and a variance from a germ line. In some embodiments, a method further comprises selecting an antibody or TCR based on one or more of sequence patterns, variance analysis, dynamics, or frequency. In some embodiments, a method further comprises selecting an antibody or TCR based on frequency.

Cloning and Expression of Antibodies, BCRs, and TCRs

"Antibody expression library" or "BCR expression library" or "TCR expression library" or "expression library" as used herein can refer to a collection of molecules (i.e. two or more molecules) at either the nucleic acid or protein level. Thus, this term can refer to a collection of expression vectors which encode a plurality of antibody, BCR, or TCR molecules (i.e. at the nucleic acid level) or can refer to a collection of antibody, BCR, or TCR molecules after they have been expressed in an appropriate expression system (i.e. at the protein level). Alternatively the expression vectors/expression library may be contained in suitable host cells in which they can be expressed. The antibody molecules which are encoded or expressed in the expression libraries of the invention can be in any appropriate format, e.g., may be whole antibody, BCR, or TCR molecules or may be antibody, BCR fragments, or TCR fragments, e.g., single chain antibodies (e.g., scFv antibodies), Fv antibodies, Fab'antibodies, (Fab')$_2$ fragments, diabodies, etc. The terms "encoding" and "coding for" as is nucleic acid sequence "encoding"/"coding for" or a DNA coding sequence of or a nucleotide sequence "encoding"/"coding for" a particular enzyme, as well as other synonymous terms, refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence includes the minimum number of bases with elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

Antibody, BCR, or TCR molecules identified by, derived from, selected from, or obtainable from the antibody, BCR, or TCR expression libraries of the invention form a yet further aspect of the invention. Again these antibody, BCR, or TCR molecules may be proteins or nucleic acids encoding antibody, BCR, or TCR molecules, which nucleic acids may in turn be incorporated into an appropriate expression vector and/or be contained in a suitable host cell.

The cDNA pool can be subjected to a PCR reaction with polynucleotides that hybridize to a constant region of the heavy chain of antibody or BCR genes and polynucleotides that hybridize to the 5' end of the $V_H$ or Vα or Vγ chain region of antibody, BCR, or TCR genes. The cDNA pool can be subjected to a PCR reaction with polynucleotides that hybridize to a constant region of the heavy chain or alpha or gamma chain of antibody, BCR, or TCR genes and polynucleotides that hybridize to region 5' to the 5' end of the $V_H$ or Vα or Vγ chain region of a barcoded polynucleotide comprising an antibody, BCR, or TCR sequence. A PCR reaction is can also set up for the amplification of the $V_L$ or Vβ or Vδ chain pool of e.g., kappa and lambda classes. The cDNA pool can be subjected to a PCR reaction with polynucleotides that hybridize to a constant region of the light chain of antibody genes and polynucleotides that hybridize to the 5' end of the $V_L$ or Vβ or Vδ chain region of antibody, BCR, or TCR genes. The cDNA pool can be subjected to a PCR reaction with polynucleotides that hybridize to a constant region of the light chain of antibody genes and polynucleotides that hybridize to region 5' to the 5' end of the $V_L$ or Vβ or Vδ chain region of a barcoded polynucleotide comprising an antibody, BCR, or TCR sequence. Such oligonucleotides or primers may be designed based on known and publicly available immunoglobulin, BCR, or TCR gene sequence database information.

In some embodiments, $V_H$ and $V_L$ or Vα and Vβ or Vγ and Vδ sequences can be conveniently obtained from a library of $V_H$ and $V_L$ or Vα and Vβ or Vγ and Vδ sequences produced by PCR amplification using one or more primers that are not specific for heavy or light chain genes and, in particular, for one or both the terminal regions of the $V_H$ and $V_L$ or Vα and Vβ or Vγ and Vδ polynucleotides. In some embodiments, $V_H$ and $V_L$ sequences can be conveniently obtained from a library of $V_H$ and $V_L$ or Vα and Vβ or Vγ and Vδ sequences produced by PCR amplification using primers specific to a region of the vessel barcoded polynucleotide. In some embodiments, $V_H$ and $V_L$ sequences can be conveniently obtained from a library of $V_H$ and $V_L$ or Vα and Vβ or Vγ and Vδ sequences produced by PCR amplification using C-gene family-specific primers or C-gene-specific primers. In some embodiments, $V_H$ and $V_L$ sequences can be conveniently obtained from a library of $V_H$ and $V_L$ or Vα and Vβ or Vγ and Vδ sequences produced by PCR amplification using a primer set with a first primer specific to a region of the vessel barcoded polynucleotide and a second primer or plurality of second primers that are C-gene family-specific primers or C-gene-specific primers. In some embodiments, $V_H$ and $V_L$ or Vα and Vβ or Vγ and Vδ sequences can be conveniently obtained from a library of $V_H$ and $V_L$ or Vα and Vβ or Vγ and Vδ sequences produced by PCR amplification using a primer set with a first primer specific to a region of the vessel barcoded polynucleotide and a second primer specific to a universal sequence.

In some embodiments, upon reverse transcription, the resulting cDNA sequences may be amplified by PCR using one or more primers specific for immunoglobulin genes or BCR genes and, in particular, for one or both the terminal regions of the $V_H$ and $V_L$ or Vα and Vβ or Vγ and Vδ polynucleotides. In some embodiments, $V_H$ and $V_L$ sequences can be obtained from a library of $V_H$ and $V_L$ or Vα and Vβ or Vγ and Vδ sequences produced by PCR amplification using V-gene family-specific primers or V-gene-specific primers (Nicholls et al., J. Immunol. Meth., 1993, 165:81; WO93/12227) or are designed according to standard art-known methods based on available sequence information. (The $V_H$ and $V_L$ or Vα and Vβ or Vγ and Vδ sequences can be ligated, usually with an intervening spacer sequence (e.g., encoding an in-frame flexible peptide spacer), forming a cassette encoding a single-chain antibody). V region sequences can be conveniently cloned as cDNAs or PCR amplification products for immunoglobulin-express sing cells. The $V_H$ and $V_L$ or Vα and Vβ or Vγ and Vδ regions are sequenced, optionally, in the methods described herein and particularly after certain steps as noted (e.g., after single cell PCR; after mammalian or other cell surface display, after FACS screening, and the like). Sequencing can be used, among other reasons, to verify that the level of diversity is at an acceptable level. Sequencing can include high-throughput sequencing, deep sequencing (in which the same gene is sequenced from a plurality of individual samples to identify differences in the sequences), or combinations of the two.

In some embodiments, it is unnecessary to physically link the natural $V_H$ and $V_L$ or Vα and Vβ or Vγ and Vδ combinations using the methods described herein. In some embodiments, cDNAs, barcoded polynucleotides, or PCR amplified barcoded cDNAs are not physically linked. In some embodiments, cDNAs, barcoded polynucleotides, or PCR amplified barcoded cDNAs are not physically linked in the same reaction or vessel.

In some embodiments, the natural $V_H$ and $V_L$ or Vα and Vβ or Vγ and Vδ combinations are physically linked, using, in addition to the cDNA primers, one primer or plurality of primers for the 5' end of the $V_H$ or Vα or Vγ gene and another primer or plurality of primers for the 5' end of the $V_L$ or Vβ or Vδ gene. These primers also contain complementary tails of extra sequence, to allow the self-assembly of the $V_H$ and $V_L$ or Vα and Vβ or Vγ and Vδ genes. After PCR amplification and linking, the chance of getting mixed products, in other words, mixed variable regions, is minimal because the amplification and linking reactions were performed within each cell. The risk of mixing can be further decreased by utilizing bulky reagents such as digoxigenin labeled nucleotides to further ensure that V region cDNA pairs do not leave the cellular compartment and intermix, but remain within the cell for PCR amplification and linking. The amplified sequences are linked by hybridization of complementary terminal sequences. After linking, sequences may be recovered from cells for use in further method steps described herein. For example, the recovered DNA can be PCR amplified using terminal primers, if necessary, and cloned into vectors which may be plasmids, phages, cosmids, phagemids, viral vectors or combinations thereof as detailed below. Convenient restriction enzyme sites may be incorporated into the hybridized sequences to facilitate cloning. These vectors may also be saved as a library of linked variable regions for later use.

To provide additional $V_H$ and $V_L$ or Vα and Vβ or Vγ and Vδ combinations, an expression system can be chosen. For example, bacteriophage expression systems allow for the random recombination of heavy- and light-chain sequences. Other suitable expression systems are known to those skilled in the art.

It should be noted that in the case of $V_H$ and $V_L$ or Vα and Vβ or Vγ and Vδ sequences derived from nonhumans, in some embodiments, it can be preferable to chimerize these sequences with a fully human Fc. As used herein "chimerized" refers to an immunoglobulin, BCR, or TCR, wherein the heavy and light chain variable regions or Vα and Vβ or Vγ and Vδ regions are not of human origin and wherein the constant regions of the heavy and light chains or Vα and Vβ or Vγ and Vδ chains are of human origin. This is affected by amplifying and cloning the variable domains into a human Fc. The human Fc can be part of the vector, or in a separate molecule, and library of Fc's could also be used. In a preferred embodiment the chimerized molecules grown in mammalian cells such as CHO cells, screened with FACS twice to enrich the cell population for cells expressing the antibody of interest. The chimerized antibodies, BCRs, or TCRs are characterized, by either sequencing followed by functional characterization, or direct functional characterization or kinetics. Growth, screening and characterization are described in detail below.

It is important to note that the above described PCR reactions are described for cloning the antibodies in the IgG form. These are preferred as they are generally associated with a more mature immune response and generally exhibit higher affinity than IgM antibodies, thereby making them more desirable for certain therapeutic and diagnostic applications. Clearly, however, polynucleotides can be designed which will allow the cloning of one or more of the other forms of immunoglobulin molecules, e.g., IgM, IgA, IgE and IgD if desired or appropriate.

After an antibody, BCR, or TCR has been identified and the appropriate populations of cells have been isolated at an appropriate time and optionally enriched as described above, the antibody, BCR, or TCR expression libraries need not be generated immediately, providing the genetic material contained in the cells can be kept intact thereby enabling the library to be made at a later date. Thus, for example the cells, a cell lysate, or nucleic acid, e.g., RNA or DNA derived therefrom, can be stored until a later date by appropriate methods, e.g., by freezing, and the expression libraries generated at a later date when desired.

Once the library of expression vectors has been generated, the encoded antibody molecules can then be expressed in an appropriate expression system and screened using appropriate techniques which are well known and documented in the art. Thus the above defined method of the invention may comprise the further steps of expressing the library of expression vectors in an appropriate expression system and screening the expressed library for antibodies with desired properties.

As indicated herein, polynucleotides prepared by the methods of the disclosure which comprise a polynucleotide encoding antibody, BCR, or TCR sequences can include, but are not limited to, those encoding the amino acid sequence of an antibody, BCR, or TCR fragment, by itself, the noncoding sequence for the entire antibody, BCR, or TCR or a portion thereof, the coding sequence for an antibody, BCR, or TCR, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, nontranslated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody or TCR comprising an antibody or TCR fragment or portion.

The primary PCR products can then optionally be subjected to a secondary PCR reaction with new polynucleotide sets that hybridize to the 5' and 3' ends of the antibody, BCR, or TCR variable domains $V_H$, $V_L$ kappa and $V_L$ lambda or Vα and Vβ or Vγ and Vδ (as appropriate depending on whether the primary PCR reaction with which the new polynucleotide sets are used was designed to amplify portions of the heavy or light chain antibody genes or Vα or Vβ TCR genes or Vγ or Vδ TCR genes). These polynucleotides advantageously include DNA sequences specific for a defined set of restriction enzymes (i.e. restriction enzyme sites) for subsequent cloning. The selected restriction enzymes must be selected so as not to cut within human antibody, BCR, or TCR V-gene segments. Such polynucleotides may be designed based on known and publicly available immunoglobulin or TCR gene sequence and restriction enzyme database information. However, preferred restriction enzyme sites to be included are NcoI, Hind III, MluI and NotI. The products of such secondary PCR reactions are repertoires of various V-heavy, V-light kappa and V-light lambda antibody fragments/domains. This type of secondary PCR reaction is therefore generally carried out when the expression library format of interest is a scFv or Fv format, wherein only the $V_H$ and $V_L$ or Vα and Vβ or Vγ and Vδ domains of an antibody or TCR are present.

PCR products can also be subjected to a PCR reaction with new primer sets that hybridize to the 5' and 3' ends of the barcoded polynucleotides. These polynucleotides can advantageously include DNA sequences specific for a defined set of restriction enzymes (i.e. restriction enzyme sites) for subsequent cloning. The selected restriction enzymes must be selected so as not to cut within human antibody or TCR V-gene segments. Such polynucleotides may be designed based on known and publicly available immunoglobulin, BCR, or TCR gene sequence and restriction enzyme database information. However, preferred restriction enzyme sites to be included are NcoI, Hind III, MluI and NotI. The products of such secondary PCR reactions are repertoires of various $V_H$, $V_L$ kappa and $V_L$ lambda antibody fragments/domains or Vα and Vβ or Vγ and Vδ TCR fragments/domains.

Heavy or light chain or Vα or Vβ chain or Vγ or Vδ chain Fv or Fab fragments, or single-chain antibodies, BCRs, or TCRs may also be used with this system. A heavy or light chain or Vα or Vβ chain or Vγ or Vδ chain can be mutagenized followed by the addition of the complementary chain to the solution. The two chains are then allowed to combine and form a functional antibody fragment. Addition of random non-specific light or heavy chain or Vα or Vβ chain or Vγ or Vδ chain sequences allows for the production of a combinatorial system to generate a library of diverse members.

Libraries of such repertoires of cloned fragments comprising the variable heavy chain or Vα chain or Vγ chain regions, or fragments thereof, and/or variable light chain or Vβ chain or Vδ chain regions, or fragments thereof, of antibody, BCR, or TCR genes derived from the B- or T-lymphocytes of immuno-challenged hosts as defined herein form further aspects of the invention. These libraries comprising cloned variable regions may optionally be inserted into expression vectors to form expression libraries.

In some embodiments, the PCR reactions can be set up so as to retain all or part of the constant regions of the various antibody, BCR, or TCR chains contained in the isolated immune cell population. This is desirable when the expression library format is a Fab format, wherein the heavy or alpha or gamma chain component comprises $V_H$ or Vα or Vγ and $C_H$ or $C\alpha$ or $C\gamma$ domains and the light chain or $V\beta$ chain or $V\delta$ chain component comprises $V_L$ or $V\beta$ or $V\delta$ chain and $C_L$ or $C\beta$ or $C\delta$ domains. Again, libraries of such cloned fragments comprising all or part of the constant regions of antibody, BCR, or TCR chains form further aspects of the invention.

These nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

The libraries disclosed herein may be used in a variety of applications. As used herein, a library comprises a plurality of molecules. In some embodiments, a library comprises a plurality of polynucleotides. In some embodiments, a library comprises a plurality of primers. In some embodiments, a library comprises a plurality of sequence reads from one or more polynucleotides, amplicons, or amplicon sets. A library can be stored and used multiple times to generate samples for analysis. Some applications include, for example, genotyping polymorphisms, studying RNA processing, and selecting clonal representatives to do sequencing according to the methods provided herein. Libraries comprising a plurality of polynucleotides, such as primers or libraries for sequencing or amplification, can be generated, wherein a plurality of polynucleotides comprises at least about 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 50,000,000, 100,000,000 or more molecular barcodes or vessel barcodes. In some embodiments, libraries of polynucleotides comprise a plurality of at least about 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 50,000,000, 100,000,000 or more unique polynucleotides, wherein each unique polynucleotide comprises one or more molecular barcodes and vessel barcodes.

Barcodes

A molecular barcode, such as an antigen molecular barcode, comprises information that is unique to a single molecule, such as a single oligonucleotide of an affinity-oligonucleotide complex or tetramer-oligonucleotide complex, or a polynucleotide molecule from a single cell or from a single vessel. A vessel barcode comprises information that is unique to polynucleotides from a single cell or present in a single vessel, compared to polynucleotides from a different single cell or present in a different single vessel. In some embodiments the unique information comprises a unique sequence of nucleotides. For example, the sequence of the molecular barcode or a vessel barcode can be determined by determining the identity and order of the unique or random sequence of nucleotides comprising the molecular barcode or a vessel barcode. In some embodiments the unique information cannot be used to identify the sequence of a target polynucleotide. For example, a molecular barcode may be attached to one target polynucleotide, but the molecular barcode cannot be used to determine the target polynucleotide to which it is attached. In some embodiments the unique information is not a known sequence linked to the identity of the sequence of a target polynucleotide. For example, a vessel barcode may be attached to one or more target polynucleotides, but the vessel barcode cannot be used to determine which of the one or more target polynucleotides to which it is attached. In some embodiments, the unique information comprises a random sequence of nucleotides. In some embodiments the unique information comprises one or more unique sequences of nucleotides on a polynucleotide. In some embodiments the unique information comprises a degenerate nucleotide sequence or degenerate barcode. A degenerate barcode can comprise a variable nucleotide base composition or sequence. For example, a degenerate bar code can be a random sequence. In some embodiments, a complement sequence of a molecular barcode or a vessel barcode is also a molecular barcode or a vessel barcode sequence.

A barcode can comprise any length of nucleotides. For example, any of the barcodes described herein can have a length within a range of from 2 to 36 nucleotides, 4 to 36 nucleotides, or from 6 to 30 nucleotides, or from 8 to 20 nucleotides, 2 to 20 nucleotides, 4 to 20 nucleotides, or from 6 to 20 nucleotides. In certain aspects, the melting temperatures of barcodes within a set are within 10° C. of one another, within 5° C. of one another, or within 2° C. of one another. In certain aspects, the melting temperatures of barcodes within a set are not within 10° C. of one another, within 5° C. of one another, or within 2° C. of one another. In some aspects, barcodes are members of a minimally cross-hybridizing set. For example, the nucleotide sequence of each member of such a set can be sufficiently different from that of every other member of the set such that no member can form a stable duplex with the complement of any other member under stringent hybridization conditions. In some embodiments, the nucleotide sequence of each member of a minimally cross-hybridizing set differs from those of every other member by at least two nucleotides. Barcode technologies are described in Winzeler et al. (1999) Science 285:901; Brenner (2000) Genome Biol. 1:1 Kumar et al. (2001) Nature Rev. 2:302; Giaever et al. (2004) Proc. Natl. Acad. Sci. USA 101:793; Eason et al. (2004) Proc. Natl. Acad. Sci. USA 101:11046; and Brenner (2004) Genome Biol. 5:240.

For example a barcode can comprise at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides. For example a barcode can comprise at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides. In some embodiments, a barcode has a particular length of nucleotides. For example, a barcode can be about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length.

In some embodiments, each barcode in a plurality of barcodes has at least about 2 nucleotides. For example, each barcode in a plurality of barcodes can be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, each barcode in a plurality of barcodes has at most about 1000 nucleotides. For example, each barcode in a plurality of barcodes can be at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length.

The number of molecular barcodes can be in excess of the total number of molecules to be labeled in a plurality of vessels. The number of vessel barcodes can be in excess of the total number of molecules to be labeled in a plurality of vessels. For example, the number of molecular barcodes or vessel barcodes can be at least about 2, 3, 4, 5, 6, 7, 8, 9, 10, 15, 20, 30, 40, 50, 60, 70, 80, 90, or 100 times greater than the total number of molecules to be labeled in a plurality of vessels.

The number of different molecular barcodes can be in excess of the total number of molecules to be labeled in a plurality of vessels. In some embodiments, the number of different molecular barcodes is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the total number of molecules to be labeled in a plurality of vessels.

The number of different molecular barcodes in a single vessel can be in excess of the number of different molecules to be labeled in the single vessel. In some embodiments, the number of different molecular barcodes in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the number of different molecules to be labeled in the single vessel.

The number of different vessel barcodes can be less than the total number of molecules to be labeled in a plurality of vessels. In some embodiments, the number of different vessel barcodes is at least about 1, 1.5, 2, 2.5, 3, 3.5, 4, 4.5, 5, 6, 7, 8, 9, 10, 15, 20, 30, 40, 50, 60, 70, 80, 90, or 100 times less than the total number of molecules to be labeled in a plurality of vessels.

The number of amplified product molecules from a vessel barcoded polynucleotide molecule in a single vessel can be in excess of the number of different molecules to be labeled in the single vessel. In some embodiments, the number of amplified product molecules from a vessel barcoded polynucleotide molecule in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the number of different molecules to be labeled in the single vessel.

The number of vessel barcoded polynucleotide molecules in a single vessel can be less than the number of different molecules to be labeled in the single vessel. In some embodiments, the number of vessel barcoded polynucleotide molecules in a single vessel is at least about 1, 1.5, 2, 2.5, 3, 3.5, 4, 4.5, 5, 6, 7, 8, 9, 10, 15, 20, 30, 40, 50, 60, 70, 80, 90, or 100 times less than the number of different molecules to be labeled in the single vessel.

The number of vessel barcoded polynucleotide molecules in a single vessel can be one molecule. The number of unamplified vessel barcoded polynucleotide molecules in a single vessel can be one molecule.

In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different molecular barcodes have the same concentration. In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different vessel barcodes have the same concentration.

In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different molecular barcodes have a different concentration. In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different vessel barcodes have a different concentration.

The molecular barcodes or vessel barcodes in a population of molecular barcodes or vessel barcodes can have at least 10, 15, 20, 25, 30, 35, 40, 45, 50, 60, 70, 80, 90, 100, 200, 300, 400, 500, 600, 700, 800, 900, 1000 or more different sequences. For example, the molecular barcodes or vessel barcodes in a population can have at least 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, 1,000,000 or more different sequences. Thus, a plurality of molecular barcodes or vessel barcodes can be used to generate at least 10, 15, 20, 25, 30, 35, 40, 45, 50, 60, 70, 80, 90, 100, 200, 300, 400, 500, 600, 700, 800, 900, 1000 or more different sequences from one or more polynucleotides, such as target polynucleotides. For example, a plurality of molecular barcodes or vessel barcodes can be used to generate at least 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$ $9\times10^{10}$, $1\times10^{11}$, $2\times10^1$, $3\times10^1$, $4\times10^{11}$, $5\times10^1$, $6\times10^1$, $7\times10^1$, $8\times10^1$, $9\times10$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more different sequences from one or more polynucleotides, such as target polynucleotides. For example, a plurality of molecular barcodes or vessel barcodes can be used to generate at least about 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800, 000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$ $9\times10^{10}$, $1\times10^{11}$, $2\times10^1$, $3\times10^1$, $4\times10^{11}$, $5\times10^1$, $6\times10^1$, $7\times10^1$, $8\times10^1$, $9\times10^1$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more different sequences from at least about 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^1$, $3\times10^1$, $4\times10^{11}$, $5\times10^1$, $6\times10^1$, $7\times10^1$, $8\times10^1$, $9\times10^1$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more target polynucleotides.

In some embodiments, one or more molecular barcodes are used to group or bin sequences. In some embodiments, one or more molecular barcodes are used to group or bin sequences, wherein the sequences in each bin contain the same molecular barcode. In some embodiments, one or more molecular barcodes or vessel barcodes are used to group or bin sequences, wherein the sequences in each bin comprise an amplicon set. In some embodiments, one or more molecular barcodes are used to group or bin sequences, wherein the sequences in each bin comprise a plurality of sequences wherein the polynucleotides from which the plurality of sequences were generated were derived from the same polynucleotide molecule in an amplification reaction.

In some embodiments, one or more vessel barcodes are used to group or bin sequences. In some embodiments, one or more vessel barcodes are used to group or bin sequences, wherein the sequences in each bin contain the same vessel barcode. In some embodiments, one or more vessel barcodes are used to group or bin sequences, wherein the sequences in each bin comprise one or more amplicon sets. In some embodiments, one or more vessel barcodes are used to group or bin sequences, wherein the sequences in each bin comprise a plurality of sequences wherein the polynucleotides from which the plurality of sequences were generated were derived from the polynucleotides from a single vessel or single cell.

In some embodiments, one or more AID sequences are used to group or bin sequences. In some embodiments, one or more AID sequences are used to group or bin sequences, wherein the sequences in each bin contain the same AID sequence. In some embodiments, one or more AID sequences are used to group or bin sequences, wherein the sequences in each bin comprise one or more amplicon sets. In some embodiments, one or more AID sequences are used to group or bin sequences, wherein the sequences in each bin comprise a plurality of sequences wherein the polynucleotides from which the plurality of sequences were generated were derived from the polynucleotides from a single vessel or single cell.

In some embodiments, one or more AMB sequences are used to group or bin sequences. In some embodiments, one or more AMB sequences are used to group or bin sequences, wherein the sequences in each bin contain the same AMB sequence. In some embodiments, one or more AMB sequences are used to group or bin sequences, wherein the sequences in each bin comprise one or more amplicon sets. In some embodiments, one or more AMB sequences are used to group or bin sequences, wherein the sequences in each bin comprise a plurality of sequences wherein the polynucleotides from which the plurality of sequences were generated were derived from the polynucleotides from a single vessel or single cell.

In some embodiments, one or more AID sequences and AMB sequences are used to group or bin sequences. In some embodiments, one or more AID sequences and AMB sequences are used to group or bin sequences, wherein the sequences in each bin contain the same AID sequence. In some embodiments, one or more AID sequences and AMB sequences are used to group or bin sequences, wherein the sequences in each bin contain the same AID sequence and a different AMB sequence. In some embodiments, one or more AID sequences and AMB sequences are used to group or bin sequences, wherein the sequences in each bin contain the same AID sequence and the same AMB sequence. In some embodiments, one or more AID sequences and AMB sequences are used to group or bin sequences, wherein the sequences in each bin comprise one or more amplicon sets. In some embodiments, one or more AID sequences and AMB sequences are used to group or bin sequences, wherein the sequences in each bin comprise a plurality of sequences wherein the polynucleotides from which the plurality of sequences were generated were derived from the same polynucleotide in an amplification reaction and from the same single cell or vessel.

In some embodiments, one or more vessel barcodes and AMB sequences are used to group or bin sequences. In some embodiments, one or more vessel barcodes and AMB sequences are used to group or bin sequences, wherein the sequences in each bin contain the same vessel barcode. In some embodiments, one or more vessel barcodes and AMB sequences are used to group or bin sequences, wherein the sequences in each bin contain the same vessel barcode and a different AMB sequence. In some embodiments, one or more vessel barcodes and AMB sequences are used to group or bin sequences, wherein the sequences in each bin contain the same vessel barcode and the same AMB sequence. In some embodiments, one or more vessel barcodes and AMB sequences are used to group or bin sequences, wherein the sequences in each bin comprise one or more amplicon sets. In some embodiments, one or more vessel barcodes and AMB sequences are used to group or bin sequences, wherein the sequences in each bin comprise a plurality of sequences wherein the polynucleotides from which the plurality of sequences were generated were derived from the same polynucleotide in an amplification reaction and from the same single cell or vessel.

In some embodiments, one or more AID sequences and vessel barcodes are used to group or bin sequences. In some embodiments, one or more AID sequences and vessel barcodes are used to group or bin sequences, wherein the sequences in each bin contain the same AID sequence. In some embodiments, one or more AID sequences and vessel barcodes are used to group or bin sequences, wherein the sequences in each bin contain the same AID sequence and a same vessel barcode. In some embodiments, one or more AID sequences and vessel barcodes are used to group or bin sequences, wherein the sequences in each bin comprise one or more amplicon sets. In some embodiments, one or more AID sequences and vessel barcodes are used to group or bin sequences, wherein the sequences in each bin comprise a plurality of sequences wherein the polynucleotides from which the plurality of sequences were generated were derived from the same polynucleotide in an amplification reaction and from the same single cell or vessel.

In some embodiments, one or more molecular barcodes and vessel barcodes are used to group or bin sequences. In some embodiments, one or more molecular barcodes and vessel barcodes are used to group or bin sequences, wherein the sequences in each bin contain the same molecular barcode and same vessel barcode. In some embodiments, one or more molecular barcodes and vessel barcodes are used to group or bin sequences, wherein the sequences in each bin comprise one or more amplicon sets. In some embodiments, one or more molecular barcodes and vessel barcodes are used to group or bin sequences, wherein the sequences in each bin comprise a plurality of sequences wherein the polynucleotides from which the plurality of sequences were generated were derived from the same polynucleotide in an amplification reaction and from the same single cell or vessel. In some embodiments, one or more molecular barcodes and vessel barcodes are not used to align sequences.

In some embodiments, one or more molecular barcodes are not used to align sequences. In some embodiments, one or more molecular barcodes are used to align sequences. In some embodiments, one or more molecular barcodes are used to group or bin sequences, and a target specific region is used to align sequences. In some embodiments, one or more vessel barcodes are not used to align sequences. In some embodiments, one or more vessel barcodes are used to align sequences. In some embodiments, one or more vessel barcodes are used to group or bin sequences, and a target specific region is used to align sequences. In some embodiments, one or more molecular barcodes and vessel barcodes are used to align sequences. In some embodiments, one or more molecular barcodes and vessel barcodes are used to group or bin sequences, and a target specific region is used to align sequences.

In some embodiments, the aligned sequences contain the same AID. In some embodiments, the aligned sequences contain the same AMB. In some embodiments, the aligned sequences contain the same AID and AMB. In some embodiments, the aligned sequences contain the same AID and vessel barcode. In some embodiments, the aligned sequences contain the same AMB and vessel barcode. In some embodiments, the aligned sequences contain the same molecular barcode. In some embodiments, the aligned sequences contain the same vessel barcode. In some embodiments, the aligned sequences contain the same molecular barcode and vessel barcode. In some embodiments, one or more molecular barcodes or vessel barcodes are used align sequences, wherein the aligned sequences comprise two or more sequences from an amplicon set. In some embodiments, one or more molecular barcodes or vessel barcodes are used to align sequences, wherein the aligned sequences comprise a plurality of sequences wherein the polynucleotides from which the plurality of sequences were generated were derived from the same polynucleotide molecule in an amplification reaction. In some embodiments, one or more molecular barcodes or vessel barcodes are used to align sequences, wherein the aligned sequences comprise a plurality of sequences wherein the polynucleotides from which the plurality of sequences were generated were derived from a single cell or single vessel.

Droplet Generation

Splitting a sample of a plurality of cells into small reaction volumes, coupled with molecular and vessel barcoding of polynucleotides from, or derived from, an individual cell from the plurality of cells can enable high throughput sequencing of a repertoire of sequences, such as biomarker sequences.

Splitting a sample of a plurality of cells into small reaction volumes, coupled with molecular and vessel barcoding of polynucleotides from, or derived from, an individual cell from the plurality of cells can enable high throughput sequencing of a repertoire of sequences, such as sequences representing a percentage of the transcriptome of an organism. For example, a repertoire of sequences can comprise a plurality of sequences representing at least about 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, 10%, 15%, 20%, 30%, 35%, 40%, 45, 50%, 55%, 60%, 65%, 70%, 75%, 80%, 85%, 90%, 95%, 98%, 99%, or 100% of the transcriptome of an organism.

Splitting a sample of immune cells into small reaction volumes, coupled with molecular and vessel barcoding of polynucleotides from, or derived from, an individual immune cell from the plurality of immune cells can enable high throughput sequencing of a repertoire of heavy and light chain sequences. These methods can also allow for pairing of the heavy and light chains after sequencing based on the barcoded sequences. Splitting a sample into small reaction volumes as described herein can also enable the use of reduced amounts of reagents, thereby lowering the material cost of the analysis.

In some cases, the reverse transcription reaction and/or the amplification reaction (e.g., PCR) are carried out in droplets, such as in droplet digital PCR. In certain aspects, the invention provides fluidic compartments to contain all or a portion of a target material. In some embodiments, a compartment is droplet. While reference is made to "droplets" throughout the specification, that term is used interchangeably with fluid compartment and fluid partition unless otherwise indicated. Except where indicated otherwise, "droplet" is used for convenience and any fluid partition or compartment may be used. The droplets used herein can include emulsion compositions (or mixtures of two or more immiscible fluids), such as described in U.S. Pat. No. 7,622,280. The droplets can be generated by devices described in WO/2010/036352. The term emulsion, as used herein, can refer to a mixture of immiscible liquids (such as oil and water). Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase. The droplets provided herein are designed to prevent mixing between compartments, with each compartment protecting its contents from evaporation and coalescing with the contents of other compartments.

The mixtures or emulsions described herein can be stable or unstable. The emulsions can be relatively stable and have minimal coalescence. Coalescence occurs when small droplets combine to form progressively larger ones. In some cases, less than 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, or 10% of droplets generated from a droplet generator coalesce with other droplets. The emulsions can also have limited flocculation, a process by which the dispersed phase comes out of suspension in flakes.

Droplets can be generated having an average diameter of about, less than about, or more than about, or at least about 0.001, 0.01, 0.05, 0.1, 1, 5, 10, 20, 30, 40, 50, 60, 70, 80, 100, 120, 130, 140, 150, 160, 180, 200, 300, 400, or 500 microns. Droplets can have an average diameter of about 0.001 to about 500, about 0.01 to about 500, about 0.1 to about 500, about 0.1 to about 100, about 0.01 to about 100, or about 1 to about 100 microns. Microfluidic methods of producing emulsion droplets using microchannel cross-flow focusing or physical agitation are known to produce either monodisperse or polydisperse emulsions. The droplets can be monodisperse droplets. The droplets can be generated such that the size of the droplets does not vary by more than plus or minus 5% of the average size of the droplets. In some cases, the droplets are generated such that the size of the droplets does not vary by more than plus or minus 2% of the average size of the droplets. A droplet generator can generate a population of droplets from a single sample, wherein none of the droplets vary in size by more than plus or minus about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

Higher mechanical stability can be useful for microfluidic manipulations and higher-shear fluidic processing (e.g., in microfluidic capillaries or through 90 degree turns, such as valves, in fluidic path). Pre- and post-thermally treated droplets or capsules can be mechanically stable to standard pipet manipulations and centrifugation.

A droplet can be formed by flowing an oil phase through an aqueous sample. The aqueous phase can comprise a buffered solution and reagents for performing an amplification reaction, including cells, nucleotides, nucleotide analogues, molecular barcoded polynucleotides, vessel barcoded polynucleotides primers, template nucleic acids, and enzymes, such as a DNA polymerase, RNA polymerase, and/or reverse transcriptase.

The aqueous phase can comprise a buffered solution and reagents for performing an amplification reaction with or without a solid surface, such as a bead. The buffered solution can comprise about, more than about, or less than about 1, 5, 10, 15, 20, 30, 50, 100, or 200 mM Tris. In some cases, the concentration of potassium chloride can be about, more than about, or less than about 10, 20, 30, 40, 50, 60, 80, 100, 200 mM. The buffered solution can comprise about 15 mM Tris and 50 mM KCl. The nucleotides can comprise deoxyribonucleotide triphosphate molecules, including dATP, dCTP, dGTP, and dTTP, in concentrations of about, more than about, or less than about 50, 100, 200, 300, 400, 500, 600, or 700 μm each. In some cases dUTP is added within the aqueous phase to a concentration of about, more than about, or less than about 50, 100, 200, 300, 400, 500, 600, or 700, 800, 900, or 1000 μm. In some cases, magnesium chloride or magnesium acetate ($MgCl_2$) is added to the aqueous phase at a concentration of about, more than about, or less than about 1.0, 2.0, 3.0, 4.0, or 5.0 mM. The concentration of $MgCl_2$ can be about 3.2 mM. In some cases, magnesium acetate or magnesium is used. In some cases, magnesium sulfate is used.

A non-specific blocking agent such as BSA or gelatin from bovine skin can be used, wherein the gelatin or BSA is present in a concentration range of approximately 0.1-0.9% w/v. Other possible blocking agents can include beta-lactoglobulin, casein, dry milk, or other common blocking agents. In some cases, preferred concentrations of BSA and gelatin are about 0.1% w/v.

Primers for amplification within the aqueous phase can have a concentration of about, more than about, or less than about 0.05, 0.1, 0.2, 0.3, 0.4, 0.5, 0.6, 0.7, 0.8, 0.9, 1.0, 1.2, 1.5, 1.7, or 2.0 μm. Primer concentration within the aqueous phase can be about 0.05 to about 2, about 0.1 to about 1.0, about 0.2 to about 1.0, about 0.3 to about 1.0, about 0.4 to about 1.0, or about 0.5 to about 1.0 μm. The concentration of primers can be about 0.5 μm. Amenable ranges for target nucleic acid concentrations in PCR include, but are not limited to between about 1 pg and about 500 ng.

In some cases, the aqueous phase can also comprise additives including, but not limited to, non-specific background/blocking nucleic acids (e.g., salmon sperm DNA), biopreservatives (e.g., sodium azide), PCR enhancers (e.g., Betaine, Trehalose, etc.), and inhibitors (e.g., RNAse inhibitors). Other additives can include, e.g., dimethyl sulfoxide (DMSO), glycerol, betaine (mono)hydrate (N,N,N-trimethylglycine=[caroxy-methyl]trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethyammonium chloride (TEA-C1) and tetrapropylammonium chloride (TPrA-C1), non-ionic detergent (e.g., Triton X-100, Tween 20, Nonidet P-40 (NP-40)), or PREXCEL-Q. In some cases, the aqueous phase can comprise 0, 1, 2, 3, 4, 5, 6, 7, 8, 9, or 10 different additives. In other cases, the aqueous phase can comprise at least 0, 1, 2, 3, 4, 5, 6, 7, 8, 9, or 10 different additives.

In some cases, a non-ionic Ethylene Oxide/Propylene Oxide block copolymer can be added to the aqueous phase in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, and Zonyl FSN. Pluronic F-68 can be present at a concentration of about 0.5% w/v.

In some cases magnesium sulfate can be substituted for magnesium chloride, at similar concentrations. A wide range of common, commercial PCR buffers from varied vendors can be substituted for the buffered solution.

The emulsion can be formulated to produce highly monodisperse droplets having a liquid-like interfacial film that can be converted by heating into microcapsules having a solid-like interfacial film; such microcapsules can behave as bioreactors able to retain their contents through a reaction process such as PCR amplification. The conversion to microcapsule form can occur upon heating. For example, such conversion can occur at a temperature of greater than about 50° C., 60° C., 70° C., 80° C., 90° C., or 95° C. In some cases this heating occurs using a thermocycler. During the heating process, a fluid or mineral oil overlay can be used to prevent evaporation. Excess continuous phase oil can or cannot be removed prior to heating. The biocompatible capsules can be resistant to coalescence and/or flocculation across a wide range of thermal and mechanical processing. Following conversion, the capsules can be stored at about, more than about, or less than about 3° C., 4° C., 5° C., 6° C., 7° C., 8° C., 9° C. 10° C., 15° C., 20° C., 25° C., 30° C., 35° C., or 40° C. These capsules can be useful in biomedical applications, such as stable, digitized encapsulation of macromolecules, particularly aqueous biological fluids containing a mix of nucleic acids or protein, or both together; drug and vaccine delivery; biomolecular libraries; clinical imaging applications, and others.

The microcapsules can contain one or more polynucleotides and can resist coalescence, particularly at high temperatures. Accordingly, PCR amplification reactions can occur at a very high density (e.g., number of reactions per unit volume). In some cases, greater than 100,000, 500,000, 1,000,000, 1,500,000, 2,000,000, 2,500,000, 5,000,000, or 10,000,000 separate reactions can occur per ml. In some cases, the reactions occur in a single well, e.g., a well of a microtiter plate, without inter-mixing between reaction volumes. The microcapsules can also contain other components necessary to enable a reverse transcription, primer extension, and/or PCR reaction to occur, e.g., primers, probes, dNTPs, DNA or RNA polymerases, etc. These capsules exhibit resistance to coalescence and flocculation across a wide range of thermal and mechanical processing.

In some cases, the amplifying step is carried out by performing digital PCR, such as microfluidic-based digital PCR or droplet digital PCR.

Droplets can be generated using microfluidic systems or devices. As used herein, the "micro-" prefix (for example, as "microchannel" or "microfluidic"), generally refers to elements or articles having widths or diameters of less than about 1 mm, and less than about 100 microns (micrometers) in some cases. In some cases, the element or article includes a channel through which a fluid can flow. Additionally, "microfluidic", as used herein, refers to a device, apparatus or system that includes at least one microscale channel.

Microfluidic systems and devices have been described in a variety of contexts, typically in the context of miniaturized laboratory (e.g., clinical) analysis. Other uses have been described as well. For example, International Patent Application Publication Nos. WO 01/89788; WO 2006/040551; WO 2006/040554; WO 2004/002627; WO 2008/063227; WO 2004/091763; WO 2005/021151; WO 2006/096571; WO 2007/089541; WO 2007/081385 and WO 2008/063227.

A droplet generally includes an amount of a first sample fluid in a second carrier fluid. Any technique known in the art for forming droplets may be used with methods of the invention. An exemplary method involves flowing a stream of the sample fluid containing the target material (e.g., immune cell) such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets containing the target material.

The carrier fluid may be any fluid that is immiscible with the sample fluid. An exemplary carrier fluid is oil. In certain embodiments, the carrier fluid includes a surfactant.

The same method may be applied to create individual droplets that contain other reagents such as reagents for an amplification reaction such as a polymerase chain reaction (PCR), or a non-PCR based amplification reaction such as multi-strand displacement amplification, or other methods known to one of ordinary skill in the art. Suitable reagents for conducting PCR-based amplification reactions are known to those of ordinary skill in the art and include, but are not limited to, DNA polymerases, forward and reverse primers, deoxynucleotide triphosphates (dNTPs), and one or more buffers.

In certain embodiments, fluidic compartments are formed by providing a first fluid partition (e.g., a droplet) comprising a target material (e.g., an immune cell and/or a solid support such as a bead) and a second fluid (e.g., as a fluid stream or within droplets). The first and second fluids are merged to form a droplet. Merging can be accomplished by application of an electric field to the two fluids. In certain embodiments, the second fluid contains reagents for conducting an amplification reaction, such as a polymerase chain reaction or a amplification reaction.

In certain aspects, the invention provides a method of making a library of uniquely barcoded heavy and light chain antibody sequences and/or alpha and beta chain TCR sequences and/or gamma and delta chain TCR sequences including obtaining a plurality of nucleic acid constructs in which each construct includes a unique N-mer and a functional N-mer. The functional N-mer can be a random N-mer, a PCR primer, a universal primer, an antibody, a sticky end, or any other sequence. The method can include making M sets of a number N of fluid compartments each containing one or more copies of a unique construct. The method can create barcode libraries of higher complexity by adding an additional barcode construct to each compartment in a set, and repeating that for each set to produce N×M compartments each containing a unique pair of constructs. The pairs can be hybridized or ligated to produce new constructs. In each construct in a barcode library, each unique N-mer can be adapted for identification by sequencing, probe hybridization, other methods, or a combination of methods.

Droplet Libraries

In general, a droplet library is made up of a number of library elements that are pooled together in a single collection. Libraries may vary in complexity from a single library element to $1 \times 10^{15}$ library elements or more. Each library element is one or more given components at a fixed concentration. The element may be, but is not limited to, cells, beads, amino acids, proteins, polypeptides, nucleic acids, polynucleotides or small molecule chemical compounds. The element may contain an identifier such as a molecular barcode, a vessel barcode, or both.

A cell library element can include, but is not limited to, hybridomas, B-cells, T-cells, primary cells, cultured cell lines, cancer cells, stem cells, or any other cell type. Cellular library elements are prepared by encapsulating a number of cells from one to tens of thousands in individual droplets. The number of cells encapsulated is usually given by Poisson statistics from the number density of cells and volume of the droplet. However, in some cases the number deviates from Poisson statistics as described in Edd et al., Lab Chip, 8(8):1262-1264, 2008. The discreet nature of cells allows for libraries to be prepared in mass with a plurality of cell variants, such as immune cells producing one antibody or TCR each, all present in a single starting media and then that media is broken up into individual droplet capsules that contain at most one cell. The cells within the individual droplets capsules are then lysed, heavy chain and light chain polynucleotides and/or alpha and beta chain polynucleotides and/or gamma and delta chain polynucleotides from the lysed cells are barcoded with molecular barcodes and vessel barcodes and amplified and then combined or pooled to form a library consisting of heavy and light chain and/or alpha and beta chain and/or gamma and delta chain library elements.

A bead based library element contains one or more beads, and may also contain other reagents, such as antibodies, enzymes or other proteins. In the case where all library elements contain different types of beads, but the same surrounding media, the library elements can all be prepared from a single starting fluid or have a variety of starting fluids. In the case of cellular libraries prepared in mass from a collection of variants, the library elements will be prepared from a variety of starting fluids. It is desirable to have exactly one cell per droplet with only a few droplets containing more than one cell when starting with a plurality of cells. In some cases, variations from Poisson statistics can be achieved to provide an enhanced loading of droplets such that there are more droplets with exactly one cell per droplet and few exceptions of empty droplets or droplets containing more than one cell.

In some embodiments, it is desirable to have exactly one vessel barcoded polynucleotide per droplet with only a few droplets containing more than one vessel barcoded polynucleotide when starting with a plurality of vessel barcoded polynucleotide. In some cases, variations from Poisson statistics can be achieved to provide an enhanced loading of droplets such that there are more droplets with exactly one vessel barcoded polynucleotide per droplet and few exceptions of empty droplets or droplets containing more than one vessel barcoded polynucleotide.

Examples of droplet libraries are collections of droplets that have different contents, ranging from beads, cells, small molecules, DNA, primers, antibodies, and barcoded polynucleotides. The droplets range in size from roughly 0.5 micron to 500 micron in diameter, which corresponds to about 1 picoliter to 1 nanoliter. However, droplets can be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the droplet library provided by the instant invention are preferably uniform in size. That is, the diameter of any droplet within the library will vary less than 5%, 4%, 3%, 2%, 1% or 0.5% when compared to the diameter of other droplets within the same library. The uniform size of the droplets in the library may be critical to maintain the stability and integrity of the droplets and also may be essential for the subsequent use of the droplets within the library for the various biological and chemical assays described herein.

The invention provides a droplet library comprising a plurality of aqueous droplets within an immiscible fluid, wherein each droplet is preferably substantially uniform in size and comprises a different library element. The invention provides a method for forming the droplet library comprising providing a single aqueous fluid comprising different library elements, encapsulating each library element into an aqueous droplet within an immiscible fluid.

In certain embodiments, different types of elements (e.g., cells or beads), are pooled in a single source contained in the same medium. After the initial pooling, the elements are then encapsulated in droplets to generate a library of droplets wherein each droplet with a different type of bead or cell is a different library element. The dilution of the initial solution enables the encapsulation process. In some embodiments, the droplets formed will either contain a single element or will not contain anything, i.e., be empty. In other embodiments, the droplets formed will contain multiple copies of a library element. The elements being encapsulated are generally variants of a type. In one example, elements are immune cells of a blood sample, and each immune cell is encapsulated to amplify and barcode the antibody sequences of the nucleotides in the immune cells.

For example, in one type of emulsion library, there are library elements that have different particles, i.e., cells or barcoded polynucleotides in a different medium and are encapsulated prior to pooling. In one example, a specified number of library elements, i.e., n number of different cells or barcoded polynucleotides, is contained within different mediums. Each of the library elements are separately emulsified and pooled, at which point each of the n number of pooled different library elements are combined and pooled into a single pool. The resultant pool contains a plurality of water-in-oil emulsion droplets each containing a different type of particle.

In some embodiments, the droplets formed will either contain a single library element or will not contain anything, i.e., be empty. In other embodiments, the droplets formed will contain multiple copies of a library element. The contents of the beads follow a Poisson distribution, where there is a discrete probability distribution that expresses the probability of a number of events occurring in a fixed period of time if these events occur with a known average rate and independently of the time since the last event. The oils and surfactants used to create the libraries prevent the exchange of the contents of the library between droplets.

Primers

Generally, one or more pairs of primers can be used in a amplification reaction; one primer of a primer pair can be a forward primer and one primer of a primer pair can be a reverse primer.

In some cases, a first pair of primers can be used in the amplification reaction; one primer of the first pair can be a forward primer complementary to a sequence of a first target polynucleotide molecule and one primer of the first pair can be reverse primer can be complementary to a second sequence of the first target polynucleotide molecule, and a first target locus can reside between the first sequence and the second sequence. In some embodiments, the first target locus comprises a $V_H$ or $V\alpha$ or $V\gamma$ sequence. In some embodiments, the first target locus comprises an AID sequence and/or an AMB sequence.

In some cases, a second pair of primers can be used in the amplification reaction; one primer of the second pair can be a forward primer complementary to a first sequence of a second target polynucleotide molecule and one primer of the second pair can be a reverse primer complementary to a second sequence of the second target polynucleotide molecule, and a second target locus can reside between the first sequence and the second sequence. In some embodiments, the second target locus comprises a $V_L$ or $V\beta$ or $V\delta$ sequence.

In some cases, a third pair of primers can be used in the amplification reaction; one primer of the third pair can be a forward primer complementary to a first sequence of a third target polynucleotide molecule and one primer of the third pair can be a reverse primer complementary to a second sequence of the third target polynucleotide molecule, and a third target locus can reside between the first sequence and the second sequence. In some embodiments, the third target locus comprises a barcode, such as a molecular barcode or vessel barcode.

The length of the forward primer and the reverse primer can depend on the sequence of the target polynucleotide and the target locus. For example, the length and/or $T_M$ of the forward primer and reverse primer can be optimized. In some case, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some cases, a primer is about 15 to about 20, about 15 to about 25, about 15 to about 30, about 15 to about 40, about 15 to about 45, about 15 to about 50, about 15 to about 55, about 15 to about 60, about 20 to about 25, about 20 to about 30, about 20 to about 35, about 20 to about 40, about 20 to about 45, about 20 to about 50, about 20 to about 55, or about 20 to about 60 nucleotides in length.

A primer can be a single-stranded DNA prior to binding a template polynucleotide. In some cases, the primer initially comprises double-stranded sequence. The appropriate length of a primer can depend on the intended use of the primer but can range from about 6 to about 50 nucleotides, or from about 15 to about 35 nucleotides. Short primer molecules can generally require cooler temperatures to form sufficiently stable hybrid complexes with a template. In some embodiments, a primer need not reflect the exact sequence of the template nucleic acid, but can be sufficiently complementary to hybridize with a template. In some cases, a primer can be partially double-stranded before binding to a template polynucleotide. A primer with double-stranded sequence can have a hairpin loop of about, more than about, or less than about 3, 4, 5, 6, 7, 8, 9, 10, 11, 12, 13, 14, 15, 16, 17, 18, 19, or 20 bases. A double stranded portion of a primer can be about, more than about, less than about, or at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 base-pairs. The design of suitable primers for the amplification of a given target sequence is well known in the art.

Primers can incorporate additional features that allow for the detection or immobilization of the primer but do not alter a basic property of the primer (e.g., acting as a point of initiation of DNA synthesis). For example, primers can contain an additional nucleic acid sequence at the 5' end which does not hybridize to a target nucleic acid, but which facilitates cloning or further amplification, or sequencing of an amplified product. For example, the additional sequence can comprise a primer binding site, such as a universal primer binding site. A region of the primer which is sufficiently complementary to a template to hybridize can be referred to herein as a hybridizing region.

In another case, a primer utilized in methods and compositions described herein can comprise one or more universal nucleosides. Non-limiting examples of universal nucleosides are 5-nitroindole and inosine, as described in U.S. Appl. Pub. Nos. 2009/0325169 and 2010/0167353.

Primers can be designed according to known parameters for avoiding secondary structures and self-hybridization. Different primer pairs can anneal and melt at about the same temperatures, for example, within 1° C., 2° C., 3° C., 4° C., 5° C., 6° C., 7° C., 8° C., 9° C. or 10° C. of another primer pair. In some cases, greater than 1, 2, 3, 4, 5, 6, 7, 8, 9, 10, 15, 20, 25, 30, 35, 40, 45, 50, 100, 200, 500, 1000, 5000, 10,000 or more primers are initially used. Such primers can hybridize to target polynucleotides described herein.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources. The primers can have an identical melting temperature. The primers can have non-identical melting temperatures. The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule ($T_M=2(A+T)+4(G+C)$). Computer programs can also be used to design primers. The $T_M$ (melting or annealing temperature) of each primer can be calculated using software programs. The annealing temperature of the primers can be recalculated and increased after any cycle of amplification, including but not limited to cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers can be incorporated into the products from each loci of interest; thus the $T_M$ can be recalculated based on both the sequences of the 5' half and the 3' half of each primer.

A primer site includes the area of the template to which a primer hybridizes. In some embodiments, primers are capable of acting as a point of initiation for template-directed nucleic acid synthesis. For example, primers can initiate template-directed nucleic acid synthesis when four different nucleotides and a polymerization agent or enzyme, such as DNA or RNA polymerase or reverse transcriptase. A primer pair includes 2 primers: a first primer with a 5' upstream region that hybridizes with a 5' end of a template sequence, and a second primer with a 3' downstream region that hybridizes with the complement of the 3' end of the template sequence. A primer set includes two or more primers: a first primer or first plurality of primers with a 5' upstream region that hybridizes with a 5' end of a template sequence or plurality of template sequences, and a second primer or second plurality of primers with a 3' downstream region that hybridizes with the complement of the 3' end of the template sequence or plurality of template sequences. In some embodiments, a primer comprises a target specific sequence. In some embodiments, a primer comprises a sample barcode sequence. In some embodiments, a primer comprises a universal priming sequence. In some embodiments, a primer comprises a PCR priming sequence. In some embodiments, a primer comprises a PCR priming sequence used to initiate amplification of a polynucleotide. (Dieffenbach, PCR Primer: A Laboratory Manual, 2nd Edition (Cold Spring Harbor Press, New York (2003)). The universal primer binding site or sequence allows the attachment of a universal primer to a polynucleotide and/or amplicon. Universal primers are well known in the art and include, but are not limited to, −47F (M13F), alfaMF, AOX3', AOX5', BGHr, CMV-30, CMV-50, CVMf, LACrmt, lambda gt10F, lambda gt10R, lambda gt11F, lambda gt11R, M13 rev, M13Forward(-20), M13Reverse, male, p10SEQPpQE, pA-120, pet4, pGAP Forward, pGLRVpr3, pGLpr2R, pKLAC14, pQEFS, pQERS, pucU1, pucU2, reversA, seqIIREStam, seqlRESzpet, seqori, seqPCR, seqpIRES-, seqpIRES+, seqpSecTag, seqpSecTag+, seqretro+PSI, SP6, T3-prom, T7-prom, and T7-termlnv. As used herein, attach can refer to both or either covalent interactions and noncovalent interactions. Attachment of the universal primer to the universal primer binding site may be used for amplification, detection, and/or sequencing of the polynucleotide and/or amplicon. The universal primer binding site may comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the universal primer binding site comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. In some embodiments, the universal primer binding site comprises 1-10, 10-20, 10-30 or 10-100 nucleotides or base pairs. In some embodiments, the universal primer binding site comprises from about 1-90, 1-80, 1-70, 1-60, 1-50, 1-40, 1-30, 1-20, 1-10, 2-90, 2-80, 2-70, 2-60, 2-50, 2-40, 2-30, 2-20, 2-10, 1-900, 1-800, 1-700, 1-600, 1-500, 1-400, 1-300, 1-200, 1-100, 2-900, 2-800, 2-700, 2-600, 2-500, 2-400, 2-300, 2-200, 2-100, 5-90, 5-80, 5-70, 5-60, 5-50, 5-40, 5-30, 5-20, 5-10, 10-90, 10-80, 10-70, 10-60, 10-50, 10-40, 10-30, 10-20, 10-10, 5-900, 5-800, 5-700, 5-600, 5-500, 5-400, 5-300, 5-200, 5-100, 10-900, 10-800, 10-700, 10-600, 10-500, 10-400, 10-300, 10-200, 10-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 nucleotides or base pairs.

Primers can have a length compatible with its use in synthesis of primer extension products. A primer can be a polynucleotide that is 8 to 200 nucleotides in length. The length of a primer can depend on the sequence of the template polynucleotide and the template locus. For example, the length and/or melting temperature ($T_M$) of a primer or primer set can be optimized. In some case, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some embodiments, primers are about 8-100 nucleotides in length, for example, 10-75, 15-60, 15-40, 18-30, 20-40, 21-50, 22-45, 25-40, 7-9, 12-15, 15-20, 15-25, 15-30, 15-45, 15-50, 15-55, 15-60, 20-25, 20-30, 20-35, 20-45, 20-50, 20-55, or 20-60 nucleotides in length and any length there between. In some embodiments, primers are at most about 10, 12, 15, 20, 21, 22, 23, 24, 25, 26, 27, 28, 29, 30, 35, 40, 45, 50, 55, 60, 65, 70, 75, 80, 85, 90, 95 or 100 nucleotides in length.

Generally, one or more pairs of primers can be used in an exponential amplification reaction; one primer of a primer pair can be a forward primer and one primer of a primer pair can be a reverse primer. In some embodiments, a first pair of primers can be used in the exponential amplification reaction; one primer of the first pair can be a forward primer complementary to a sequence of a first template polynucleotide molecule and one primer of the first pair can be a reverse primer complementary to a second sequence of the first template polynucleotide molecule, and a first template locus can reside between the first sequence and the second sequence. In some embodiments, a second pair of primers can be used in the amplification reaction; one primer of the second pair can be a forward primer complementary to a first sequence of a second target polynucleotide molecule and one primer of the second pair can be a reverse primer complementary to a second sequence of the second target polynucleotide molecule, and a second target locus can reside between the first sequence and the second sequence. In some embodiments, the second target locus comprises a variable light chain antibody sequence. In some embodiments, a third pair of primers can be used in the amplification reaction; one primer of the third pair can be a forward primer complementary to a first sequence of a third template polynucleotide molecule and one primer of the third pair can be a reverse primer complementary to a second sequence of the third template polynucleotide molecule, and a third template locus can reside between the first sequence and the second sequence.

The one or more primers can anneal to at least a portion of a plurality of template polynucleotides. The one or more primers can anneal to the 3' end and/or 5' end of the plurality of template polynucleotides. The one or more primers can anneal to an internal region of the plurality of template polynucleotides. The internal region can be at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends or 5' ends the plurality of template polynucleotides. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. In some embodiments, the one or more custom primers anneal to an SBC, a target specific region, complements thereof, or any combination thereof. The one or more primers can comprise a universal primer. The one or more primers primer can be designed to amplify or perform primer extension, reverse transcription, linear extension, non-exponential amplification, exponential amplification, PCR, or any other amplification method of one or more target or template polynucleotides The target specific region can comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides or base pairs. In another example, the target specific region comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. in some embodiments, the target specific region comprises from about 5-10, 10-15, 10-20, 10-30, 15-30, 10-75, 15-60, 15-40, 18-30, 20-40, 21-50, 22-45, 25-40, 7-9, 12-15, 15-20, 15-25, 15-30, 15-45, 15-50, 15-55, 15-60, 20-25, 20-30, 20-35, 20-45, 20-50, 20-55, 20-60, 2-900, 2-800, 2-700, 2-600, 2-500, 2-400, 2-300, 2-200, 2-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 nucleotides or base pairs.

Primers can be designed according to known parameters for avoiding secondary structures and self-hybridization. In some embodiments, different primer pairs can anneal and melt at about the same temperatures, for example, within 1° C., 2° C., 3° C., 4° C., 5° C., 6° C., 7° C., 8° C., 9° C. or 10° C. of another primer pair. In some embodiments, one or more primers in a plurality of primers can anneal and melt at about the same temperatures, for example, within 1, 2, 3, 4, 5, 6, 7, 8, 9 or 10° C. of another primer in the plurality of primers. In some embodiments, one or more primers in a plurality can anneal and melt at different temperatures than another primer in the plurality of primers.

A plurality of primers for one or more steps of the methods described herein can comprise a plurality of primers comprising about, at most about, or at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 50,000,000, 100,000,000 different primers. For example, each primer in a plurality of primers can comprise a different target or template specific region or sequence.

Reverse Transcription

In some cases, the target polynucleotides are prepared from an RNA by reverse transcription. In some cases, the target polynucleotides are prepared from a DNA by primer extension, such as using a polymerase.

The methods described herein can be used in coupled reverse transcription-PCR (reverse transcription-PCR). For example, reverse transcription and PCR can be carried out in two distinct steps. First a cDNA copy of the sample mRNA can be synthesized using either a polynucleotide dT primer, a sequence specific primer, a universal primer, or any primer described herein.

Reverse transcription and PCR can be carried out in a single closed vessel reaction. For example, three primers can be employed, one for reverse transcription and two for PCR. The primer for reverse transcription can bind to the mRNA 3' to the position of the PCR amplicon. Although not essential, the reverse transcription primer can include RNA residues or modified analogs such as 2'-O-methyl RNA bases, which will not form a substrate for RNase H when hybridized to the mRNA.

The temperature to carry out the reverse transcription reaction depends on the reverse transcriptase being used. In some cases, a thermostable reverse transcriptase is used and the reverse transcription reaction is carried out at about 37° C. to about 75° C., at about 37° C. to about 50° C., at about 37° C. to about 55° C., at about 37° C. to about 60° C., at about 55° C. to about 75° C., at about 55° C. to about 60° C., at about 37° C., or at about 60° C. In some cases, a reverse transcriptase that transfers 3 or more non-template terminal nucleotides to an end of the transcribed product is used.

A reverse transcription reaction and the PCR reaction described herein can be carried out in various formats known in the art, such as in tubes, microtiter plates, microfluidic devices, or, preferably, droplets.

A reverse transcription reaction can be carried out in volumes ranging from 5 µL to 100 µL, or in 10 µL to 20 µL reaction volumes. In droplets, reaction volumes can range from 1 pL to 100 nL, or 10 pL to 1 nL. In some cases, the reverse transcription reaction is carried out in a droplet having a volume that is about or less than 1 nL. In some cases, a PCR reaction is in a droplet having a reaction volume ranges from 1 pL to 100 nL preferably 10 pL to 1 nL. In some cases, the PCR reaction is carried out in a droplet having a volume that is about or less than 1 nL. In some cases, a reverse transcription reaction and a PCR reaction are carried out in the same droplet having a reaction volume ranges from 1 pL to 100 nL or 10 pL to 1 nL. In some cases, the reverse transcription reaction and the PCR reaction are carried out in a droplet having a volume that is about or less than 1 nL or a volume that is about or less than 1 pL. In some cases, a reverse transcription reaction and a PCR reaction are carried out in a different droplet. In some cases, a reverse transcription reaction and a PCR reaction are carried out in a plurality of droplets each having a reaction volume ranges from 1 pL to 100 nL or 10 pL to 1 nL. In some cases, the reverse transcription reaction and the PCR reaction are carried out in a plurality of droplets each having a volume that is about or less than 1 nL.

In some cases, a first PCR reaction is in a first droplet having a reaction volume ranges from 1 pL to 100 nL preferably 10 pL to 1 nL and a second PCR reaction is in a second droplet having a reaction volume ranges from 1 pL to 100 nL preferably 10 pL to 1 nL. In some cases, a first PCR reaction is in a first droplet having a volume that is about or less than 1 nL, and a second PCR reaction is in a second droplet having a volume that is about or less than 1 nL.

In some cases, a first PCR reaction and a second PCR reaction are carried out in a plurality of droplets each having a reaction volume ranges from 1 pL to 100 nL or 10 pL to 1 nL. In some cases, a first PCR reaction and a second PCR reaction are carried out in a plurality of droplets each having a volume that is about or less than 1 nL.

Target polynucleotides, such as RNA, can be reverse transcribed into cDNA using one or more reverse transcription primers. The one or more reverse transcription primers can comprise a region complementary to a region of the RNA, such as a constant region (e.g., a heavy or light chain constant region or a poly-A tail of mRNA). In some embodiments, the reverse transcription primers can comprise a first reverse transcription primer with a region complementary to a constant region of a first RNA, and a second reverse transcription primer with a region complementary to a constant region of a second RNA. In some embodiments, the reverse transcription primers can comprise a first reverse transcription primer with a region complementary to a constant region of a first RNA, and one or more reverse transcription primers with a region complementary to a constant region of one or more RNAs, respectively.

In some embodiments, reverse transcription primers do not comprise a barcode.

Reverse transcription primers can further comprise a region that is not complementary to a region of the RNA. In some embodiments, the region that is not complementary to a region of the RNA is 5' to a region of the primers that is complementary to the RNA. In some embodiments, the region that is not complementary to a region of the RNA is 3' to a region of the primers that is complementary to the RNA. In some embodiments, the region that is not complementary to a region of the RNA is a 5' overhang region. In some embodiments, the region that is not complementary to a region of the RNA comprises a priming site for amplification and/or a sequencing reaction. Using the one or more primers described herein, the RNA molecules are reverse transcribed using suitable reagents known in the art.

After performing the reverse transcription reactions of the RNA molecules, the resulting cDNA molecules can be barcoded with a molecular barcode and a vessel barcode and amplified by one or more PCR reactions, such as a first and/or a second PCR reaction. The first and/or second PCR reaction can utilize a pair of primers or a plurality of primer pairs. The first and/or second PCR reaction can utilize a plurality of forward/reverse primers and a reverse primer. The first and/or second PCR reaction can utilize a plurality of forward/reverse primers and a forward primer. A first and/or second primer of a plurality of forward/reverse primers can be a forward/reverse primer containing a region complementary to the cDNA molecules or barcoded cDNA molecules. A first and/or second primer of a plurality of forward/reverse primers can be a forward/reverse primer containing a region complementary to the barcoded cDNA molecules.

In some embodiments, a plurality of forward/reverse primers comprises one or more forward/reverse primers wherein each of the forward/reverse primers in the plurality of forward/reverse primers comprises a region complementary to one or more upstream or downstream regions to a V segment of the cDNAs or barcoded cDNAs. For example, a plurality of forward/reverse primers comprises a forward/reverse primer comprising a region complementary to a upstream or downstream region to a V segment of the cDNAs or barcoded cDNAs and one or more other forward/reverse primers comprising a region complementary to one or more other upstream or downstream regions to a V segment of the cDNAs or barcoded cDNAs. For example, a plurality of forward/reverse primers comprises a first and/or second forward/reverse primer comprising a region complementary to a first and/or second upstream or downstream region to a V segment of the cDNAs or barcoded cDNAs and a second forward/reverse primer comprising a region complementary to a second upstream or downstream region to a V segment of the cDNAs or barcoded cDNAs. For example, a plurality of forward/reverse primers comprises a first and/or second forward/reverse primer comprising a region complementary to a first and/or second upstream or downstream region to a V segment of the cDNAs or barcoded cDNAs, a second forward/reverse primer comprising a region complementary to a second upstream or downstream region to a V segment of the cDNAs or barcoded cDNAs, and a third forward/reverse primer comprising a region complementary to a third upstream or downstream region to a V segment of the cDNAs or barcoded cDNAs, etc. The primers in the plurality of forward/reverse primers can be used to anneal to all possible upstream or downstream regions of all V segments expressed by the cells, such as immune B-cells or T-cells, in the sample.

In some embodiments, a plurality of forward/reverse primers comprises one or more forward/reverse primers wherein each of the forward/reverse primers in the plurality of forward/reverse primers comprises a region complementary to one or more upstream or downstream regions to a C segment of the cDNAs or barcoded cDNAs. For example, a plurality of forward/reverse primers comprises a forward/reverse primer comprising a region complementary to a upstream or downstream region to a C segment of the cDNAs or barcoded cDNAs and one or more other forward/reverse primers comprising a region complementary to one or more other upstream or downstream regions to a C segment of the cDNAs or barcoded cDNAs. For example, a plurality of forward/reverse primers comprises a first and/or second forward/reverse primer comprising a region complementary to a first and/or second upstream or downstream region to a C segment of the cDNAs or barcoded cDNAs and a second forward/reverse primer comprising a region complementary to a second upstream or downstream region to a C segment of the cDNAs or barcoded cDNAs. For example, a plurality of forward/reverse primers comprises a first and/or second forward/reverse primer comprising a region complementary to a first and/or second upstream or downstream region to a C segment of the cDNAs or barcoded cDNAs, a second forward/reverse primer comprising a region complementary to a second upstream or downstream region to a C segment of the cDNAs or barcoded cDNAs, and a third forward/reverse primer comprising a region complementary to a third upstream or downstream region to a C segment of the cDNAs or barcoded cDNAs, etc. The primers in the plurality of forward/reverse primers can be used to anneal to all possible upstream or downstream regions of all C segments expressed by the cells, such as immune B-cells or T-cells, in the sample.

In some embodiments, a plurality of forward/reverse primers comprises one or more forward/reverse primers wherein each of the forward/reverse primers in the plurality of forward/reverse primers comprises a region complementary to one or more upstream or downstream regions to a molecular barcode of the barcoded cDNAs. For example, a plurality of forward/reverse primers comprises a forward/reverse primer comprising a region complementary to a upstream or downstream region to a molecular barcode of the barcoded cDNAs and one or more other forward/reverse primers comprising a region complementary to one or more other upstream or downstream regions to a molecular barcode of the barcoded cDNAs. For example, a plurality of forward/reverse primers comprises a first and/or second forward/reverse primer comprising a region complementary to a first and/or second upstream or downstream region to a molecular barcode of the barcoded cDNAs and a second forward/reverse primer comprising a region complementary to a second upstream or downstream region to a molecular barcode of the barcoded cDNAs. For example, a plurality of forward/reverse primers comprises a first and/or second forward/reverse primer comprising a region complementary to a first and/or second upstream or downstream region to a molecular barcode of the barcoded cDNAs, a second forward/reverse primer comprising a region complementary to a second upstream or downstream region to a molecular barcode of the barcoded cDNAs, and a third forward/reverse primer comprising a region complementary to a third upstream or downstream region to a molecular barcode of the barcoded cDNAs, etc. The plurality of forward/reverse primers can be used to anneal to all possible upstream or downstream regions of all molecular barcodes expressed by the cells, such as immune B-cells or T-cells, in the sample.

In some embodiments, a plurality of forward/reverse primers comprises one or more forward/reverse primers wherein each of the forward/reverse primers in the plurality of forward/reverse primers comprises a region complementary to one or more upstream or downstream regions to a vessel barcode of the barcoded cDNAs. For example, a plurality of forward/reverse primers comprises a forward/reverse primer comprising a region complementary to a upstream or downstream region to a vessel barcode of the barcoded cDNAs and one or more other forward/reverse primers comprising a region complementary to one or more other upstream or downstream regions to a vessel barcode of the barcoded cDNAs. For example, a plurality of forward/reverse primers comprises a first and/or second forward/reverse primer comprising a region complementary to a first and/or second upstream or downstream region to a vessel barcode of the barcoded cDNAs and a second forward/reverse primer comprising a region complementary to a second upstream or downstream region to a vessel barcode of the barcoded cDNAs. For example, a plurality of forward/reverse primers comprises a first and/or second forward/reverse primer comprising a region complementary to a first and/or second upstream or downstream region to a vessel barcode of the barcoded cDNAs, a second forward/reverse primer comprising a region complementary to a second upstream or downstream region to a vessel barcode of the barcoded cDNAs, and a third forward/reverse primer comprising a region complementary to a third upstream or downstream region to a vessel barcode of the barcoded cDNAs, etc. The primers in the plurality of forward/reverse primers can be used to anneal to all possible upstream or downstream regions of all vessel barcodes expressed by the cells, such as immune B-cells or T-cells, in the sample.

The forward/reverse primers in the plurality of forward/reverse primers further comprise a region that is not complementary to a region of the RNA. In some embodiments, the region that is not complementary to a region of the RNA is 5' to a region of the forward/reverse primers that is complementary to the RNA (i.e. a upstream or downstream regions of a V segment). In some embodiments, the region that is not complementary to a region of the RNA is 3' to a region of the forward/reverse primers that is complementary to the RNA. In some embodiments, the region that is not complementary to a region of the RNA is a 5' overhang region. In some embodiments, the region that is not complementary to a region of the RNA comprises a priming site for amplification and/or a second sequencing reaction. In some embodiments, the region that is not complementary to a region of the RNA comprises a priming site for amplification and/or a third sequencing reaction. In some embodiments, the region that is not complementary to a region of the RNA comprises a priming site for a second and a third sequencing reaction. In some embodiments, the sequence of the priming site for the second and the third sequencing reaction are the same. Using the one or more forward/reverse primers and a reverse primer as described herein, the cDNA molecules are amplified using suitable reagents known in the art. In some embodiments, a region is complementary to a region of the RNA, such as the constant region or a poly-A tail of mRNA.

In some embodiments, a plurality of forward/reverse primers comprises one or more forward/reverse primers wherein each of the forward/reverse primers in the plurality of forward/reverse primers comprises a region complementary to one or more upstream or downstream regions to a vessel barcode of the barcoded oligonucleotides of affinity-oligonucleotide conjugates or tetramer-oligonucleotide conjugates. In some embodiments, a plurality of forward/reverse primers comprises one or more forward/reverse primers wherein each of the forward/reverse primers in the plurality of forward/reverse primers comprises a region complementary to one or more upstream or downstream regions to an AID of the barcoded oligonucleotides of affinity-oligonucleotide conjugates or tetramer-oligonucleotide conjugates. In some embodiments, a plurality of forward/reverse primers comprises one or more forward/reverse primers wherein each of the forward/reverse primers in the plurality of forward/reverse primers comprises a region complementary to one or more upstream or downstream regions to an AMB of the barcoded oligonucleotides of affinity-oligonucleotide conjugates or tetramer-oligonucleotide conjugates. For example, a plurality of forward/reverse primers comprises a forward/reverse primer comprising a region complementary to a upstream or downstream region to a vessel barcode, AID, and/or AMB of the barcoded oligonucleotides of affinity-oligonucleotide conjugates or tetramer-oligonucleotide conjugates and one or more other forward/reverse primers comprising a region complementary to one or more other upstream or downstream regions to a vessel barcode, AID, and/or AMB of the barcoded oligonucleotides of affinity-oligonucleotide conjugates or tetramer-oligonucleotide conjugates. For example, a plurality of forward/reverse primers comprises a first and/or second forward/reverse primer comprising a region complementary to a first and/or second upstream or downstream region to a vessel barcode, AID, and/or AMB of the barcoded oligonucleotides of affinity-oligonucleotide conjugates or tetramer-oligonucleotide conjugates and a second forward/reverse primer comprising a region complementary to a second upstream or downstream region to a vessel barcode, AID, and/or AMB of the barcoded oligonucleotides of affinity-oligonucleotide conjugates or tetramer-oligonucleotide conjugates. For example, a plurality of forward/reverse primers comprises a first and/or second forward/ reverse primer comprising a region complementary to a first and/or second upstream or downstream region to a vessel barcode, AID, and/or AMB of the barcoded oligonucleotides of affinity-oligonucleotide conjugates or tetramer-oligonucleotide conjugates, a second forward/reverse primer comprising a region complementary to a second upstream or downstream region to a vessel barcode, AID, and/or AMB of the barcoded oligonucleotides of affinity-oligonucleotide conjugates or tetramer-oligonucleotide conjugates, and a third forward/reverse primer comprising a region complementary to a third upstream or downstream region to a vessel barcode, AID, and/or AMB of the barcoded oligonucleotides of affinity-oligonucleotide conjugates or tetramer-oligonucleotide conjugates, etc.

Amplification

After a vessel barcode has been added to a target polynucleotide, the target polynucleotide can be amplified. For example, after a vessel barcode has been added to an oligonucleotide of an affinity-oligonucleotide conjugate or tetramer-oligonucleotide conjugate, the oligonucleotide can be amplified. For example, after a vessel barcode has been added to cell polynucleotide, the vessel barcoded cell polynucleotide can be amplified.

An amplification reaction can comprise one or more additives. In some cases, the one or more additives are dimethyl sulfoxide (DMSO), glycerol, betaine (mono)hydrate (N,N,N-trimethylglycine=[caroxy-methyl]trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some cases, an amplification reaction comprises 0, 1, 2, 3, 4, 5, 6, 7, 8, 9, or 10 different additives. In other cases, an amplification reaction comprises at least 0, 1, 2, 3, 4, 5, 6, 7, 8, 9, or 10 different additives.

Thermocycling reactions can be performed on samples contained in reaction volumes (e.g., droplets). Droplets can be polydisperse or preferably monodisperse, generated through agitation, sonication or microfluidically through a T-channel junction or other means by those familiar with the art. Densities can exceed 20,000 droplets/40 ul (1 nL droplets), 200,000 droplets/40 ul (100 pL droplets). The droplets can remain intact during thermocycling. Droplets can remain intact during thermocycling at densities of greater than about 10,000 droplets/µL, 100,000 droplets/µL, 200,000 droplets/µL, 300,000 droplets/µL, 400,000 droplets/µL, 500,000 droplets/µL, 600,000 droplets/µL, 700,000 droplets/µL, 800,000 droplets/µL, 900,000 droplets/µL or 1,000,000 droplets/µL. In other cases, two or more droplets do not coalesce during thermocycling. In other cases, greater than 100 or greater than 1,000 droplets do not coalesce during thermocycling.

Any DNA polymerase that catalyzes primer extension can be used, including but not limited to E. coli DNA polymerase, Klenow fragment of E. coli DNA polymerase 1, T7 DNA polymerase, T4 DNA polymerase, Taq polymerase, Pfu DNA polymerase, Vent DNA polymerase, bacteriophage 29, REDTaq™, Genomic DNA polymerase, or sequenase. In some cases, a thermostable DNA polymerase is used. A hot start PCR can also be performed wherein the reaction is heated to 95° C. for two minutes prior to addition of the polymerase or the polymerase can be kept inactive until the first heating step in cycle 1. Hot start PCR can be used to minimize nonspecific amplification. Any number of PCR cycles can be used to amplify the DNA, e.g., about, more than about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 cycles. The number of amplification cycles can be about 1-45, 10-45, 20-45, 30-45, 35-45, 10-40, 10-30, 10-25, 10-20, 10-15, 20-35, 25-35, 30-35, or 35-40.

Amplification of target nucleic acids can be performed by any means known in the art. Target nucleic acids can be amplified by polymerase chain reaction (PCR) or isothermal DNA amplification. Examples of PCR techniques that can be used include, but are not limited to, quantitative PCR, quantitative fluorescent PCR (QF-PCR), multiplex fluorescent PCR (MF-PCR), real time PCR (reverse transcription-PCR), single cell PCR, restriction fragment length polymorphism PCR (PCR-RFLP), PCR-RFLP/reverse transcription-PCR-RFLP, hot start PCR, nested PCR, in situ polony PCR, in situ rolling circle amplification (RCA), digital PCR (dPCR), droplet digital PCR (ddPCR), bridge PCR, picoliter PCR and emulsion PCR. Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate polynucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938, as well as include Q beta replicase mediated RNA amplification. Amplification can be isothermal amplification, e.g., isothermal linear amplification.

In some embodiments, amplification does not occur on a solid support. In some embodiments, amplification does not occur on a solid support in a droplet. In some embodiments, amplification does occur on a solid support when the amplification is not in a droplet.

Sequencing

After performing one or more of the methods or method steps described herein, a library of polynucleotides generated can be sequenced.

Sequencing can be performed by any sequencing method known in the art. In some embodiments, sequencing can be performed in high throughput. Suitable next generation sequencing technologies include the 454 Life Sciences platform (Roche, Branford, Conn.) (Margulies et al., Nature, 437, 376-380 (2005)); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al., Genome Res. 16, 383-393 (2006); and U.S. Pat. Nos. 6,306,597, 7,598,035, 7,232,656), or DNA Sequencing by Ligation, SOLiD System (Applied Biosystems/Life Technologies; U.S. Pat. Nos. 6,797,470, 7,083,917, 7,166,434, 7,320,865, 7,332,285, 7,364,858, and 7,429,453); or the Helicos True Single Molecule DNA sequencing technology (Harris et al., Science, 320, 106-109 (2008); and U.S. Pat. Nos. 7,037,687, 7,645,596, 7,169,560, and 7,769,400), the single molecule, real-time (SMRTTm) technology of Pacific Biosciences, and sequencing (Soni et al., Clin. Chem. 53, 1996-2001 (2007)). These systems allow multiplexed parallel sequencing of many polynucleotides isolated from a sample (Dear, Brief Funct. Genomic Proteomic, 1(4), 397-416 (2003) and McCaughan et al., J. Pathol., 220, 297-306 (2010)). In some embodiments, polynucleotides are sequenced by sequencing by ligation of dye-modified probes, pyrosequencing, or single-molecule sequencing. Determining the sequence of a polynucleotide may be performed by sequencing methods such as Helioscope™ single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent™, Ion semiconductor sequencing, Single Molecule SMRT™ sequencing, Polony sequencing, DNA nanoball sequencing, and VisiGen Biotechnologies approach. Alternatively, determining the sequence of polynucleotides may use sequencing platforms, including, but not limited to, Genome Analyzer IIx, HiSeq, and MiSeq offered by Illumina, Single Molecule Real Time (SMRT™) technology, such as the PacBio RS system offered by Pacific Biosciences (California) and the Solexa Sequencer, True Single Molecule Sequencing (tSMS™) technology such as the HeliScope™ Sequencer offered by Helicos Inc. (Cambridge, Mass.). Sequencing can comprise MiSeq sequencing. Sequencing can comprise HiSeq sequencing. In some embodiments, determining the sequence of a polynucleotide comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of a polynucleotide can be determined by electron microscopy or a chemical-sensitive field effect transistor (chemFET) array.

A method can further comprise sequencing one or more polynucleotides in the library. A method can further comprise aligning one or more polynucleotide sequences, sequence reads, amplicon sequences, or amplicon set sequences in the library to each other.

Aligning can comprise comparing a test sequence, such as a sequence read, to one or more other test sequences, reference sequences, or a combination thereof. In some embodiments, aligning can be used to determine a consensus sequence from a plurality of sequences or aligned sequences. In some embodiments, aligning comprises determining a consensus sequence from a plurality of sequences that each has an identical molecular barcode or vessel barcode. In some embodiments, the length of a sequence aligned for comparison purposes is at least 30%, at least 40%, at least 50%, at least 60%, at least 70%, at least 80%, at least 90%, or at least 95%, of the length of a reference sequence. The actual comparison of the two or more sequences can be accomplished by well-known methods, for example, using a mathematical algorithm. A non-limiting example of such a mathematical algorithm is described in Karlin, S. and Altschul, S., Proc. Natl. Acad. Sci. USA, 90-5873-5877 (1993). Such an algorithm is incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In some embodiments, the percent identity between two amino acid sequences can be accomplished using, for example, the GAP program in the GCG software package (Accelrys, Cambridge, UK).

Sequencing can comprise sequencing at least about 10, 20, 30, 40, 50, 60, 70, 80, 90, 100 or more nucleotides or base pairs of the polynucleotides. In some embodiments, sequencing comprises sequencing at least about 200, 300, 400, 500, 600, 700, 800, 900, 1000, or more nucleotides or base pairs of the polynucleotides. In other instances, sequencing comprises sequencing at least about 1500, 2000, 3000, 4000, 5000, 6000, 7000, 8000, 9000, 10,000, or more nucleotides or base pairs of the polynucleotides.

Sequencing can comprise at least about 200, 300, 400, 500, 600, 700, 800, 900, 1000 or more sequencing reads per run. As used herein, a sequence read comprises a sequence of nucleotides determined from a sequence or stream of data generated by a sequencing technique. In some embodiments, sequencing comprises sequencing at least about 1500, 2000, 3000, 4000, 5000, 6000, 7000, 8000, 9000, 10,000, or more sequencing reads per run. Sequencing can comprise more than, less than, or equal to about 1,000,000,000 sequencing reads per run. Sequencing can comprise more than, less than, or equal to about 200,000,000 reads per run.

Enzymes

The methods and kits disclosed herein may comprise one or more enzymes. Examples of enzymes include, but are not limited to, ligases, reverse transcriptases, polymerases, and restriction nucleases.

In some embodiments, attachment of an adaptor to polynucleotides comprises the use of one or more ligases. Examples of ligases include, but are not limited to, DNA ligases such as DNA ligase I, DNA ligase III, DNA ligase IV, and T4 DNA ligase, and RNA ligases such as T4 RNA ligase I and T4 RNA ligase II.

The methods and kits disclosed herein may further comprise the use of one or more reverse transcriptases. In some embodiments, the reverse transcriptase is a HIV-1 reverse transcriptase, M-MLV reverse transcriptase, AMV reverse transcriptase, and telomerase reverse transcriptase. In some embodiments, the reverse transcriptase is M-MLV reverse transcriptase.

In some embodiments, the methods and kits disclosed herein comprise the use of one or more proteases.

In some embodiments, the methods and kits disclosed herein comprise the use of one or more polymerases. Examples of polymerases include, but are not limited to, DNA polymerases and RNA polymerases. In some embodiments, the DNA polymerase is a DNA polymerase I, DNA polymerase II, DNA polymerase III holoenzyme, and DNA polymerase IV. Commercially available DNA polymerases include, but are not limited to, Bst 2.0 DNA Polymerase, Bst 2.0 WarmStart™ DNA Polymerase, Bst DNA Polymerase, *Sulfolobus* DNA Polymerase IV, Taq DNA Polymerase, 9°N™m DNA Polymerase, Deep VentR™ (exo-) DNA Polymerase, Deep VentR™ DNA Polymerase, Hemo KlenTaq™, LongAmp® Taq DNA Polymerase, OneTaq® DNA Polymerase, Phusion® DNA Polymerase, Q5™ High-Fidelity DNA Polymerase, Therminator™ γ DNA Polymerase, Therminator™ DNA Polymerase, Therminator™ II DNA Polymerase, Therminator™ III DNA Polymerase, VentR® DNA Polymerase, VentR® (exo-) DNA Polymerase, Bsu DNA Polymerase, phi29 DNA Polymerase, T4 DNA Polymerase, T7 DNA Polymerase, Terminal Transferase, Titanium® Taq Polymerase, KAPA Taq DNA Polymerase and KAPA Taq Hot Start DNA Polymerase.

In some embodiments, the polymerase is an RNA polymerases such as RNA polymerase I, RNA polymerase II, RNA polymerase III, *E. coli* Poly(A) polymerase, phi6 RNA polymerase (RdRP), Poly(U) polymerase, SP6 RNA polymerase, and T7 RNA polymerase.

Additional Reagents

The methods and kits disclosed herein may comprise the use of one or more reagents. Examples of reagents include, but are not limited to, PCR reagents, ligation reagents, reverse transcription reagents, enzyme reagents, hybridization reagents, sample preparation reagents, affinity capture reagents, solid supports such as beads, and reagents for nucleic acid purification and/or isolation.

In other embodiments, the methods, kits, and compositions disclosed herein may comprise a support. In some embodiments, the methods, kits, and compositions disclosed herein do not comprise a support. Typically, a solid support comprises one or more materials comprising one or more rigid or semi-rigid surfaces. In some embodiments, the support is a non-solid support. The support or substrate may comprise a membrane, paper, plastic, coated surface, flat surface, glass, slide, chip, or any combination thereof. In some embodiments, one or more surfaces of a support are substantially flat, although in some embodiments it may be desirable to physically separate synthesis regions for different compounds with, for example, wells, raised regions, pins, etched trenches, or the like. In some embodiments, solid supports comprise beads, resins, gels, microspheres, or other geometric configurations. Alternatively, solid supports can comprises silica chips, microparticles, nanoparticles, plates, and arrays. The solid support can comprise the use of beads that self-assemble in microwells. For example, the solid support comprises Illumina's BeadArray Technology. Alternatively, the solid support comprises Abbott Molecular's Bead Array technology, and Applied Microarray's FlexiPlex™ system. In other instances, the solid support is a plate. Examples of plates include, but are not limited to, MSD multi-array plates, MSD Multi-Spot® plates, microplate, ProteOn microplate, AlphaPlate, DELFIA plate, IsoPlate, and LumaPlate. In some embodiments, a support can comprise a plurality of beads. In some embodiments, a support can comprise an array. In some embodiments, a support can comprise a glass slide. Methods, substrates, and techniques applicable to polymers (U.S. Pat. Nos. 5,744,305, 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752; US Patent Pub. Nos. 20090149340, 20080038559, 20050074787; and in PCT Publication Nos. WO 00/58516, WO 99/36760, and WO 01/58593). The attachment of the polynucleotides to a support may comprise amine-thiol crosslinking, maleimide crosslinking, N-hydroxysuccinimide or N-hydroxysulfosuccinimide, Zenon or SiteClick. Attaching the labeled nucleic acids to the support may comprise attaching biotin to the plurality of polynucleotides and coating the one or more beads with streptavidin. In some embodiments, the solid support is a bead. Examples of beads include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, polynucleotide dT conjugated beads, silica beads, silica-like beads, anti-biotin microbead, anti-fluorochrome microbead, and BcMag™ Carboxy-Terminated Magnetic Beads. The diameter of the beads may be about 5 µm, 10 µm, 20 µm, 25 µm, 30 µm, 35 µm, 40 µm, 45 µm or 50 µm. The solid support may be an array or microarray. The solid support may comprise discrete regions. The solid support may be an array, e.g., an addressable array.

A solid support can comprise virtually any insoluble or solid material, and often a solid support composition is selected that is insoluble in water. For example, a solid support can comprise or consist essentially of silica gel, glass (e.g., controlled-pore glass (CPG)), nylon, Sephadex®, Sepharose®, cellulose, a metal surface (e.g., steel, gold, silver, aluminum, silicon and copper), a magnetic material, a plastic material (e.g., polyethylene, polypropylene, polyamide, polyester, polyvinylidene difluoride (PVDF)) and the like. Examples of beads for use according to the embodiments can include an affinity moiety that allows the bead to interact with a nucleic acid molecule. A solid phase (e.g., a bead) can comprise a member of a binding pair (e.g., avidin, streptavidin or derivative thereof). For instance, the bead may be a streptavidin-coated bead and a nucleic acid molecule for immobilization on the bead can include a biotin moiety. In some cases, each polynucleotide molecule can include two affinity moieties, such as biotin, to further stabilize the polynucleotide. Beads can include additional features for use in immobilizing nucleic acids or that can be used in a downstream screening or selection processes. For example, the bead may include an affinity portion, a fluorescent label or a fluorescent quencher. In some cases, the bead can be magnetic. In some instances, the solid support is a bead. Examples of beads include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, polynucleotide-dT conjugated beads, silica beads, silica-like beads, anti-biotin microbead, anti-fluoro chrome microbead, and BcMag™ Carboxy-Terminated Magnetic Beads. Beads or particles may be swellable (e.g., polymeric beads such as Wang resin) or non-swellable (e.g., CPG). In some embodiments a solid phase is substantially hydrophilic. In some embodiments a solid phase (e.g., a bead) is substantially hydrophobic. In some embodiments a solid phase comprises a member of a binding pair (e.g., avidin, streptavidin or derivative thereof) and is substantially hydrophobic or substantially hydrophilic. In some embodiments, a solid phase comprises a member of a binding pair (e.g., avidin, streptavidin or derivative thereof) and has a binding capacity greater than about 1350 picomoles of free capture agent (e.g., free biotin) per mg solid support. In some embodiments the binding capacity of solid phase comprising a member of a binding pair is greater than 800, 900, 1000, 1100, 1200, 1250, 1300, 1350, 1400, 1450, 1500, 1600, 1800, 2000 picomoles of free capture agent per mg solid support. Other examples of beads that are suitable for the invention are gold colloids or beads such as polystyrene beads or silica beads. Substantially any bead radii may be used. Examples of beads may include beads having a radius ranging from 150 nanometers to 10 microns. Other sizes may also be used.

The methods and kits disclosed herein may comprise the use of one or more buffers. Examples of buffers include, but are not limited to, wash buffers, ligation buffers, hybridization buffers, amplification buffers, and reverse transcription buffers. In some embodiments, the hybridization buffer is a commercially available buffer, such as TMAC Hyb solution, SSPE hybridization solution, and ECONO™ hybridization buffer. The buffers disclosed herein may comprise one or more detergents.

The methods and kits disclosed herein may comprise the use of one or more carriers. Carriers may enhance or improve the efficiency of one or more reactions disclosed herein (e.g., ligation reaction, reverse transcription, amplification, hybridization). Carriers may decrease or prevent non-specific loss of the molecules or any products thereof (e.g., a polynucleotide and/or amplicon). For example, the carrier may decrease non-specific loss of a polynucleotide through absorption to surfaces. The carrier may decrease the affinity of a polynucleotide to a surface or substrate (e.g., container, Eppendorf tube, pipet tip). Alternatively, the carrier may increase the affinity of a polynucleotide to a surface or substrate (e.g., bead, array, glass, slide, chip). Carriers may protect the polynucleotide from degradation. For example, carriers may protect an RNA molecule from ribonucleases. Alternatively, carriers may protect a DNA molecule from a DNase. Examples of carriers include, but are not limited to, polynucleotides such as DNA and/or RNA, or polypeptides. Examples of DNA carriers include plasmids, vectors, polyadenylated DNA, and DNA polynucleotides. Examples of RNA carriers include polyadenylated RNA, phage RNA, phage MS2 RNA, *E. coli* RNA, yeast RNA, yeast tRNA, mammalian RNA, mammalian tRNA, short polyadenylated synthetic ribonucleotides and RNA polynucleotides. The RNA carrier may be a polyadenylated RNA. Alternatively, the RNA carrier may be a non-polyadenylated RNA. In some embodiments, the carrier is from a bacteria, yeast, or virus. For example, the carrier may be a polynucleotide or a polypeptide derived from a bacteria, yeast or virus. For example, the carrier is a protein from *Bacillus subtilis*. In another example, the carrier is a polynucleotide from *Escherichia coli*. Alternatively, the carrier is a polynucleotide or peptide from a mammal (e.g., human, mouse, goat, rat, cow, sheep, pig, dog, or rabbit), avian, amphibian, or reptile.

The methods and kits disclosed herein may comprise the use of one or more control agents. Control agents may include control polynucleotides, inactive enzymes, non-specific competitors. Alternatively, the control agents comprise bright hybridization, bright probe controls, nucleic acid templates, spike-in controls, PCR amplification controls. The PCR amplification controls may be positive controls. In other instances, the PCR amplification controls are negative controls. The nucleic acid template controls may be of known concentrations. The control agents may comprise one or more labels.

Spike-in controls may be templates that are added to a reaction or sample. For example, a spike-in template may be added to an amplification reaction. The spike-in template may be added to the amplification reaction any time after the first amplification cycle. In some embodiments, the spike-in template is added to an amplification reaction after cycle number 2, 3, 4, 5, 6, 7, 8, 9, 10, 11, 12, 13, 14, 15, 20, 25, 30, 35, 40, 45, or 50. The spike-in template may be added to the amplification reaction any time before the last amplification cycle. The spike-in template may comprise one or more nucleotides or nucleic acid base pairs. The spike-in template may comprise DNA, RNA, or any combination thereof. The spike-in template may comprise one or more labels.

Disclosed herein are molecules, materials, compositions, and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. For example, if a nucleotide or nucleic acid is disclosed and discussed and a number of modifications that can be made to a number of molecules including the nucleotide or nucleic acid are discussed, each and every combination and permutation of nucleotide or nucleic acid and the modifications that are possible are specifically contemplated unless specifically indicated to the contrary. This concept applies to all aspects of this application including, but not limited to, steps in methods of making and using the disclosed methods and compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

While some embodiments described herein have been shown and described herein, such embodiments are provided by way of example only. Numerous variations, changes, and substitutions will now occur to those skilled in the art without departing from the disclosure provided herein. It should be understood that various alternatives to the embodiments described herein can be employed in practicing the methods described herein.

Unless otherwise explained, all technical and scientific terms used herein have the same meaning as commonly understood by one of ordinary skill in the art to which this disclosure belongs. The following references contain embodiments of the methods and compositions that can be used herein: The Merck Manual of Diagnosis and Therapy, 18th Edition, published by Merck Research Laboratories, 2006 (ISBN 0-9119102); Benjamin Lewin, Genes IX, published by Jones & Bartlett Publishing, 2007 (ISBN-13: 9780763740634); Kendrew et al. (eds.), The Encyclopedia of Mol. Biology, published by Blackwell Science Ltd., 1994 (ISBN 0-632-02182-9); and Robert A. Meyers (ed.), Mol. Biology and Biotechnology: a Comprehensive Desk Reference, published by VCH Publishers, Inc., 1995 (ISBN 1-56081-569-8).

Standard procedures of the present disclosure are described, e.g., in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl (eds.), Academic Press Inc., San Diego, USA (1987)). Current Protocols in Molecular Biology (CPMB) (Fred M. Ausubel, et al. ed., John Wiley and Sons, Inc.), Current Protocols in Protein Science (CPPS) (John E. Coligan, et al., ed., John Wiley and Sons, Inc.), Current Protocols in Immunology (CPI) (John E. Coligan, et al., ed. John Wiley and Sons, Inc.), Current Protocols in Cell Biology (CPCB) (Juan S. Bonifacino et al. ed., John Wiley and Sons, Inc.), Culture of Animal Cells: A Manual of Basic Technique by R. Ian Freshney, Publisher: Wiley-Liss; 5th edition (2005), and Animal Cell Culture Methods (Methods in Cell Biology, Vol. 57, Jennie P. Mather and David Barnes editors, Academic Press, 1st edition, 1998).

EXAMPLES

Example 1

Immunotyping of Single T-lymphocytes in a Population of T-cells

The immunophenotyping methods described herein were validated by analyzing both CD4 and CD8 mRNA and surface protein expression in human T lymphocytes (FIG. 1). Canonically, mature T-cells are expected to be either the CD4 subtype or the CD8 subtype. A CD4 subtype should express CD4 mRNA and CD4 protein together, but should express either CD8 mRNA or CD8 protein. A CD8 subtype should express CD8 mRNA and CD8 protein together, but should express either CD4 mRNA or CD4 protein.

30,000 T-cells were incubated with both a CD4-specific antibody-oligonucleotide comprising a CD4 Antigen ID sequence and a CD8-specific antibody-oligonucleotide comprising a CD8 Antigen ID sequence. The CD4, CD8 and TCR mRNA content of the T-cells were also analyzed in a single-cell emulsion experiment. The T-cell receptor alpha, T-cell receptor beta, CD4 and CD8 mRNA were reverse transcribed to cDNA and a droplet-specific barcode sequence was fused to both the cDNA and antibody-conjugated oligonucleotides through a polymerase chain reaction. This DNA was extracted from the emulsion and analyzed with next generation sequencing.

Almost all droplet-barcodes (related to a single cell) were associated with either the CD4-specific Antigen ID or the CD8-specific Antigen ID. Substantial agreement was found between the mRNA and surface protein-based assignments (FIG. 3).

Example 2

Sequencing of the immune repertoire has wide applications in basic immunology, autoimmunity, infectious disease and oncology. While many studies have investigated BCR and TCR diversity in circulating blood, there is growing interest in the immune receptors of TILs, whose functions are highly relevant to cancer growth or regression yet variable and often uncharacterized. A critical step towards a better understanding of TILs will be recovery and functional characterization of their BCRs and TCRs, since this may allow the identification of new tumor-associated antigens. Tumor antigens are critically required to develop cancer vaccines, understand the role of checkpoint inhibitors, and advance chimeric antigen receptor T-cell (CAR-T) therapy in solid tumors. However, despite decades of technical progress in immune sequencing, no study has recovered full-length, natively paired BCRs (heavy and light chains) and TCRs (alpha and beta chains) from a heterogeneous sample such as a tumor without in vitro culture or cell sorting, steps that restrict and bias the observed repertoire. The technical challenge is particularly high since primary uncultured immune cells can contain 100-fold less receptor RNA than in vitro stimulated cells. To allow comprehensive analysis of natively paired BCRs and TCRs from complex heterogeneous samples a microfluidic emulsion-based method was developed for parallel isolation and DNA barcoding of large numbers of single cells. Up to a million cells per hour are isolated in individual ~65 picoliter emulsion droplets. Within the droplets cells are lysed, target mRNA is reverse transcribed with target-specific primers and a two-step DNA barcoding process attaches both molecule-specific and droplet-specific barcodes to the cDNAs.

After subsequent recovery and next generation sequencing, the dual barcoding strategy allows clustering of sequence reads into both their molecules and cells of origin. This allows extensive correction of errors and amplification biases, clone counting at both the mRNA and cellular levels, heavy chain isotype determination, and importantly, recovery of full-length, natively paired V(D)J sequences of BCR and TCRs simultaneously at extremely high throughput.

Tumor-infiltrating lymphocytes (TILs) are critical to anti-cancer immune responses, but are challenging to study due to their unpredictable abundance, phenotypes and function. A method for deep TIL characterization without the need for cell-sorting, stimulation or culture was developed by the inventors. The emulsion-based, single-cell barcoding method captures natively paired B-cell and T-cell receptor (BCR and TCR) sequences from lymphocytes among millions of input cells. In contrast to previous approaches the recovered variable regions are full-length and can be accompanied by additional mRNA and protein targets. The method was validated with 3 million B-cells from healthy human blood and 350,000 B-cells from an HIV patient before processing 400,000 unsorted cells from an ovarian adenocarcinoma, recovering paired BCRs and TCRs from over 11,000 TILs. Our results represent the deepest sampling of any paired BCR or TCR repertoire as well as the first demonstration of simultaneous RNA sequencing and protein measurements from single-cells in emulsion.

Example 3

Large Scale Recovery of B-cell $V_H V_L$ Pairs from a Healthy Blood Sample

The technology was initially developed and pairing capability and throughput was assessed with 3 million B-cells isolated by negative bead enrichment from peripheral blood of a healthy volunteer. The emulsion was split across six separate fractions which were processed in parallel and not remixed prior to sequencing. The emulsion was loaded at 0.2 cells per droplet, giving a Poisson expectation that ~90% of occupied droplets contain single cells, which was consistent with emulsion droplet observations (FIG. 5A). After emulsion breaking and additional library processing steps paired-end 325+300 bp sequencing was performed with Illumina MiSeq. To process the sequencing data, the droplet and molecular barcodes were used together to collect PCR replicate reads from each original mRNA molecule, and determined a consensus for each mRNA keeping only mRNA sequences built from at least two reads. Forward and reverse reads were stitched to generate full-length products comprising the 5' UTR, complete V(D)J sequence, and constant region sufficient for isotype determination. Rearranged immunoglobulin heavy and light chain sequences were annotated with IMGT High-VQuest and/or IgBLAST.

The resulting dataset contained 324,988 droplet barcodes that were associated with at least one heavy chain ($V_H$) and one light chain ($V_L$) mRNA, with 229,869 distinct $V_H$ clonal lineages present as estimated by heavy chain clustering analysis. Since this raw set includes data from multi-cell as well as single-cell droplets, data from single-cell droplets was enriched by filtering out droplet barcodes linked to non-unanimous heavy or light chain V(D)J sequences (FIG. 5B). This step is made possible by the high diversity of typical immune repertoires, in which $V_H$ or $V_L$ mRNAs from two random cells will almost never match. The resulting enriched dataset comprised 259,368 $V_H V_L$ droplet barcodes and contained 182,745 $V_H$ clonal lineages, representing comfortably the deepest sampling of a paired immune repertoire to date. Precision of the $V_H V_L$ pairings by identifying incidences of clonal expansion was directly estimated, since clonally related cells should show consistency in their $V_H V_L$ pairings. 2,604 $V_H$ clones were identified that were observed in more than one emulsion fraction with high confidence to be clonally expanded cells. The consistency of $V_L$ sequences paired with these $V_H$ clones across fractions was very high and indicated a pairing precision of 96.1%, allowing high confidence in the entire filtered dataset of 259,368 $V_H V_L$ pairs. The cross-fraction $V_H$ and $V_L$ sequences were invariably associated with different droplet and molecular barcodes in each fraction and thus did not represent library cross-contamination. The analysis may underestimate pairing precision since some B-cells are known to express multiple light chains. 75.0% of the 259,368 filtered $V_H V_L$ droplet barcodes or "$V_H V_L$ pairs" contained IgM and/or IgD (FIG. 5C), which were frequently observed together as expected given the typical IgM$^+$IgD$^+$ phenotype of naïve B-cells. Lower but substantial fractions of IgA (18.3%) and IgG (6.6%) $V_H V_L$ pairs were also found. All $V_H$ isotypes were paired with either Igκ or Igλ in a ~3:2 ratio. Among the 182,745 $V_H$ clonal lineages clone expansion was assessed in two ways: the number of droplet barcodes associated with a clone and observation of the clone across emulsion fractions. Clones seen in multiple droplet barcodes could reflect clonal expansion or multi-barcode droplets, which are expected in ~37% of droplets given the initial λ=1 Poisson dispersal of barcodes into droplets. However, any clone represented by >8 droplet barcodes is likely to be genuinely expanded (Poisson probability in a single droplet <10-6). While overall 6.0% of clones were seen in more than one fraction, for the clones seen in more than 8 droplet barcodes (0.7% overall), 99% of them were seen in more than one fraction. The 100 most frequent clones (30-137 droplet barcodes each, FIG. 5D) were all seen in at least five of six fractions. A combination of barcode counting and independent fraction analysis thus allows detection of rare expanded lineages amongst a vast background of non-expanded clones. Notably however, even the most abundant expanded clone was present at less than one cell in a thousand, exemplifying the huge diversity of human peripheral immune repertoires.

Figure 2:
FIG. 2 depicts an exemplary design of oligonucleotide tag conjugated to an antibody. Each colored block represents a portion of the complete oligonucleotide sequence. The fusion sequence is used for enzymatic attachment of a droplet-specific DNA barcode inside the emulsion reaction. Only one possible arrangement of the sequences is shown, although other arrangements are compatible with the method described.
Figure 3B:
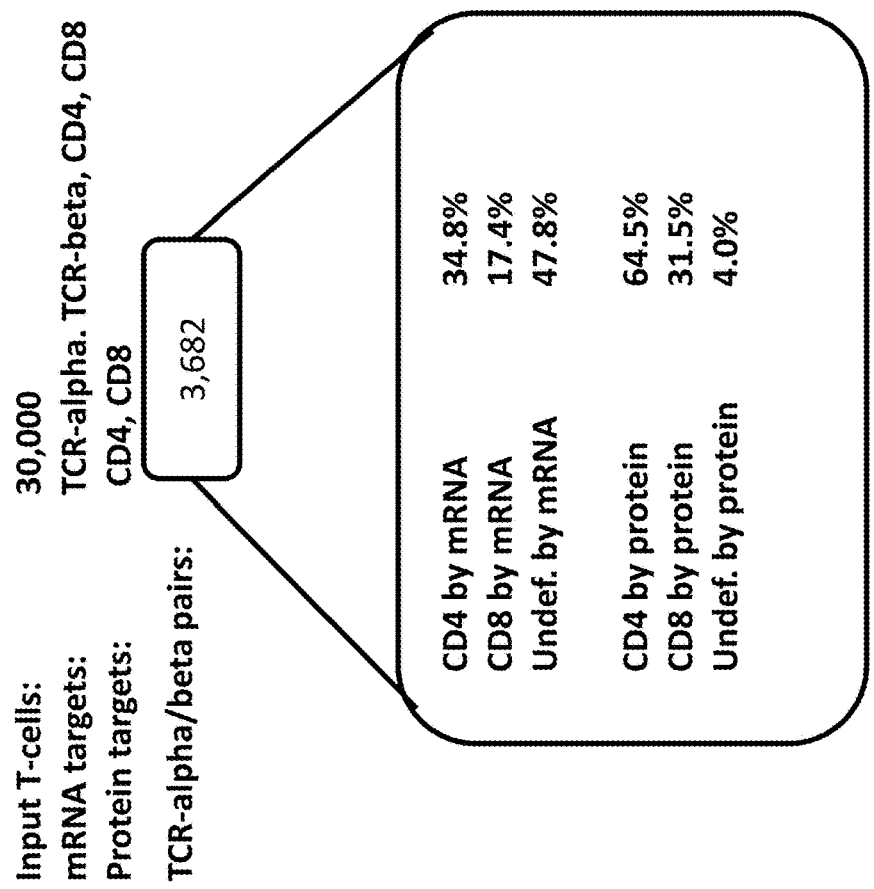
FIG. 3B depicts an exemplary CD4 and CD8 mRNA and protein measurements on 3,682 droplet barcode TCR VαVβ pairs generated from healthy human T-cells.
Figure 3A:
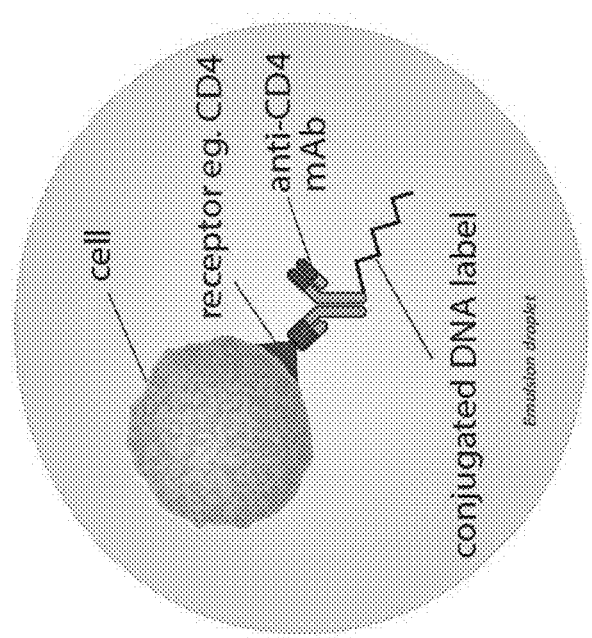
FIG. 3A depicts an exemplary co-capture of immune receptor sequences with additional mRNA and protein targets. Surface protein targets are quantified by pre-incubating cells with DNA-labeled staining antibodies prior to emulsion sequencing.
Figure 3C:
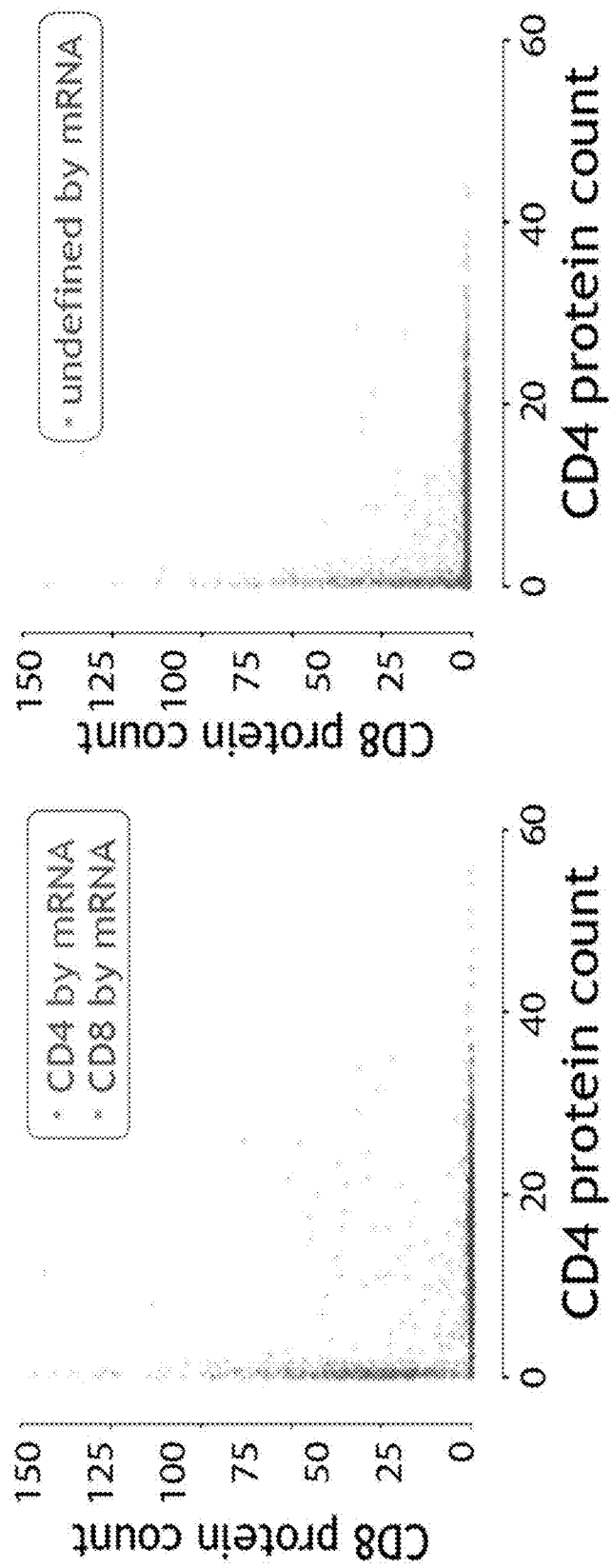
FIG. 3C depicts an exemplary concordance between mRNA and protein measurements (each point is a droplet barcode linked to a TCR VαVβ pair).
Figure 3E:
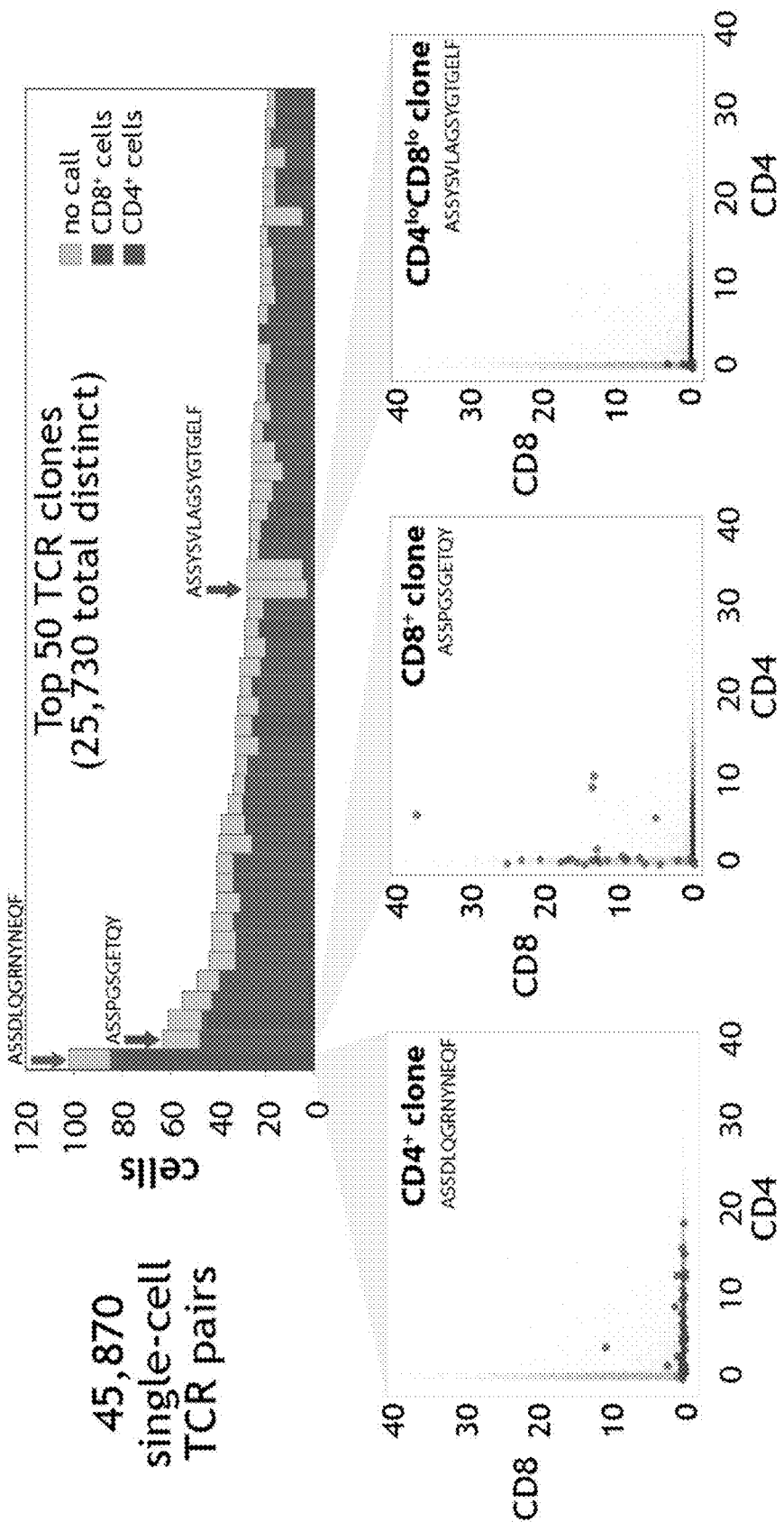
FIG. 3E depicts exemplary results from 45,870 single cell TCR pairs using an affinity-oligonucleotide conjugate targeting CD4 and an affinity-oligonucleotide conjugate targeting CD8.
Figure 4:
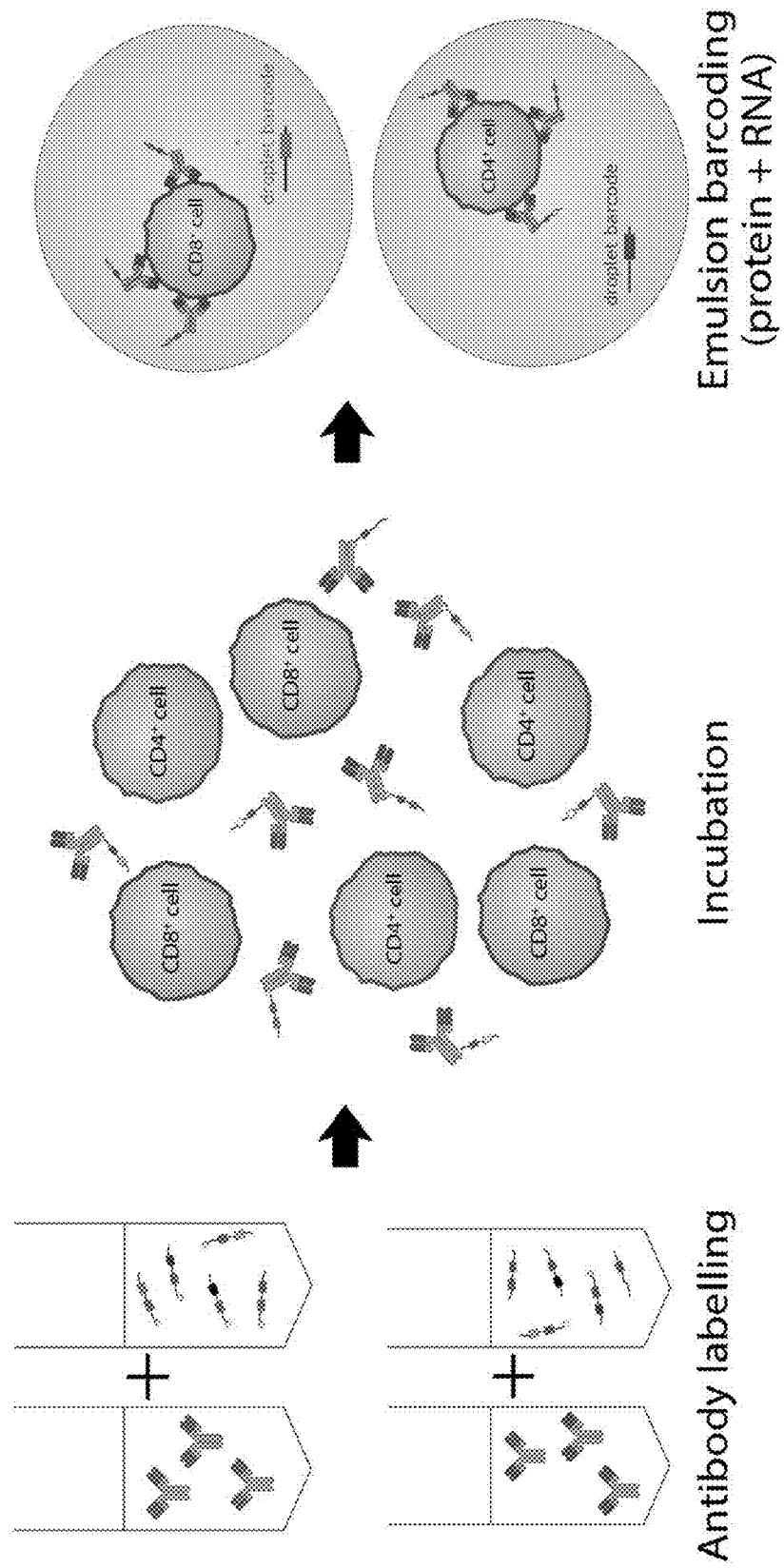
FIG. 4 depicts a schematic of an exemplary method using an affinity-oligonucleotide conjugate targeting CD4 and an affinity-oligonucleotide conjugate targeting CD8.
Figure 9A:
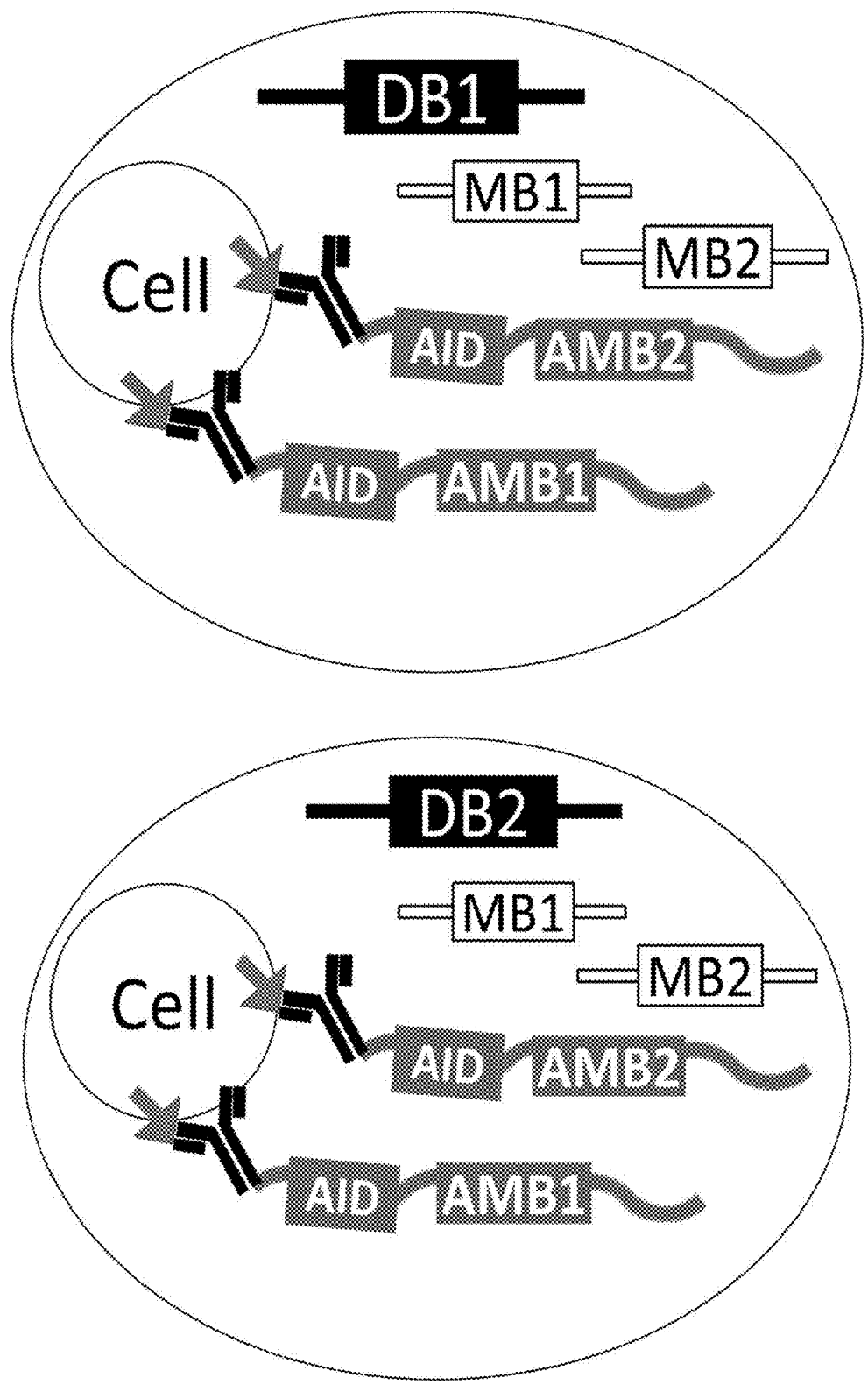
FIG. 9A, FIG. 9B, FIG. 9C, FIG. 9D, and FIG. 9E exemplify a method of immunophenotyping using antibody-oligonucleotide conjugates.
Figure 9B:
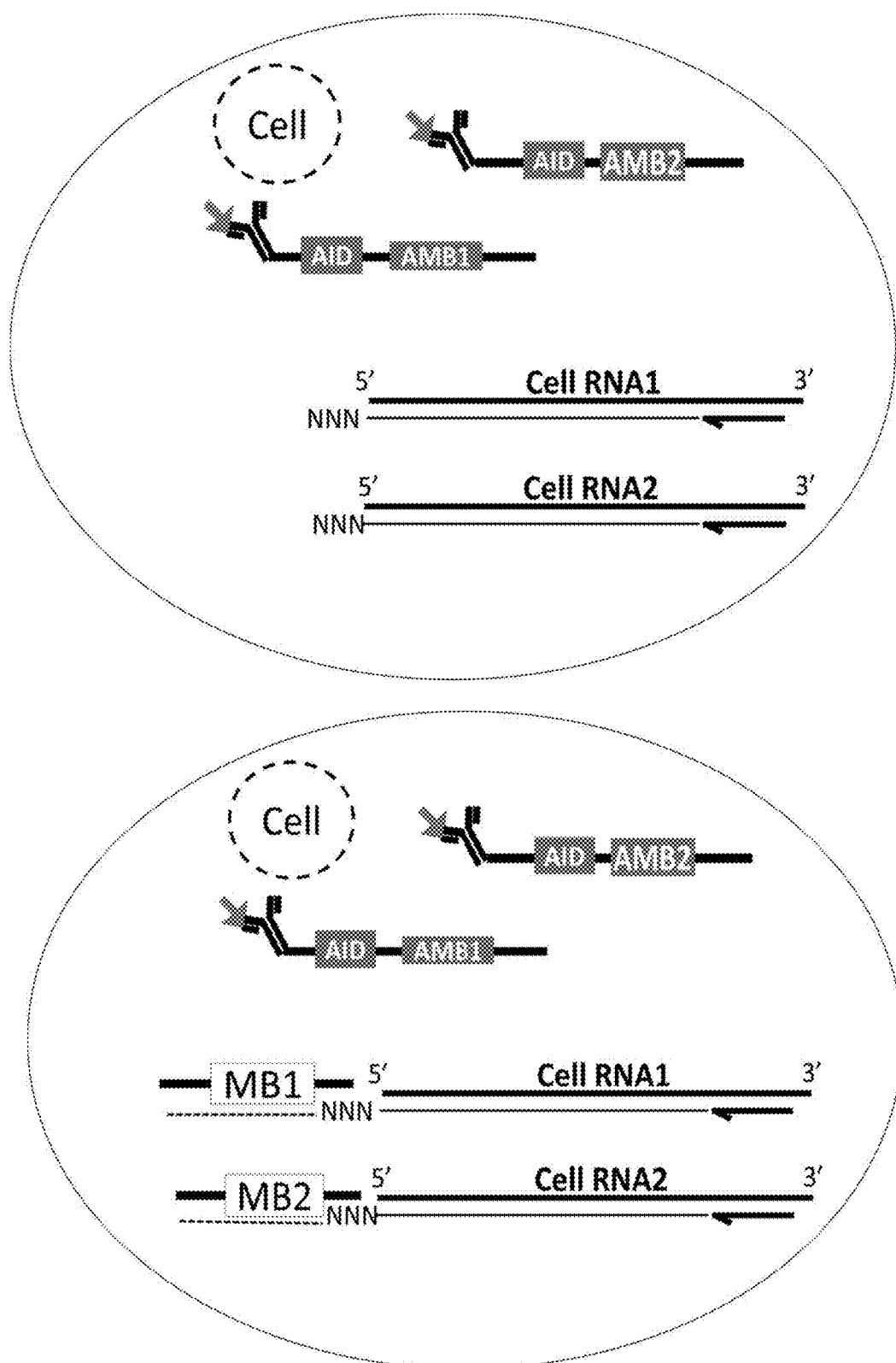
Figure 9C:
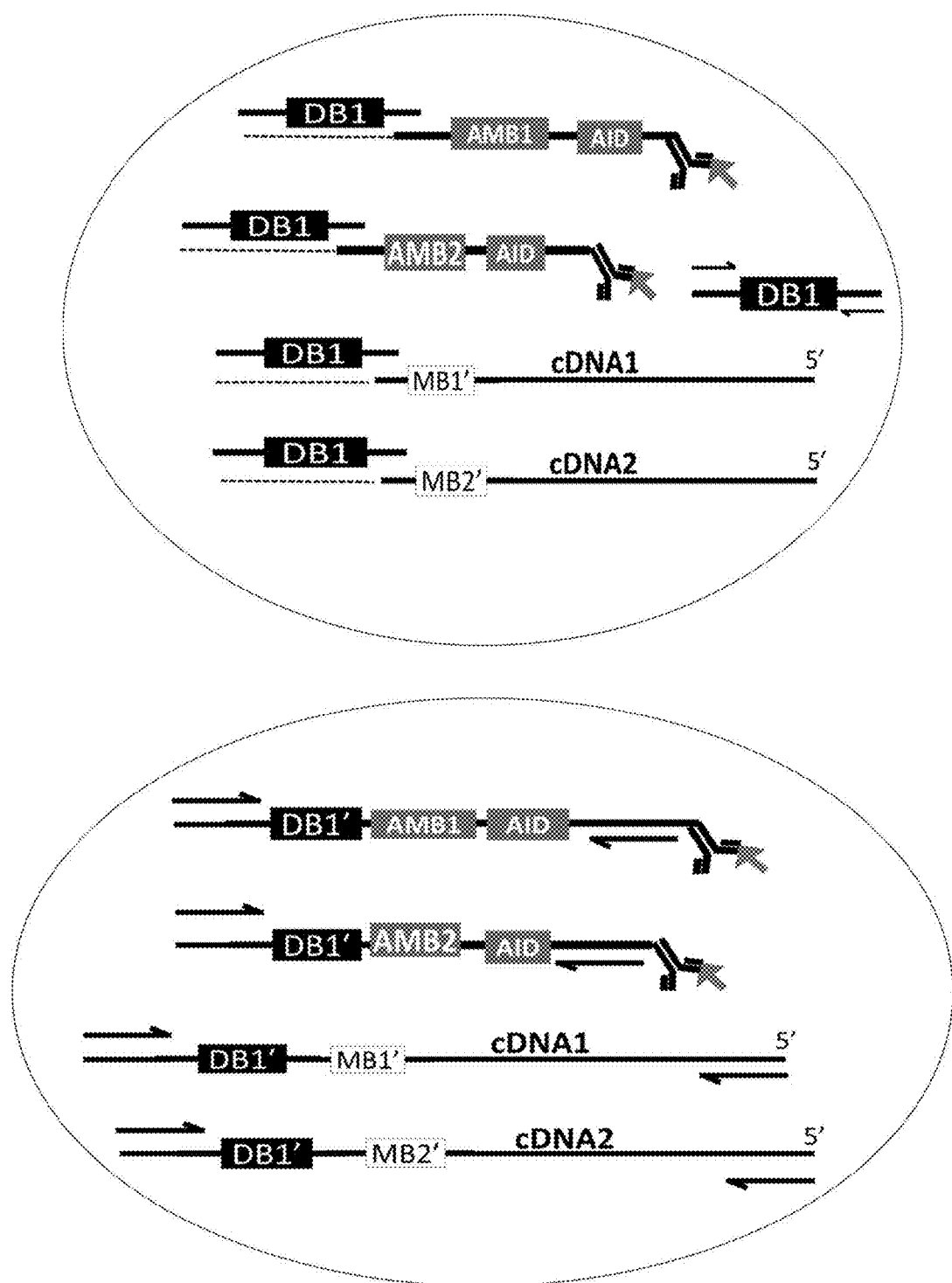
Figure 9D:
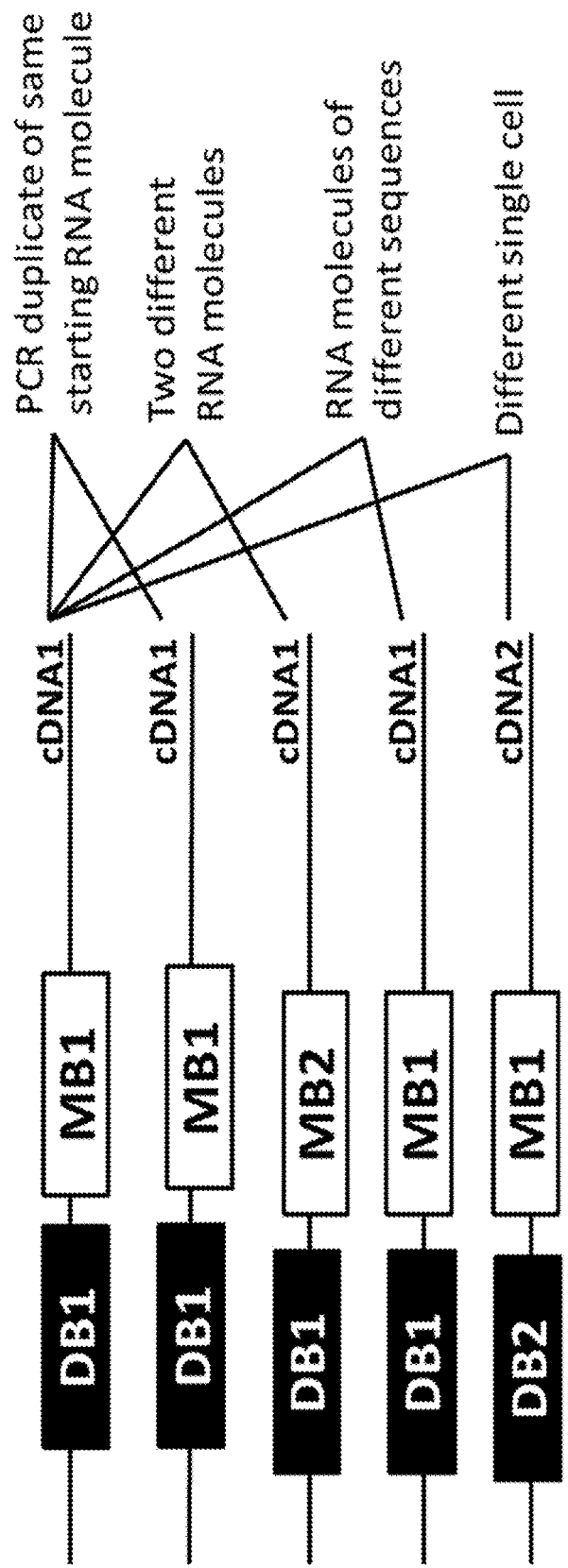
Figure 9E:
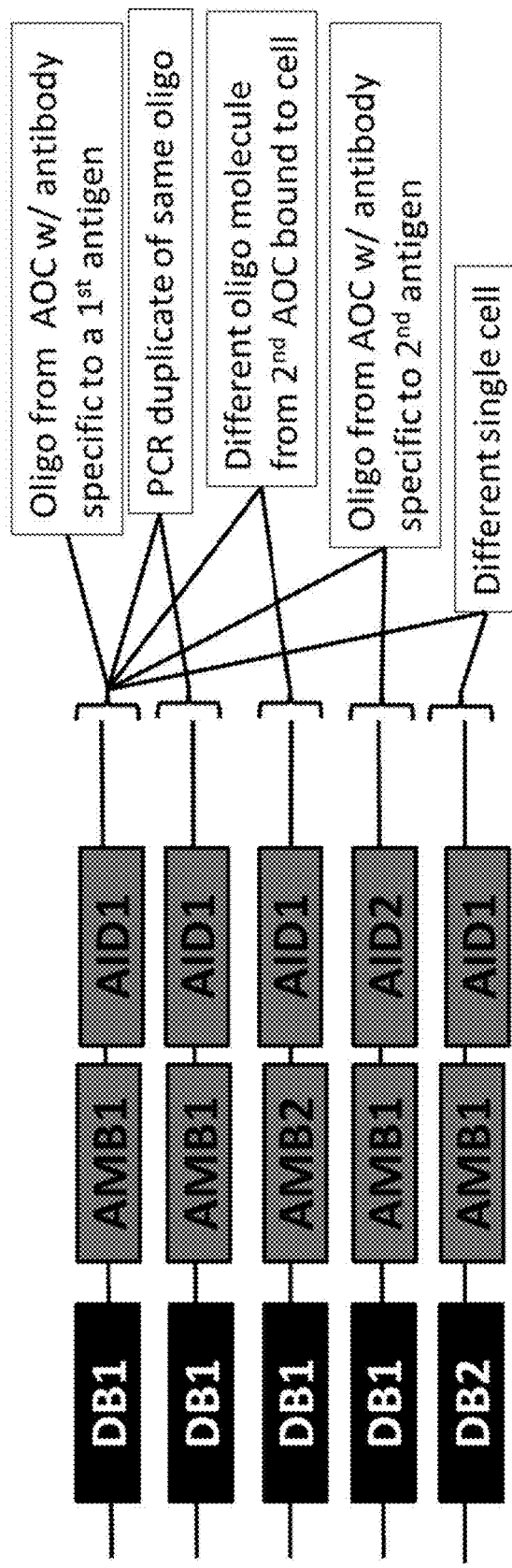
Figure 10A:
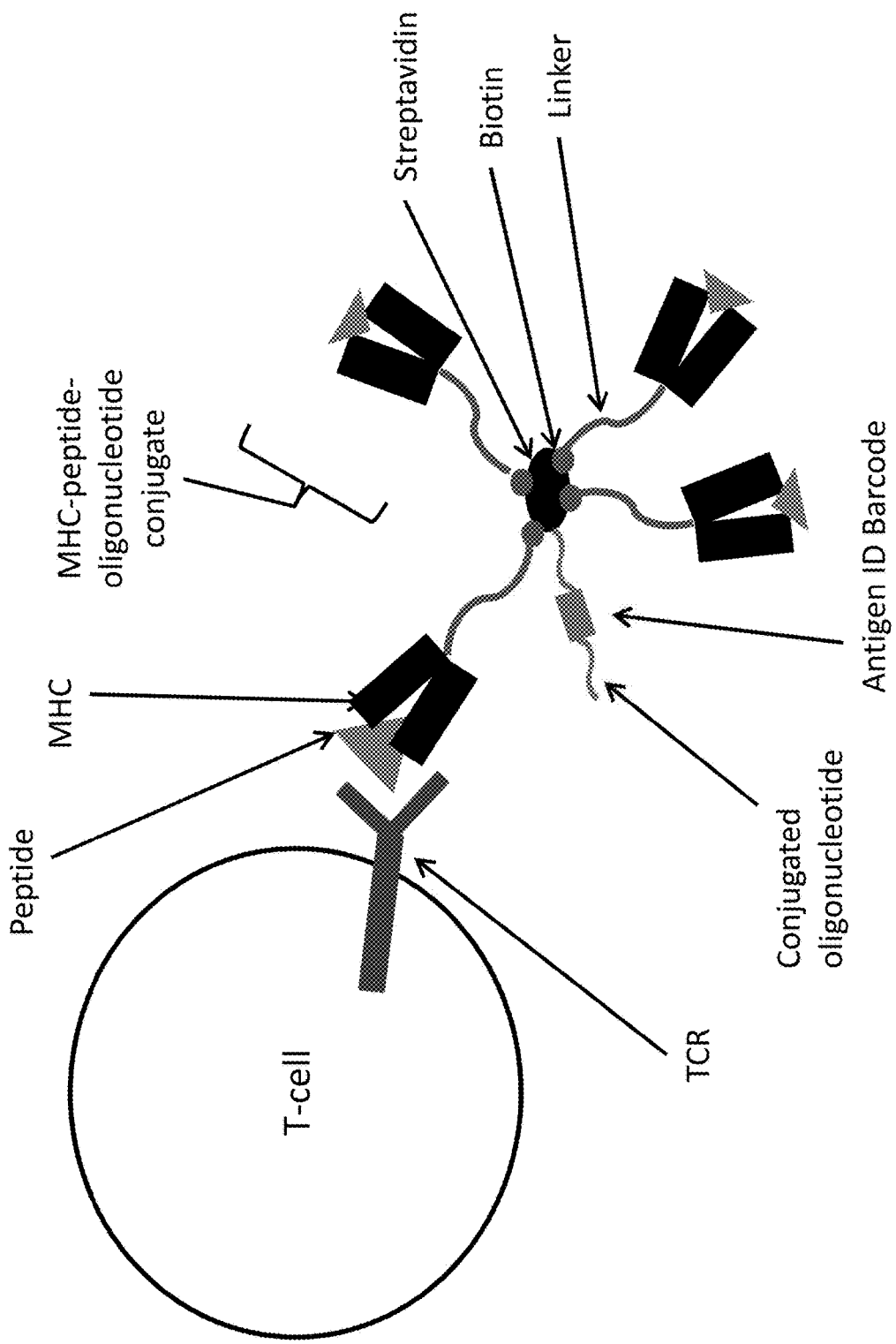
FIG. 10A depicts a schematic of an exemplary affinity-oligonucleotide conjugate of the methods described herein. As depicted, an exemplary affinity-oligonucleotide conjugate may comprise an MHC-peptide affinity portion. In some aspects, such conjugates may be referred to as tetramer-oligonucleotide conjugates.
Figure 10B:
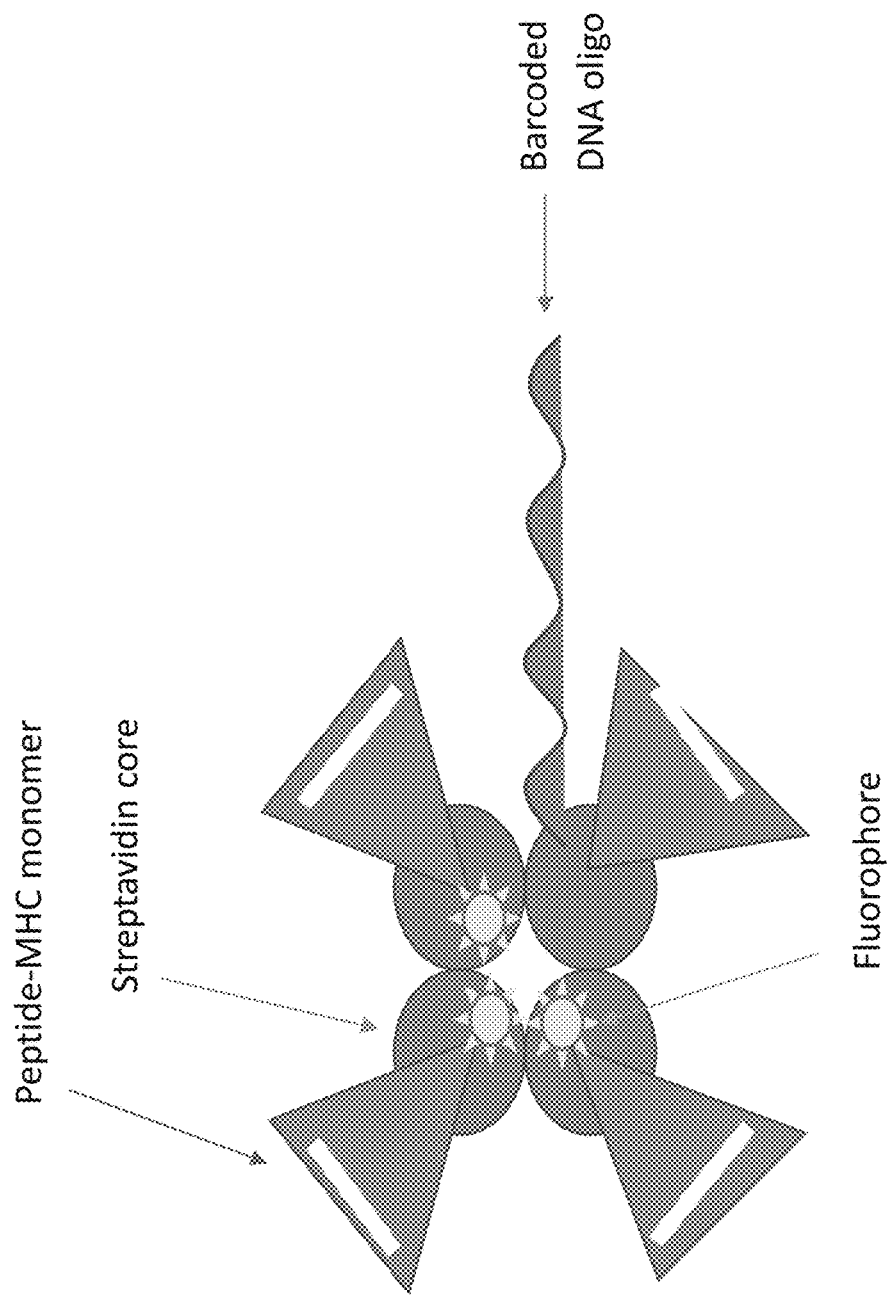
FIG. 10B depicts a schematic of an exemplary affinity-oligonucleotide conjugate of the methods described herein. In some aspects, such conjugates may be referred to as tetramer-oligonucleotide conjugates.
Figure 11A:
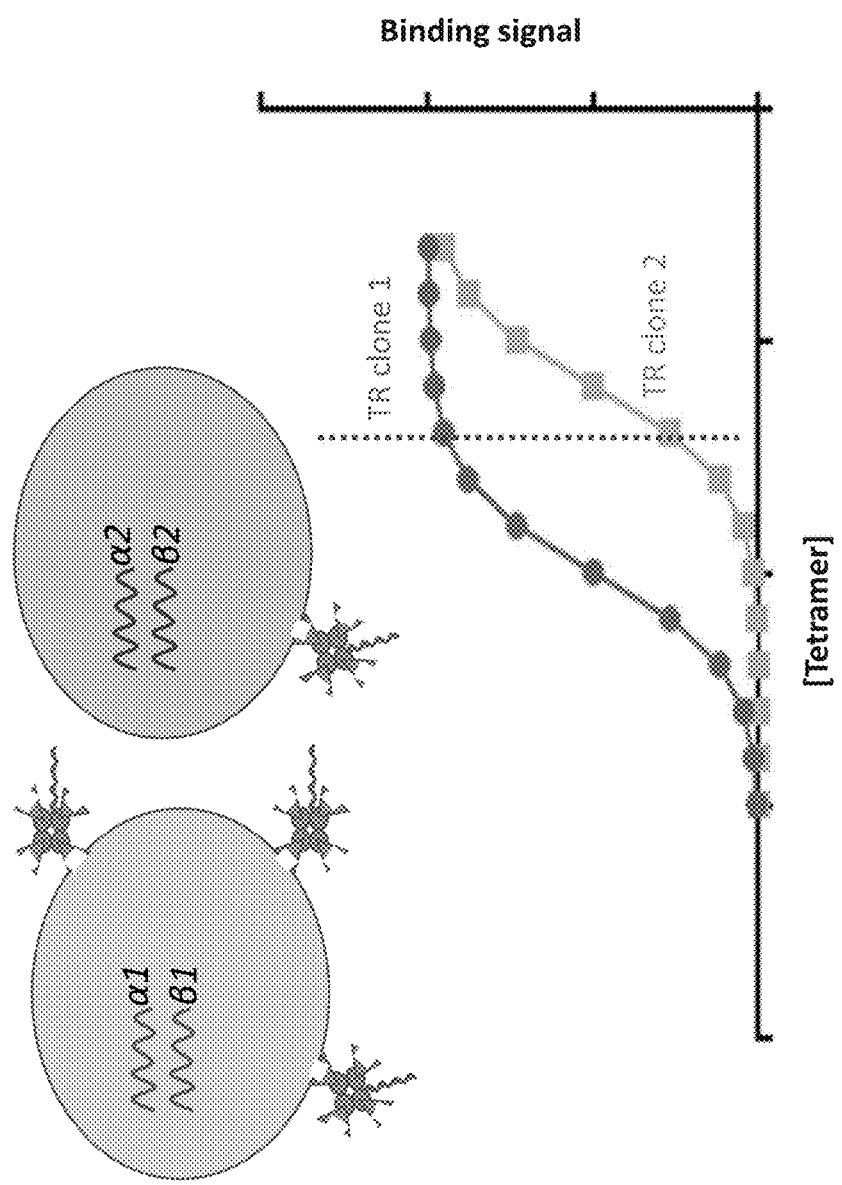
FIG. 11A depicts an exemplary graph of binding signal for two exemplary affinity-oligonucleotide conjugates of the methods described herein that contain an affinity portion that binds to a TCR.
Figure 12B:
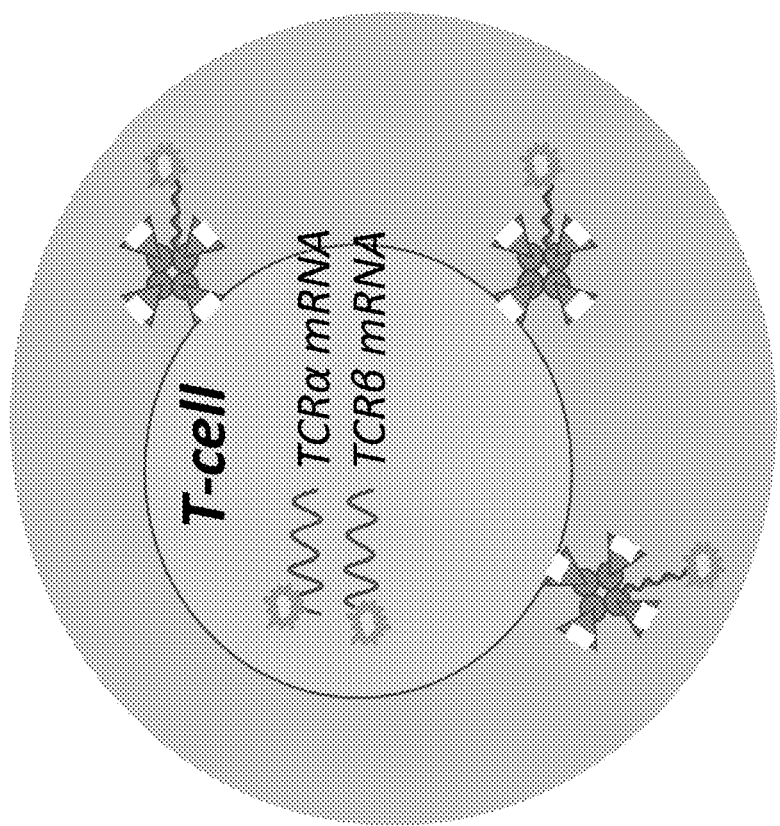
FIG. 12B depicts an exemplary schematic of a T-cell in a droplet bound to an exemplary affinity-oligonucleotide conjugate of the methods described herein. Nucleic acids in the droplet are marked with droplet-identifying sequence and incorporated into a next-generation sequencing library.
Figure 12A:
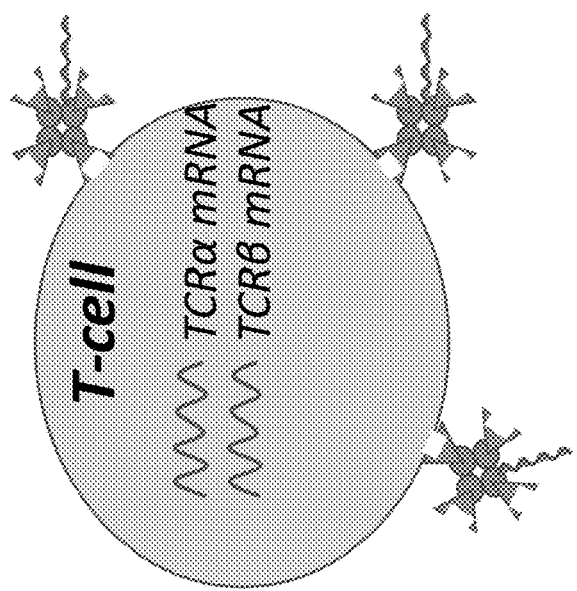
FIG. 12A depicts an exemplary schematic of a T-cell bound to an exemplary affinity-oligonucleotide conjugate of the methods described herein.
Figure 13:
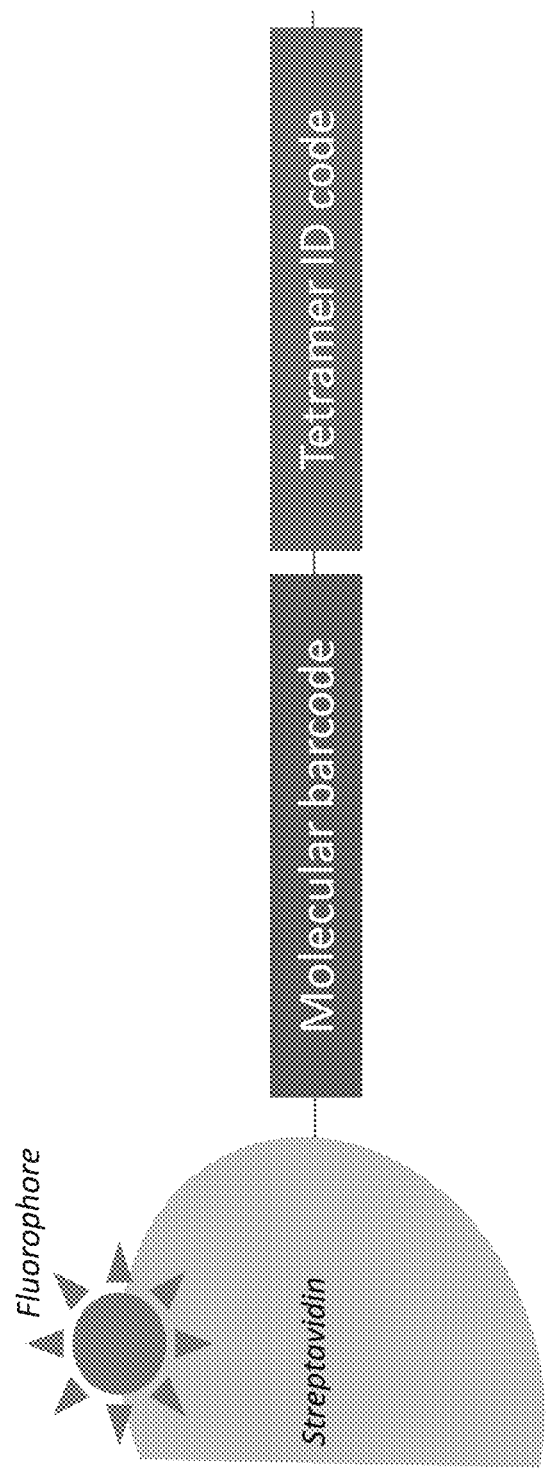
FIG. 13 depicts an exemplary schematic of an oligonucleotide tag conjugated to an exemplary affinity-oligonucleotide conjugate tetramer. The tetramer ID is a short constant DNA sequence that corresponds to a tetramer batch and allows multiplexing of different targets, such as peptide-MHC targets, in single experiment. The molecular barcode is a degenerate sequence that allows for molecular counting for quantification of bound tetramers.
Figure 14:
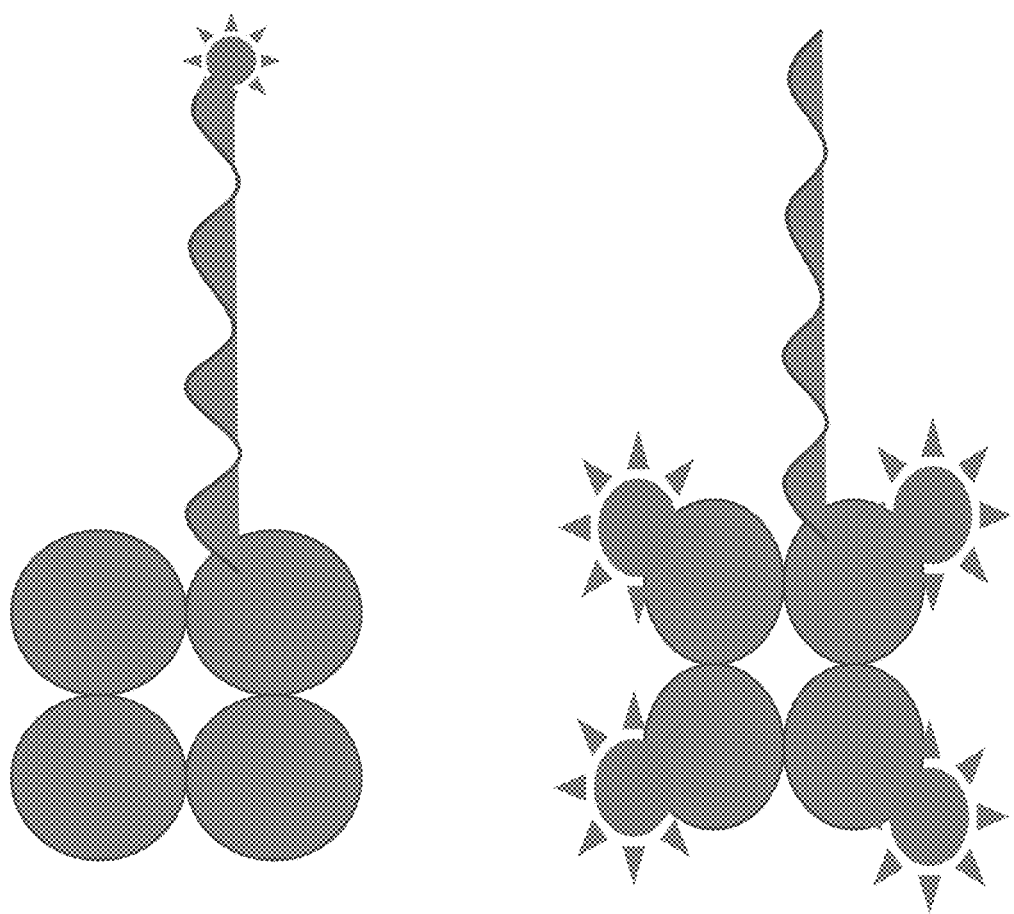
FIG. 14 depicts schematics of an exemplary affinity-oligonucleotide conjugate generated from DNA-labeled MHC tetramer reagents (tetramer-oligonucleotide conjugate). In one embodiment, a Cy5-linked DNA oligonucleotide is synthesized and conjugated to streptavidin or neutravidin. In one embodiment, a non-fluorescent DNA oligonucleotide is conjugated to an APC-streptavidin. In one embodiment, a mixture of non-fluorescent DNA oligonucleotide and streptavidin or neutravidin is conjugated to an activated APC.
Figure 15:
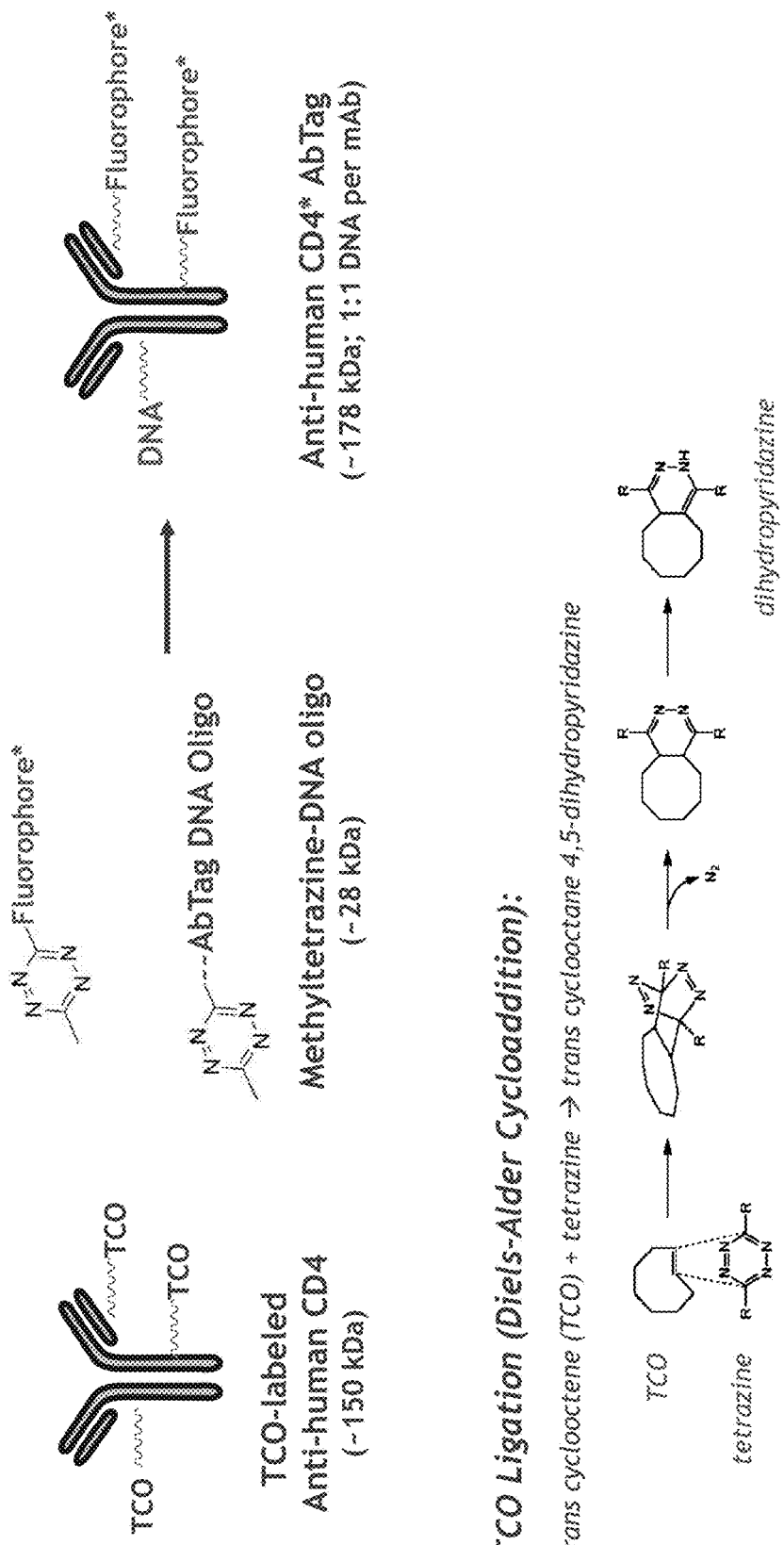
FIG. 15 depicts an exemplary method of conjugating an oligonucleotide to an affinity portion of an affinity-oligonucleotide conjugate using click-chemistry.
Figure 16:
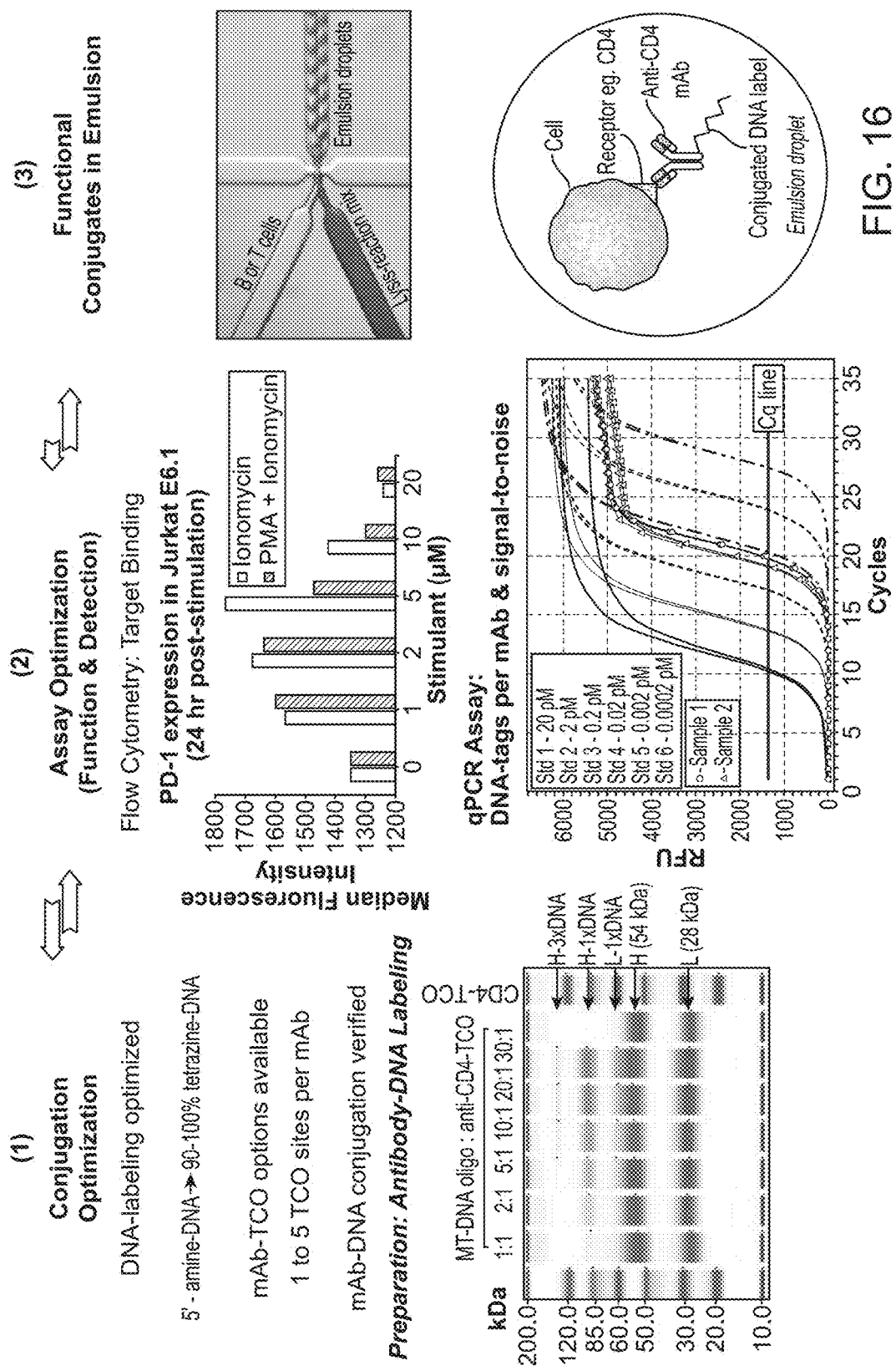
FIG. 16 depicts a schematic of an exemplary workflow for preparing and characterizing exemplary affinity-oligonucleotides.
Figure 17:
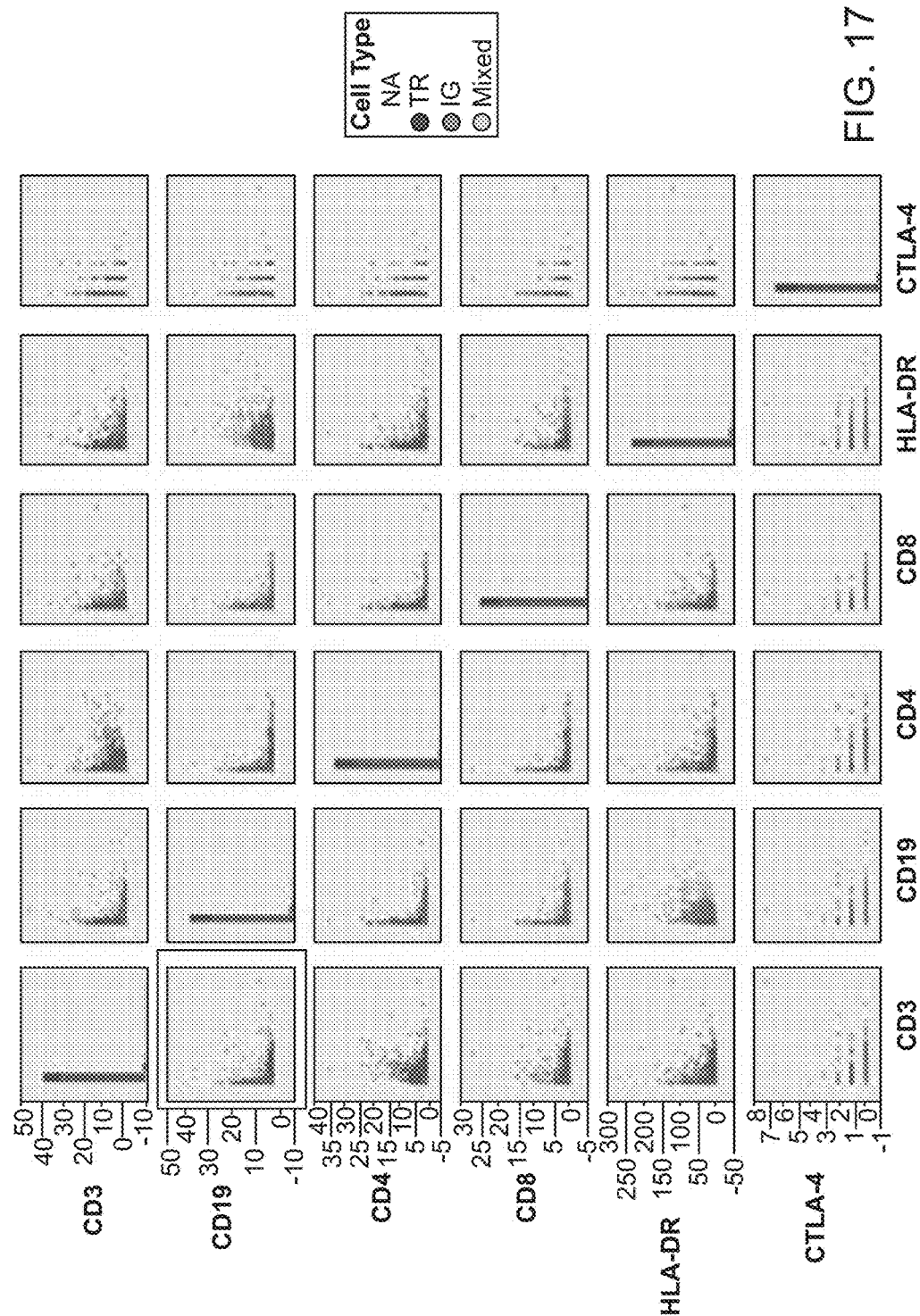
FIG. 17 depicts results from an exemplary method described herein using 6 different affinity-oligonucleotide conjugates targeting CD3, CD19, CD4, CD8, HLA-DR, and CTLA-4. Each point is a droplet barcode/single cell. Cell identity was revealed by the type of receptor pair recovered (TCR=T-cell; Ig=B-cell).

The number of captured mRNAs of each $V_H$ and $V_L$ chain within pairs as an estimate of expression level (FIG. 5E). Generally less than ten heavy chain (mean 2.0) and light chain (mean 4.0) mRNAs were captured per droplet barcode, a small population of droplet barcodes with dozens to hundreds of captured heavy and light chain mRNAs per cell was observed, almost exclusively from IgG and IgA expressing cells. Interestingly the degree of $V_H$ and $V_L$ mutation within pairs was strongly correlated both within each isotype (e.g., $V_H$ vs $V_L$ for IgG) and between isotypes (e.g., IgG vs IgM) (FIG. 2F). Furthermore, IgG and IgA pairs were almost all substantially mutated in both their $V_H$ and $V_L$ chains, whereas IgM and IgD pairs mostly showed little $V_H$ or $V_L$ mutation. These results are consistent with the mechanism of B-cell activation leading to class-switching from IgM and IgD to IgG or IgA, increased immunoglobulin expression and somatic hypermutation that affects both heavy and light chain loci in the cell. In addition to this observation that highly mutated $V_H$ chains tend to be paired with highly mutated $V_L$ chains, this method is capable of generating large numbers of full-length, natively paired BCRs from resting human B-cell repertoires.

Example 4

Recovery of Known Low Frequency $V_HV_L$ Pairs from an HIV Elite Controller

As a further validation of the pairing sensitivity and accuracy of the assay, a sample was processed where several rare (<1 cell in 10,000) native $V_HV_L$ pairings are already and publically known. Peripheral B-cells from an HIV elite controller patient were obtained whose memory B cells have been mined heavily in recent years for antibodies displaying HIV neutralization activity. 350,000 B-cells were processed to generate a total of 38,620 filtered $V_HV_L$ pairs. Interestingly, this individual showed a greater proportion of IgG than the previous healthy sample (FIG. 3A) or typical healthy peripheral B-cell repertoires. $V_H$ sequences from this dataset were compared to all reported broadly neutralizing antibodies (bNAbs) from this individual including PGT121 and found eight close or identical $V_H$ sequences, indicating that this family of bNAbs represents less than 0.03% of circulating B-cells. Crucially, all light chains paired to these heavy chains were of the expected and similarly rare bNAb lineage, displaying the same Igλ-V3-21/J3 rearrangement and hallmark triple codon insertion as previously reported, supporting the high accuracy and sensitivity of our method. Furthermore, on a phylogenetic tree of all known and newly generated PGT121-like $V_HV_L$ pairs from this individual (FIG. 3B), the $V_H$ and $V_L$ trees show strikingly similar topology with paired $V_H$ and $V_L$ sequences occupying mirror-like positions, likely reflecting shared phylogenetic history. The variant pairs discovered here fit well with this rule. Interestingly, two published antibodies PGT122 and PGT123 appear as exceptions; support for these two pairings was not found, but instead PGT122$V_H$:PGT123$V_L$-like, and PGT123$V_H$:PGT 122$V_L$-like pairs were found, addressing the unverified pairing in the original report. DNA encoding the complete V(D)J regions of 8 novel PGT-like $V_HV_L$ pairs were synthesized, expressed the antibodies as full IgG and tested their ability to neutralize multiple pseudostrains of HIV (FIG. 6C). The antibodies expressed well and all showed strong neutralizing activity against the virus, demonstrating the utility of our approach in rapidly generating natively paired functional antibody variants from a relevant biological sample.

Example 5

B-cell and T-cell Receptor Pairs from Tumor Infiltrating Lymphocytes

Having validated emulsion barcoding for high throughput recovery of paired receptors, immune receptors were recovered directly from a tumor. A protease-dissociated resected ovarian adenocarcinoma sample was taken and entered 400,000 unsorted cells into emulsion. CD3/CD19 staining of a separate aliquot of the sample suggested substantial numbers of infiltrating B (~5%) and T cells (~20%) among the material. Single cell dispersal in the emulsion was similar to purified cells albeit with some limited clumping visible, and extensive variation in cell size and shape within the droplets as expected given the cell type heterogeneity of the sample (FIG. 7A).

Primers targeting the constant regions of T-cell receptor alpha and beta chains together were used with the BCR primers used previously, and following sequencing and stringent filtering recovered thousands of droplet barcodes linked to BCR or TCR products. To assess single cell precision all possible combinations of the four target loci ($V_H$, $V_L$, Vα, Vβ) within droplet barcodes were counted (FIG. 7B). The vast majority (97.9%) of droplet barcodes with more than one target chain contained biologically expected pairings of BCR $V_H$+$V_L$ or TCR Vα+Vβ with only 2.1% containing mixed BCR-TCR combinations. Since barcoding of products is unbiased with respect to target chain, this result allows a high degree of confidence in the resulting 6,056 BCR $V_HV_L$ and 5,217 TCR VαVβ pairs. The BCRs showed striking dominance of IgG (>80%) compared to other isotypes (FIG. 7C), although all were present (IgE<0.05% only). Kappa and lambda light chains were present in similar ratios to the peripheral blood datasets.

Similarly to peripheral blood a correlation was observed between BCR isotype and mutation level of both $V_H$ and $V_L$ chains, with IgG and IgA pairs showing greater $V_H$ and $V_L$ mutation than IgD and IgM, and a general correlation of mutation between $V_H$ and $V_L$ within each isotype (FIG. 7D). Interestingly, while IgD, IgM and IgA pairs showed very similar mutational distributions between the tumor and peripheral blood datasets (FIG. 5F), the tumor IgG fraction also contained a substantial proportion of little to non-mutated sequences that was not observed in the peripheral blood. For TCRs, and for BCRs containing IgD, similar numbers of captured mRNAs were observed per droplet barcode to the BCR results from peripheral blood (FIG. 7E, mostly <10 per droplet barcode). In stark contrast, the tumor-derived IgM, IgA and IgG pairs showed a 10 to 100-fold increased average expression level with hundreds or thousands of target mRNAs captured in many of the droplet barcodes. The diversity of the captured TIL-TCR and BCR repertoires was then assessed (FIG. 7F). Among the 5,217 total TCR pairs 2,423 distinct TCR beta clones were observed. Seven clones were present at a frequency >1% with the top clone representing 16.9% of all droplet barcodes. Among the 6,056 total BCR pairs 1,518 distinct heavy chain clones were observed, with 15 clones at >1% frequency but none >5%. While this represents substantially more restricted diversity than the healthy peripheral BCR repertoire (where no clone was present in greater than 0.06% frequency), the presence of so many class-switched, mutated and highly expressed clones in the tumor sample demonstrates the necessity of a deep and sensitive sampling approach for TIL characterization. These method allows rapid retrieval of large numbers of TIL immune receptor pairs, from both B and T cells simultaneously, without the need for prior sorting or exogenous activation of defined TIL populations.

Example 6

Capture of Additional Phenotypic Markers of Interest

Pairing of receptor chains by droplet barcoding potentially allows capture of additional targets besides immune receptors. To investigate this possibility healthy T-cells into CD4$^+$ and CD8$^+$ populations were separated by magnetic bead enrichment and entered 20,000 cells of each type into separate emulsion runs, with primers targeting TCR alpha and beta chains and CD4 and CD8 mRNAs. After sequencing, 47.0% of 3,861 droplet barcodes containing TCR Vα and Vβ ("TCR pairs") from CD4$^+$ isolated cells were linked to CD4 mRNA, while only 0.3% were linked to CD8 mRNA. Conversely, 50.6% of 2,235 TCR pairs from CD8$^+$ isolated cells were associated with CD8 mRNA, while only 0.6% were linked to CD4 mRNA. This demonstrates the high specificity but limited sensitivity of an mRNA-based approach to cell phenotyping, similar to a previous report. In contrast, proteins such as cell surface receptors are usually present in far higher numbers (1,000-100,000 per cell) than their coding mRNAs, potentially making them easier to detect as well as being potentially more directly relevant to cell phenotype. To measure target protein levels on each cell custom oligonucleotide DNA labels were conjugated to anti-human CD4 and CD8 antibodies, and incubated the labeled antibodies with an unseparated mixture of CD4$^+$ and CD8$^+$ T-cells before entry of 30,000 cells into an emulsion (FIG. 8A). The DNA labels carry antibody-specific sequence tags as well as molecular barcodes and sequence complementarity to the amplified droplet barcodes, allowing emulsion droplet barcoding and molecular counting similarly to that done for mRNAs. The DNA labels were targeted as well as TCR, CD4 and CD8 mRNAs simultaneously. After sequencing and filtering 3,682 droplet barcodes were identified with high confidence TCR VαVβ pairs. Consistent with the previous experiment, roughly half (52%) of the TCR pairs could be assigned CD4 or CD8 status based on mRNA (FIG. 8B). However, over 95% of droplet barcodes could be assigned CD4 or CD8 based on protein status, with average molecular counts per droplet considerably higher for CD4/8 proteins (mean 20.5) than CD4/8 mRNAs (mean 1.0). Concordance between mRNA and protein signals was high (FIG. 8C): 96.0% of droplets given both mRNA and protein calls were in agreement. In some rare instances, both CD4 and CD8 proteins were detected, likely a result of droplets that contained two or more cells. Emulsion barcoding allows, for the first time, direct linking of single cell immune receptors to mRNA and protein markers of interest, all at high throughput. Application of this approach to TILs with an expanded, immune-oncology relevant marker set such as anti-PD-1 and anti-CTLA-4 is warranted.

Example 7

Human Samples

The blood sample for healthy repertoire validation was collected under the approval of the Personal Genome Project. PBMCs for the HIV bNAb experiment were obtained from donor 17, an HIV-1 infected donor from the IAVI Protocol G cohort. All human HIV samples were collected with written informed consent under clinical protocols approved by the Republic of Rwanda National Ethics Committee, the Emory University Institutional Review Board, the University of Zambia Research Ethics Committee, the Charing Cross Research Ethics Committee, the UVRI Science and Ethics Committee, the University of New South Wales Research Ethics Committee. St. Vincent's Hospital and Eastern Sydney Area Health Service, Kenyatta National Hospital Ethics and Research Committee, University of Cape Town Research Ethics Committee, the International Institutional Review Board, the Mahidol University Ethics Committee, the Walter Reed Army Institute of Research (WRAIR) Institutional Review Board, and the Ivory Coast Comite "National d'Ethique des Sciences de la Vie et de la Sante" (CNESVS). Cryopreserved, dissociated resected ovarian adenocarcinoma from a single donor was obtained from Conversant Biologics with written informed consent under an IRB approved protocol.

Example 8

Cell Preparation

For the study of 3 million healthy B-cells, 50 mL blood was drawn into Vacutainer CPT Cell Preparation Tubes with sodium heparin (BD), centrifuged for 20 min at 1800×g, washed twice in cell preparation buffer (1x PBS supplemented with 2% fetal bovine serum and 2 mM EDTA), using spins at 200×g to remove platelets, and the resulting PBMCs were cryopreserved in RPMI-1640 medium (Life Technologies)+20% fetal bovine serum+10% DMSO at −80° C. until needed. Prior to emulsion generation, PBMCs were thawed, washed twice in cell preparation buffer and counted. B-cells were isolated using a negative selection-based human B-cell enrichment kit (Stem Cell Technologies) according to the manufacturer's instructions. Cells were passed through a 20 m cell strainer and diluted to $6.2×10^6$ cells/mL (3-million B-cell experiment) or $3.1×10^6$ cells/mL (PGT-donor and ovarian tumor experiments) in cell preparation buffer.

Example 9

Immune Receptor Barcoding in Emulsion

The emulsion generation platform consisted of three Mitos P-Pumps (Dolomite Microfluidics) driven by a single air compressor, each with a Mitos Flow Rate sensor, to allow computer-controlled flow of two aqueous phases and one fluorophilic oil continuous phase into a fluorophilically-coated quartz Dolomite Small 2-Reagent chip. One aqueous input channel contained the cells at the required density to produce the desired cells-per-droplet occupancy level, while the second aqueous channel contained lysis and reaction mix, consisting of AbPair™ reaction buffer and oligonucleotides (www.abvitro.com/catalog AV2070-1S and AV2080-1S), 5 units/µL MuMLV-based reverse transcriptase (Thermo Scientific) and 0.1 units/µL Herculase II PCR polymerase. A 100 µL Hamilton Microliter syringe was used to overload a 100-µL internal diameter PEEK tubing sample loop in two injections of ~100 µL each of LR mix. A 100 µL Hamilton Gastight syringe was used to load ~110 µL of the cell suspension into a ~100 µL, 0.2 mm internal diameter FEP tubing loop. The emulsion was formed by focused flow jetting of the aqueous phases at identical flow rates through the 2-reagent chip with simultaneous oil flow from the two oil channels in the chip. The emulsion leaving the chip exit channel was dripped into 0.2 mL PCR strip tubes (Eppendorf) on a cold block, after which excess oil was removed by pipetting from the bottom of the tube, 40 µL of overlay solution was added (25 mM Na-EDTA, pH 8.0) and tubes were transferred to a standard thermocycler for the transcript tagging reaction. During a 45 min reverse transcription (RT) step, RNA is reverse transcribed at 42° C. with target-specific RT primers, with template-switch-based addition of a universal adaptor sequence containing a randomized molecular barcode. Following RT, emulsions were subjected to 40 cycles of thermocycling (each cycle: 82° C. for 10 sec, 65° C. for 25 sec) to perform PCR amplification of the droplet barcode templates, which were diluted in the initial lysis and reaction mix to 30,000 cp/µL, generating a concentration in the final mixture of 15,000 cp/µL or ~1 per ~65 pl droplet. One end of the droplet barcode comprises the Illumina read 2 ("P7") primer site, whereas the other end matches the common sequence of the universal adaptor oligonucleotide. Therefore, during PCR, template-switched cDNAs can anneal to amplified droplet barcode strands and become spliced by overlap extension to produce full-length products containing target, molecular barcode and droplet barcode sequences.

Example 10

Emulsion Breaking, Cleanup, Downstream PCRs, Pooling and Sequencing

After thermocycling, the overlay solution was removed by pipetting and 40 μL emulsion breaking solution (1:1 FC-40:perfluorooctanol) were added together with 15 μL lysate clearing solution (12.5 μL Qiagen Protease, 2.5 μL 0.5 M Na-EDTA, pH 8.0). After inverting 10 times to break the emulsion, the mixture was incubated for 15 minutes at 50° C. and 3 minutes at 95° C. to inactivate the protease. After centrifugation at 15,000×g for 1 min to isolate the aqueous phase, the recovered material was rigorously purified to remove oligonucleotides, reagents and excess droplet barcode PCR products. Since full length products contain biotin due to 5' biotinylation of the RT primer, they can be efficiently separated from excess droplet barcode PCR products by cleanup on streptavidin beads, thus minimizing downstream PCR recombination artifacts, a common problem in extension-by-overlap approaches. First products were purified using AMPure XP beads (Agencourt) using manufacturer's instructions at a 1:1 ratio, followed by cleanup using streptavidin beads (New England Biolabs) also using manufacturer's instructions, followed by elution in deionized water at 95° C., followed by a second cleanup with AMPure XP beads at a 1:1 ratio. Products were then entered into a target enrichment PCR in which primers specific to the constant regions of the B- or T-cell receptor targets were used together with a primer specific to the universal end of the droplet barcode sequence. This reverse primer also contained a six-base index barcode for multiplexed sequencing on the MiSeq instrument according to the manufacturer's instructions. Thus, only full-length, droplet-barcoded target sequences are amplified in this step. All targets were first amplified together for seven cycles of 98° C. 10 seconds; 64° C. 20 seconds; 72° C. 15 seconds, using Q5 Hot Start polymerase (New England Biolabs) under manufacturer-recommended conditions, including a 2 minute 98° C. polymerase activation step at the beginning of the reaction. This was followed by AMPure XP cleanup at a 1.5:1 beads:PCR ratio. A second seven-cycle targeting each chain ($V_H$, $V_L$, $V\alpha$, $V\beta$) separately was then performed, using the same thermocycling conditions as before, followed by AMPure XP cleanup. A final PCR with the same thermocycling conditions and 5-15 cycles (depending on yield as judged by qPCR) to add the full-length Illumina sequencing adaptors and generate enough material for TapeStation D1000 (Agilent) quantification was then performed. Libraries were then pooled and sequenced on the V3 2×300 bp MiSeq platform (Illumina).

Example 11

Modifications to the MiSeq Platform

Reconstruction of the complete variable V(D)J region of BCR or TCR requires stitching the two paired-end Illumina reads. To improve this process the forward read of the 2×300 bp kit was extended to 325 bp. 10% phiX spike-in was used to alleviate issues of limited library diversity, since immune receptor libraries have limited diversity in the constant region primer sites.

Example 12

Overview of Bioinformatics Processing of Reads

Illumina MiSeq reads were processed using custom pipelines built around the pRESTO package (version 0.4) to generate full length consensus sequences for mRNA molecules from each droplet, annotated with IgBLAST and/or IMGT/HighV-QUEST, and further aligned, filtered, and processed with custom scripts and the Change-O package to generate statistics.

Example 13

Read Processing and Annotation, Isotype Assignment

Raw read processing, V(D)J annotation and clonal assignment was performed with custom pipelines utilizing the pRESTO and Change-O packages. Briefly, raw Illumina paired-end 325+300 bp reads were quality-controlled, primer-trimmed, and droplet-specific (DB) and molecule-specific barcodes (MB) identified via fuzzy matching of primer sites. Together, DB and MB uniquely specify a molecule of origin, and this unique molecular identifier (UMI) was used to group agreeing PCR replicate reads (minimum of two) hailing from the same molecule to generate a consensus for each mRNA sequence. Isotype-specific priming was confirmed by fuzzy matching of known isotype-specific constant regions within primer-trimmed sequences. V(D)J germline segments and rearrangement structure was determined using IgBLAST and confirmed with IMGT/HighV-QUEST where appropriate, parsed by Change-O and custom scripts.

Clones were assigned via single-linkage clustering within groups of functional V(D)J sequences having matching IGHV gene, IGHJ gene, and junction length as implemented in Change-O. For the 3 million circulating cell dataset, a weighted intraclonal distance of 4.0, using a symmetrized transition/transversion model was used as the nearest-neighbor distance cutoff within clones.

Example 14

Droplet Immune Receptor Inclusion Filtering and Pairing Fidelity Calculation Precision of B-cell sequence recovery from droplets can be assessed in two ways with this barcoding method: using intra-droplet mRNA sequence agreement, and via cross-fraction pairing agreement. Within each droplet, multiple mRNAs are captured per locus; expressed V(D)J sequences from one cell should agree. The presence of more than one productive VDJ and one productive VJ sequence per droplet is flagged bioinformatically as putative immune receptor inclusion or multi-cell occupancy, using a cutoff of 2% sequence diversity (mean pairwise nucleotide differences pi55<0.02) of multiple aligned V(D)J segments to define sequence agreement. Heavy and light chain consensus sequences were built for each allelically excluded droplet, and were used for clone definition and cross-fraction pairing analysis. For the 3 million circulating B-cell dataset, each $V_H$ lineage is associated with one (in the ideal case) of >20,000 light chain clones in the dataset. Among 259,368 immune-locus-excluded droplets with $V_H V_L$ pairs, 10,870 VDJ heavy locus rearrangement clusters were present in at least two of six physically separated emulsion fractions. These clusters represent either expanded lineages or independent but similar rearrangement of the same VJ exons. Where a VDJ rearrangement is paired with a consistent VJ rearrangement across two replicates, both experiments independently produced a true positive (33,157 of 35,922 possible pairwise comparisons for 2,604 clones with rarer rearrangements). Thus, the precision for each replicate is 96.1% (0.923^0.5).

Example 15

HIV bNAb Candidate Sequence Discovery

New natively paired broadly-neutralizing antibodies (BNAbs) to HIV were discovered by mining our 38,620 $V_H V_L$ pairs for similarity to known bNAb HCDR3s, VDJ sequences and Donor 17 lineages culled from the literature using tblastx, MUSCLE, and PhyML, followed by manual inspection of phylogenetic trees of full V(D)J amino acid sequence to select antibody candidates interspersing with known bNAb sequences.

Example 16

HIV bNAb Protein Expression and Purification

Antibody sequences were synthesized and cloned into previously described heavy and light chain vectors. Heavy and light chain plasmids were co-transfected (1:1 ratio) in 293 FreeStyle cells using 293fectin (Invitrogen) according to the manufacturer's protocol. Antibody supernatants were harvested four days following transfection and purified by protein-A affinity chromatography. Purified antibodies were buffer exchanged into PBS before use in further assays.

Example 17

Pseudovirus Production and Neutralization Assays

Pseudoviruses were generated by transfection of 293T cells with an HIV-1 Env expressing plasmid and an Env-deficient genomic backbone plasmid (pSG3AEnv). Pseudoviruses were harvested 72 hr post-transfection for use in neutralization assays. Neutralizing activity was assessed using a single round of replication pseudovirus assay and TZM-B1 target cells. Briefly, TZM-B1 cells were seeded in a 96 well flat bottom plate. To this plate was added pseudovirus, which was preincubated with serial dilutions of antibody for 1 hr at 37° C. Luciferase reporter gene expression was quantified 72 hr after infection upon lysis and addition of Bright-Glo Luciferase substrate (Promega). To determine $IC_{50}$ values, dose-response curves were fit by nonlinear regression.

Example 18

Ovarian Tumor Target Chain Identification

After simultaneous BCR and TCR capture from ovarian dissociated tumor tissue in emulsion, reads were filtered using molecular and droplet barcodes as previously described, but then looked for the presence of each of the four possible target chain types (BCR $V_H$, BCR $V_L$, TCR Vα, TCR Vβ). Target chains were retained if they were supported by at least two mRNAs, each with at least two sequencing reads. All droplet barcodes containing only BCR $V_H V_L$ or TCR VαVβ pairs were analyzed further. BCR heavy chain and TCR beta chain clones were called based on distinct CDR3 amino acid sequences.

Example 19

Protein Detection in Emulsion Through DNA-labelled Antibody Staining

Single-stranded, 200 bp DNA oligonucleotides were designed to contain unique 5 bp antigen ID sequences and were modified with a 5' amino group (Integrated DNA Technologies). Mouse monoclonal, anti-human CD4 (BioLegend, #300516) and CD8a (BioLegend, #301018) antibodies were conjugated to DNA oligonucleotide tags using the Thunder-Link kit (Innova Biosciences) according to manufacturer's protocol. For cell labeling prior to emulsion, two million negatively selected T-cells from peripheral blood were diluted in 400 µL cell buffer+2 mM EDTA+0.05% sodium azide. Single stranded salmon sperm DNA was added to cells to a final concentration of 200 µg/mL and cells were rotated at room temperature for five minutes. A mixture of CD4 and CD8a DNA-labeled antibodies (each to a final concentration of 5 nM) was added to the cells and incubated at room temperature for 30 minutes. Cells were washed three times with cell Buffer+2 mM EDTA+0.05% sodium azide+200 µg/mL single stranded salmon sperm DNA. Cells were resuspended in cell buffer+0.05% sodium azide prior to entry into emulsion analysis. 30,000 cells were used for emulsion sequencing.

Example 20

Tetramer-Oligonucleotide Conjugate Staining

Figure 18:
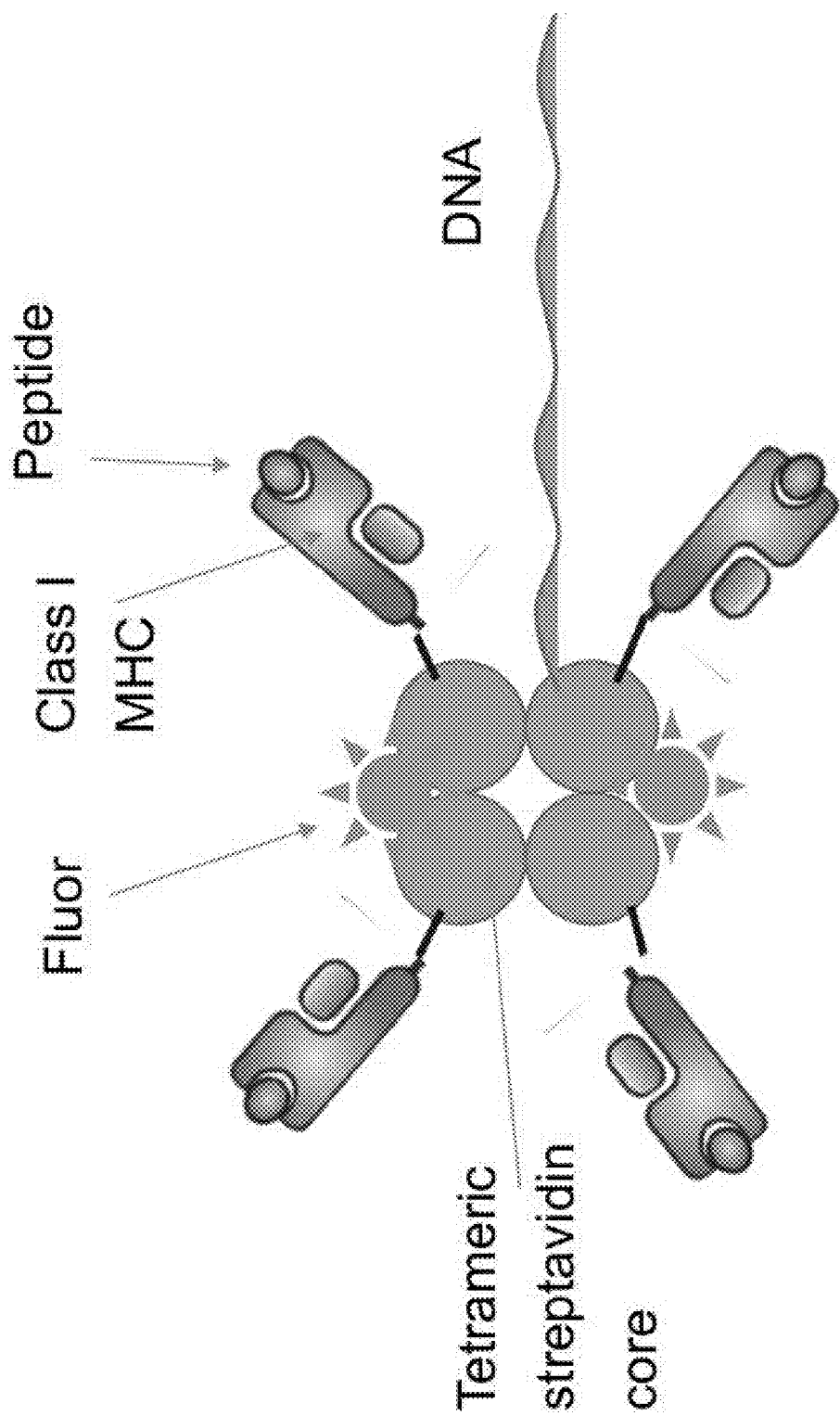
FIG. 18 depicts a further view an exemplary tetramer-oligonucleotide conjugate. In some embodiments, a tetramer-oligonucleotide comprises a fluorophore (Fluor). In some embodiments, a tetramer-oligonucleotide does not comprise a fluorophore.

A tetramer-oligonucleotide comprised of four MHC-peptide complexes each with a streptavidin core and a fluorophore was generated. Each tetramer oligonucleotide further comprised a molecular barcode and/or a tetramer ID code for use in quantification as described below. An exemplary fluor-labeled tetramer-oligonucleotide conjugate is shown in FIG. 18.

Figure 19:
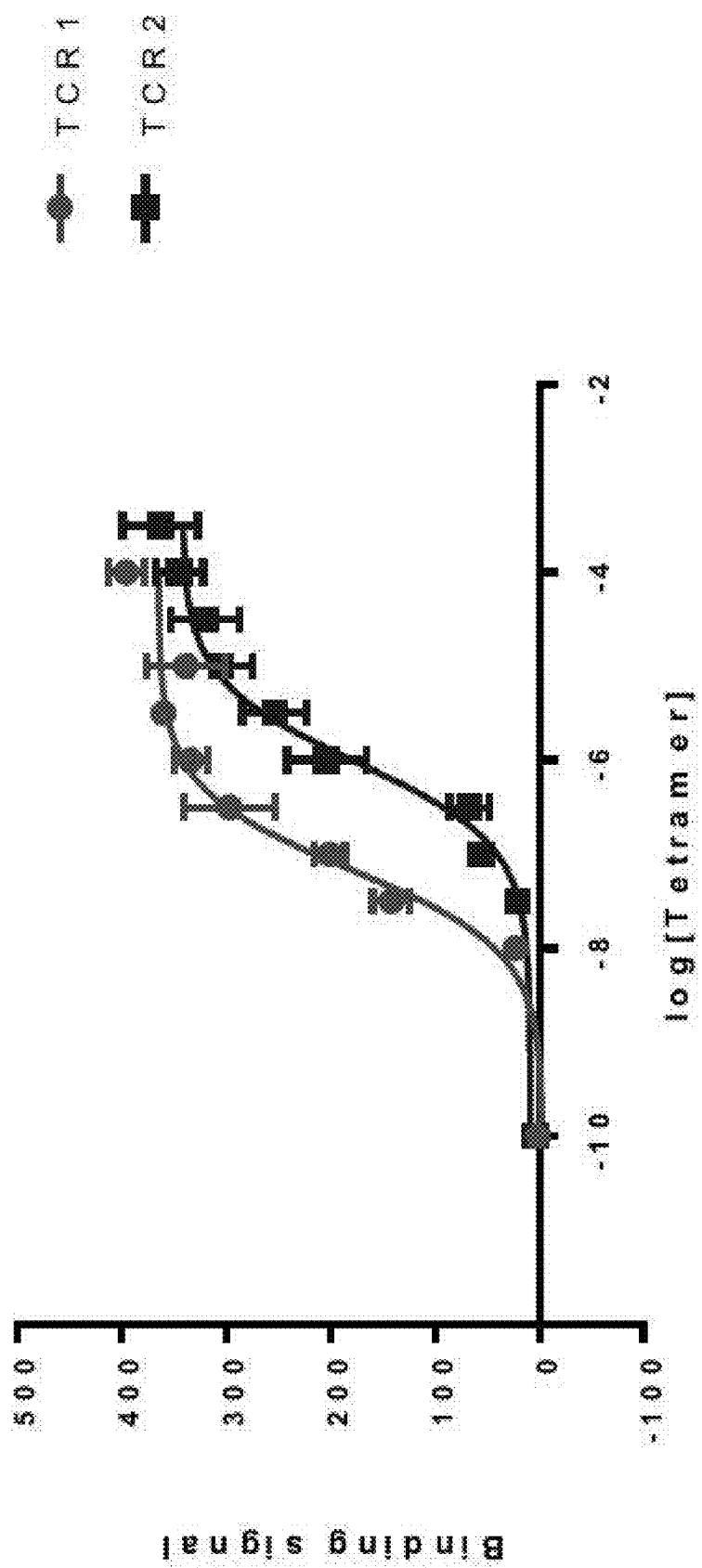
FIG. 19 depicts exemplary binding curves for two exemplary tetramer-oligonucleotide conjugates of the methods described herein that contain a MHC-peptide affinity portion that binds to a TCR.
Figure 20:
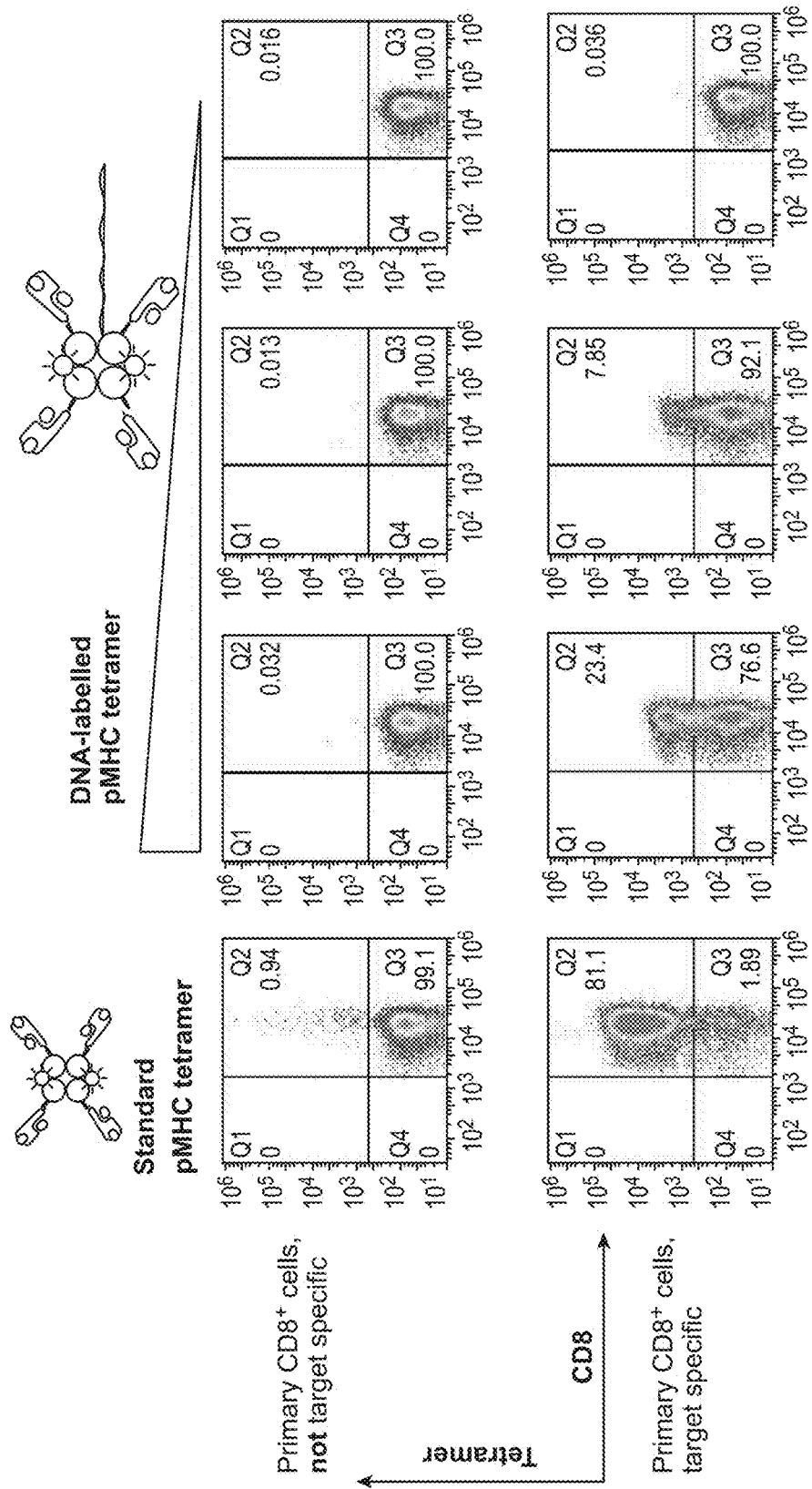
FIG. 20 depicts flow cytometry plots wherein target-specific primary CD8+ T cells or non-target specific primary CD8+ T cells were incubated with either standard pMHC tetramer reagent or DNA labelled pMHC tetramer (tetramer-oligonucleotide conjugate). DNA-labelled pMHC tetramer was used at decreasing concentrations, as shown by the triangle directly above the rightmost three columns of panels.

An exemplary method for determining affinity of two different TCRs is described herein. Two populations of T-cells with a known differing affinity for a MHC-peptide are incubated with various concentrations of tetramer-oligonucleotide conjugate comprising the MHC-peptide tetramer (pMHC). The unbound tetramer-oligonucleotide is washed away, and the cells are entered into emulsion analysis and sequenced. Binding signal is calculated based on sequence reads of the oligonucleotide of the tetramer-oligonucleotide conjugate for each T-cell at each concentration of tetramer-oligonucleotide conjugate (FIG. 19). T-cells incubated with a higher concentration of tetramer-oligonucleotide conjugate are expected to show a higher binding signal. T-cells with TCRs that have a higher affinity for the MHC-peptide of the tetramer-oligonucleotide conjugate are expected to exhibit a higher binding signal as compared to the T-cells with TCRs that had a lower affinity for the MHC-peptide of the tetramer-oligonucleotide conjugate at the same concentration of tetramer-oligonucleotide conjugate within the workable range of the assay. For example, in FIG. 19 between the concentrations of log [Tetramer]−8 and −4, the binding signal for TCR1 is above that of TCR2, indicating that in this assay TCR1 would be expected to have a higher affinity for the tetramer reagent used.

Example 21

Tetramer-Oligonucleotide Conjugate Staining Compared with Conventional MHC-peptide Tetramer Staining Target-specific T cells were generated to provide a positive control for testing binding specificity of exemplary tetramer-oligonucleotide conjugate reagents as described herein. An exemplary method for generating target-specific T cells is generally described by Ho et al., *J. Immunol. Methods*, 310:1-2, 40-52. Briefly, dendritic cells are derived from adherent fractions of peripheral blood mononuclear cell (PBMC) samples obtained from normal human donors with HLA-A02:01 by culturing over two days in the presence of GM-CSF and IL-4, followed by incubation beginning at day 3 in the presence of pro-inflammatory cytokines to produce mature dendritic cells. On Day 4, the resulting mature dendritic cells are harvested, washed and pulsed with the desired target-derived peptide to be used in the MHC-peptide tetramer (pMHC). On Day 5, autologous CD8+ T-cells from normal human donors are incubated with the peptide-pulsed dendritic cells. On Day 8, IFNγ in the cultures is measured as an indicator for cultures containing antigen-specific T-cells. Cells from reactive co-cultures are selected and re-stimulated two or three times with peptide-pulsed dendritic cells to enrich for antigen-specific T-cells. In some embodiments, these antigen specific T-cells are generated from such enriched populations by cell sorting and/or limiting dilution cloning essentially as described by Ho et al. 2006. CD8+ T-cells which are not target specific were used as a T-cell control population.

Figure 21:
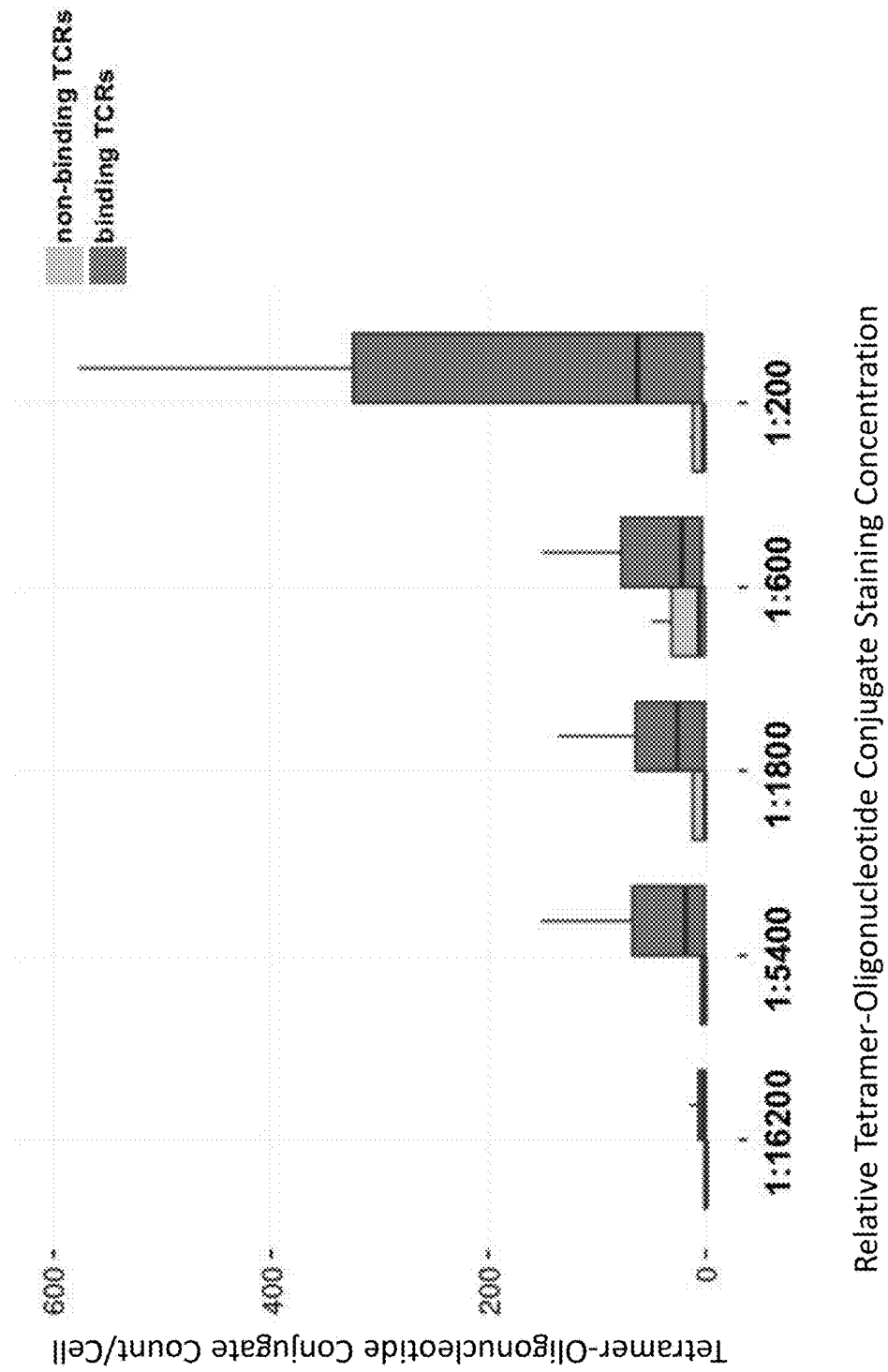
FIG. 21 depicts a comparison of tetramer-oligonucleotide conjugate count per cell between cells displaying non-binding TCRs (for example, TCRs that are not specifically recognized by the tetramer-oligonucleotide conjugate reagent) and binding TCRs (for example, TCRs that are specifically recognized by the tetramer-oligonucleotide conjugate reagent). Increasing concentrations of tetramer-oligonucleotide conjugate were used as indicated along the X axis.

The target specific CD8+ T-cells and the non-specific CD8+ T-cell control population were incubated with either a fluor-labeled standard MHC-peptide tetramer or various decreasing concentrations of a fluor-labeled tetramer-oligonucleotide conjugate. After incubation, the presence of cells staining positive for standard MHC-peptide tetramer or tetramer-oligonucleotide conjugate were identified by flow cytometry. Both the standard MHC-peptide tetramer and the tetramer-oligonucleotide conjugate incubated with the non-specific CD8+ T-cells showed little to no positive staining (FIG. 21, top row flow cytometry plots). The standard MHC-peptide tetramer incubated with the target specific CD8+ T-cells showed a strong double positive MHC-peptide tetramer+CD8+ cell population (FIG. 21, bottom row, left flow cytometry plot). The tetramer-oligonucleotide conjugate incubated with the target specific CD8+ T-cells showed a strong double positive tetramer-oligonucleotide conjugate+CD8+ cell population, in which this double positive population decreased with decreased tetramer-oligonucleotide conjugate concentration (FIG. 21, bottom row, right three flow cytometry plots). This indicated that tetramer-oligonucleotide conjugates bound to target specific T-cells similarly to standard MHC-peptide tetramers, and that the tetramer-oligonucleotide conjugates binding to target specific T-cells was tetramer-oligonucleotide conjugate concentration dependent.

Example 22

Tetramer-Oligonucleotide Conjugate Binding Signal

Target-specific (binding TCRs) or non-specific T cells (non-binding TCRs), generally as described in Example 21, were also used to assess the bound tetramer-oligonucleotide conjugate count per cell. The non-binding TCRs cell population and the binding TCRs cell population were separately incubated with various concentrations of tetramer-oligonucleotide conjugate comprising an MHC-peptide tetramer recognized by the TCRs of the binding TCR population as well as at least one unique oligonucleotide sequence (e.g., a molecular barcode, a tetramer ID code, and/or an antigen ID code). The unbound tetramer-oligonucleotide was washed away, and the cells were entered into emulsion analysis and were sequenced. Binding signal was calculated based on the number of sequence reads of the oligonucleotide for each tetramer at each concentration of tetramer-oligonucleotide conjugate, which is represented in graphic form in FIG. 21. The results shown in FIG. 21 indicate that tetramer-oligonucleotide conjugates are capable of specifically recognizing and binding to TCRs on primary target T cells in a dose-dependent manner.

What is claimed is:

1. A method of selecting a T cell receptor (TCR), comprising:
   (a) forming a plurality of vessels, wherein a vessel of the plurality of vessels comprises at least one pMHC-oligonucleotide conjugate molecule and a single T cell of a plurality of T cells;
   (b) attaching a vessel barcoded polynucleotide or complement thereof to:
      (i) an oligonucleotide portion of the pMHC-oligonucleotide conjugate molecule within the vessel of the plurality of vessels, and
      (ii) a TCR polynucleotide from the single T cell; and
   (c) sequencing the oligonucleotide portion or a complement thereof and the TCR polynucleotide or a complement thereof, thereby generating sequence information, wherein the attaching of step (b) occurs within the vessel.

2. The method of claim 1, wherein a pMHC portion of the pMHC-oligonucleotide conjugate molecule comprises a multimer of the pMHC.

3. The method of claim 1, wherein the pMHC oligonucleotide conjugate molecule comprises a detection portion.

4. The method of claim 1, wherein the method further comprises prior to step (a), obtaining an enriched T cell population comprising T cells bound to pMHC-oligonucleotide conjugate molecules.

5. The method of claim 4, wherein the method further comprises washing the enriched T cell population.

6. The method of claim 1, wherein the method further comprises isolating the single T cell in the vessel.

7. The method of claim 4, wherein the T cells are bound to the pMHC-oligonucleotide conjugate molecules before obtaining the enriched T cell population.

8. The method of claim 6, wherein the method further comprises lysing the single T cell after the single T cell is isolated in the vessel.

9. The method of claim 1, wherein the vessel barcoded polynucleotide or complement thereof comprises a vessel barcode sequence, and wherein the vessel barcode sequence of each vessel barcoded polynucleotide or complement thereof in any single vessel of the plurality of vessels is unique.

10. The method of claim 1, wherein the method further comprises amplifying the oligonucleotide portion or complement thereof.

11. The method of claim 1, wherein the method further comprises amplifying the TCR polynucleotide or complement thereof.

12. The method of claim 1, wherein the vessel barcoded polynucleotide or complement thereof comprises a vessel barcode sequence, and wherein the vessel barcode sequence of the vessel barcoded polynucleotide or complement thereof attached to the TCR polynucleotide and the vessel barcode sequence of the vessel barcoded polynucleotide or complement thereof attached to the oligonucleotide portion are the same.

13. The method of claim 1, wherein the method further comprises pooling oligonucleotide portions, amplified products thereof or complements thereof, and TCR polynucleotides or complements thereof, from two or more vessels of the plurality of vessels.

14. The method of claim 1, further comprising determining a binding affinity of a TCR encoded by the TCR polynucleotide to the pMHC-oligonucleotide conjugate molecule based on the sequence information.

15. The method of claim 1, wherein the method further comprises determining the number of pMHC-oligonucleotide conjugate molecules bound to the single T cell.

16. The method of claim 1, wherein the sequence information comprises TCR polynucleotide sequence reads, vessel barcode sequence reads, and oligonucleotide sequence reads.

17. The method of claim 16, wherein the method further comprises comparing the oligonucleotide sequence reads to the TCR polynucleotide sequence reads.

18. The method of claim 16, wherein the method further comprises selecting a TCR based on the oligonucleotide sequence reads.

19. The method of claim 1, wherein the oligonucleotide portion of the pMHC-oligonuleotide conjugate molecule comprises a tetramer molecular barcode (TMB) sequence that is unique to a single pMHC-oligonucleotide conjugate molecule of a plurality of pMHC-oligonucleotide conjugate molecules.

20. The method of claim 19, wherein a number of pMHC-oligonucleotide conjugate molecules bound to the single T cell is determined from the sequence information.

21. The method of claim 19, wherein the sequence information comprises tetramer molecular barcode sequence reads.

22. The method of claim 21, wherein the number of pMHC-oligonucleotide conjugate molecules bound to the single T cell is determined from the tetramer molecular barcode sequence reads.

23. The method of claim 16, wherein the method further comprises analyzing TMB sequences of the oligonucleotide sequence reads.

24. The method of claim 23, wherein the method further comprises analyzing tetramer identification (TID) sequences of the oligonucleotide sequence reads.

25. The method of claim 1, wherein the oligonucleotide portion comprises a tetramer identification (TID) sequence.

26. The method of claim 25, wherein the TID sequence is barcoded to a peptide or a pMHC portion of the pMHC-oligonucleotide conjugate molecule.

27. The method of claim 25, wherein the sequence information comprises the TID sequence or a complement thereof and a copy number of molecules having the TID sequence.

28. The method of claim 24, wherein the analyzing comprises determining a frequency of one or more vessel barcode sequences, one or more TID sequences, one or more TMB sequences, or a combination thereof.

29. The method of claim 24, wherein the method further comprises comparing TID sequences of oligonucleotide sequence reads to TMB sequences of oligonucleotide sequence reads.

30. A method of determining the binding affinity of a T cell receptor (TCR) comprising
   (a) incubating a plurality of pMHC-oligonucleotide conjugate molecules with a plurality of T cells;
   (b) forming a vessel comprising at least one of the plurality of pMHC-oligonucleotide conjugate molecules and at least one of the plurality of T cells;
   (c) attaching a vessel barcoded polynucleotide or complement thereof to an oligonucleotide portion of the pMHC-oligonucleotide conjugate molecules within the vessel;
   (d) quantifying the pMHC-oligonucleotide conjugate molecules within the vessel by sequencing the oligonucleotide portion or a complement thereof of the pMHC-oligonucleotide conjugate molecules, thereby generating sequence information; and
(e) determining a binding affinity of a TCR to a pMHC oligonucleotide conjugate molecule based on the sequence information.

31. A composition comprising a plurality of vessels, wherein a vessel of the plurality of vessels comprises
(a) a single T cell from a sample comprising a plurality of T cells;
(b) a vessel barcoded polynucleotide comprising a vessel barcode sequence; and
(c) a pMHC-oligonucleotide conjugate that binds to a TCR of the single T cell.

* * * * *

SEQUENCE LISTING

```
<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 1

His His His His His His
1               5

<210> SEQ ID NO 2
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 2

Ala Ser Ser Asp Leu Gln Gly Arg Asn Tyr Asn Glu Gln Phe
1               5                   10

<210> SEQ ID NO 3
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ala Ser Ser Pro Gly Ser Gly Glu Thr Gln Tyr
1               5                   10

<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ala Ser Ser Tyr Ser Val Leu Ala Gly Ser Tyr Gly Thr Gly Glu Leu
1               5                   10                  15

Phe

<210> SEQ ID NO 5
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
tacattgata gtca                                                         14

<210> SEQ ID NO 6
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
tcattttata cttc                                                         14

<210> SEQ ID NO 7
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
attattaaaa gact                                                         14
```

```
<210> SEQ ID NO 8
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
aatctctctt gaat                                                       14

<210> SEQ ID NO 9
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
tagttttcga aaga                                                       14

<210> SEQ ID NO 10
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
aacgtcctgt aaac                                                       14

<210> SEQ ID NO 11
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
cggcacttca ttgt                                                       14

<210> SEQ ID NO 12
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
ccacagccaa ccag                                                       14
```